(12) United States Patent
Lin et al.

(10) Patent No.: US 11,504,441 B2
(45) Date of Patent: Nov. 22, 2022

(54) RADIOLABELED COMPOUNDS TARGETING THE PROSTATE-SPECIFIC MEMBRANE ANTIGEN

(71) Applicants: PROVINCIAL HEALTH SERVICES AUTHORITY, Vancouver (CA); THE UNIVERSITY OF BRITISH COLUMBIA, Vancouver (CA)

(72) Inventors: Kuo-Shyan Lin, Richmond (CA); François Bénard, Vancouver (CA); Hsiou-Ting Kuo, Sherbrooke (CA); Zhengxing Zhang, Vancouver (CA); David Perrin, Vancouver (CA)

(73) Assignees: PROVINCIAL HEALTH SERVICES AUTHORITY, Vancouver (CA); THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 17/371,587

(22) Filed: Jul. 9, 2021

(65) Prior Publication Data
US 2021/0338851 A1 Nov. 4, 2021

Related U.S. Application Data

(63) Continuation of application No. PCT/CA2020/050864, filed on Jun. 19, 2020.

(60) Provisional application No. 63/006,643, filed on Apr. 7, 2020, provisional application No. 62/865,088, filed on Jun. 21, 2019.

(51) Int. Cl.
| | | |
|---|---|---|
| A61K 51/00 | (2006.01) | |
| A61M 36/14 | (2006.01) | |
| A61K 51/08 | (2006.01) | |
| A61P 35/00 | (2006.01) | |
| A61K 51/04 | (2006.01) | |
| C07D 257/02 | (2006.01) | |
| C07B 59/00 | (2006.01) | |

(52) U.S. Cl.
CPC ........ *A61K 51/088* (2013.01); *A61K 51/0482* (2013.01); *A61K 51/0497* (2013.01); *A61P 35/00* (2018.01); *A61K 51/0402* (2013.01); *C07B 59/004* (2013.01); *C07D 257/02* (2013.01)

(58) Field of Classification Search
CPC .............. A61K 51/088; A61K 51/0482; A61K 51/0497; A61K 51/0402; A61P 35/00; C07B 59/004; C07D 257/02
See application file for complete search history.

(56) References Cited

U.S. PATENT DOCUMENTS

| | | | |
|---|---|---|---|
| 5,650,134 A | 7/1997 | Albert et al. | |
| 8,114,381 B2 | 2/2012 | Perrin et al. | |
| 8,153,101 B2 | 4/2012 | McBride et al. | |
| 8,574,546 B2 | 11/2013 | Perrin et al. | |
| 8,691,761 B2 | 4/2014 | Rivier et al. | |
| 10,150,804 B2 | 12/2018 | Benard et al. | |
| 10,471,160 B2 | 11/2019 | Eder et al. | |
| 10,688,200 B2 | 6/2020 | Kung et al. | |
| 10,882,871 B2 * | 1/2021 | Benard ............. | A61K 51/0453 |
| 2014/0147381 A1 | 5/2014 | Espenan | |
| 2019/0008988 A1 | 1/2019 | Eder et al. | |
| 2020/0339625 A1 | 10/2020 | Lin et al. | |

FOREIGN PATENT DOCUMENTS

| | | |
|---|---|---|
| CN | 106967152 A | 7/2017 |
| EP | 3 064 224 A1 | 9/2016 |
| WO | WO 2005/077967 A1 | 8/2005 |
| WO | WO 2008/053360 A2 | 5/2008 |
| WO | WO 2008/058192 A2 | 5/2008 |
| WO | WO 2009/002529 A2 | 12/2008 |
| WO | WO 2009/012596 A1 | 1/2009 |
| WO | WO 2010/014933 A2 | 2/2010 |
| WO | WO 2012/094334 A1 | 7/2012 |
| WO | WO 2012/118909 A1 | 9/2012 |
| WO | WO 2013/028664 A1 | 2/2013 |
| WO | WO 2013/028791 A1 | 2/2013 |
| WO | WO 2014/078484 A1 | 5/2014 |
| WO | WO 2014/134716 A1 | 9/2014 |
| WO | WO 2015/055318 A1 | 4/2015 |
| WO | WO 2015/073678 A1 | 5/2015 |
| WO | WO 2015/100498 A1 | 7/2015 |
| WO | WO 2015/135082 A1 | 9/2015 |
| WO | WO 2017/117687 A1 | 7/2017 |
| WO | WO 2018/098390 A1 | 5/2018 |
| WO | WO 2018/215627 A1 | 11/2018 |
| WO | WO 2018/223180 A1 | 12/2018 |
| WO | WO 2019/075583 A1 | 4/2019 |

(Continued)

OTHER PUBLICATIONS

Kuo et al. (J. Nucl. Med. May 1, 2018, 59 (suppl 1) 7).*

(Continued)

*Primary Examiner* — Michael G. Hartley
*Assistant Examiner* — Melissa J Perreira
(74) *Attorney, Agent, or Firm* — Cooley LLP

(57) ABSTRACT

A compound comprising a prostate specific membrane antigen (PSMA)-targeting moiety of the following formula or of a salt or a solvate thereof. $R^0$ is O or S. Each of $R^{1a}$, $R^{1b}$ and $R^{1c}$ may be —$CO_2H$, —$SO_2H$, —$SO_3H$, —$PO_2H$, or —$PO_3H_2$, for example. $R^2$ may be methylene or a derivative thereof, propylene or a derivative thereof, or a derivative of ethylene, optionally substituted. $R^3$ is a linker. When the PSMA-targeting moiety is linked to a radiolabeling group, the compound may be used as an imaging agent or therapeutic agent for PSMA-expressing diseases/conditions.

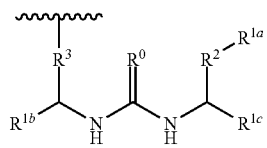

20 Claims, 14 Drawing Sheets

(56) References Cited

FOREIGN PATENT DOCUMENTS

| | | |
|---|---|---|
| WO | WO 2019/115547 A1 | 6/2019 |
| WO | WO 2019/204335 A1 | 10/2019 |
| WO | WO 2020/065045 A1 | 4/2020 |
| WO | WO 2020/109523 A1 | 6/2020 |
| WO | WO 2020/124237 A1 | 6/2020 |

OTHER PUBLICATIONS

Kuo et al. (J. Nucl. Med. 2019, 60, 1160-1166).*

Afshar-Oromieh et al., "Repeated PSMA-targeting radioligand therapy of metastatic prostate cancer with 131I-MIP-1095," Eur. J. Nucl. Med. Mol. Imaging, 44, 950-959 (2017).

Ahmadzadehfar et al., "Overall survival and response pattern of castration-resistant metastatic prostate cancer to multiple cycles of radioligand therapy using [177Lu]Lu-PSMA-617," Eur. J. Nucl. Med. Mol. Imaging, 44, 1448-1454 (2017).

Antunes et al., "Influence of Different Spacers on the Biological Profile of a DOTA-Somatostatin Analogue," Bioconjugate Chemistry, 2007, vol. 18, pp. 84-92.

Apostolidis et al., "Production of Ac-225 from Th-229 for targeted α therapy," Anal. Chem., 77, 6288-6291 (2005).

Bander et al., "Phase I trial of $^{177}$lutetium-labeled J591, a monoclonal antibody to prostate-specific membrane antigen, in patients with androgen-independent prostate cancer," J. Clin. Oncol., 23, 4591-4601 (2005).

Banerjee et al., "$^{64}$Cu-Labeled Inhibitors of Prostate-Specific Membrane Antigen for PET Imaging of Prostate Cancer," Journal of Medicinal Chemistry, 2014, vol. 57, pp. 2657-2669.

Banerjee et al., "$^{68}$Ga-Labeled Inhibitors of Prostate-Specific Membrane Antigen (PSMA) for Imaging Prostate Cancer," Journal of Medicinal Chemistry, 2010, vol. 53, pp. 5333-5341.

Banerjee et al., "Clinical applications of Gallium-68," Applied Radiation and Isotopes, 2013, vol. 76, pp. 2-13.

Benesova et al., "Linker modification strategies to control the prostate-specific membrane antigen (PSMA)-targeting and pharmacokinetic properties of DOTA-conjugated PSMA inhibitors," J. Med. Chem, 59, 1761-1775 (2016).

Benesova et al., "Albumin-binding PSMA ligands: optimization of the tissue distribution profile," Mol. Pharmaceutics, 15, 934-946 (2018).

Benesova et al., "Preclinical evaluation of a tailor-made DOTA-conjugated PSMA inhibitor with optimized linker moiety for imaging and endoradiotherapy of prostate cancer," J. Nucl. Med., 56, 914-920 (2015).

Berge et al., "Pharmaceutical Salts," Journal of Pharmaceutical Sciences, Jan. 1977, vol. 66, No. 1, pp. 1-19.

Bouvet et al., "Automated synthesis of [$^{18}$F]DCFPyL via direct radiofluorination and validation in preclinical prostate cancer models," EJNMMI Research, 2016, vol. 6, Article 40, 15 pages.

Bräuer et al., "$^{177}$Lu-PSMA-617 radioligand therapy and outcome in patients with metastasized castration-resistant prostate cancer," Eur. J. Nucl. Med. Mol. Imaging, 44, 1663-1670 (2017).

Breeman et al., "Somatostatin receptor-mediated imaging and therapy: basic science, current knowledge, limitations and future perspectives," European Journal of Nuclear Medicine, Sep. 2001, vol. 28, No. 9, pp. 1421-1429.

Buchmann et al., "Comparison of $^{68}$Ga-DOTATOC PET and $^{111}$In-DTPAOC (Octreoscan)SPECT in patients with neuroendocrine tumours," Eur J Nucl Med Mol Imaging., 2007, vol. 34, pp. 1617-1626.

Cai et al., "RGD-based PET tracers for imaging receptor integrin $\alpha_v\beta_3$ expression," Journal of Labelled Compounds and Radiopharmaceuticals, 2013, vol. 56, pp. 264-279.

Carter et al., "Prostate-specific membrane antigen is a hydrolase with substrate and pharmacologic characteristics of a neuropeptidase," Proc. Natl. Acad. Sci. U.S.A., 93, 749-753 (1996).

Chatalic et al., "Towards personalized treatment of prostate cancer: PSMA I&T, a promising prostate-specific membrane antigen-targeted theranostic agent" Theranostics, 6, 849-861 (2016).

Chen et al., "2-(3-{1-Carboxy-5-[(6-[$^{18}$F]Fluoro-Pyridine-3-Carbonyl)-Amino]-Pentyl}-Ureido)-Pentanedioic Acid, [$^{18}$F]DCFPyL, a PSMA-Based PET Imaging Agent for Prostate Cancer," Clinical Cancer Research, Dec. 2011, vol. 17, No. 24, pp. 7645-7653.

Chin et al., "First Experience with Clinical-Grade [$^{18}$F]FPP(RGD)$_2$: An Automated Multi-step Radiosynthesis for Clinical PET Studies," Mol Imaging Biol., 2012, vol. 14, pp. 88-95.

Choy, C. J. et al., "$^{177}$Lu-Labeled phosphoramidate-based PSMA inhibitors: The effect of an albumin binder on biodistribution and therapeutic efficacy in prostate tumor-bearing mice," Theranostics, 7, 1928-1939 (2017), and supplemental information, 33 pages.

Dumelin et al, "A portable albumin binder from a DNA-encoded chemical library," Angew Chem. Int. Ed, 47, 3196-3201 (2008).

Eberl et al., "High beam current operation of a PETtrace™ cyclotron for $^{18}$F production," Applied Radiation and Isotopes, 2012, vol. 70, pp. 922-930.

Eder et al., "$^{68}$Ga-Complex Lipophilicity and the Targeting Property of a Urea-Based PSMA Inhibitor for PET Imaging," Bioconjugate Chemistry, 2012, vol. 23, pp. 688-697.

Extended Search Report for European Patent Application No. 15733077.0, dated Jun. 19, 2017, 6 pages.

Extended Search Report for European Patent Application No. 17735797.7, dated Aug. 13, 2019, 8 pages.

Fani et al., "Unexpected Sensitivity of sst$^2$ Antagonists to N-Terminal Radiometal Modifications," The Journal of Nuclear Medicine, Sep. 2012, vol. 53, No. 9, pp. 1481-1489.

Fendler et al., "Preliminary experience with dosimetry, response and patient reported outcome after $^{177}$Lu-PSMA-617 therapy for metastatic castration-resistant prostate cancer," Oncotarget, 8, 3581-3590 (2017).

Gabriel et al., "$^{68}$Ga-DOTA-Tyr$^3$-Octreotide PET in Neuroendocrine Tumors: Comparison with Somatostatin Receptor Scintigraphy and CT," The Journal of Nuclear Medicine, Apr. 2007, vol. 48, No. 4, pp. 508-518.

Gabriel et al., "An Intrapatient Comparison of $^{99m}$Tc-EDDA/HYNIC-TOC with $^{111}$In-DTPA Octreotide for Diagnosis of Somatostatin Receptor-Expressing Tumors," The Journal of Nuclear Medicine, May 2003, vol. 44, No. 5, pp. 708-716.

Ginj et al., "Design, Synthesis, and Biological Evaluation of Somatostatin-Based Radiopeptides," Chemistry & Biology, Oct. 2006, vol. 13, pp. 1081-1090.

Guo et al., "Preparation and Biological Evaluation of $^{64}$Cu Labeled Tyr$^3$-Octreotate using a Phosphonic Acid-Based Cross-Bridged Macrocyclic Chelator," Bioconjugate Chemistry, 2012, vol. 23, pp. 1470-1477.

Harada et al., "Synthesis and biological evaluation of novel $^{18}$F-labeled probes targeting prostate-specific membrane antigen for positron emission tomography of prostate cancer," J. Nucl. Med., 57, 1978-1984 (2016).

Heck et al., "Systemic radioligand therapy with $^{177}$Lu labeled prostate specific membrane antigen ligand for imaging and therapy in patients with metastatic castration resistant prostate cancer," J. Urol., 196, 382-391 (2016).

Henze et al., "PET Imaging of Somatostatin Receptors Using [$^{68}$GA]DOTA-D-Phe$^1$-Tyr$^3$-Octreotide: Firest Results in Patients with Meningiomas," The Journal of Nuclear Medicine, Jul. 2001, vol. 42, No. 7, pp. 1053-1056.

Hofman et al., "[$^{177}$Lu]-PSMA-617 radionuclide treatment in patients with metastatic castration-resistant prostate cancer (LuPSMA trial): a single-centre, single-arm, phase 2 study," Lancet Oncol., 19, 825-833 (2018).

Horiuchi et al., "Discovery of novel thieno[2,3-d]pyrimidin-4-yl hydrazone-based inhibitors of Cyclin D1-CDK4: Synthesis, biological evaluation and structure-activity relationships. Part 2" Bioorganic & Medicinal Chemistry, 2009, vol. 17, pp. 7850-7860.

Huggins et al., "Studies on Prostatic Cancer II. The Effects of Castration on Advanced Carcinoma of the Prostate Gland," Archives of Surgery, 1941, vol. 43, No. 2, pp. 209-223.

(56) References Cited

OTHER PUBLICATIONS

International Search Report and Written Opinion dated Jan. 30, 2019 in PCT International Application No. PCT/CA2018/051336, 8 pages.
International Search Report and Written Opinion for International (PCT) Patent Application No. PCT/CA2015/000002, dated May 4, 2015, 10 pages.
International Search Report and Written Opinion of the International Searching Authority for International Application No. PCT/CA2019/051853, dated Feb. 18, 2020, 8 pages.
International Search Report and Written Opinion of the International Searching Authority for International Application No. PCT/CA2020/050509, dated Jun. 11, 2020, 13 pages.
International Search Report and Written Opinion prepared by the Canadian Intellectual Property Office dated Mar. 31, 2017, for International Application No. PCT/CA2017/050026, 10 pages.
Kayani "A Comparison of $^{68}$Ga-DOTATATE and $^{18}$F-FDG PET/CT in Pulmonary Neuroendocrine Tumors," The Journal of Nuclear Medicine, Dec. 2009, vol. 50, No. 12, pp. 1927-1932.
Keenan et al., "RADAR realistic animal model series for dose assessment," J Nucl Med.;51:471-476 (2010).
Kelly et al., "Dual-target binding ligands with modulated pharmacokinetics for endoradiotherapy of prostate cancer," J. Nucl. Med., 58,1442-1449 (2017).
Kelly et al., "Trifunctional PSMA-targeting constructs for prostate cancer with unprecedented localization to LNCaP tumors," Eur. J. Nucl. Med. Mol. Imaging, 45:1841-1851 (2018) doi: 10.1007/S00259-018-4004-5.
Kemerink et al., "Effect of the positron range of $^{18}$F, $^{68}$Ga and $^{124}$I on PET/CT in lung equivalent materials," Eur J Nucl Med Mol Imaging, 2011, vol. 38, pp. 940-948.
Kirschner, "Radiation dosimetry of 131I-19-iodocholesterol: the pitfalls of using tissue concentration data," The author's reply. J Nucl Med. ;16:248-249 (1975).
Kopka et al. "Glu-Ureido-Based Inhibitors of Prostate-Specific Membrane Antigen: Lessons Learned During the Development of a Novel Class of Low-Molecular-Weight Theranostic Radiotracers," The Journal of Nuclear Medicine, Sep. 2017, vol. 58, No. 9 (Supple), pp. 17S-26S.
Kratochwil et al., "$^{225}$Ac-PSMA-617 for PSMA-targeted α-radiation therapy of metastatic castrationresistant prostate cancer," J. Nucl. Med., 57, 1941-1944 (2016).
Kratochwil et al., "PSMA-targeted radionuclide therapy of metastatic castration-resistant prostate cancer with $^{177}$Lu-labeled PSMA-617," J. Nucl. Med, 57, 1170-1176 (2016).
Krausz et al., "SPECT/CT hybrid imaging with $^{111}$In-pentetreotide in assessment of neuroendocrine tumours," Clinical Endocrinology, 2003, vol. 59, pp. 565-573.
Kularatne et al., "Prostate-Specific Membrane Antigen Targeted Imaging and Therapy of Prostate Cancer Using a PSMA Inhibitor as a Homing Ligand," Molecular Pharmaceutics, 2009, vol. 6, No. 3, pp. 780-789.
Kuo et al., "Enhancing Treatment efficacy of $^{177}$Lu-PSMA-617 with the conjugation of an Albuminbinding motif: Preclinical dosimetry and endoradiotherapy studies" Mol. Pharmaceutics, 15, pp. 5183-5191 (2018).
Kuo et al., "Effects of linker modification on tumor-to-kidney contrast of 68Ga-labeled PSMA-targeted imaging probes," Mol. Pharmaceutics, 2018, 15, 3502-3511 doi: 10.1021/acs.molpharmaceut.8b00499.
Kwekkeboom et al. "Peptide Receptor Radionuclide Therapy in Patients With Gastroenteropancreatic Neuroendocrine Tumors," Seminars in Nuclear Medicine, Mar. 2010, vol. 40, No. 2, pp. 78-88.
Kwekkeboom et al. "Somatostatin receptor-based imaging and therapy of gastroenteropancreatic neuroendocrine tumors," Endocr Relat Cancer., 2010, vol. 17, pp. R53-R73.
LaForest et al. "Image quality with non-standard nuclides in PET," QJ Nucl Med Mol Imaging, 2008, vol. 52, pp. 151-158.

Laverman et al., "A Novel Facile Method of Labeling Octreotide with $^{18}$F-Fluorine," The Journal of Nuclear Medicine, Mar. 2010, vol. 51(3), pp. 454-461.
Laverman et al., "Optimized labeling of NOTA-conjugated octreotide with F-18," Tumor Biol., 2012, vol. 33, pp. 427-434.
Leyton et al., "Targeting Somatostatin Receptors: Preclinical Evaluation of Novel $^{18}$F-Fluoroethyltriazole-Tyr$^3$-Octreotate Analogs for PET," The Journal of Nuclear Medicine, Sep. 2011, vol. 52(9), pp. 1441-1448.
Li et al., "One-step and one-pot-two-step radiosynthesis of cyclo-RGD-$^{18}$F-aryltrifluoroboronate conjugates for functional imaging," Am. J. Nucl. Med. Mol. Imaging, 2013, vol. 3(1), pp. 44-56 (32 pages).
Liu et al., ""Kit-like" radiosynthesis and biological evaluation of an F-labeled 4-(2-Aminoethyl)-benzenesulfonamide (AEBS) trimer for imaging carbonic anhydrase IX expression with positron emission tomography," World Molecular Imaging Congress, Sep. 19, 2013—poster, 1 page.
Liu et al., "$^{18}$F-trifluoroborate derivatives of [des-arg$^{10}$]kallidin for imaging bradykinin b1 receptor expression with positron emission tomography," Molecular Pharmaceutics, 2015, vol. 12, No. 3, pp. 974-982.
Liu et al., "An Organotrifluoroborate for Broadly Applicable One-Step $^{18}$F-Labeling," Angewandte Chemie International Edition, Sep. 2014, vol. 53, No. 44, p. 11876-11880.
Liu et al., "Facile synthesis and biological evaluation of an 18F-labeled 4-(2-aminoethyl) benzenesulfonamide (AEBS) trimer for imaging carbonic anhydrase IX expression with positron emission tomography," World Molecular Imaging Congress, Sep. 19, 2013, Presentation No. LBAP 029, 2 pages.
Liu et al., "From Minutes to Years: Predicting Organotrifluoroborate Solvolysis Rates," Chemistry—A European Journal, Mar. 2015, vol. 21, No. 10, pp. 3924-3928.
Liu et al., "Kit-like $^{18}$F-labeling of RGD-$^{19}$F-Aryltrifluroborate in high yield and at extraordinarily high specific activity with preliminary in vivo tumor imaging," Nuclear Medicine and Biology, vol. 40, 2013, pp. 841-849.
Liu et al., "Preclinical evaluation of a high affinity 18F-trifluoroborate octreotate derivative for somatostatin receptor imaging—poster," UBC, 2014, 1 page.
Liu et al., "Preclinical Evaluation of a High-Affinity $^{18}$F-Trifluoroborate Octreotate Derivative for Somatostatin Receptor Imaging," Journal of Nuclear Medicine, Sep. 2014, vol. 55(9), pp. 1499-1505.
Liu et al., "Preclinical Evaluation of a Novel 18F-Labelled Somatostatin Receptor-Binding Peptide—Abstract Proof," ScholarOne, Inc., 2014, Control ID: 1931699, 4 pages.
Liu et al., "Preclinical evaluation of a novel $^{18}$F-labelled somatostatin receptor-binding peptide," The Journal of Nuclear Medicine, 2014, vol. 55 (Supplement 1):1089, 1 page.
Liu et al., "Rapid, one-step, high yielding $^{18}$F-labeling of an aryltrifluoroborate bioconjugate by isotope exchange at very high specific activity," Journal of Labelled Compounds and Radiopharmaceuticals, 2012, vol. 55, pp. 491-496.
Liu et al., "Stoichiometric Leverage: Rapid 18F-Aryltrifluoroborate Radiosynthesis at High Specific Activity for Click Conjugation," Angew. Chem. Int. Ed., 2013, vol. 52, pp. 2303-2307.
Liu et al., "Simple Bioconjugate chemistry serves great clinical advances: albumin as a versatile platform for diagnosis and precision therapy," Chem. Soc. Rev, 45, 1432-1456 (2016).
Maresca et al., "A Series of Halogenated Heterodimeric Inhibitors of Prostate Specific Membrane Antigen (PSMA) as Radiolabeled Probes for Targeting Prostate Cancer," Journal of Medicinal Chemistry, 2009, vol. 52, No. 2, pp. 347-357.
Matteson et al., "Iodomethaneboronic Esters and Aminomethaneboronic Esters," Journal of Organometallic Chemistry, 1979, vol. 170, pp. 259-264.
Means et al. "Chemical Modifications of Proteins: History and Applications," Bioconjugate Chemistry, 1990, vol. 1, No. 1, pp. 2-12.
Meckel et al., "DOTA based bisphosphonate with an albumin binding moiety for delayed body clearance for bone targeting," Nucl. Med. Biol., 43, 670-678 (2016).

(56) References Cited

OTHER PUBLICATIONS

Mukherjee et al., "Mechanistic Studies on the Substrate-Tolerant Lanthipeptide Synthetase ProcM," Journal of the American Chemical Society, 2014, vol. 136, pp. 10450-10459.
Müller et al., "DOTA conjugate with an albumin-binding entity enables the first folic acid-targeted $^{177}$Lu-radionuclide tumor therapy in mice," J. Nucl. Med, 54, 124-131 (2013).
Poeppel et al., "$^{68}$GA-DOTATOC Versus $^{68}$Ga-DOTATATE PET/CT in Functional Imaging of Neuroendocrine Tumors," The Journal of Nuclear Medicine, Dec. 2011, vol. 52(12), pp. 1864-1870.
Poethko et al., "Two-Step Methodology for High-Yield Routine Radiohalogenation of Peptides: $^{18}$F-Labeled RGD and Octreotide Analogs," The Journal of Nuclear Medicine, May 2004, vol. 45 No. 5, pp. 892-902.
Pourghisian et al., "$^{18}$F-AmBF$_3$-MJ9: a novel radiofluorinated bombesin derivative for prostate cancer imaging," Bioorganic & Medicinal Chemistry, 2015, vol. 23, No. 7, pp. 1500-1506.
Price and Orvig, "Matching chelators to radiometals for radiopharmaceuticals," Chem. Soc. Rev., 43, 260-290 (2014).
Pyka et al., "$^{68}$Ga-PSMA-HBED-CC PET for Differential Diagnosis of Suggestive Lung Lesions in Patients with Prostate Cancer," Journal of Nuclear Medicine, 2016, vol. 57, pp. 367-371.
Pyka et al., "[68Ga]PSMA-HBED PET for differential diagnosis of suspicious lung lesions in patients with prostate cancer," J Nucl Med. Nov. 19, 2015, 26 pages, doi: 10.2967/jnumed.115.164442.
Rahbar et al, "German multicenter study investigating 177Lu-PSMA-617 radioligand therapy in advanced prostate cancer patients," J. Nucl. Med., 58, 85-90 (2017).
Rahbar et al., "Radioligand therapy with $^{177}$Lu-PSMA-617 as a novel therapeutic option in patients with metastatic castration resistant prostate cancer," Clin. Nucl. Med., 41, 522-528 (2016).
Reubi et al., "Affinity profiles for human somatostatin receptor subtypes SST1-SST5 of somatostatin radiotracers selected for scintigraphic and radiotherapeutic use," European Journal of Nuclear Medicine, Mar. 2000, vol. 27, No. 3, pp. 273-282.
Rowe et al., "Imaging of metastatic clear cell renal cell carcinoma with PSMA-targeted 18F-DCFPyL PET/CT," Annals of Nuclear Medicine, Dec. 2015, vol. 29, No. 10, pp. 877-882.
Roxin et al., "A metal-free DOTA-conjugated $^{18}$F-labeledradiotracer: [$^{18}$F]DOTA-AMBFi LLP2A for imaging VLA-4 Over-expression in murine melanoma with improved tumor uptake and greatly enhanced renal clearance," Bioconjugate Chem. 2019, 30, 1210-1219.
Roxin et al., "Preliminary evaluation of 18F-labeled LLP2A-trifluoroborate conjugates as VLA-4 (α4β1 integrin) specific radiotracers for PET imaging of melanoma" Nuclear Medicine and Biology 61 (2018) 11-20.
Sathekge et al., "$^{68}$Ga-PSMA imaging of metastatic breast cancer," European Journal of Nuclear Medicine and Molecular Imaging, Aug. 2015, vol. 42, No. 9, pp. 1482-1483.
Schottelius et al., "[$^{111}$In]PSMA-I&T: expanding the spectrum of PSMA-I&T applications towards SPECT and radioguided surgery," EJNMMI Research, 2015, vol. 5, Article 68, 5 pages.
Silver et al., "Prostate-specific membrane antigen expression in normal and malignant human tissues," Clin. Cancer Res., 3, 81-85 (1997).
Sokoloff et al., "A dual-monoclonal sandwich assay for prostate-specific membrane antigen: levels in tissues, seminal fluid and urine," Prostate, 43, 150-157 (2000).
Sprague et al., "Preparation and Biological Evaluation of Copper-64-Labeled Tyr3-Octreotate Using a Cross-Bridged Macrocyclic Chelator," Clinical Cancer Research, Dec. 2004, vol. 10, pp. 8674-8682.
Stabin et al., "OLINDA/EXM: the second-generation personal computer software for internal dose assessment in nuclear medicine," J Nucl Med.;46:1023-1027 (2005).
Stabin et al., "RADAR reference adult, pediatric, and pregnant female phantom series for internal and external dosimetry," J Nucl Med.; 53:1807-1813 (2012).
Stabin et al., "Re-evaluation of absorbed fractions for photons and electrons in spheres of various sizes," J Nucl. Med.; 41:149-160 (2000).
Storch et al., "Evaluation of [$^{99m}$Tc/EDDA/HYNIC$^0$]Octreotide Derivatives Compared with [$^{111}$In-DOTA$^0$,Tyr$^3$,Thr$^8$]Octreotide and [$^{111}$In-DTPA$^0$]Octreotide: Does Tumor or Pancreas Uptake Correlate with the Rate of Internalization?" The Journal of Nuclear Medicine, Sep. 2005, vol. 46, No. 9, pp. 1561-1569.
Thiele, N.A. et al., "An Eighteen-Membered Macrocyclic Ligand for Actinium-225 Targeted Alpha Therapy," Angewandte, vol. 56, Issue 46, pp. 14712-14717 (2017).
Umbricht et al., "Preclinical development of novel PSMA-targeting radioligands: Modulation of albuminbinding properties to improve prostate cancer therapy," Mol. Pharmaceutics, 15, 2297-2306 (2018).
Uribe et al., "Accuracy of $^{177}$Lu activity quantification in SPECT imaging: a phantom study," EJNMMI Phys.;4:2 (2017), 20 pages.
Vallabhajosula et al., "Preclinical Evaluation of Technetium-99m-Labeled Somatostatin Receptor-Binding Peptides," The Journal of Nuclear Medicine, Jun. 1996, vol. 37, No. 6, pp. 1016-1022.
Verburg et al., "First evidence of PSMA expression in differentiated thyroid cancer using [$^{68}$Ga]PSMA_HBED-CC PET/CT," European Journal of Nuclear Medicine and Molecular Imaging, 2015, vol. 42, pp. 1622-1623.
Virgolinl et al., "Somatostatin Receptor Subtype Specificity and in Vivo Binding of a Novel Tumor Tracer. $^{99m}$Tc-P829$^1$," Cancer Research, May 1998, vol. 58, pp. 1850-1859.
Walsh, K. M. "Brookhaven National Laboratory: Radioisotopes for medical imaging and disease treatment," J. Nucl. Med., 58, 11N-12N (2017).
Wängler et al., "One-Step $^{18}$F-Labeling of Carbohydrate-Conjugated Octreotate-Derivatives Containing a Silicon-Fluoride-Acceptor (SiFA): In Vitro and in Vivo Evaluation as Tumor Imaging Agents for Positron Emission Tomography," Bioconjugate Chem., 2010, vol. 21(12), pp. 2289-2296.
Wessels, "Bone marrow dosimetry using blood-based models for radiolabeled antibody therapy: a multiinstitutional comparison," J Nucl Med. ;45(10):1725-1733 (2004).
Wester et al., "PET imaging of somatostatin receptors: design, synthesis and preclinical evaluation of a novel 18F-labelled, carbohydrated analogue of octreotide," European Journal of Nuclear Medicine and Molecular Imaging, Jan. 2003, vol. 30, No. 1, pp. 117-122.
Wirtz et al., "Synthesis and in vitro and in vivo evaluation of urea-based PSMA inhibitors with increased lipophilicity," EJNMMI Research 8:84. Structures 10, 11 (2018).
Yadav et al, "$^{177}$Lu-DKFZ-PSMA-617 therapy in metastatic castration resistant prostate cancer: safety, efficacy, and quality of life assessment," Eur. J. Nucl. Med. Mol. Imaging, 44, 81-91 (2017).
Zhan et al., "Hydration of the Fluoride Anion: Structures and Absolute Hydration Free Energy from First-Principles Electronic Structure Calculations," J Phys Chem A., 2004, vol. 108, pp. 2020-2029.
Zhou et al., "A Fluorogenic Probe for the Copper(I)-Catalyzed Azide-Alkyne Ligation Reaction: Modulation of the Fluorescence Emission via 3(n,π*)-(π,π*) Inversion," Journal of the American Chemical Society, Jul. 2004, vol. 126, No. 29, pp. 8862-8863.
Extended Search Report for European Patent Application No. 18868855.0, dated Jul. 7, 2021, 13 pages.
International Search Report and Written Opinion of the International Searching Authority for International Application No. PCT/CA2020/050864, dated Sep. 18, 2020, 8 pages.

\* cited by examiner (PRIOR ART)

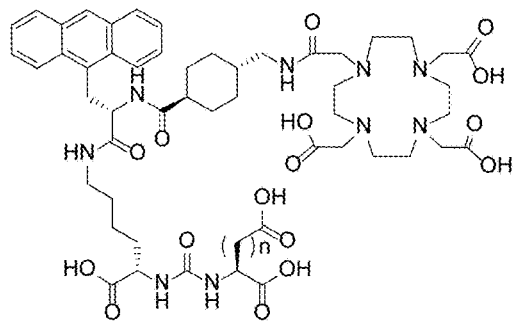
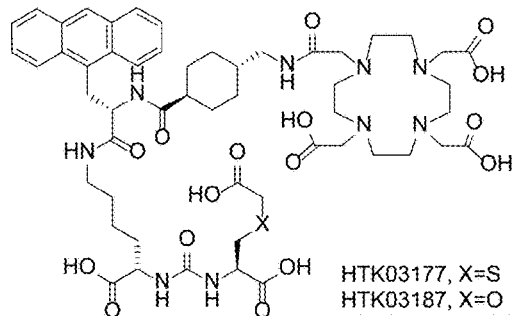
HTK03161: n=1; HTK03041: n=2
HTK03149: n=3
HTK03189 (A and B): n=4 (D- or L-form)
HTK03177, X=S
HTK03187, X=O
HTK04018, X=SO$_2$
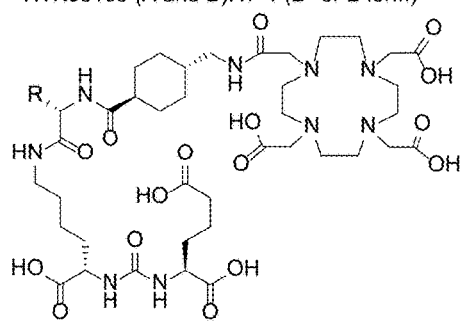
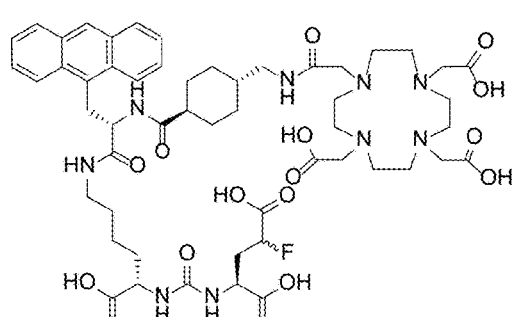
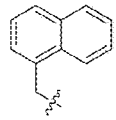 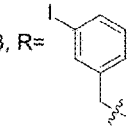
HTK03169, R=    HTK04053, R=
HTK04033, (R)-fluoro
HTK04040, (S)-fluoro
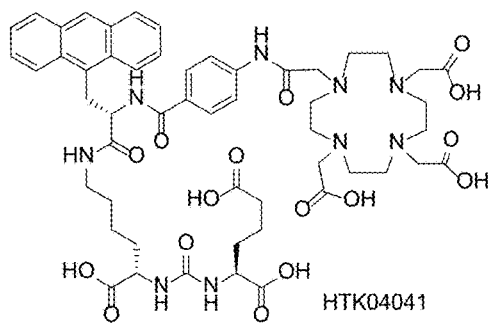
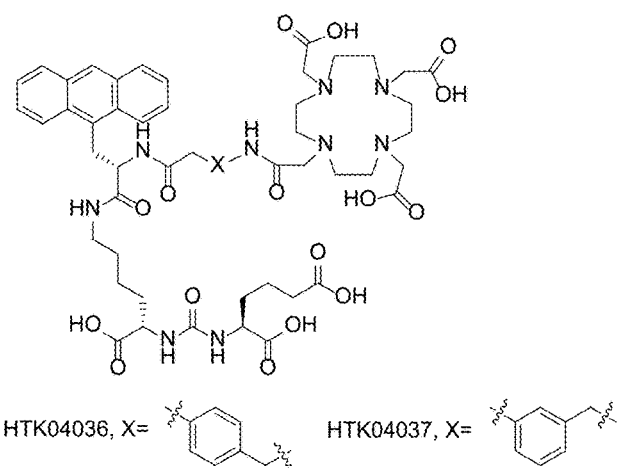
HTK04041    HTK04036, X=    HTK04037, X=
Fig. 6 (continued on next sheet)

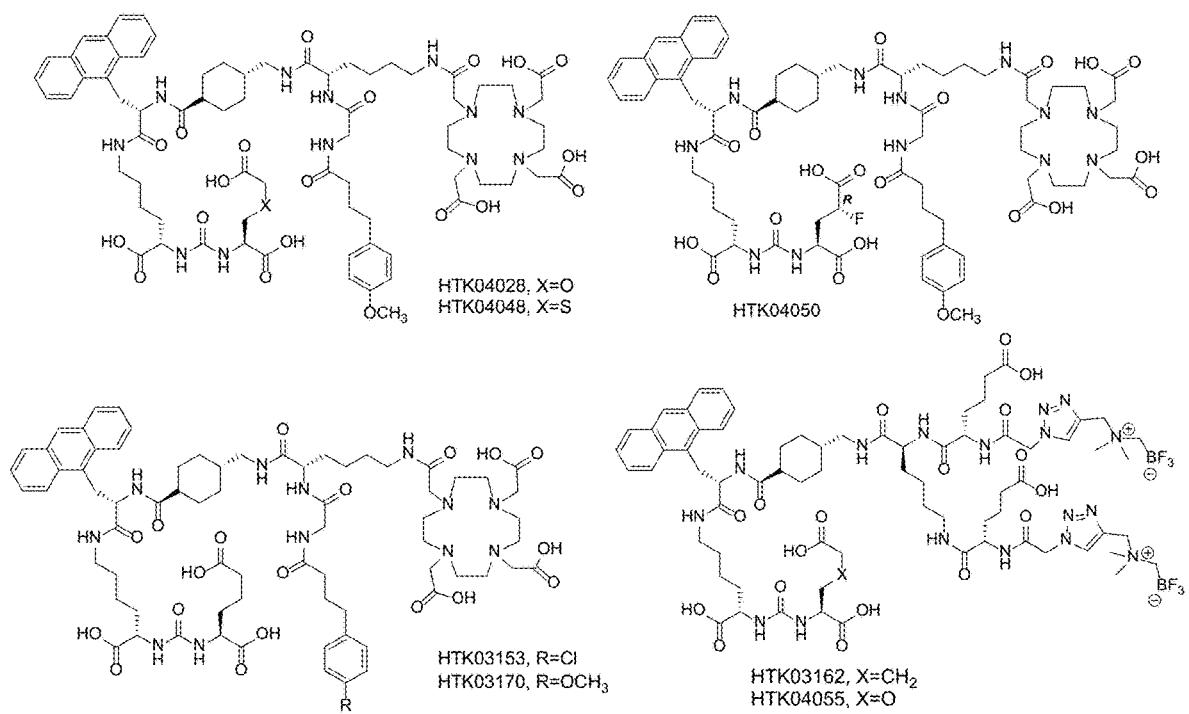
Fig. 6 (continued from previous sheet)

RADIOLABELED COMPOUNDS TARGETING THE PROSTATE-SPECIFIC MEMBRANE ANTIGEN

CROSS-REFERENCE TO RELATED APPLICATIONS

This application is a continuation of International Application No. PCT/CA2020/050864, filed Jun. 19, 2020, which claims the benefit of U.S. Provisional Application No. 62/865,088, filed Jun. 21, 2019, and U.S. Provisional Application No. 63/006,643, filed Apr. 7, 2020, the disclosure of each of which is incorporated by reference herein in its entirety.

FIELD OF INVENTION

The present invention relates to radiolabeled compounds for in vivo imaging or treatment of diseases or conditions characterized by expression of prostate-specific membrane antigen, particularly compounds with low uptake in salivary glands and/or kidneys.

BACKGROUND OF THE INVENTION

Prostate-specific membrane antigen (PSMA) is a transmembrane protein that catalyzes the hydrolysis of N-acetylaspartylglutamate to glutamate and N-acetylaspartate. PSMA is selectively overexpressed in certain diseases and conditions compared to most normal tissues. For example, PSMA is overexpressed up to 1,000-fold in prostate tumors and metastases. Due to its pathological expression pattern, various radiolabeled PSMA-targeting constructs have been designed and evaluated for imaging of PSMA-expressing tissues and/or for therapy of diseases or conditions characterized by PSMA expression.

A number of radiolabeled PSMA-targeting derivatives of lysine-urea-glutamate (Lys-ureido-Glu) have been developed, including $^{18}$F-DCFBC, $^{18}$F-DCFPyL, $^{68}$Ga-PSMA-HBED-CC, $^{68}$Ga-PSMA-617, $^{68}$Ga-PSMA I & T (see FIG. 1) as well as versions of the foregoing labeled with alpha emitters (such as $^{225}$Ac) or beta emitters (such as $^{177}$Lu or $^{90}$Y).

In clinical trials, PSMA-617 radiolabeled with therapeutic radionuclides, such as $^{177}$Lu and $^{225}$AC, has shown promise as an effective systemic treatment for metastatic castration resistant prostate cancer (mCRPC). However, dry mouth (xerostomia), altered taste and adverse renal events are common side effects of this treatment, due to high salivary gland and kidney accumulation of the radiotracer (Hofman et al., 2018 *The Lancet* 16(6):825-833; Rathke et al. 2019 *Eur J Nucl Med Mol Imaging* 46(1):139-147; Sathekge et al. 2019 *Eur J Nucl Med Mol Imaging* 46(1):129-138). Radiotracer accumulation in the kidneys and salivary gland is therefore a limiting factor that reduces the maximal cumulative administered activity that can be safely given to patients, which limits the potential therapeutic effectiveness of Lys-urea-Glu based radiopharmaceuticals (Violet et al. 2019 *J Nucl Med.* 60(4):517-523). There is therefore a need for new radiolabeled PSMA-targeting compounds, particularly compounds that have low accumulation in the salivary glands and/or kidneys.

No admission is necessarily intended, nor should it be construed, that any of the preceding information constitutes prior art against the present invention.

SUMMARY

Various embodiments disclosed herein relate to a compound, wherein the compound has Formula I or a salt or a solvate of Formula I:

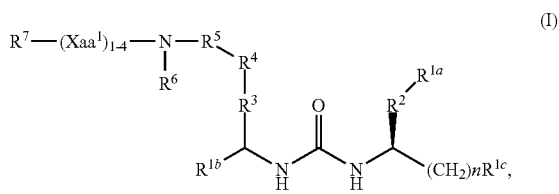

wherein:
n is 0 or 1;
each of $R^{1a}$, $R^{1b}$ and $R^{1c}$ is independently —$CO_2H$, —$SO_2H$, —$SO_3H$, —$SO_4H$, —$PO_2H$, —$PO_3H$ or —$PO_4H$;
when n is 0, $R^2$ is —$CH_2$—, —CHOH—, —CHF—, —$CH_2$CHOH—, —$CH_2$CHF—, —$CH_2$CHOHCH$_2$—, —$CH_2$CHFCH$_2$—, —(CH$_2$)$_2$CHOH—, —(CH$_2$)$_2$CHF—, —(CH$_2$)$_3$—, —$CH_2$OCH$_2$— or —$CH_2$SCH$_2$—;
when n is 1, $R^2$ is —$CH_2$—, —CHOH—, —CHF—, —$CH_2$CHOH—, —$CH_2$CHF— or —(CH$_2$)$_2$—;
$R^3$ is a linear or branched, cyclic or acyclic, and/or aromatic or non-aromatic $C_1$-$C_{20}$ alkylenyl or alkenylenyl, or a linear or branched, cyclic or acyclic, and/or aromatic or non-aromatic $X_2$-$X_{20}$ heteroalkylenyl or heteroalkenylenyl;
$R^4$: —O—, —S—, —NHC(O)—, —C(O)NH—,

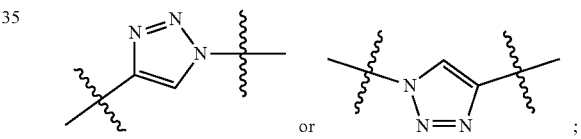

$R^5$ is a linear or branched, cyclic or acyclic, and/or aromatic or non-aromatic $C_1$-$C_{30}$ alkylenyl, alkenylenyl or alkynylenyl, or is a linear or branched, cyclic or acyclic, and/or aromatic or non-aromatic $X_2$-$X_{30}$ heteroalkylenyl, heteroalkenylenyl or heteroalkynylenyl;
$R^6$ is hydrogen or methyl;
$Xaa^1$ is an amino acid of formula —N($R^8$)$R^9$C(O)—, wherein each $R^8$ is independently hydrogen or methyl, and wherein each $R^9$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl;
at least one $R^9$ or $R^5$ is

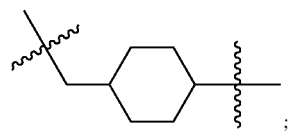 [SMILES: *CC1CCC(*)CC1]

at least one $R^9$ or $R^5$ is —(CH$_2$)$_{0-3}$CH($R^{10}$)(CH$_2$)$_{0-3}$—, wherein $R^{10}$ is a linear or branched, cyclic or acyclic, and/or aromatic or non-aromatic $C_2$-$C_{19}$ alkyl, alkenyl or alkynyl, or $R^{10}$ is a linear or branched, cyclic or acyclic, and/or aromatic or non-aromatic $X_2$-$X_{19}$ heteroalkyl, heteroalkenyl or heteroalkynyl having only 1-3 heteroatoms;

$R^7$ is $R^X$—$(Xaa^2)_{0-4}$—,

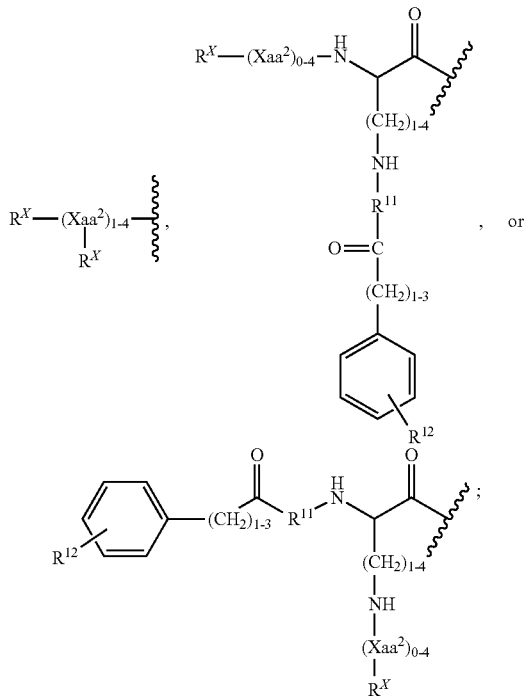

$R^{11}$ is absent,

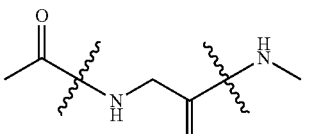

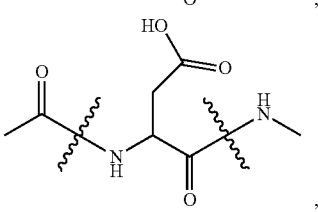

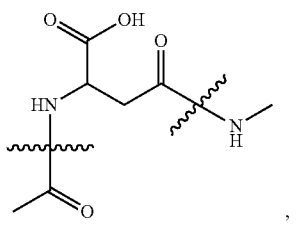

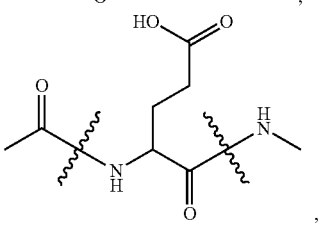

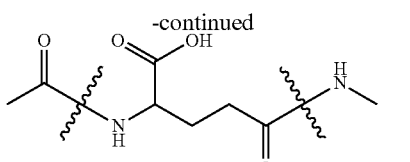

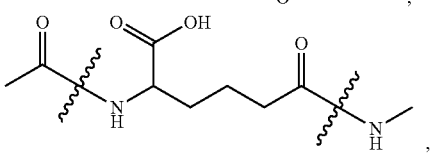

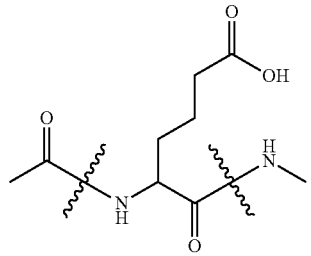

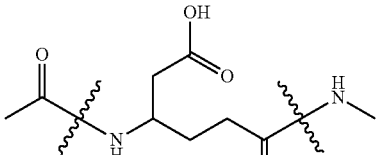

, or

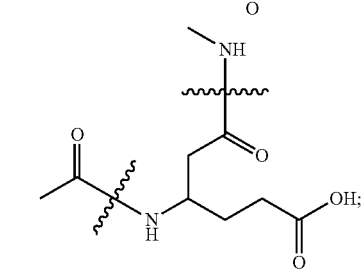

$R^{12}$ is I, Br, F, Cl, H, OH, $OCH_3$, $NH_2$, $NO_2$ or $CH_3$;

$Xaa^2$, when present, is —$N(R^{13})R^{14}C(O)$—, wherein each $R^{13}$ is independently hydrogen or methyl, and wherein each $R^{14}$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl; and each $R^X$ is a radiolabeling group independently selected from: a radiometal chelator optionally bound by a radiometal; an aryl substituted with a radioisotope; a prosthetic group containing a trifluoroborate; and a prosthetic group containing a silicon-fluorine-acceptor moiety.

Various embodiments disclosed herein relate to a compound, wherein the compound has Formula II or a salt or a solvate of Formula II:

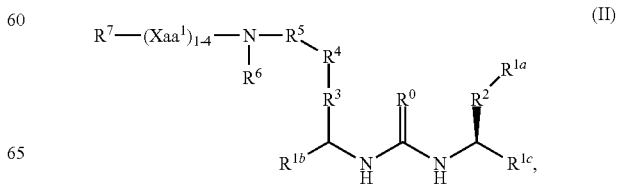

(II)

wherein:

$R^0$ is O or S;

$R^{1a}$ is —CO$_2$H, —SO$_2$H, —SO$_3$H, —PO$_2$H, —PO$_3$H$_2$, OPO$_3$H$_2$, OSO$_3$H, —B(OH)$_2$, or

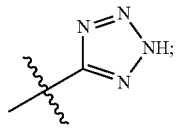 [SMILES: *c1nn[nH]n1]

$R^{1b}$ is —CO$_2$H, —SO$_2$H, —SO$_3$H, —PO$_2$H, —PO$_3$H$_2$, —B(OH)$_2$, or

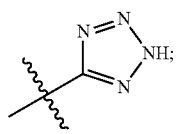 [SMILES: *c1nn[nH]n1]

$R^{1c}$ is —CO$_2$H, —SO$_2$H, —SO$_3$H, —PO$_2$H, —PO$_3$H$_2$, —B(OH)$_2$, or

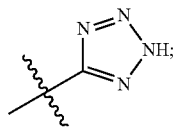

$R^2$ is —CH$_2$—, —CH(OH)—, —CHF—, —CF$_2$—, —CH(CH$_3$)—, —C(CH$_3$)$_2$—, —CH$_2$CH(OH)—, —CH$_2$CHF—, —CHFCH$_2$—, —CF$_2$CH$_2$—, —CH$_2$CF$_2$—, —CH(OH)CH$_2$—, —CH(CH$_3$)CH$_2$—, —CH$_2$CH(CH$_3$)—, —C(CH$_3$)$_2$CH$_2$—, —CH$_2$C(CH$_3$)$_2$—, —CH$_2$CH(OH)CH$_2$—, —CH$_2$CHFCH$_2$—, —(CH$_2$)$_2$CH(OH)—, —(CH$_2$)$_2$CHF—, —(CH$_2$)$_3$—, —CH$_2$OCH$_2$—, —CH$_2$SCH$_2$—, —CHFCH$_2$CH$_2$—, —CH(OH)CH$_2$CH$_2$—, —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —CH$_2$—NH—C(O)—, —C(O)—NH—CH$_2$—, —C(O)—NH—CH(CH$_3$)—, or —C(O)—NH—C(CH$_3$)$_2$—;

$R^3$ is a linear or branched, cyclic or acyclic, and/or aromatic or non-aromatic C$_1$-C$_{20}$ alkylenyl, alkenylenyl, or alkynylenyl, or a linear or branched, cyclic or acyclic, and/or aromatic or non-aromatic X$_2$-X$_{20}$ heteroalkylenyl, heteroalkenylenyl, or heteroalkynylenyl;

$R^4$ is —O—, —S—, —Se—, —S(O)—, —S(O)$_2$—, —NHC(O)—, —C(O)NH—,

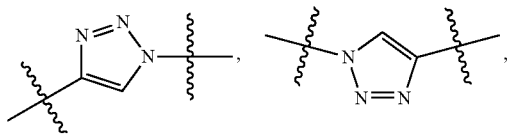 [SMILES: *c1cn(*)nn1 ; *c1cn(*)nn1]

—C(O)—(NH)$_2$—C(O)—, —OC(O)NH, —NHC(O)O—, —NHC(O)NH—, —OC(S)NH, —NHC(S)O—, —NHC(S)NH—, —NHC(O)C(O)NH—, —S—S—, —S—CH$_2$—S—, —NH—NH—C(O)—, —C(O)—NH—NH;

$R^5$ is a linear or branched, cyclic or acyclic, and/or aromatic or non-aromatic C$_1$-C$_{30}$ alkylenyl, alkenylenyl or alkynylenyl, or is a linear or branched, cyclic or acyclic, and/or aromatic or non-aromatic X$_2$-X$_{30}$ heteroalkylenyl, heteroalkenylenyl or heteroalkynylenyl;

$R^6$ is hydrogen or methyl or ethyl;

Xaa$^1$ is an amino acid of formula —N(R$^8$)R$^9$C(O)—, wherein each R$^8$ is independently hydrogen or methyl, and wherein each R$^9$ is independently: a linear or branched, cyclic or acyclic, and/or aromatic or non-aromatic C$_1$-C$_{20}$ alkylenyl, alkenylenyl or alkynylenyl; or a linear or branched, cyclic or acyclic, and/or aromatic or non-aromatic X$_2$-X$_{20}$ heteroalkylenyl, heteroalkenylenyl or heteroalkynylenyl;

at least one R$^9$ or R$^5$ is —(CH$_2$)$_{0-3}$CH(R$^{10}$)(CH$_2$)$_{0-3}$, wherein R$^{10}$ is:

a linear or branched, cyclic or acyclic, and/or aromatic or non-aromatic C$_2$-C$_{19}$ alkyl, alkenyl or alkynyl; a linear or branched, cyclic or acyclic, and/or aromatic or non-aromatic X$_2$-X$_{19}$ heteroalkyl, heteroalkenyl or heteroalkynyl having only 1-3 heteroatoms;

CH$_2$R$^{23}$, in which R$^{23}$ is an optionally substituted C$_4$-C$_{16}$ aromatic ring or partially or fully aromatic fused ring system, wherein 0-3 carbons in the aromatic ring or the partially or fully aromatic fused ring system are replaced with N, S and/or O heteroatoms, and wherein the optional substitutions are selected from OH, NH$_2$, NO$_2$, halogen, C$_1$-C$_6$ alkyl, and/or C$_1$-C$_6$ alkoxyl groups; or selected from:

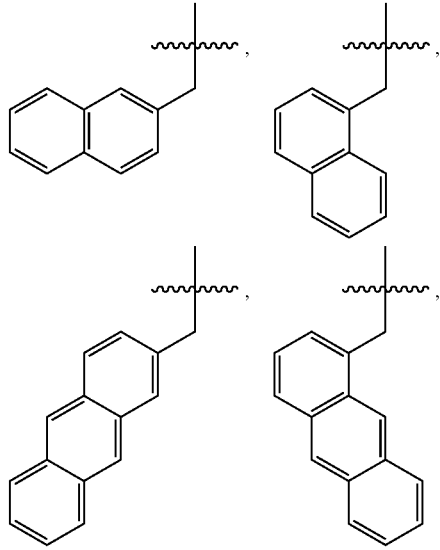

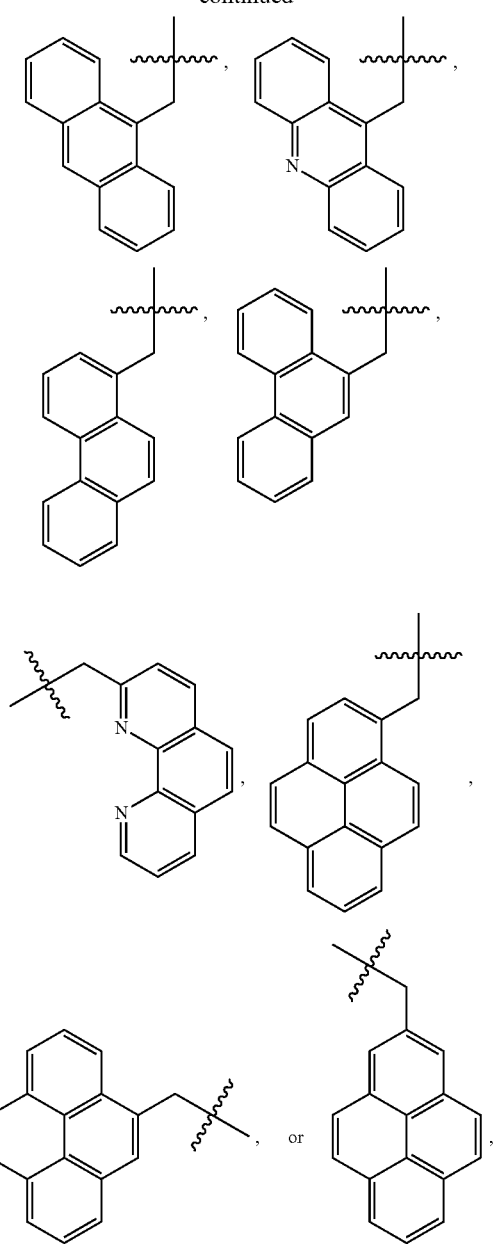

optionally modified with one, more than one, or a combination of: halogen, OMe, SMe, $NH_2$, $NO_2$, CN, OH, or additional endocyclic ring nitrogen atoms;

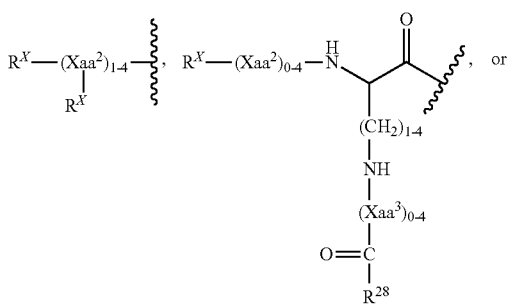

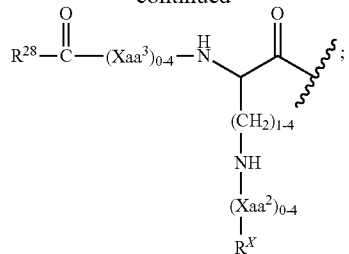

$R^7$ is $R^X$—$(Xaa^2)_{0-4}$, $R^{28}$ is an albumin binder;

$Xaa^2$ and $Xaa^3$, when present, are independently —$N(R^{13})R^{14}C(O)$—, wherein each $R^{13}$ is independently hydrogen or methyl, and wherein each $R^{14}$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl; and each $R^X$ is a radiolabeling group independently selected from: a radiometal chelator optionally bound by a radiometal; an aryl or heteroaryl substituted with a radiohalogen; a prosthetic group containing a trifluoroborate; a prosthetic group containing a silicon-fluorine-acceptor moiety; or a prosthetic group containing a fluorophosphate, fluorosulfate, sulfonylfluoride, or a combination thereof.

In some embodiments of the compound, salt or solvate of Formula II:

$R^0$ is O;

each of $R^{1a}$, $R^{1b}$ and $R^{1c}$ is independently —$CO_2H$, —$SO_2H$, —$SO_3H$, —$SO_4H$, —$PO_2H$, —$PO_3H$ or —$PO_4H$;

$R^2$ is —$CH_2$—, —$CH(OH)$—, —$CHF$—, —$CF_2$—, —$CH(CH_3)$—, —$C(CH_3)_2$—, —$CH_2CH(OH)$—, —$CH_2CHF$—, —$CHFCH_2$—, —$CF_2CH_2$—, —$CH_2CF_2$—, —$CH(OH)CH_2$—, —$CH(CH_3)CH_2$—, —$CH_2CH(CH_3)$—, —$C(CH_3)_2CH_2$—, —$CH_2C(CH_3)_2$—, —$CH_2CH(OH)CH_2$—, —$CH_2CHFCH_2$—, —$(CH_2)_2CH(OH)$—, —$(CH_2)_2CHF$—, —$(CH_2)_3$—, —$CH_2OCH_2$—, —$CH_2SCH_2$—, —$CHFCH_2CH_2$—, —$CH(OH)CH_2CH_2$—, —$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—, —$CH(CH_3)$—O—$CH_2$—, —$C(CH_3)_2$—O—$CH_2$—, —$CH_2$—O—$CH(CH_3)$—, —$CH_2$—O—$C(CH_3)_2$—, —$CH_2$—$S(O)$—$CH_2$—, —$CH_2$—$S(O)_2$—$CH_2$—, —$CH(CH_3)$—S—$CH_2$—, —$C(CH_3)_2$—S—$CH_2$—, —$CH_2$—S—$CH(CH_3)$—, —$CH_2$—S—$C(CH_3)_2$—, —$CH(CH_3)$—$S(O)$—$CH_2$—, —$C(CH_3)_2$—$S(O)$—$CH_2$—, —$CH_2$—$S(O)$—$CH(CH_3)$—, —$CH_2$—$S(O)$—$C(CH_3)_2$—, —$CH(CH_3)$—$S(O)_2$—$CH_2$—, —$C(CH_3)_2$—$S(O)_2$—$CH_2$—, —$CH_2$—$S(O)_2$—$CH(CH_3)$—, —$CH_2$—$S(O)_2$—$C(CH_3)_2$—, —$CH_2$—NH—$C(O)$—, —$C(O)$—NH—$CH_2$—, —$C(O)$—NH—$CH(CH_3)$—, or —$C(O)$—NH—$C(CH_3)_2$—;

$R^3$ is a linear or branched, cyclic or acyclic, and/or aromatic or non-aromatic $C_1$-$C_{20}$ alkylenyl or alkenylenyl, or a linear or branched, cyclic or acyclic, and/or aromatic or non-aromatic $X_2$-$X_{20}$ heteroalkylenyl or heteroalkenylenyl;

$R^4$ is —O—, —S—, —S(O)—, —S(O)$_2$—, —NHC(O)—, —C(O)NH—,

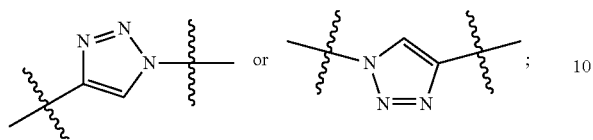 or ;

$R^5$ is a linear or branched, cyclic or acyclic, and/or aromatic or non-aromatic $C_1$-$C_{30}$ alkylenyl, alkenylenyl or alkynylenyl, or is a linear or branched, cyclic or acyclic, and/or aromatic or non-aromatic $X_2$-$X_{30}$ heteroalkylenyl, heteroalkenylenyl or heteroalkynylenyl;

$R^6$ is hydrogen or methyl;

$Xaa^1$ is an amino acid of formula —N($R^8$)$R^9$C(O)—, wherein each $R^8$ is independently hydrogen or methyl, and wherein each $R^9$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl;

at least one $R^9$ or $R^5$ is —(CH$_2$)$_{0-3}$CH($R^{10}$)(CH$_2$)$_{0-3}$—, wherein $R^{10}$ is: a linear or branched, cyclic or acyclic, and/or aromatic or non-aromatic $C_2$-$C_{19}$ alkyl, alkenyl or alkynyl; a linear or branched, cyclic or acyclic, and/or aromatic or non-aromatic $X_2$-$X_{19}$ heteroalkyl, heteroalkenyl or heteroalkynyl having only 1-3 heteroatoms; or —CH$_2$R$^{23}$, in which $R^{23}$ is an optionally substituted $C_4$-$C_{16}$ aromatic ring or partially or fully aromatic fused ring system, wherein 0-3 carbons in the aromatic ring or the partially or fully aromatic fused ring system are replaced with N, S and/or O heteroatoms, and wherein the optional substitutions are selected from OH, NH$_2$, NO$_2$, halogen, $C_1$-$C_6$ alkyl, and/or $C_1$-$C_6$ alkoxyl groups;

$R^7$ is $R^X$—(Xaa$^2$)$_{0-4}$,

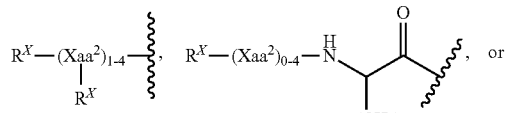

$R^{11}$ is absent,

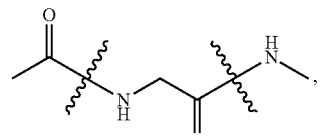

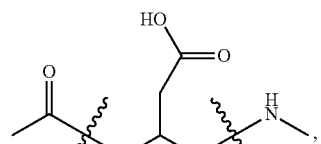

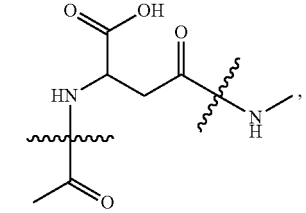

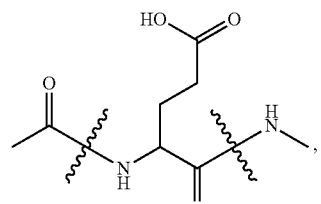

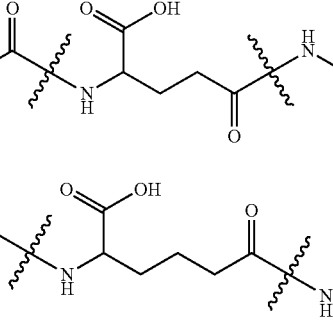

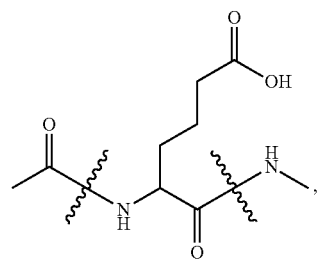

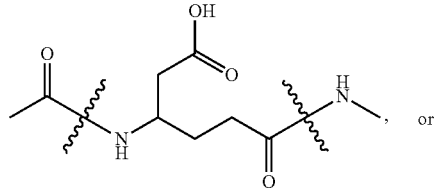

-continued

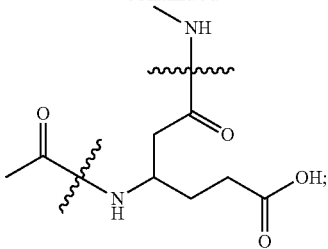

$R^{12}$ is I, Br, F, Cl, H, OH, OCH$_3$, NH$_2$, NO$_2$ or CH$_3$;

Xaa$^2$, when present, is —N(R$^{13}$)R$^{14}$C(O)—, wherein each R$^{13}$ is independently hydrogen or methyl, and wherein each R$^{14}$ is independently: a linear or branched, cyclic or acyclic, and/or aromatic or non-aromatic C$_1$-C$_{20}$ alkylenyl, alkenylenyl or alkynylenyl; or a linear or branched, cyclic or acyclic, and/or aromatic or non-aromatic X$_2$-X$_{20}$ heteroalkylenyl, heteroalkenylenyl or heteroalkynylenyl; and each R$^X$ is a radiolabeling group independently selected from: a radiometal chelator optionally bound by a radiometal; an aryl substituted with a radioisotope; a prosthetic group containing a trifluoroborate; and a prosthetic group containing a silicon-fluorine-acceptor moiety.

Various embodiments disclosed herein relate to a compound comprising a prostate specific membrane antigen (PSMA)-targeting moiety of Formula III or of a salt or a solvate of Formula III:

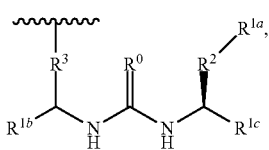

(III)

wherein:

R$^0$ is O or S;

R$^{1a}$ is —CO$_2$H, —SO$_2$H, —SO$_3$H, —PO$_2$H, —PO$_3$H$_2$, OPO$_3$H$_2$, OSO$_3$H, —B(OH)$_2$, or

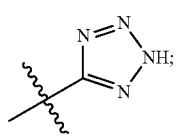 [SMILES: *c1nn[nH]n1]

R$^{1b}$ is —CO$_2$H, —SO$_2$H, —SO$_3$H, —PO$_2$H, —PO$_3$H$_2$, —B(OH)$_2$, or

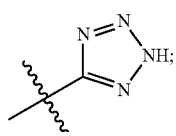 [SMILES: *c1nn[nH]n1]

R$^{1c}$ is —CO$_2$H, —SO$_2$H, —SO$_3$H, —PO$_2$H, —PO$_3$H$_2$, —B(OH)$_2$, or

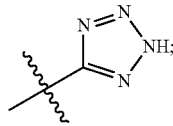 [SMILES: *c1nn[nH]n1]

R$^2$ is —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$, —C(O)—NH—CH$_2$—, —C(O)—NH—CH(CH$_3$)—, or —C(O)—NH—C(CH$_3$)$_2$; and R$^3$ is a linker.

In some embodiments of the compound, salt or solvate of Formula III:

R$^0$ is O;

each of R$^{1a}$, R$^{1b}$ and R$^{1c}$ is independently —CO$_2$H, —SO$_2$H, —SO$_3$H, —SO$_4$H, —PO$_2$H, —PO$_3$H or —PO$_4$H;

R$^2$ is —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —C(O)—NH—CH$_2$—, —C(O)—NH—CH(CH$_3$)—, —C(O)—NH—C(CH$_3$)$_2$—, —CH$_2$CH(COOH)CH$_2$—, or —CH$_2$CH$_2$CH(COOH)—; and R$^3$ is a linker.

Various embodiments disclosed herein relate to a compound, wherein the compound has Formula IV or a salt or a solvate of Formula IV:

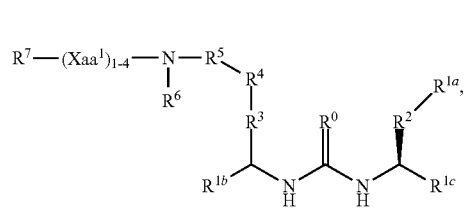

(IV)

wherein:

R$^0$ is S or O;

R$^{1a}$ is —CO$_2$H, —SO$_2$H, —SO$_3$H, —PO$_2$H, —PO$_3$H$_2$, —OPO$_3$H$_2$, —OSO$_3$H, —B(OH)$_2$, or

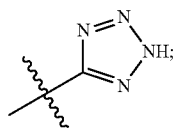 [SMILES: *c1nn[nH]n1]

$R^{1b}$ is —CO$_2$H, —SO$_2$H, —SO$_3$H, —PO$_2$H, —PO$_3$H$_2$, —B(OH)$_2$, or

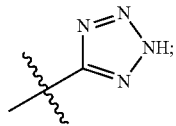 [SMILES: *c1nn[nH]n1]

$R^{1c}$ is —CO$_2$H, —SO$_2$H, —SO$_3$H, —PO$_2$H, —PO$_3$H$_2$, —B(OH)$_2$, or

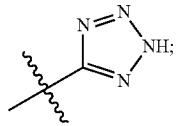 [SMILES: *c1nn[nH]n1]

$R^2$ is —CH$_2$—, —CH(OH)—, —CHF—, —CF$_2$—, —CH(CH$_3$)—, —C(CH$_3$)$_2$—, —CH$_2$CH(OH)—, —CH$_2$CHF—, —CHFCH$_2$—, —CF$_2$CH$_2$—, —CH$_2$CF$_2$—, —CH(OH)CH$_2$—, —CH(CH$_3$)CH$_2$—, —CH$_2$CH(CH$_3$)—, —C(CH$_3$)$_2$CH$_2$—, —CH$_2$C(CH$_3$)$_2$—, —CH$_2$CH(OH)CH$_2$—, —CH$_2$CHFCH$_2$—, —(CH$_2$)$_2$CH(OH)—, —(CH$_2$)$_2$CHF—, —(CH$_2$)$_3$—, —CH$_2$OCH$_2$—, —CH$_2$SCH$_2$—, —CHFCH$_2$CH$_2$—, —CH(OH)CH$_2$CH$_2$—, —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—, CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —CH$_2$—NH—C(O)—, —C(O)—NH—CH$_2$—, —C(O)—NH—CH(CH$_3$)—, —C(O)—NH—C(CH$_3$)$_2$—, —CH$_2$SeCH$_2$—, —CH(COOH)—, —CH$_2$CH(COOH)—, —CH$_2$CH(COOH)CH$_2$—, —CH$_2$CH$_2$CH(COOH)—, —CH=CH—, —CH=CHCH$_2$—, —C≡CCH$_2$—, —HC[CH$_2$]CH—, or —HC[CH$_2$]CHCH$_2$—, wherein HC[CH$_2$]CH represents a cyclopropyl ring;

$R^3$ is a linear or branched, cyclic or acyclic, and/or aromatic or non-aromatic C$_1$-C$_{20}$ alkylenyl or alkenylenyl, or a linear or branched, cyclic or acyclic, and/or aromatic or non-aromatic X$_2$-X$_{20}$ heteroalkylenyl or heteroalkenylenyl;

$R^4$ is —O—, —S—, —Se—, —S(O)—, —S(O)$_2$—, —NHC(O)—, —C(O)NH—,

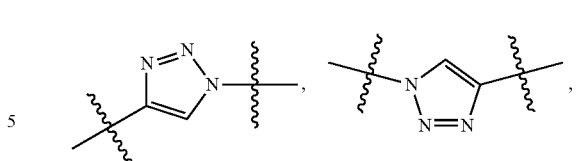

—C(O)—(NH)$_2$—C(O)—, —OC(O)NH, —NHC(O)O—, —NHC(O)NH—, —OC(S)NH, —NHC(S)O—, —NHC(S)NH—, —NHC(O)C(O)NH—, —S—S—, —S—CH$_2$—S—, —NH—NH—C(O)—, —C(O)—NH—NH—,

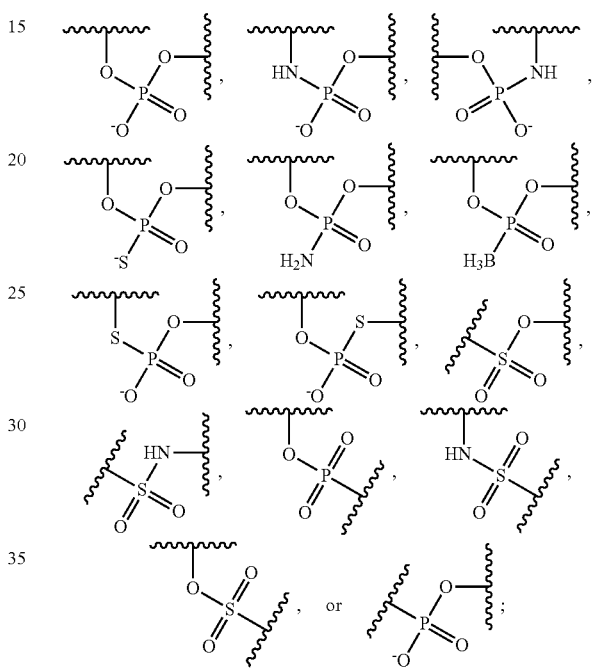

$R^5$ is a linear or branched, cyclic or acyclic, and/or aromatic or non-aromatic C$_1$-C$_{30}$ alkylenyl, alkenylenyl or alkynylenyl, or is a linear or branched, cyclic or acyclic, and/or aromatic or non-aromatic X$_2$-X$_{30}$ heteroalkylenyl, heteroalkenylenyl or heteroalkynylenyl;

$R^6$ is hydrogen or methyl or ethyl;

Xaa$^1$ is an amino acid of formula —N(R$^8$)R$^9$C(O)—, wherein each R$^8$ is independently hydrogen or methyl, and wherein each R$^9$ is independently: a linear or branched, cyclic or acyclic, and/or aromatic or non-aromatic C$_1$-C$_{20}$ alkylenyl, alkenylenyl or alkynylenyl; or a linear or branched, cyclic or acyclic, and/or aromatic or non-aromatic X$_2$-X$_{20}$ heteroalkylenyl, heteroalkenylenyl or heteroalkynylenyl;

at least one R$^9$ or R$^5$ is (CH$_2$)$_{0-3}$CH(R$^{10}$)(CH$_2$)$_{0-3}$, wherein R$^{10}$ is:

a linear or branched, cyclic or acyclic, and/or aromatic or non-aromatic C$_2$-C$_{19}$ alkyl, alkenyl or alkynyl; a linear or branched, cyclic or acyclic, and/or aromatic or non-aromatic X$_2$-X$_{19}$ heteroalkyl, heteroalkenyl or heteroalkynyl having only 1-3 heteroatoms;

—CH$_2$R$^{23}$, in which R$^{23}$ is an optionally substituted C$_4$-C$_{16}$ aromatic ring or partially or fully aromatic fused ring system, wherein 0-3 carbons in the aromatic ring or the partially or fully aromatic fused ring system are replaced with N, S and/or O heteroatoms, and wherein the optional substitutions are selected from OH, NH$_2$, NO$_2$, halogen, C$_1$-C$_6$ alkyl, and/or C$_1$-C$_6$ alkoxyl groups; or selected from:

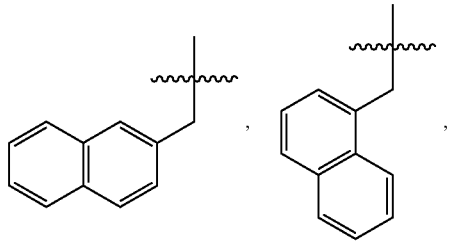

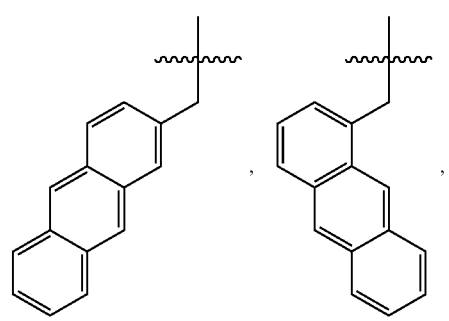

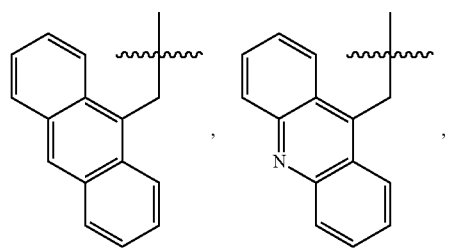

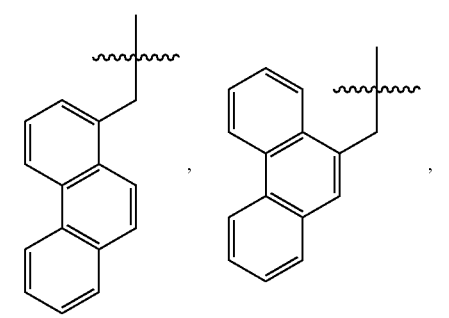

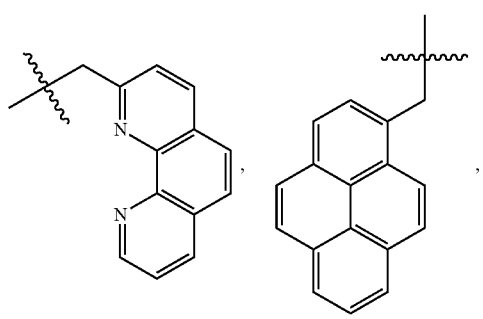

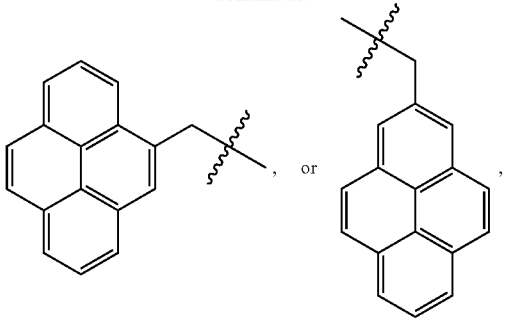

optionally modified with one, more than one, or a combination of: halogen, OMe, SMe, NH$_2$, NO$_2$, CN, OH, or additional endocyclic ring nitrogen atoms;

R$^7$ is R$^X$—(Xaa$^2$)$_{0-4}$—,

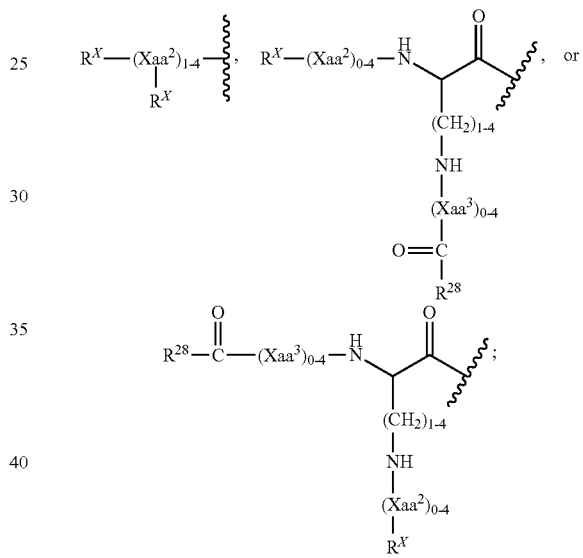

R$^{28}$ is an albumin binder;

Xaa$^2$ and Xaa$^3$, when present, are independently —N(R$^{13}$)R$^{14}$C(O)—, wherein each R$^{13}$ is independently hydrogen or methyl, and wherein each R$^{14}$ is independently: a linear or branched, cyclic or acyclic, and/or aromatic or non-aromatic C$_1$-C$_{20}$ alkylenyl, alkenylenyl or alkynylenyl; or a linear or branched, cyclic or acyclic, and/or aromatic or non-aromatic X$_2$-X$_{20}$ heteroalkylenyl, heteroalkenylenyl or heteroalkynylenyl; and each R$^X$ is a radiolabeling group independently selected from: a radiometal chelator optionally bound by a metal; an aryl or heteroaryl substituted with a radioisotope; a prosthetic group containing a trifluoroborate; or a prosthetic group containing a silicon-fluorine-acceptor moiety, a fluorophosphate, a fluorosulfate, or a sulfonylfluoride;

and wherein any one or any combination of amide linkages within R$^7$—(Xaa$^1$)$_{1-4}$—N(R$^6$)—R$^6$—R$^4$—R$^3$ is optionally replaced by one or a combination selected from the group consisting of —O—, —S—, —Se—, —S(O)—, —S(O)$_2$—, —NHC(O)—, —C(O)NH—,

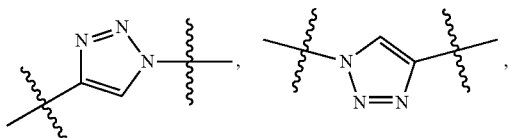 [SMILES: *c1cn(*)nn1 ; *c1cn(*)nn1]

—C(O)—(NH)₂—C(O)—, —OC(O)NH, —NHC(O)O—, —NHC(O)NH—, —OC(S)NH, —NHC(S)O—, —NHC(S)NH—, —NHC(O)C(O)NH—, —S—S—, —S—CH₂—S—, —NH—NH—C(O)—, and —C(O)—NH—NH—.

Various embodiments disclosed herein relate to a compound, wherein the compound has Formula V or a salt or a solvate of Formula V:

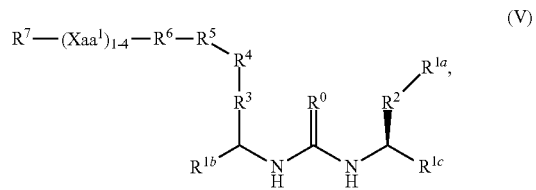

(V)

wherein:

$R^0$ is S or O;

$R^{1a}$ is —CO₂H, —SO₂H, —SO₃H, —PO₂H, —PO₃H₂, —OPO₃H₂, —OSO₃H, —B(OH)₂, or

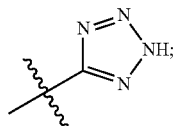 [SMILES: *c1nn[nH]n1]

$R^{1b}$ is —CO₂H, —SO₂H, —SO₃H, —PO₂H, —PO₃H₂, —B(OH)₂, or

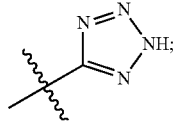

$R^{1c}$ is —CO₂H, —SO₂H, —SO₃H, —PO₂H, —PO₃H₂, —B(OH)₂, or

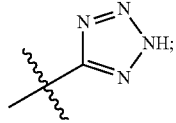 [SMILES: *c1nn[nH]n1]

$R^2$ is —CH₂—, —CH(OH)—, —CHF—, —CF₂—, —CH(CH₃)—, —C(CH₃)₂—, —CH₂CH(OH)—, —CH₂CHF—, —CHFCH₂—, —CF₂CH₂—, —CH₂CF₂—, —CH(OH)CH₂—, —CH(CH₃)CH₂—, —CH₂CH(CH₃)—, —C(CH₃)₂CH₂—, —CH₂C(CH₃)₂—, —CH₂CH(OH)CH₂—, —CH₂CHFCH₂—, —(CH₂)₂CH(OH)—, —(CH₂)₂CHF—, —(CH₂)₃—, —CH₂OCH₂—, —CH₂SCH₂—, —CHFCH₂CH₂—, —CH(OH)CH₂CH₂—, —CH(CH₃)CH₂CH₂—, —CH₂CH(CH₃)CH₂—, —CH₂CH₂CH(CH₃)—, —C(CH₃)₂CH₂CH₂—, —CH₂C(CH₃)₂CH₂—, —CH₂CH₂C(CH₃)₂—, —CH(CH₃)—O—CH₂—, —C(CH₃)₂—O—CH₂—, —CH₂—O—CH(CH₃)—, —CH₂—O—C(CH₃)₂—, —CH₂—S(O)—CH₂—, —CH₂—S(O)₂—CH₂—, —CH(CH₃)—S—CH₂—, —C(CH₃)₂—S—CH₂—, —CH₂—S—CH(CH₃)—, —CH₂—S—C(CH₃)₂—, —CH(CH₃)—S(O)—, CH₂—, —C(CH₃)₂—S(O)—CH₂—, —CH₂—S(O)—CH(CH₃)—, —CH₂—S(O)—C(CH₃)₂—, —CH(CH₃)—S(O)₂—CH₂—, —C(CH₃)₂—S(O)₂—CH₂—, —CH₂—S(O)₂—CH(CH₃)—, —CH₂—S(O)₂—C(CH₃)₂—, —CH₂—NH—C(O)—, —C(O)—NH—CH₂—, —C(O)—NH—CH(CH₃)—, —C(O)—NH—C(CH₃)₂—, —CH₂SeCH₂—, —CH(COOH)—, —CH₂CH(COOH)—, —CH₂CH(COOH)CH₂—, —CH₂CH₂CH(COOH)—, —CH=CH—, —CH=CHCH₂—, —C≡CCH₂—, —HC[CH₂]CH—, or —HC[CH₂]CHCH₂—, wherein HC[CH₂]CH represents a cyclopropyl ring;

$R^3$ is a linear or branched, cyclic or acyclic, and/or aromatic or non-aromatic $C_1$-$C_{20}$ alkylenyl or alkenylenyl, or a linear or branched, cyclic or acyclic, and/or aromatic or non-aromatic $X_2$-$X_{20}$ heteroalkylenyl or heteroalkenylenyl;

$R^4$ is —O—, —S—, —Se—, S(O)—, —S(O)₂—, —NHC(O)—, —C(O)NH—,

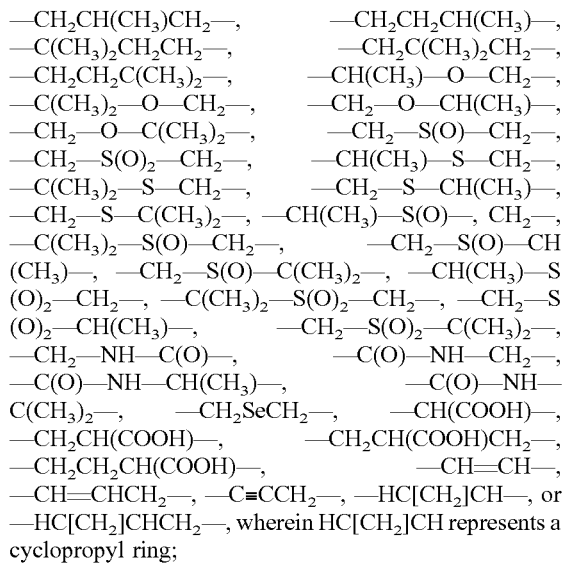

—C(O)—(NH)₂—C(O)—, —OC(O)NH, —NHC(O)O—, —NHC(O)NH—, —OC(S)NH, —NHC(S)O—, —NHC(S)NH—, —NHC(O)C(O)NH—, —S—S—, —S—CH₂—S—, —NH—NH—C(O)—, —C(O)—NH—NH—,

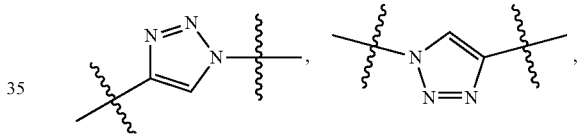

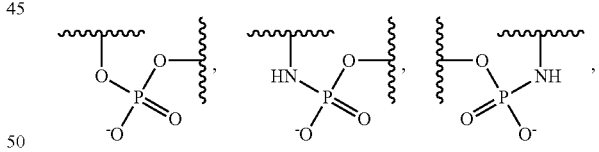

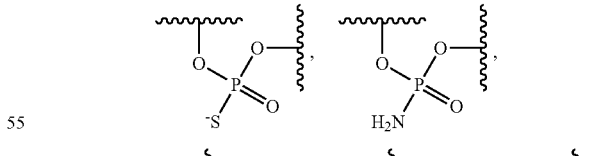

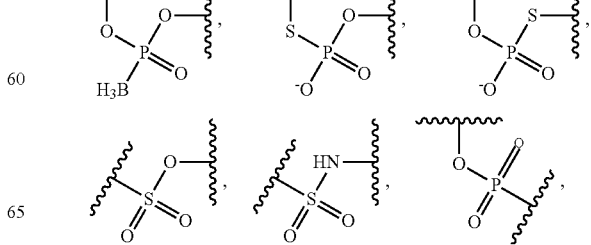

-continued

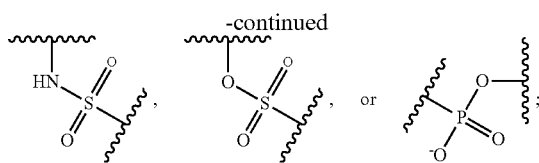

R[5] is a linear or branched, cyclic or acyclic, and/or aromatic or non-aromatic $C_1$-$C_{30}$ alkylenyl, alkenylenyl or alkynylenyl, or is a linear or branched, cyclic or acyclic, and/or aromatic or non-aromatic $X_2$-$X_{30}$ heteroalkylenyl, heteroalkenylenyl or heteroalkynylenyl R[6] is optionally in carbonyl, a phosphoryl or a sulfonyl group that is linked to the alpha-nitrogen in Xaa[1] to respectively give an amide, phosphoramidate/phosphonamidate, or sulfonamide linkage; or alternatively is: —NHC(O)—, —(NH)$_2$—C(O)—, —C(O)—(NH)$_2$—C(O)—, —OC(O)—, —OC(S)—, —NHC(S)—, —NHC(O)C(O)—, —NH—NH—C(O)—, to enjoin the alpha-nitrogen in Xaa[1].

Xaa[1] is an amino acid of formula —N(R[8])R[9]C(O)—, wherein each R[8] is independently hydrogen or methyl, and wherein each R[9] is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl;

at least one R[9] or R[5] is —(CH$_2$)$_{0-3}$CH(R[10])(CH$_2$)$_{0-3}$, wherein R[10] is:

a linear or branched, cyclic or acyclic, and/or aromatic or non-aromatic $C_2$-$C_{19}$ alkyl, alkenyl or alkynyl; a linear or branched, cyclic or acyclic, and/or aromatic or non-aromatic $X_2$-$X_{19}$ heteroalkyl, heteroalkenyl or heteroalkynyl having only 1-3 heteroatoms;

—CH$_2$R[23], in which R[23] is an optionally substituted $C_4$-$C_{16}$ aromatic ring or partially or fully aromatic fused ring system, wherein 0-3 carbons in the aromatic ring or the partially or fully aromatic fused ring system are replaced with N, S and/or O heteroatoms, and wherein the optional substitutions are selected from OH, NH$_2$, NO$_2$, halogen, $C_1$-$C_6$ alkyl, and/or $C_1$-$C_6$ alkoxyl groups; or selected from:

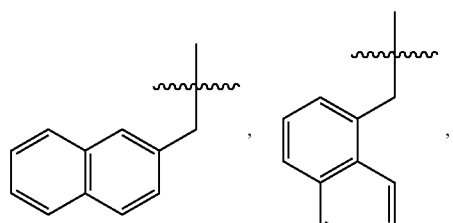

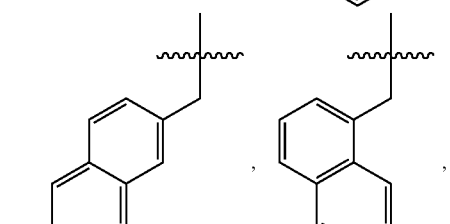

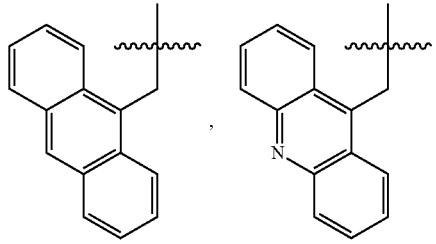

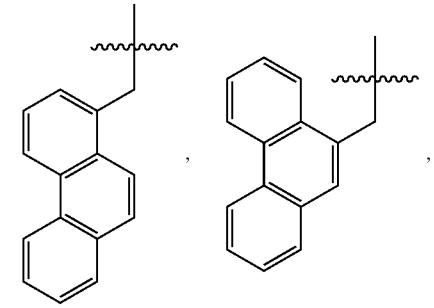

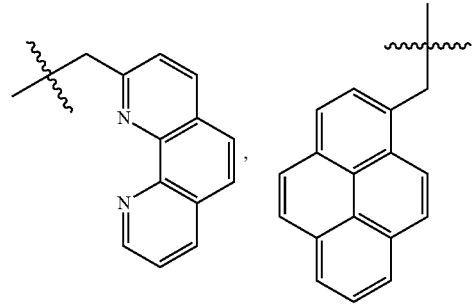

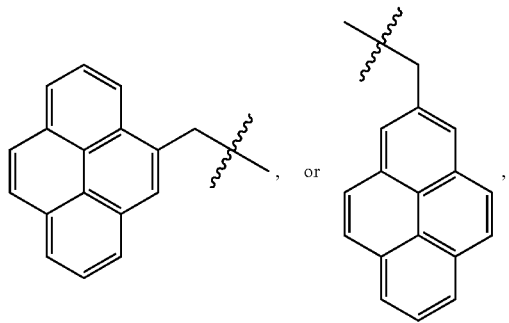

optionally modified with one, more than one, or a combination of: halogen, OMe, SMe, NH$_2$, NO$_2$, CN, OH, or additional endocyclic ring nitrogen atoms;

R[7] is R[X]—(Xaa[2])$_{0-4}$,

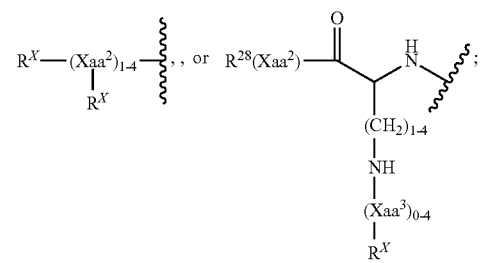

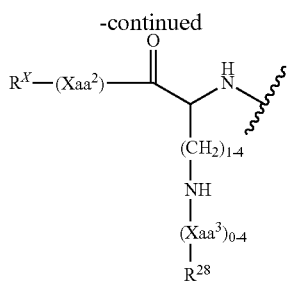

$R^{28}$ is an albumin binder;

Xaa² and Xaa³, when present, are independently —N(R¹³)R¹⁴C(O)—, wherein each $R^{13}$ is independently hydrogen or methyl, and wherein each $R^{14}$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl; and each $R^X$ is a radiolabeling group independently selected from: a radiometal chelator optionally bound by a metal; an aryl or heteroaryl substituted with a radioisotope; a prosthetic group containing a trifluoroborate; or a prosthetic group containing a silicon-fluorine-acceptor moiety, a fluorophosphate, a fluorosulfate, or a sulfonylfluoride.

Various embodiments may be used for imaging PSMA-expressing tissues in a subject. Various embodiments may be used for treatment of a PSMA-expressing condition or disease in a subject.

BRIEF DESCRIPTION OF THE DRAWINGS

The features of the invention will become apparent from the following description in which reference is made to the appended drawings wherein:

FIG. 6 shows the chemical structures of compounds HTK03041, HTK03149, HTK03169, HTK03161, HTK03177, HTK03187, HTK03153, HTK03170, HTK03189A, HTK03189B, HTK04033, HTK04036, HTK04037, HTK04040, HTK04041, HTK04053, HTK03162, and HTK04055.

DETAILED DESCRIPTION

Figure 1:
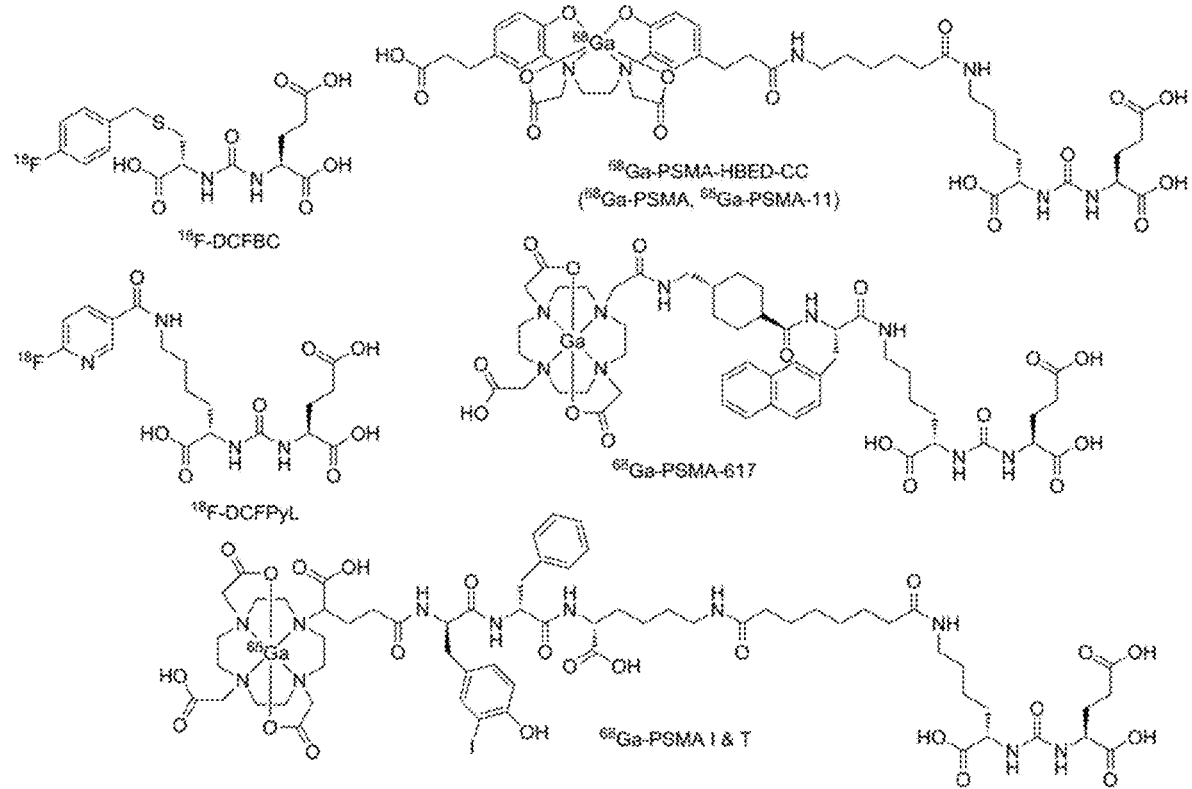
FIG. 1 shows examples of prior art PSMA-targeting compounds for prostate cancer imaging.

As used herein, the terms "comprising," "having", "including" and "containing," and grammatical variations thereof, are inclusive or open-ended and do not exclude additional, unrecited elements and/or method steps, even if a feature/component defined as a part thereof consists or consists essentially of specified feature(s)/component(s). The term "consisting essentially of" if used herein in connection with a compound, composition, use or method, denotes that additional elements and/or method steps may be present, but that these additions do not materially affect the manner in which the recited compound, composition, method or use functions. The term "consisting of" if used herein in connection with a feature of a composition, use or method, excludes the presence of additional elements and/or method steps in that feature. A compound, composition, use or method described herein as comprising certain elements and/or steps may also, in certain embodiments consist essentially of those elements and/or steps, and in other embodiments consist of those elements and/or steps, whether or not these embodiments are specifically referred to. A use or method described herein as comprising certain elements and/or steps may also, in certain embodiments consist essentially of those elements and/or steps, and in other embodiments consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the context clearly dictates otherwise. The use of the word "a" or "an" when used herein in conjunction with the term "comprising" may mean "one," but it is also consistent with the meaning of "one or more," "at least one" and "one or more than one."

In this disclosure, the recitation of numerical ranges by endpoints includes all numbers subsumed within that range including all whole numbers, all integers and, where suitable, all fractional intermediates (e.g., 1 to 5 may include 1, 1.5, 2, 2.75, 3, 3.80, 4, and 5 etc.).

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a method, product, use, composition, compound, et cetera.

As used herein, the terms "treat", "treatment", "therapeutic" and the like includes ameliorating symptoms, reducing disease progression, improving prognosis and reducing recurrence.

As used herein, the term "diagnostic agent" includes an "imaging agent". As such, a "diagnostic radiometal" includes radiometals that are suitable for use as imaging agents.

The term "subject" refers to an animal (e.g. a mammal or a non-mammal animal). The subject may be a human or a non-human primate. The subject may be a laboratory mammal (e.g., mouse, rat, rabbit, hamster and the like). The subject may be an agricultural animal (e.g., equine, ovine, bovine, porcine, camelid and the like) or a domestic animal (e.g., canine, feline and the like). In some embodiments, the subject is a human.

The compounds disclosed herein may also include base-free forms, salts or pharmaceutically acceptable salts thereof. Unless otherwise specified, the compounds claimed and described herein are meant to include all racemic mixtures and all individual enantiomers or combinations thereof, whether or not they are explicitly represented herein.

The compounds disclosed herein may be shown as having one or more charged groups, may be shown with ionizable groups in an uncharged (e.g. protonated) state or may be shown without specifying formal charges. As will be appreciated by the person of skill in the art, the ionization state of certain groups within a compound (e.g. without limitation, $CO_2H$, $PO_3H_2$, $SO_2H$, $SO_3H$, $SO_4H$, $OPO_3H_2$ and the like) is dependent, inter alia, on the pKa of that group and the pH at that location. For example, but without limitation, a carboxylic acid group (i.e. COOH) would be understood to usually be deprotonated (and negatively charged) at neutral pH and at most physiological pH values, unless the protonated state is stabilized. Likewise, $OSO_3H$ (i.e. $SO_4H$) groups, $SO_2H$ groups, $SO_3H$ groups, $OPO_3H_2$ (i.e. $PO_4H_2$) groups and $PO_3H$ groups would generally be deprotonated (and negatively charged) at neutral and physiological pH values.

As used herein, the terms "salt" and "solvate" have their usual meaning in chemistry. As such, when the compound is a salt or solvate, it is associated with a suitable counter-ion. It is well known in the art how to prepare salts or to exchange counter-ions. Generally, such salts can be prepared by reacting free acid forms of these compounds with a stoichiometric amount of a suitable base (e.g. without limitation, Na, Ca, Mg, or K hydroxide, carbonate, bicarbonate, or the like), or by reacting free base forms of these compounds with a stoichiometric amount of a suitable acid. Such reactions are generally carried out in water or in an organic solvent, or in a mixture of the two. Counter-ions may be changed, for example, by ion-exchange techniques such as ion-exchange chromatography. All zwitterions, salts, solvates and counter-ions are intended, unless a particular form is specifically indicated.

In certain embodiments, the salt or counter-ion may be pharmaceutically acceptable, for administration to a subject.

More generally, with respect to any pharmaceutical composition disclosed herein, non-limiting examples of suitable excipients include any suitable buffers, stabilizing agents, salts, antioxidants, complexing agents, tonicity agents, cryoprotectants, lyoprotectants, suspending agents, emulsifying agents, antimicrobial agents, preservatives, chelating agents, binding agents, surfactants, wetting agents, non-aqueous vehicles such as fixed oils, or polymers for sustained or controlled release. See, for example, Berge et al. 1977. (J. Pharm Sci. 66:1-19), or Remington—The Science and Practice of Pharmacy, 21st edition (Gennaro et al editors. Lippincott Williams & Wilkins Philadelphia), each of which is incorporated by reference in its entirety.

As used herein, the expression "Xy-Xz", where y and z are integers (e.g. $X_1$-$X_{15}$, $X_1$-$X_{30}$, $X_1$-$X_{100}$, and the like), refers to the number of carbons (for alkyls, whether saturated or unsaturated, or aryls) in a compound, R-group or substituent, or refers to the number of carbons plus heteroatoms (for heteroalkyls, whether saturated or unsaturated, or heteroaryls) in a compound, R-group or substituent. Heteroatoms may include any, some or all possible heteroatoms. For example, in some embodiments, the heteroatoms are selected from N, O, S, P and Se. In some embodiments, the heteroatoms are selected from N, O, S and P. Such embodiments are non-limiting. Alkyls and aryls may alternatively be referred to using the expression "Cy-Cz", where y and z are integers (e.g. $C_3$-$C_{15}$ and the like).

Unless explicitly stated otherwise, the terms "alkyl" and "heteroalkyl" each includes any reasonable combination of the following: (1) saturated alkyls as well as unsaturated (including partially unsaturated) alkyls (e.g. alkenyls and alkynyls); (2) linear or branched; (3) acyclic or cyclic (aromatic or nonaromatic), the latter of which may include multi-cyclic (fused rings, multiple non-fused rings or a combination thereof); and (4) unsubstituted or substituted. For example, an alkyl or heteroalkyl (i.e. "alkyl/heteroalkyl") may be saturated, branched and cyclic, or unsaturated, branched and cyclic, or linear and unsaturated, or any other reasonable combination according to the skill of the person of skill in the art. If unspecified, the size of the alkyl/heteroalkyl is what would be considered reasonable to the person of skill in the art. For example, but without limitation, if unspecified, the size of an alkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroalkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons and heteroatoms in length, subject to the common general knowledge of the person of skill in the art. In the context of the expression "alkyl, alkenyl or alkynyl" and similar expressions, the "alkyl" would be understood to be a saturated alkyl. Likewise, in the context of the expression "heteroalkyl, heteroalkenyl or heteroalkynyl" and similar expressions, the "heteroalkyl" would be understood to be a saturated heteroalkyl.

As used herein, in the context of an alkyl/heteroalkyl group of a compound, the term "linear" may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl.

As used herein, the term "branched" may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

The term "alkylenyl" refers to a divalent analog of an alkyl group. In the context of the expression "alkylenyl, alkenylenyl or alkynylenyl", "alkylenyl or alkenylenyl" and similar expressions, the "alkylenyl" would be understood to be a saturated alkylenyl. The term "heteroalkylenyl" refers to a divalent analog of a heteroalkyl group. In the context of the expression "heteroalkylenyl, heteroalkenylenyl or heteroalkynylenyl", "heteroalkylenyl or heteroalkenylenyl" and similar expressions, the "heteroalkylenyl" would be understood to be a saturated heteroalkylenyl.

As used herein, the term "saturated" when referring to a chemical entity may be used as it is normally understood to a person of skill in the art and generally refers to a chemical entity that comprises only single bonds, and may include linear, branched, and/or cyclic groups. Non-limiting examples of a saturated $C_1$-$C_{20}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, I-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl, t-decyl, cyclopropanyl, cyclobutanyl, cyclopentanyl, cyclohexanyl, cycloheptanyl, cyclooctanyl, cyclononanyl, cyclodecanyl, and the like. Unless otherwise specified, a $C_1$-$C_{20}$ alkylenyl therefore encompasses, without limitation, all divalent analogs of the above-listed saturated alkyl groups.

As used herein, the term "unsaturated" when referring to a chemical entity may be used as it is normally understood to a person of skill in the art and generally refers to a chemical entity that comprises at least one double or triple bond, and may include linear, branched, and/or cyclic groups. Non-limiting examples of a $C_2$-$C_{20}$ alkenyl group may include vinyl, allyl, isopropenyl, I-propene-2-yl, 1-butene-I-yl, 1-butene-2-yl, I-butene-3-yl, 2-butene-I-yl, 2-butene-2-yl, octenyl, decenyl, cyclopropenyl, cyclobutenyl, cyclopentenyl, cyclohexenyl, cycloheptenyl, cyclooctenyl, cyclononanenyl, cyclodecanenyl, and the like. Unless otherwise specified, a $C_1$-$C_{20}$ alkenylenyl therefore encompasses, without limitation, all divalent analogs of the above-listed alkenyl groups. Non-limiting examples of a $C_2$-$C_{20}$ alkynyl group may include ethynyl, propynyl, butynyl, pentynyl, hexynyl, heptynyl, octynyl, nonynyl, decynyl, and the like. Unless otherwise specified, a $C_1$-$C_{20}$ alkynylenyl therefore encompasses, without limitation, all divalent analogs of the above-listed alkynyl groups. Without limitation, the above-defined saturated $C_1$-$C_{20}$ alkyl groups, $C_2$-$C_{20}$ alkenyl groups and $C_2$-$C_{20}$ alkynyl groups are all encompassed within the term "$X_1$-$X_{20}$ alkyl", unless otherwise indicated. Without limitation, the above-defined saturated $C_1$-$C_{20}$ alkylenyl groups, $C_2$-$C_{20}$ alkenylenyl groups and $C_2$-$C_{20}$ alkynylenyl groups are all encompassed within the term "$X_1$-$X_{20}$ alkylenyl", unless otherwise indicated.

Without limitation, the term "$X_1$-$X_{20}$ heteroalkyl" would encompass each of the above-defined saturated $C_1$-$C_{20}$ alkyl groups, $C_2$-$C_{20}$ alkenyl groups and $C_2$-$C_{20}$ alkynyl groups, where one or more of the carbon atoms is independently replaced with a heteroatom. Likewise, without limitation, the term "$X_1$-$X_{20}$ heteroalkylenyl" would encompass each of the above-defined saturated $C_1$-$C_{20}$ alkylenyl groups, $C_2$-$C_{20}$ alkenylenyl groups and $C_2$-$C_{20}$ alkynylenyl groups, where one or more of the carbon atoms is independently replaced with a heteroatom. The person of skill in the art would understand that various combinations of different heteroatoms may be used. Non-limiting examples of non-aromatic heterocyclic groups include aziridinyl, azetidinyl, diazetidinyl, pyrrolidinyl, pyrrolinyl, piperidinyl, piperazinyl, imidazolinyl, pyrazolidinyl, imidazolydinyl, phthalimidyl, succinimidyl, oxiranyl, tetrahydropyranyl, oxetanyl, dioxanyl, thietanyl, thiepinyl, morpholinyl, oxathiolanyl, and the like.

Unless further specified, an "aryl" group includes both single aromatic rings as well as fused rings containing at least one aromatic ring. non-limiting examples of $C_3$-$C_{20}$ aryl groups include phenyl (Ph), pentalenyl, indenyl, naphthyl and azulenyl. Non-limiting examples of $X_3$-$X_{20}$ aromatic heterocyclic groups include pyrrolyl, imidazolyl, pyrazolyl, pyridinyl, pyridazinyl, pyrimidinyl, pirazinyl, quinolinyl, isoquinolinyl, acridinyl, indolyl, isoindolyl, indolizinyl, purinyl, carbazolyl, indazolyl, phthalazinyl, naphthyridinyl, quinoxalinyl, quinazolinyl, cinnolinyl, pteridinyl, phenanthridinyl, phenazinyl, phenanthrolinyl, perimidinyl, furyl, dibenzofuryl, xanthenyl, benzofuryl, thiophenyl, thianthrenyl, benzothiophenyl, phosphorinyl, phosphinolinyl, phosphindolyl, thiazolyl, oxazolyl, isoxazolyl, and the like.

As used herein, the term "substituted" is used as it would normally be understood to a person of skill in the art and generally refers to a compound or chemical entity that has one chemical group replaced with a different chemical group. Unless otherwise specified, a substituted alkyl is an alkyl in which one or more hydrogen atom(s) are independently each replaced with an atom that is not hydrogen. For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g. alkyl, heteroalkyl, aryl, heteroaryl and the like) may be substituted with any chemical group reasonable to the person of skill in the art. For example, but without limitation, a hydrogen bonded to a carbon or heteroatom (e.g. N) may be substituted with halide (e.g. F, I, Br, Cl), amine, amide, oxo, hydroxyl, thiol, phosphate, phosphonate, sulfate, $SO_2H$, $SO_3H$, alkyls, heteroalkyls, aryl, heteroaryl, ketones, carboxaldehyde, carboxylates, carboxamides, nitriles, monohalomethyl, dihalomethyl or trihalomethyl.

As used herein, the term "unsubstituted" is used as it would normally be understood to a person of skill in the art. Non-limiting examples of unsubstituted alkyls include methyl, ethyl, tert-butyl, pentyl and the like. The expression "optionally substituted" is used interchangeably with the expression "unsubstituted or substituted".

In the structures provided herein, hydrogen may or may not be shown. In some embodiments, hydrogens (whether shown or implicit) may be protium (i.e. $^1$H), deuterium (i.e. $^2$H) or combinations of $^1$H and $^2$H. Methods for exchanging $^1$H with $^2$H are well known in the art. For solvent-exchangeable hydrogens, the exchange of $^1$H with $^2$H occurs readily in the presence of a suitable deuterium source, without any catalyst. The use of acid, base or metal catalysts, coupled with conditions of increased temperature and pressure, can facilitate the exchange of non-exchangeable hydrogen atoms, generally resulting in the exchange of all $^1$H to $^2$H in a molecule.

The term "Xaa" refers to an amino acid residue in a peptide chain or an amino acid that is otherwise part of a compound. Amino acids have both an amino group and a carboxylic acid group, either or both of which can be used for covalent attachment. In attaching to the remainder of the compound, the amino group and/or the carboxylic acid group may be converted to an amide or other structure; e.g. a carboxylic acid group of a first amino acid is converted to an amide (i.e. a peptide bond) when bonded to the amino group of a second amino acid. As such, Xaa may have the formula $N(R^a)R^bC(O)$, where $R^a$ and $R^b$ are R-groups. $R^a$ will typically be hydrogen or methyl. The amino acid residues of a peptide may comprise typical peptide (amide) bonds and may further comprise bonds between side chain functional groups and the side chain or main chain functional group of another amino acid. For example, the side chain carboxylate of one amino acid residue in the peptide (e.g. Asp, Glu, etc.) may be bonded to and the amine of another amino acid residue in the peptide (e.g. Dap, Dab, Orn, Lys). Further details are provided below. Unless otherwise indicated, "Xaa" may be any amino acid, including proteinogenic and nonproteinogenic amino acids. Non-limiting examples of nonproteinogenic amino acids are shown in Table 1 and include: D-amino acids (including without limitation any D-form of the following amino acids), ornithine (Orn), 3-(1-naphtyl)alanine (Nal), 3-(2-naphtyl)alanine (2-Nal), α-aminobutyric acid, norvaline, norleucine (Nle), homonorleucine, beta-(1,2,3-triazol-4-yl)-L-alanine, 1,2,4-triazole-3-alanine, Phe(4-F), Phe(4-Cl), Phe(4-Br), Phe(4-I), Phe(4-NH$_2$), Phe(4-NO$_2$), homoarginine (hArg), 2-amino-4-guanidinobutyric acid (Agb), 2-amino-3-guanidinopropionic acid (Agp), β-alanine, 4-aminobutyric acid, 5-aminovaleric acid, 6-aminohexanoic acid, 7-aminoheptanoic acid, 8-aminooctanoic acid, 9-aminononanoic acid, 10-aminodecanoic acid, 2-aminooctanoic acid, 2-amino-3-(anthracen-2-yl)propanoic acid, 2-amino-3-(anthracen-9-yl)propanoic acid, 2-amino-3-(pyren-1-yl)propanoic acid, Trp(5-Br), Trp(5-OCH$_3$), Trp(6-F), Trp(5-OH) or Trp(CHO), 2-aminoadipic acid (2-Aad), 3-aminoadipic acid (3-Aad), propargylglycine (Pra), homopropargylglycine (Hpg), beta-homopropargylglycine (Bpg), 2,3-diaminopropionic acid (Dap), 2,4-diaminobutyric acid (Dab), azidolysine (Lys(N$_3$)), azido-ornithine (Orn(N$_3$)), 2-amino-4-azidobutanoic acid Dab(N$_3$), Dap(N$_3$), 2-(5'-azidopentyl)alanine, 2-(6'-azidohexyl)alanine, 4-amino-1-carboxymethyl-piperidine (Pip), 4-(2-aminoethyl)-1-carboxymethyl-piperazine (Acp), and tranexamic acid. If not specified as an L- or D-amino acid, an amino acid shall be understood to encompass both L- and D-amino acids.

TABLE 1

List of non-limiting examples of non-proteinogenic amino acids.

| | |
|---|---|
| Any D-amino acid of a proteinogenic amino acid | 10-aminodecanoic acid |
| ornithine (Orn) | 2-aminooctanoic acid |
| 3-(1-naphtyl)alanine (Nal) | 2-amino-3-(anthracen-2-yl)propanoic acid |
| 3-(2-naphtyl)alanine (2-Nal) | 2-amino-3-(anthracen-9-yl)propanoic acid |
| α-aminobutyric acid | 2-amino-3-(pyren-1-yl)propanoic acid |
| norvaline | Trp(5-Br), |
| norleucine (Nle) | Trp(5-OCH$_3$), |
| homonorleucine | Trp(6-F), |
| beta-(1,2,3-triazol-4-yl)-L-alanine | Trp(5-OH) |
| 1,2,4-triazole-3-alanine | Trp(CHO), |
| Phe(4-F), Phe(2-F), Phe(3-F), | 2-aminoadipic acid (2-Aad) |
| Phe(4-Cl), Phe(2-Cl), Phe(3-Cl), | 3-aminoadipic acid (3-Aad) |
| Phe(4-Br), Phe(2-Br), Phe(3-Br), | propargylglycine (Pra) |
| Phe(4-I), Phe(2-I), Phe(2-I), | homopropargylglycine (Hpg) |
| Phe(4-NH$_2$), Phe(2-NH$_2$), Phe(3-NH$_2$), | beta-homopropargylglycine (Bpg) |
| Phe(4-NO$_2$), Phe(2-NO$_2$), Phe(2-NO$_2$), | 2,3-diaminopropionic acid (Dap) |
| homoarginine (hArg) | 2,4-diaminobutyric acid (Dab) |
| 4-(2-aminoethyl)-1-carboxymethyl-piperazine (Acp) | azidolysine (Lys(N$_3$)) |
| 2-(5'-azidopentyl)alanine, 2-(6'-azidohexyl)alanine | azido-ornithine (Orn(N$_3$)) |
| 2-amino-4-guanidinobutyric acid (Agb) | amino-4-azidobutanoic acid Dab(N$_3$) |
| 2-amino-3-guanidinopropionic acid (Agp) | tranexamic acid |
| β-alanine | 4-amino-1-carboxymethyl-piperidine (Pip) |
| 4-aminobutyric acid | NH$_2$(CH$_2$)$_2$O(CH$_2$)$_2$C(O)OH |
| 5-aminovaleric acid | NH$_2$(CH$_2$)$_2$[O(CH$_2$)$_2$]$_2$C(O)OH |
| 6-aminohexanoic acid | NH$_2$(CH$_2$)$_2$[O(CH$_2$)$_2$]$_3$C(O)OH |
| 7-aminoheptanoic acid | NH$_2$(CH$_2$)$_2$[O(CH$_2$)$_2$]$_4$C(O)OH |
| 8-aminooctanoic acid | NH$_2$(CH$_2$)$_2$[O(CH$_2$)$_2$]$_5$C(O)OH |
| 9-aminononanoic acid | NH$_2$(CH$_2$)$_2$[O(CH$_2$)$_2$]$_6$C(O)OH |

The wavy line "~~" symbol shown through or at the end of a bond in a chemical formula (e.g. in the definitions $R^4$, $R^6$, $R^7$, $R^9$ and $R^{11}$ of Formula I etc.) is intended to define the R group on one side of the wavy line, without modifying the definition of the structure on the opposite side of the wavy line. Where an R group is bonded on two or more sides (e.g. $R^{11}$), any atoms shown outside the wavy lines are intended to clarify orientation of the R group. As such, only the atoms between the two wavy lines constitute the definition of the R group. When atoms are not shown outside the wavy lines, or for a chemical group shown without wavy lines but does have bonds on multiple sides (e.g. —C(O)NH—, and the like), the chemical group should be read from left to right matching the orientation in the formula that the group relates to (e.g. for formula —$R^a$—$R^b$—$R^c$—, the definition of $R^b$ as —C(O)NH— would be incorporated into the formula as —$R^a$—C(O)NH—$R^c$— not as —$R^a$—NHC(O)—$R^c$—).

In various aspects, there is disclosed a compound of Formula I (as defined below), Formula II (as defined below), Formula IV (as defined below), or Formula V (as defined below), or a compound that comprises a PSMA-targeting moiety of Formula III (as defined below), including salts or solvates of the foregoing.

The following definitions apply to Formula I compounds (and salts/solvates thereof).

In some embodiments, the compound is of Formula I or is a salt or solvate of Formula I:

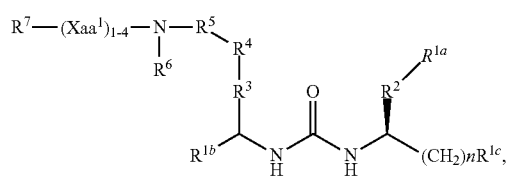

(I)

wherein:
n is 0 or 1;
each of $R^{1a}$, $R^{1b}$ and $R^{1c}$ is independently —$CO_2H$, —$SO_2H$, —$SO_3H$, —$SO_4H$, —$PO_2H$, —$PO_3H$ or —$PO_4H$;
when n is 0, $R^2$ is —$CH_2$—, —CHOH—, —CHF—, —$CH_2$CHOH—, —$CH_2$CHF—, —$CH_2$CHOHCH$_2$—, —$CH_2$CHFCH$_2$—, —(CH$_2$)$_2$CHOH—, —(CH$_2$)$_2$CHF—, —(CH$_2$)$_3$—, —$CH_2$OCH$_2$— or —$CH_2$SCH$_2$—;
when n is 1, $R^2$ is —$CH_2$—, —CHOH—, —CHF—, —$CH_2$CHOH—, —$CH_2$CHF— or —(CH$_2$)$_2$—;
$R^3$ is a linear or branched, cyclic or acyclic, and/or aromatic or non-aromatic $C_1$-$C_{20}$ alkylenyl or alkenylenyl, or a linear or branched, cyclic or acyclic, and/or aromatic or non-aromatic $X_2$-$X_{20}$ heteroalkylenyl or heteroalkenylenyl;
$R^4$ is —O—, —S—, —NHC(O)—, —C(O)NH—,

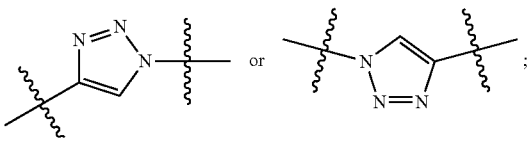 [SMILES: *c1cn(*)nn1 ; *c1cn(*)nn1]

$R^5$ is a linear or branched, cyclic or acyclic, and/or aromatic or non-aromatic $C_1$-$C_{30}$ alkylenyl, alkenylenyl or alkynylenyl, or is a linear or branched, cyclic or acyclic, and/or aromatic or non-aromatic $X_2$-$X_{30}$ heteroalkylenyl, heteroalkenylenyl or heteroalkynylenyl;
$R^6$ is hydrogen or methyl;
Xaa$^1$ is an amino acid of formula —N($R^8$)$R^9$C(O)—, wherein each $R^8$ is independently hydrogen or methyl, and wherein each $R^9$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl;

at least one $R^9$ or $R^5$ is

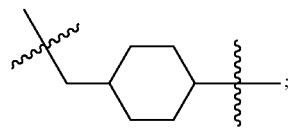

at least one $R^9$ or $R^5$ is —(CH$_2$)$_{0-3}$CH($R^{10}$)(CH$_2$)$_{0-3}$, wherein $R^{10}$ is a linear or branched, cyclic or acyclic, and/or aromatic or non-aromatic $C_2$-$C_{19}$ alkyl, alkenyl or alkynyl, or $R^{10}$ is a linear or branched, cyclic or acyclic, and/or aromatic or non-aromatic $X_2$-$X_{19}$ heteroalkyl, heteroalkenyl or heteroalkynyl having only 1-3 heteroatoms;
$R^7$ is $R^X$—(Xaa$^2$)$_{0-4}$,

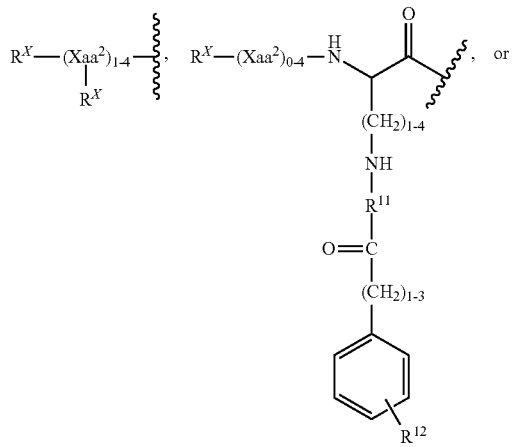

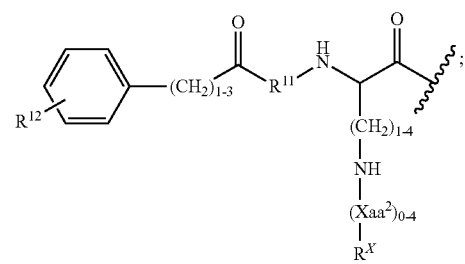

$R^{11}$ is absent,

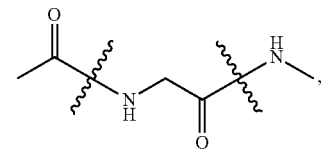

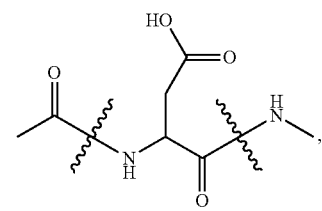

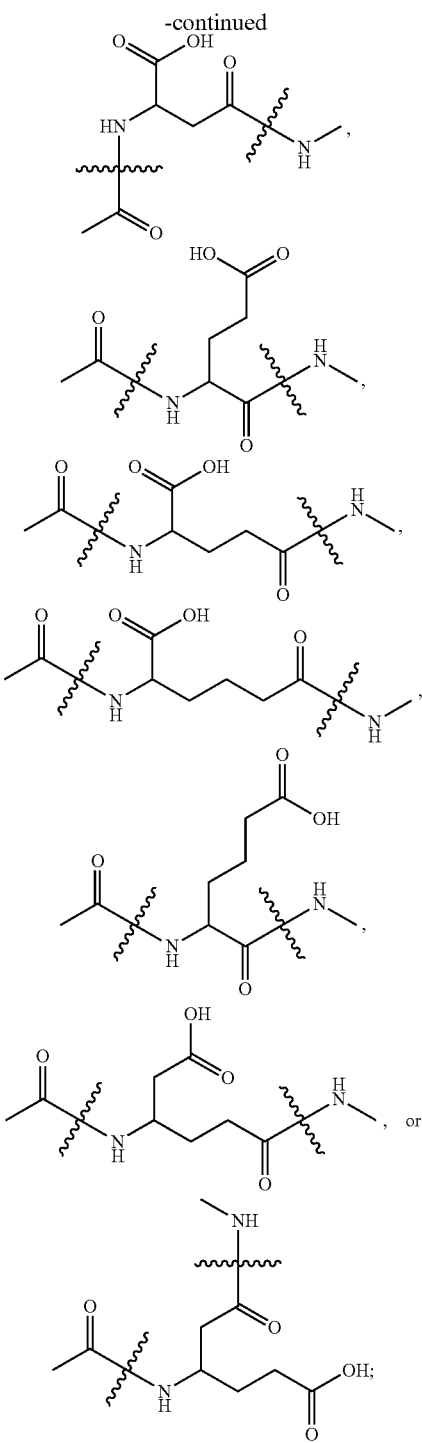

$R^{12}$ is I, Br, F, Cl, H, OH, OCH$_3$, NH$_2$, NO$_2$ or CH$_3$;

Xaa$^2$, when present, is —N(R$^{13}$)R$^{14}$C(O)—, wherein each R$^{13}$ is independently hydrogen or methyl, and wherein each R$^{14}$ is independently: a linear or branched, cyclic or acyclic, and/or aromatic or non-aromatic C$_1$-C$_{20}$ alkylenyl, alkenylenyl or alkynylenyl; or a linear or branched, cyclic or acyclic, and/or aromatic or non-aromatic X$_2$-X$_{20}$ heteroalkylenyl, heteroalkenylenyl or heteroalkynylenyl; and each R$^X$ is a radiolabeling group independently selected from: a radiometal chelator optionally bound by a radiometal; an aryl substituted with a radioisotope; a prosthetic group containing a trifluoroborate; and a prosthetic group containing a silicon-fluorine-acceptor moiety.

In some embodiments, the compound of is a salt or solvate of Formula I.

In some embodiments, the compound of Formula I is a compound of Formula Ia:

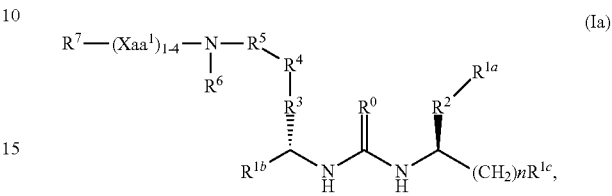

(Ia)

wherein R$^{1a}$, R$^{1b}$, R$^{1c}$, R$^2$, R$^3$, R$^4$, R$^5$, R$^6$, Xaa$^1$ and R$^7$ are as defined for Formula I. In some embodiments, the compound is a salt or solvate of Formula Ia.

In some embodiments, n is 0. In some embodiments, n is 1.

In some embodiments, R$^{1a}$ is —CO$_2$H. In some embodiments, R$^{1b}$ is —CO$_2$H. In some embodiments, R$^{1c}$ is —CO$_2$H. In some embodiments, R$^{1a}$ and R$^{1b}$ are each —CO$_2$H. In some embodiments, R$^{1a}$ and R$^{1c}$ are each —CO$_2$H. In some embodiments, R$^{1b}$ and R$^{1c}$ are each —CO$_2$H. In some embodiments, R$^{1a}$, R$^{1b}$ and R$^{1c}$ are each —CO$_2$H.

In some embodiments, R$^2$ is —CH$_2$OCH$_2$— or —CH$_2$SCH$_2$—.

In some embodiments, n is 0 and R$^2$ is —CH$_2$—. In some embodiments, n is 0 and R$^2$—CHOH—. In some embodiments, n is 0 and R$^2$ is —CHF—. In some embodiments, n is 0 and R$^2$ is —CH$_2$CHOH—. In some embodiments, n is 0 and R$^2$ is —CH$_2$CHF—. In some embodiments, n is 0 and R$^2$ is —CH$_2$CHOHCH$_2$—. In some embodiments, n is 0 and R$^2$ is —CH$_2$CHFCH$_2$—. In some embodiments, n is 0 and R$^2$ is —(CH$_2$)$_2$CHOH—. In some embodiments, n is 0 and R$^2$ is —(CH$_2$)$_2$CHF—. In some embodiments, n is 0 and R$^2$ is —(CH$_2$)$_3$—. In some embodiments, n is 0 and R$^2$ is —CH$_2$OCH$_2$—. In some embodiments, n is 0 and R$^2$ is —CH$_2$SCH$_2$—.

In some embodiments, n is 1 and R$^2$ is —CH$_2$—. In some embodiments, n is 1 and R$^2$ is —CHOH—. In some embodiments, n is 1 and R$^2$ is —CHF—. In some embodiments, n is 1 and R$^2$ is —CH$_2$CHOH—. In some embodiments, n is 1 and R$^2$ is —CH$_2$CHF—. In some embodiments, n is 1 and R$^2$ is —(CH$_2$)$_2$—.

In some embodiments, n is 0, R$^{1a}$ is —CO$_2$H and R$^2$ is —(CH(CH$_2$)$_3$—. In some embodiments, n is 0, R$^{1a}$ is —CO$_2$H and R$^2$ is —CH$_2$—. In some embodiments, n is 0, R$^{1a}$ is —CO$_2$H, R$^{1b}$ is —CO$_2$H, R$^{1c}$ is —CO$_2$H, and R$^2$ is —(CH$_2$)$_3$—. In some embodiments, n is 0, R$^{1a}$ is —CO$_2$H and R$^2$ is —CH$_2$—.

In some embodiments, R$^3$ is a linear acyclic C$_3$-C$_{15}$ alkylenyl. In some embodiments, R$^3$ is a linear acyclic C$_3$-C$_{15}$ heteroalkylenyl having 1-5 N, S and/or O heteroatoms. In some embodiments, R$^3$ is a linear acyclic saturated C$_3$-C$_{10}$ alkylenyl, optionally substituted with 1-5 amine, amide, oxo, hydroxyl, thiol, methyl or ethyl groups. In some embodiments, R$^3$ is —(CH$_2$)$_{3-15}$—. In some embodiments, R$^3$ is —CH$_2$—. In some embodiments, R$^3$ is —(CH$_2$)$_2$—. In some embodiments, R$^3$ is —(CH$_2$)$_3$—. In some embodiments, R$^3$ is —(CH$_2$)$_4$—. In some embodiments, R$^3$ is —$(CH_2)_5$—. In some embodiments, $R^3$ is —$CH_2$—O—$CH_2$—. In some embodiments, $R^3$ is —$CH_2$—S—$CH_2$—.

In some embodiments, $R^4$ is —O—. In some embodiments, $R^4$ is —S—. In some embodiments, $R^4$ is —NHC(O)—. In some embodiments, $R^4$ is —C(O)NH—. In some embodiments, $R^4$ is

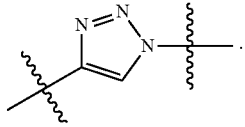

In some embodiments, $R^4$ is

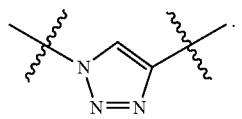 [SMILES: *c1cn(*)nn1]

In some embodiments, $R^3$ is —$(CH_2)_{3-15}$— and $R^4$ is —C(O)NH—. In some embodiments, $R^3$ is —$(CH_2)_{3-5}$— and $R^4$ is —C(O)NH—. In some embodiments, $R^3$ is —$(CH_2)_4$— and $R^4$ is —C(O)NH—.

In some embodiments, $R^5$ is —$(CH_2)_{0-3}CH(R^{10})(CH_2)_{0-3}$—. In some embodiments, $R^5$ is —$CH(R^{10})$—. In some embodiments, $R^5$ is —$CH_2CH(R^{10})$—. In some embodiments, $R^5$ is —$CH(R^{10})CH_2$—. In some embodiments, $R^5$ is —$CH(R^{10})$—.

In some embodiments, $R^{10}$ is an alkenyl containing either a $C_6$-$C_{16}$ aryl or $X_6$-$X_{16}$ heteroaryl having 1-3 heteroatoms independently selected from N, S and/or O. In some embodiments, the $C_6$-$C_{16}$ aryl is benzyl. In some embodiments, the $X_6$-$X_{16}$ heteroaryl is benzyloxyl or benzylthio. In some embodiments, $R^{10}$ is:

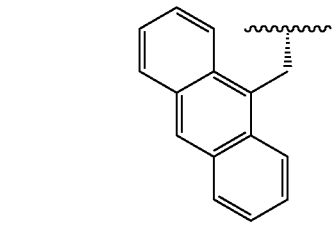

In some embodiments, $R^{10}$

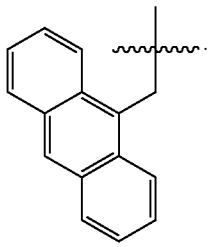

In some embodiments, $R^{10}$ is:

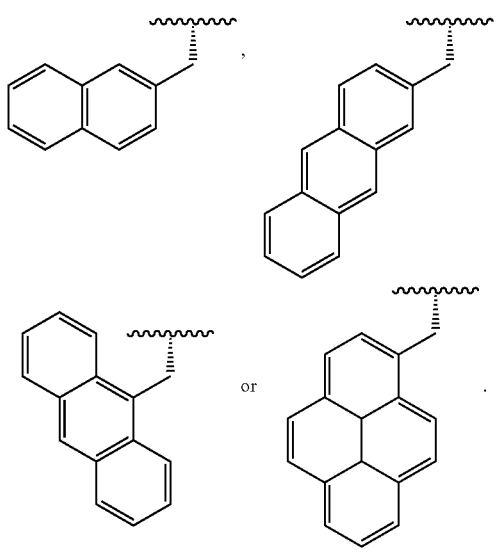

In some embodiments, $R^{10}$ is

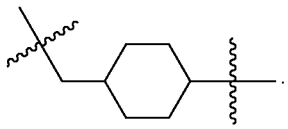 [SMILES: *CC1CCC(*)CC1]

In some embodiments, $R^5$ is —$CH(R^{10})$— wherein $R^{10}$ is as defined in any embodiment above.

In some embodiments, $R^5$ is —$(CH_2)_{0-3}CH(R^{10})(CH_2)_{0-3}$— and $R^{10}$ is —$(CH_2)_5CH_3$. In some embodiments, $R^5$ is —$CH(R^{10})$— and $R^{10}$ is —$(CH_2)_5CH_3$.

In some embodiments, $R^5$ is

In some embodiments, $R^5$ is

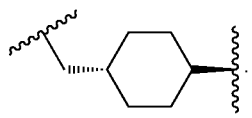

In some embodiments, $R^6$ is hydrogen. In some embodiments, $R^6$ is methyl.

In some embodiments, $(Xaa^1)_{1-4}$ consists of a single amino acid residue. In some embodiments, $(Xaa^1)_{1-4}$ is a dipeptide, wherein each $Xaa^1$ may be the same or different. In some embodiments, $(Xaa^1)_{1-4}$ is a tripeptide, wherein each $Xaa^1$ may be the same, different or a combination thereof. In some embodiments, $(Xaa^1)_{1-4}$ consists of 4 amino acid residues connected by peptide bonds, wherein each $Xaa^1$ may be the same, different or a combination thereof. In some embodiments, each $Xaa^1$ is independently selected from proteinogenic amino acids and the non-proteinogenic amino acids listed in Table 1, wherein each peptide backbone amino group is optionally methylated. In some embodiments, at least one $R^9$ is

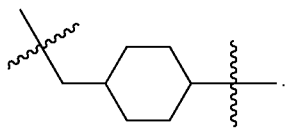 [SMILES: *CC1CCC(*)CC1]

In some embodiments, at least one $R^9$ is

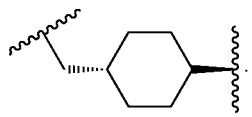

In some embodiments, at least one $R^8$ is hydrogen. In some embodiments, all $R^8$ are hydrogen. In some embodiments, at least one $Xaa^1$ is a tranexamic acid residue. In some embodiments, $(Xaa^1)_{1-4}$ consists of a single tranexamic acid residue.

In some embodiments, $R^3$ is $-(CH_2)_4-$ and $-(Xaa^1)_{1-4}N(R^6)R^5R^4-$ is

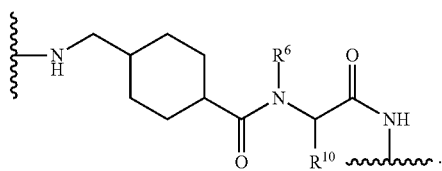

In some embodiments, $R^3$ is $-(CH_2)_4-$ and $-(Xaa^1)_{1-4}N(R^6)R^5R^4-$ is

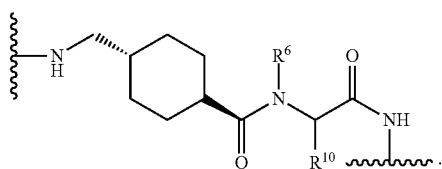

The following definitions apply to Formula II compounds (and salts/solvates thereof).

In some embodiments, the compound is a compound of Formula II or is a salt or a solvate of Formula II:

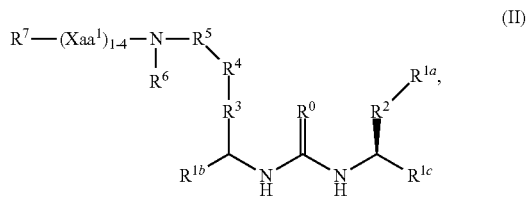

(II)

wherein:

$R^0$ is O or S;

$R^{1a}$ is $-CO_2H$, $-SO_2H$, $-SO_3H$, $-PO_2H$, $-PO_3H_2$, $-OPO_3H_2$, $-OSO_3H$, $-B(OH)_2$, or

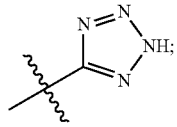 [SMILES: *c1nn[nH]n1]

$R^{1b}$ is $-CO_2H$, $-SO_2H$, $-SO_3H$, $-PO_2H$, $-PO_3H_2$, $-B(OH)_2$, or

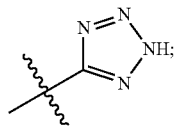 [SMILES: *c1nn[nH]n1]

$R^{1c}$ is $-CO_2H$, $-SO_2H$, $-SO_3H$, $-PO_2H$, $-PO_3H_2$, $-B(OH)_2$, or

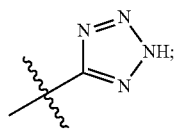 [SMILES: *c1nn[nH]n1]

$R^2$ is $-CH_2-$, $-CH(OH)-$, $-CHF-$, $-CF_2-$, $-CH(CH_3)-$, $-C(CH_3)_2-$, $-CH_2CH(OH)-$, $-CH_2CHF-$, $-CHFCH_2-$, $-CF_2CH_2-$, $-CH_2CF_2-$, $-CH(OH)CH_2-$, $-CH(CH_3)CH_2-$, $-CH_2CH(CH_3)-$, $-C(CH_3)_2CH_2-$, $-CH_2C(CH_3)_2-$, $-CH_2CH(OH)CH_2-$, $-CH_2CHFCH_2-$, $-(CH_2)_2CH(OH)-$, $-(CH_2)_2CHF-$, $-(CH_2)_3-$, $-CH_2OCH_2-$, $-CH_2SCH_2-$, $-CHFCH_2CH_2-$, $-CH(OH)CH_2CH_2-$, $-CH(CH_3)CH_2CH_2-$, $-CH_2CH(CH_3)CH_2-$, $-CH_2CH_2CH(CH_3)-$, $-C(CH_3)_2CH_2CH_2-$, $-CH_2C(CH_3)_2CH_2-$, $-CH_2CH_2C(CH_3)_2-$, $-CH(CH_3)-O-CH_2-$, $-C(CH_3)_2-O-CH_2-$, $-CH_2-O-CH(CH_3)-$, $-CH_2-O-C(CH_3)_2-$, $-CH_2-S(O)-CH_2-$, $-CH_2-S(O)_2-CH_2-$, $-CH(CH_3)-S-CH_2-$, $-C(CH_3)_2-S-CH_2-$, $-CH_2-S-CH(CH_3)-$, $-CH_2-S-C(CH_3)_2-$, $-CH(CH_3)-S(O)-CH_2-$, $-C(CH_3)_2-S(O)-CH_2-$, $-CH_2-S(O)-CH(CH_3)-$, $-CH_2-S(O)-C(CH_3)_2-$, $-CH(CH_3)-S$ (O)₂—CH₂—, —C(CH₃)₂—S(O)₂—CH₂—, —CH₂—S(O)₂—CH(CH₃)—, —CH₂—S(O)₂—C(CH₃)₂—, —CH₂—NH—C(O)—, —C(O)—NH—CH₂—, —C(O)—NH—CH(CH₃)—, or —C(O)—NH—C(CH₃)₂—;

$R^3$ is a linear or branched, cyclic or acyclic, and/or aromatic or non-aromatic $C_1$-$C_{20}$ alkylenyl, alkenylenyl, or alkynylenyl, or a linear or branched, cyclic or acyclic, and/or aromatic or non-aromatic $X_2$-$X_{20}$ heteroalkylenyl, heteroalkenylenyl, or heteroalkynylenyl;

$R^4$ is —O—, —S—, —Se—, —S(O)—, —S(O)₂—, —NHC(O)—, —C(O)NH—,

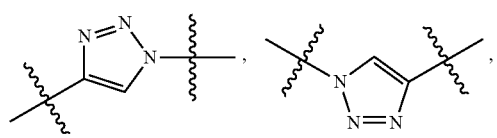 [SMILES: *c1cn(*)nn1 ; *c1cn(*)nn1]

—C(O)—(NH)₂—C(O)—, —OC(O)NH, —NHC(O)O—, —NHC(O)NH—, —OC(S)NH—, —NHC(S)O—, —NHC(S)NH—, —NHC(O)C(O)NH—, —S—S—, —S—CH₂—S, —NH—NH—C(O)—, —C(O)—NH—NH;

$R^5$ is a linear or branched, cyclic or acyclic, and/or aromatic or non-aromatic $C_1$-$C_{30}$ alkylenyl, alkenylenyl or alkynylenyl, or is a linear or branched, cyclic or acyclic, and/or aromatic or non-aromatic $X_2$-$X_{30}$ heteroalkylenyl, heteroalkenylenyl or heteroalkynylenyl;

$R^6$ is hydrogen or methyl or ethyl;

$Xaa^1$ is an amino acid of formula —N($R^8$)$R^9$C(O)—, wherein each $R^8$ is independently hydrogen or methyl, and wherein each $R^9$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl;

at least one $R^9$ or $R^5$ is —(CH₂)$_{0-3}$CH($R^{10}$)(CH₂)$_{0-3}$, wherein $R^{10}$ is:

a linear or branched, cyclic or acyclic, and/or aromatic or non-aromatic $C_2$-$C_{19}$ alkyl, alkenyl or alkynyl; a linear or branched, cyclic or acyclic, and/or aromatic or non-aromatic $X_2$-$X_{19}$ heteroalkyl, heteroalkenyl or heteroalkynyl having only 1-3 heteroatoms;

—CH₂$R^{23}$, in which $R^{23}$ is an optionally substituted $C_4$-$C_{16}$ aromatic ring or partially or fully aromatic fused ring system, wherein 0-3 carbons in the aromatic ring or the partially or fully aromatic fused ring system are replaced with N, S and/or O heteroatoms, and wherein the optional substitutions are selected from OH, NH₂, NO₂, halogen, $C_1$-$C_6$ alkyl, and/or $C_1$-$C_6$ alkoxyl groups; or selected from

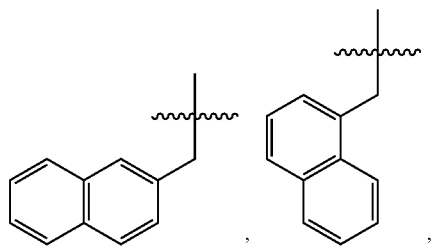

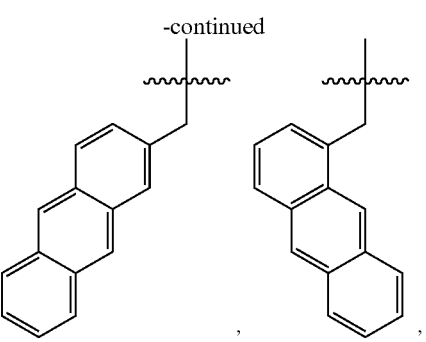

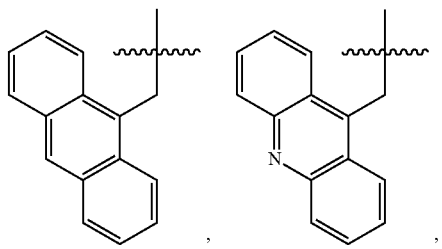

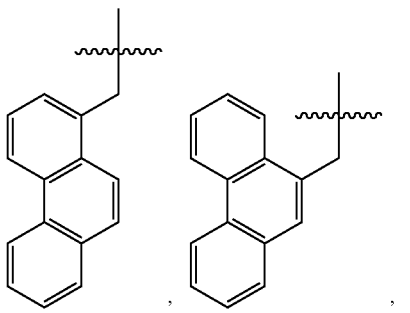

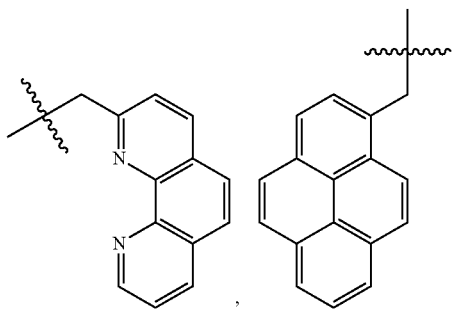

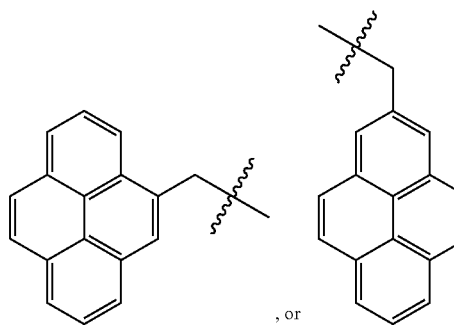

optionally modified with one, more than one, or a combination of: halogen, OMe, SMe, NH₂, NO₂, CN, OH, or one or more additional endocyclic ring nitrogen atoms;

$R^7$ is $R^X$—$(Xaa^2)_{0-4}$—,

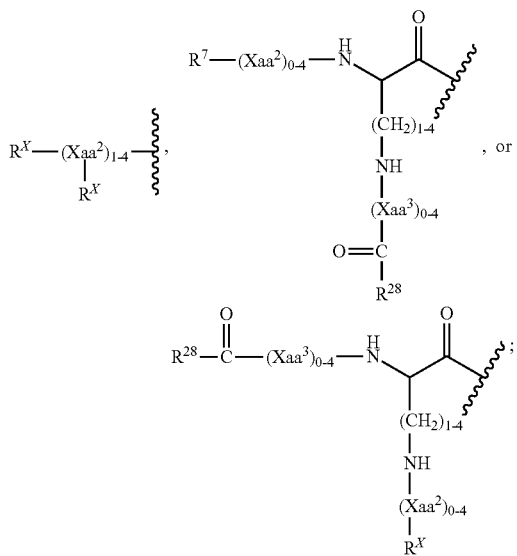

$R^{28}$ is an albumin binder;

$Xaa^2$ and $Xaa^3$, when present, are independently —N($R^{13}$)$R^{14}$C(O)— wherein each $R^{13}$ is independently hydrogen or methyl, and wherein each $R^{14}$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl; and each $R^X$ is a radiolabeling group independently selected from: a radiometal chelator optionally bound by a radiometal; an aryl or heteroaryl substituted with a radiohalogen; a prosthetic group containing a trifluoroborate; a prosthetic group containing a silicon-fluorine-acceptor moiety; or a prosthetic group containing a fluorophosphate, fluorosulfate, sulfonylfluoride, or a combination thereof.

In some embodiments, the compound of Formula II is a compound of Formula IIa:

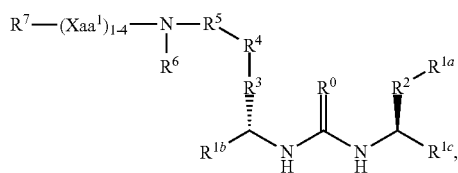

(IIa)

wherein $R^{1a}$, $R^{1b}$, $R^{1c}$, $R^2$, $R^{3}$, $R^4$, $R^5$, $R^6$, $Xaa^1$ and $R^7$ are as defined for Formula II. In some embodiments, the compound is a salt or solvate of Formula IIa.

In some embodiments, $R^2$ is —CH$_2$—. In some embodiments, $R^2$ is —CH(OH)—. In some embodiments, $R^2$ is —CHF—. In some embodiments, $R^2$ is —CF$_2$—. In some embodiments, $R^2$ is —CH(CH$_3$)—. In some embodiments, $R^2$ is —C(CH$_3$)$_2$—.

In some embodiments, $R^2$ is —CH$_2$CH(OH)—. In some embodiments, $R^2$ is —CH$_2$CHF—. In some embodiments, $R^2$ is —CHFCH$_2$—. In some embodiments, $R^2$ is —CF$_2$CH$_2$—. In some embodiments, $R^2$ is —CH$_2$CF$_2$—. In some embodiments, $R^2$ is —CH(OH)CH$_2$—. In some embodiments, $R^2$ is —CH(CH$_3$)CH$_2$—. In some embodiments, $R^2$ is —CH$_2$CH(CH$_3$)—. In some embodiments, $R^2$ is —C(CH$_3$)$_2$CH$_2$—. In some embodiments, $R^2$ is —CH$_2$C(CH$_3$)$_2$—.

In some embodiments, $R^2$ is —CH$_2$—, —CH(OH)—, —CHF—, —CF$_2$—, —CH(CH$_3$)—, —C(CH$_3$)$_2$—, —CH$_2$CH(OH)—, —CH$_2$CHF—, —CHFCH$_2$—, —CF$_2$CH$_2$—, —CH$_2$CF$_2$—, —CH(OH)CH$_2$—, —CH(CH$_3$)CH$_2$—, —CH$_2$CH(CH$_3$)—, —C(CH$_3$)$_2$CH$_2$—, —CH$_2$C(CH$_3$)$_2$—, —CH$_2$CH(OH)CH$_2$—, —CH$_2$CHFCH$_2$—, —(CH$_2$)$_2$CH(OH)—, —(CH$_2$)$_2$CHF—, —(CH$_2$)$_3$—, —CH$_2$OCH$_2$—, —CH$_2$SCH$_2$—, —CHFCH$_2$CH$_2$—, —CH(OH)CH$_2$CH$_2$—, —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —C(O)—NH—CH$_2$—, —C(O)—NH—CH(CH$_3$)—, or —C(O)—NH—C(CH$_3$)$_2$—.

In some embodiments, $R^2$ is —CH$_2$CH(OH)CH$_2$—, —CH$_2$CHFCH$_2$—, —(CH$_2$)$_2$CH(OH)—, —(CH$_2$)$_2$CHF—, —(CH$_2$)$_3$—, —CH$_2$OCH$_2$—, —CH$_2$SCH$_2$—, —CHFCH$_2$CH$_2$—, —CH(OH)CH$_2$CH$_2$—, —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —CH$_2$—NH—C(O)—, —C(O)—NH—CH$_2$—, —C(O)—NH—CH(CH$_3$)—, —C(O)—NH—C(CH$_3$)$_2$—, —CH$_2$CH(COOH)CH$_2$—, or —CH$_2$CH$_2$CH(COOH)—. In some embodiments, $R^2$ is —CH$_2$OCH$_2$— or —CH$_2$SCH$_2$—.

In some embodiments, $R^2$ is —CH$_2$—, —CH(OH)—, —CHF—, —CF$_2$—, —CH(CH$_3$)—, —C(CH$_3$)$_2$—, —CHFCH$_2$—, —CF$_2$CH$_2$—, —CH(OH)CH$_2$—, —CH(CH$_3$)CH$_2$—, —C(CH$_3$)$_2$CH$_2$—, —(CH$_2$)$_2$CH(OH)—, —(CH$_2$)$_2$CHF—, —(CH$_2$)$_3$—, —CH$_2$OCH$_2$—, —CH$_2$SCH$_2$—, —CHFCH$_2$CH$_2$—, —CH(OH)CH$_2$CH$_2$—, —CH(CH$_3$)CH$_2$CH$_2$—, —CH$_2$CH$_2$CH(CH$_3$)—, —C(CH$_3$)$_2$CH$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —CH$_2$—NH—C (O)—, —C(O)—NH—CH$_2$—, —C(O)—NH—CH(CH$_3$)—, or —C(O)—NH—C(CH$_3$)$_2$—.

In some embodiments, R$^2$ is —(CH$_2$)$_2$CHF—, —(CH$_2$)$_3$—, —CH$_2$OCH$_2$—, —CH$_2$SCH$_2$—, —CHFCH$_2$CH$_2$—, —CH(OH)CH$_2$CH$_2$—, —CH(CH$_3$)CH$_2$CH$_2$—, —CH$_2$CH$_2$CH(CH$_3$)—, —C(CH$_3$)$_2$CH$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —C(O)—NH—CH$_2$—, —C(O)—NH—CH(CH$_3$)—, or —C(O)—NH—C(CH$_3$)$_2$—.

In some embodiments, R$^2$ is —CH$_2$CH(OH)—, —CH$_2$CHF—, —CH$_2$CH(CH$_3$)—, —CH$_2$CH(COOH)—, —CH$_2$CH(OH)CH$_2$—, —CH$_2$CH(F)CH$_2$—, or —CH$_2$CH(CH$_3$)CH$_2$—, wherein the second carbon in R$^2$ has R-configuration. In some embodiments, R$^2$ is —CH$_2$CH(OH)—, —CH$_2$CHF—, or —CH$_2$CH(CH$_3$)—, wherein the second carbon in R$^2$ has R-configuration. In some embodiments, R$^2$ is —CH$_2$CHF—, wherein the second carbon in R$^2$ has R-configuration.

In some embodiments, R$^2$ is —CH$_2$CH(OH)CH$_2$—. In some embodiments, R$^2$ is —CH$_2$CHFCH$_2$—. In some embodiments, R$^2$ is —(CH$_2$)$_2$CH(OH)—. In some embodiments, R$^2$ is —(CH$_2$)$_2$CHF—. In some embodiments, R$^2$ is —(CH$_2$)$_3$—. In some embodiments, R$^2$ is —CH$_2$OCH$_2$—. In some embodiments, R$^2$ is —CH$_2$SCH$_2$—. In some embodiments, R$^2$ is —CHFCH$_2$CH$_2$—. In some embodiments, R$^2$ is —CH(OH)CH$_2$CH$_2$—. In some embodiments, R$^2$ is —CH(CH$_3$)CH$_2$CH$_2$—. In some embodiments, R$^2$ is —CH$_2$CH(CH$_3$)CH$_2$—. In some embodiments, R$^2$ is —CH$_2$CH$_2$CH(CH$_3$)—. In some embodiments, R$^2$ is —C(CH$_3$)$_2$CH$_2$CH$_2$—. In some embodiments, R$^2$ is —CH$_2$C(CH$_3$)$_2$CH$_2$—. In some embodiments, R$^2$ is —CH$_2$CH$_2$C(CH$_3$)$_2$—. In some embodiments, R$^2$ is —CH(CH$_3$)—O—CH$_2$—. In some embodiments, R$^2$ is —C(CH$_3$)$_2$—O—CH$_2$—. In some embodiments, R$^2$ is —CH$_2$—O—CH(CH$_3$)—. In some embodiments, R$^2$ is —CH$_2$—O—C(CH$_3$)$_2$—. In some embodiments, R$^2$ is —CH$_2$—S(O)—CH$_2$—. In some embodiments, R$^2$ is —CH$_2$—S(O)$_2$—CH$_2$—. In some embodiments, R$^2$ is —CH(CH$_3$)—S—CH$_2$—. In some embodiments, R$^2$ is —C(CH$_3$)$_2$—S—CH$_2$—. In some embodiments, R$^2$ is —CH$_2$—S—CH(CH$_3$)—. In some embodiments, R$^2$ is —CH$_2$—S—C(CH$_3$)$_2$—. In some embodiments, R$^2$ is —CH(CH$_3$)—S(O)—CH$_2$—. In some embodiments, R$^2$ is —C(CH$_3$)$_2$—S(O)—CH$_2$—. In some embodiments, R$^2$ is —CH$_2$—S(O)—CH(CH$_3$)—. In some embodiments, R$^2$ is —CH$_2$—S(O)—C(CH$_3$)$_2$—. In some embodiments, R$^2$ is —CH(CH$_3$)—S(O)$_2$—CH$_2$—. In some embodiments, R$^2$ is —C(CH$_3$)$_2$—S(O)$_2$—CH$_2$—. In some embodiments, R$^2$ is —CH$_2$—S(O)$_2$—CH(CH$_3$)—. In some embodiments, R$^2$ is —CH$_2$—S(O)$_2$—C(CH$_3$)$_2$—. In some embodiments, R$^2$ is —CH$_2$—NH—C(O)—. In some embodiments, R$^2$ is —C(O)—NH—CH$_2$—. In some embodiments, R$^2$ is —C(O)—NH—CH(CH$_3$)—. In some embodiments, R$^2$ is —C(O)—NH—C(CH$_3$)$_2$—.

The following definitions apply to Formula III.

In some embodiments, the compound is a compound comprising a prostate specific membrane antigen (PSMA)-targeting moiety of Formula III or of a salt or a solvate of Formula III:

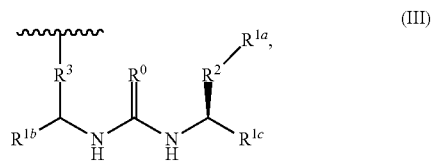

wherein:
R$^0$ is O or S;
R$^{1a}$ is —CO$_2$H, —SO$_2$H, —SO$_3$H, —PO$_2$H, —PO$_3$H$_2$, —OPO$_3$H$_2$, —OSO$_3$H, —B(OH)$_2$, or

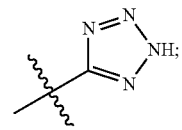 [SMILES: *c1nn[nH]n1]

R$^{1b}$ is —CO$_2$H, —SO$_2$H, —SO$_3$H, —PO$_2$H, —PO$_3$H$_2$, —B(OH)$_2$, or

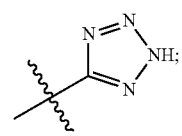 [SMILES: *c1nn[nH]n1]

R$^{1c}$ is —CO$_2$H, —SO$_2$H, —SO$_3$H, —PO$_2$H, —PO$_3$H$_2$, —B(OH)$_2$, or

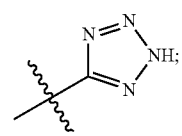 [SMILES: *c1nn[nH]n1]

R$^2$ is —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$, —C(O)—NH—CH$_2$—, —C(O)—NH—CH(CH$_3$)—, or —C(O)—NH—C(CH$_3$)$_2$—; and
R$^3$ is a linker.

In some embodiments, the PSMA-targeting moiety of Formula III is a PSMA-targeting moiety of Formula IIIa:

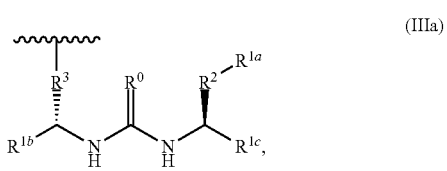

wherein $R^{1a}$, $R^{1b}$, $R^{1c}$, $R^2$, and $R^3$ are as defined for Formula III. In some embodiments, the PSMA-targeting moiety is a salt or solvate of Formula IIIa.

The linker ($R^3$) may be any linker. In some embodiments, $R^3$ is a linear or branched, cyclic or acyclic, and/or aromatic or non-aromatic $C_1$-$C_{20}$ alkylenyl, alkenylenyl, or alkynylenyl, or a linear or branched, cyclic or acyclic, and/or aromatic or non-aromatic $X_2$-$X_{20}$ heteroalkylenyl, heteroalkenylenyl, or heteroalkynylenyl. In some embodiments, $R^3$ is a linear or branched, cyclic or acyclic, and/or aromatic or non-aromatic $C_1$-$C_{20}$ alkylenyl or alkenylenyl, or a linear or branched, cyclic or acyclic, and/or aromatic or non-aromatic $X_2$-$X_{20}$ heteroalkylenyl or heteroalkenylenyl. In some embodiments, $R^3$ is a linear or branched peptide linker.

In some embodiments, $R^2$ is —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, or —CH$_2$—S(O)$_2$—C(CH$_3$)$_2$.

In some embodiments, $R^2$ is —CH(CH$_3$)CH$_2$CH$_2$—. In some embodiments, $R^2$ is —CH$_2$CH(CH$_3$)CH$_2$—. In some embodiments, $R^2$ is —CH$_2$CH$_2$CH(CH$_3$)—. In some embodiments, $R^2$ is —C(CH$_3$)$_2$CH$_2$CH$_2$—. In some embodiments, $R^2$ is —CH$_2$C(CH$_3$)$_2$CH$_2$—. In some embodiments, $R^2$ is —CH$_2$CH$_2$C(CH$_3$)$_2$—. In some embodiments, $R^2$ is —CH(CH$_3$)—O—CH$_2$—. In some embodiments, $R^2$ is —C(CH$_3$)$_2$—O—CH$_2$—. In some embodiments, $R^2$ is —CH$_2$—O—CH(CH$_3$)—. In some embodiments, $R^2$ is —CH$_2$—O—C(CH$_3$)$_2$—. In some embodiments, $R^2$ is —CH$_2$—S(O)—CH$_2$—. In some embodiments, $R^2$ is —CH$_2$—S(O)$_2$—CH$_2$—. In some embodiments, $R^2$ is —CH(CH$_3$)—S—CH$_2$—. In some embodiments, $R^2$ is —C(CH$_3$)$_2$—S—CH$_2$—. In some embodiments, $R^2$ is —CH$_2$—S—CH(CH$_3$)—. In some embodiments, $R^2$ is —CH$_2$—S—C(CH$_3$)$_2$—. In some embodiments, $R^2$ is —CH(CH$_3$)—S(O)—CH$_2$—. In some embodiments, $R^2$ is —C(CH$_3$)$_2$—S(O)—CH$_2$—. In some embodiments, $R^2$ is —CH$_2$—S(O)—CH(CH$_3$)—. In some embodiments, $R^2$ is —CH$_2$—S(O)—C(CH$_3$)$_2$—. In some embodiments, $R^2$ is —CH(CH$_3$)—S(O)$_2$—CH$_2$—. In some embodiments, $R^2$ is —C(CH$_3$)$_2$—S(O)$_2$—CH$_2$—. In some embodiments, $R^2$ is —CH$_2$—S(O)$_2$—CH(CH$_3$)—. In some embodiments, $R^2$ is —CH$_2$—S(O)$_2$—C(CH$_3$)$_2$—. In some embodiments, $R^2$ is —C(O)—NH—CH$_2$—. In some embodiments, $R^2$ is —C(O)—NH—CH(CH$_3$)—. In some embodiments, $R^2$ is —C(O)—NH—C(CH$_3$)$_2$—.

In some embodiments, $R^2$ is —CH$_2$CH(CH$_3$)CH$_2$—, wherein the second carbon in $R^2$ has R-configuration.

In some embodiments, the compound further comprises one or more radiolabeling groups connected to the linker, independently selected from: a radiometal chelator optionally bound by a radiometal; an aryl or heteroaryl substituted with a radiohalogen; a prosthetic group containing a trifluoroborate; or a prosthetic group containing a silicon-fluorine-acceptor moiety, a fluorophosphate, a fluorosulfate, or a sulfonylfluoride. In some embodiments, the compound comprises a radiometal chelator. In some embodiments, the radiometal chelator is bound by a radiometal. In some embodiments, the compound comprises an aryl substituted with a radiohalogen. In some embodiments, the compound comprises a prosthetic group containing a trifluoroborate. In some embodiments, the compound comprises a prosthetic group containing a silicon-fluorine-acceptor moiety. In some embodiments, the compound comprises a prosthetic group containing a fluorophosphate. In some embodiments, the compound comprises a prosthetic group containing a fluorosulfate. In some embodiments, the compound comprises a prosthetic group containing a sulfonylfluoride. In some embodiments, a fluorine in the aforementioned groups is $^{18}$F.

In some embodiments, the one or more radiolabeling groups comprise: a radiometal chelator optionally bound by a radiometal; and a prosthetic group containing a trifluoroborate, optionally wherein 1, 2 or 3 fluorines in the trifluoroborate are $^{18}$F.

In some embodiments, the compound comprising a PSMA-targeting moiety of Formula III is a compound of Formula II (or Formula IIa) or is a salt or solvate of Formula II (or Formula IIa), wherein $R^2$ is —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$S(O)CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —C(O)—NH—CH$_2$—, —C(O)—NH—CH(CH$_3$)—, or —C(O)—NH—C(CH$_3$)$_2$—.

Unless otherwise specified, the following definitions apply to any of Formula II/IIa compounds (or salts/solvates thereof) as well as any compounds comprising a PSMA-targeting moiety of Formula III/IIIa (or a salts/solvates thereof). The following definitions therefore apply to compounds comprising Formula III/IIIa PSMA-targeting moieties, including but not necessarily limited to when such compounds are Formula II/IIa compounds.

In some embodiments, $R^0$ is O. In other embodiments, $R^0$ is S.

In some embodiments, $R^{1a}$ is —CO$_2$H, —SO$_2$H, —SO$_3$H, —PO$_2$H, —PO$_3$H$_2$, —OPO$_3$H$_2$, or —OSO$_3$H. In some embodiments, $R^{2a}$ is —CO$_2$H, —SO$_2$H, —SO$_3$H, —PO$_2$H, or —PO$_3$H$_2$. In some embodiments, $R^{3a}$ is —CO$_2$H, —SO$_2$H, —SO$_3$H, —PO$_2$H, or —PO$_3$H$_2$. In some embodiments, $R^{1a}$ is —CO$_2$H. In some embodiments, $R^{1b}$ is —CO$_2$H. In some embodiments, $R^{1c}$ is —CO$_2$H. In some embodiments, $R^{1a}$ and $R^{1b}$ are each —CO$_2$H. In some embodiments, $R^{1a}$ and $R^{1c}$ are each —CO$_2$H. In some embodiments, $R^{1b}$ and $R^{1c}$ are each —CO$_2$H. In some embodiments, $R^{1a}$, $R^{1b}$ and $R^{1c}$ are each —CO$_2$H. In some embodiments, $R^{1a}$, $R^{1b}$ and $R^{1c}$ are anionic or metallated salts of the foregoing.

In some embodiments, $R^3$ is a linear or branched, cyclic or acyclic, and/or aromatic or non-aromatic $C_1$-$C_{20}$ alkylenyl or alkenylenyl, or a linear or branched, cyclic or acyclic, and/or aromatic or non-aromatic $X_2$-$X_{20}$ heteroalkylenyl or heteroalkenylenyl.

In some embodiments, $R^3$ is a linear acyclic $C_3$-$C_{15}$ alkylenyl. In some embodiments, $R^3$ is a linear acyclic $C_3$-$C_{15}$ alkylenyl in which 1-5 carbons are replaced with N, S and/or O heteroatoms. In some embodiments, $R^3$ is a linear acyclic saturated $C_3$-$C_{10}$ alkylenyl, optionally substituted with 1-5 amine, amide, oxo, hydroxyl, thiol, methyl or ethyl groups. In some embodiments, $R^3$ is —(CH$_2$)$_{3-15}$—. In some embodiments, $R^3$ is —CH$_2$—. In some embodiments, $R^3$ is —(CH$_2$)$_2$—. In some embodiments, $R^3$ is —(CH$_2$)$_3$—. In some embodiments, $R^3$ is —(CH$_2$)$_4$—. In some embodiments, $R^3$ is —(CH$_2$)$_5$—. In some embodiments, $R^3$ is —CH$_2$—O—CH$_2$—. In some embodiments, $R^3$ is —CH$_2$—S—CH$_2$—. In some embodiments, $R^3$ is —CH=CH—. In some embodiments, $R^3$ is —CH$_2$—C≡C—. In some embodiments, $R^3$ is a linear C$_3$-C$_5$ alkenylenyl and/or alkynylenyl.

In some embodiments, $R^4$ is —O—. In some embodiments, $R^4$ is —S—. In some embodiments, $R^4$ is —NHC(O)—. In some embodiments, $R^4$ is —C(O)NH—. In some embodiments, $R^4$ is

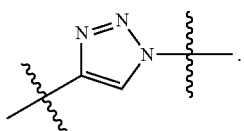 [SMILES: *c1cn(*)nn1]

In some embodiments, $R^4$ is

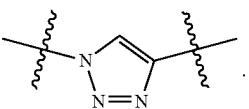 [SMILES: *c1cn(*)nn1]

In some embodiments, $R^4$ is —S—(O)—. In some embodiments, $R^4$ is —S(O)$_2$—. In some embodiments, $R^4$ is —C(O)—(NH)$_2$—C(O)—. In some embodiments, $R^4$ is —OC(O)NH—. In some embodiments, $R^4$ is —NHC(O)C—. In some embodiments, $R^4$ is —NHC(O)NH—. In some embodiments, $R^4$ is —OC(S)NH. In some embodiments, $R^4$ is —NHC(S)O—. In some embodiments, $R^4$ is —NHC(S)NH—. In some embodiments, $R^4$ is —NHC(O)C(O)NH—. In some embodiments, $R^4$ is S—S. In some embodiments, $R^4$ is S—CH$_2$—S. In some embodiments, $R^4$ is —NH—NH—C(O)—. In some embodiments, $R^4$ is or —C(O)—NH—NH—.

In some embodiments, $R^3$ is —(CH$_2$)$_{3-15}$— and $R^4$ is —C(O)NH—. In some embodiments, $R^3$ is —(CH$_2$)$_{3-5}$— and $R^4$ is —C(O)NH—. In some embodiments, $R^3$ is —(CH$_2$)$_4$— and $R^4$ is —C(O)NH—.

In some embodiments, $R^5$ is —(CH$_2$)$_{0-3}$CH(R$^{10}$)(CH$_2$)$_{0-3}$—. In some embodiments, $R^5$ is —CH(R$^{10}$)—. In some embodiments, $R^5$ is —CH$_2$CH(R$^{10}$)—. In some embodiments, $R^5$ is —CH(R$^{10}$)CH$_2$—. In some embodiments, $R^5$ is —CH(R$^{10}$)—.

In some embodiments, $R^{10}$ is a linear or branched, cyclic or acyclic, and/or aromatic or non-aromatic C$_2$-C$_{19}$ alkyl, alkenyl or alkynyl; a linear or branched, cyclic or acyclic, and/or aromatic or non-aromatic X$_2$-X$_{19}$ heteroalkyl, heteroalkenyl or heteroalkynyl having only 1-3 heteroatoms.

In some embodiments, $R^{10}$ is —CH$_2$R$^{23}$, in which R$^{23}$ is an optionally substituted C$_4$-C$_{16}$ aromatic ring or partially or fully aromatic fused ring system, wherein 0-3 carbons in the aromatic ring or the partially or fully aromatic fused ring system are replaced with N, S and/or O heteroatoms, and wherein the optional substitutions are selected from OH, NH$_2$, NO$_2$, halogen, C$_1$-C$_6$ alkyl, and/or C$_1$-C$_6$ alkoxyl groups.

In some embodiments, $R^{10}$ is

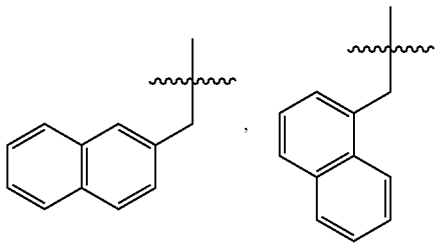

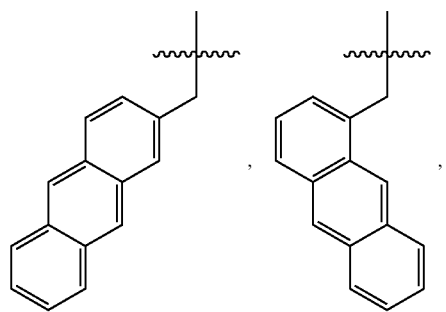

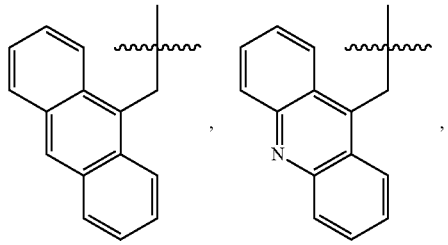

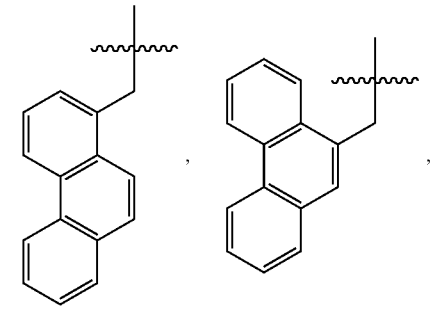

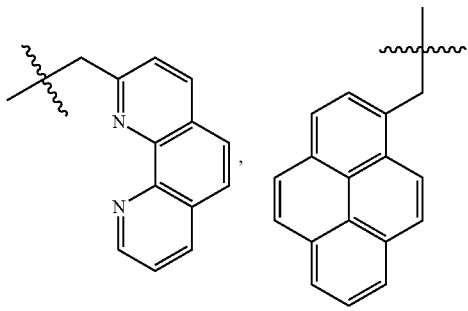

-continued

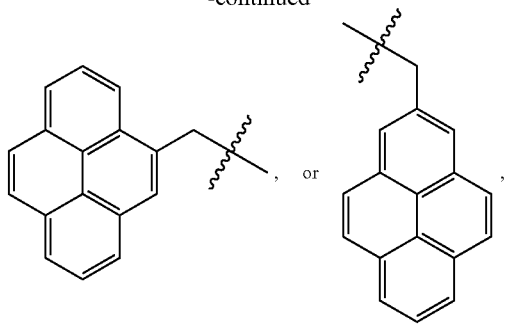

optionally modified with one, more than one, or a combination of: halogen, OMe, SMe, $NH_2$, $NO_2$, CN, OH, or one or more additional endocyclic ring nitrogen atoms.

In some embodiments, $R^{10}$ is an alkenyl containing either a $C_6$-$C_{16}$ aryl or $X_6$-$X_{16}$ heteroaryl having 1-3 heteroatoms independently selected from N, S and/or O. In some embodiments, the $C_6$-$C_{16}$ aryl is benzyl. In some embodiments, the $X_6$-$X_{16}$ heteroaryl is benzyloxyl or benzylthio.

In some embodiments, $R^{10}$ is:

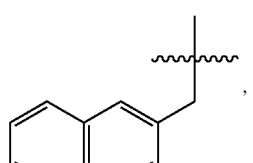

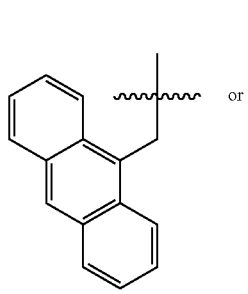 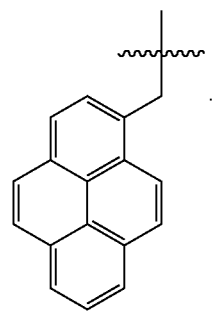

In some embodiments, $R^{10}$ is

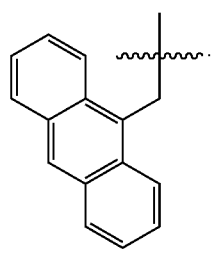 [SMILES: *Cc1c2ccccc2cc2ccccc12]

In some embodiments, $R^{10}$ is

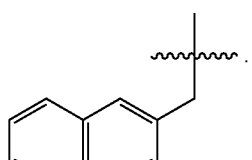

In some embodiments, $R^{10}$ is

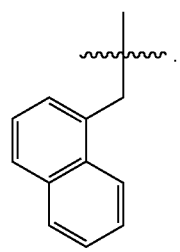 [SMILES: *Cc1cccc2ccccc12]

In some embodiments, $R^{10}$ is

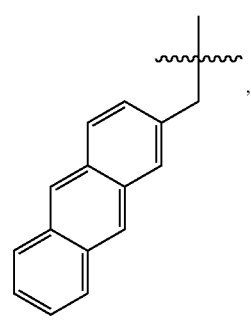 [SMILES: *Cc1ccc2cc3ccccc3cc2c1]

In some embodiments, $R^{10}$ is

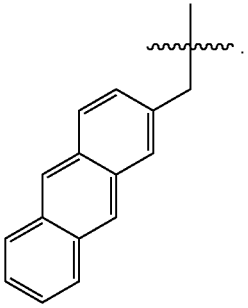

In some embodiments, $R^{10}$ is

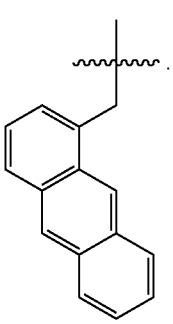 [SMILES: *Cc1cccc2cc3ccccc3cc12]

In some embodiments, $R^{10}$ is

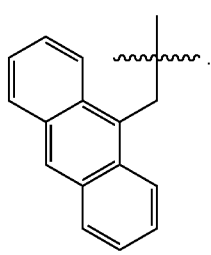 [SMILES: *Cc1c2ccccc2cc2ccccc12]

In some embodiments, $R^{10}$ is
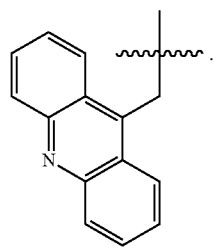
In some embodiments, $R^{10}$ is
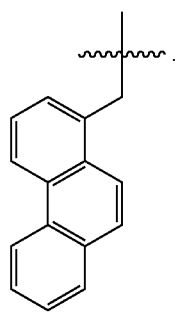 [SMILES: *Cc1cccc2c1ccc1ccccc12]
In some embodiments, $R^{10}$ is
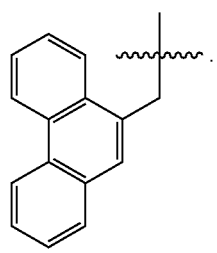
In some embodiments, $R^{10}$ is
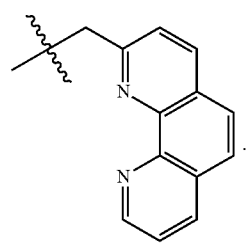
In some embodiments, $R^{10}$ is
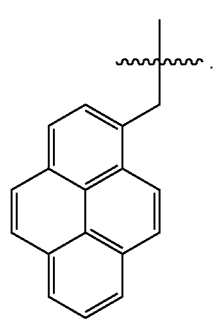
In some embodiments, $R^{10}$ is
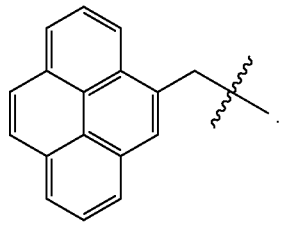 [SMILES: *Cc1cc2cccc3ccc4cccc1c4c32]
In some embodiments, $R^{10}$ is
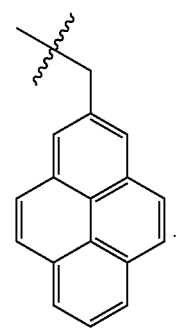
In some embodiments, $R^{10}$ is
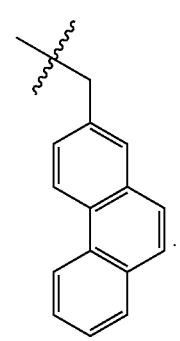 [SMILES: *Cc1ccc2c(ccc3ccccc32)c1]
In some embodiments, $R^{10}$ is
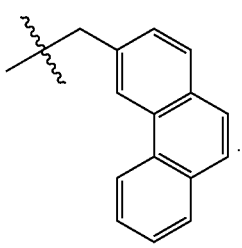 [SMILES: *Cc1ccc2ccc3ccccc3c2c1]
In some embodiments, $R^{10}$ is. In some embodiments, $R^{10}$ is
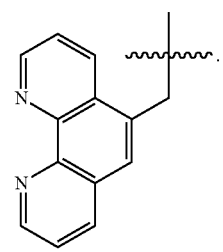 [SMILES: *Cc1cc2cccnc2c2ncccc12]

In some embodiments, $R^{10}$ is

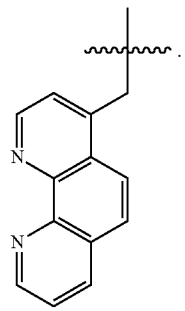 [SMILES: *Cc1ccnc2c1ccc1cccnc12]

In some embodiments, $R^{10}$ is:

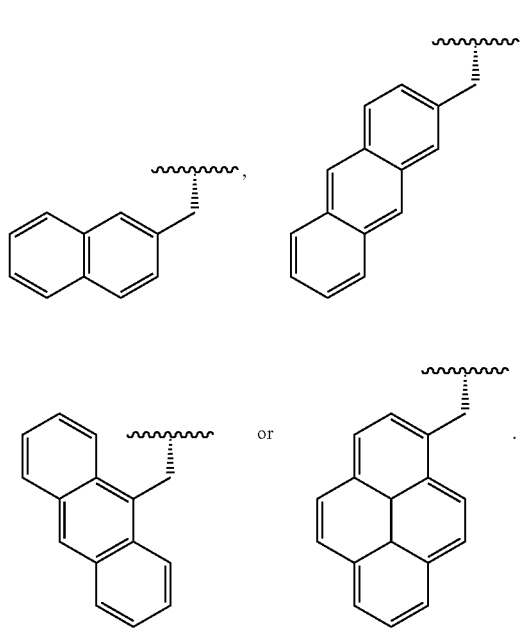

In some embodiments, $R^{10}$ is

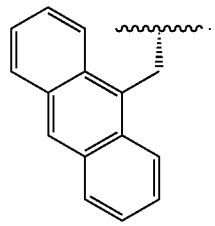

In some embodiments, $R^5$ is —CH($R^{10}$)— wherein $R^{10}$ is as defined in any embodiment above.

In some embodiments, $R^5$ is —(CH$_2$)$_{0-3}$CH($R^{10}$)(CH$_2$)$_{0-3}$— and $R^{10}$ is —(CH$_2$)$_5$CH$_3$. In some embodiments, $R^5$ is —CH($R^{10}$)— and $R^{10}$ is —(CH$_2$)$_5$CH$_3$. In some embodiments, $R^5$ is —(CH$_2$)$_{0-3}$CH($R^{10}$)(CH$_2$)$_{0-3}$—.

In some embodiments, $R^{10}$ is —CH$^2$—$R^{23}$. In some embodiments, $R^{23}$ is phenyl substituted with 1 or 2 iodo groups and optionally further substituted with 1 oxy group. In some embodiments, $R^5$ is —(CH$_2$)$_{0-3}$CH($R^{10}$)(CH$_2$)$_{0-3}$— wherein $R^{10}$ is —CH$_2$$R^{23}$ and $R^{23}$ is phenyl substituted with 1 or 2 iodo groups and optionally further substituted with 1 oxy group. In some embodiments, $R^{23}$ is

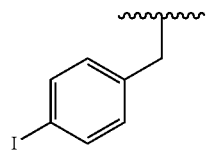

In some embodiments, $R^{23}$ is

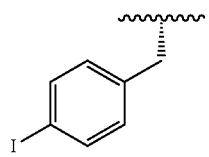

In some embodiments, $R^{23}$ is

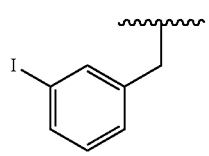

In some embodiments, $R^{23}$ is $R^{23}$ is 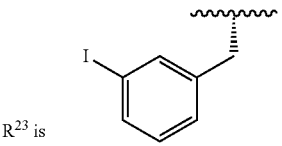

In some embodiments, $R^{23}$ is

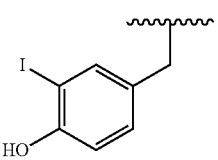

In some embodiments, $R^{23}$ is

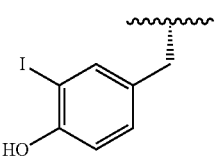

In some embodiments, $R^{23}$ is

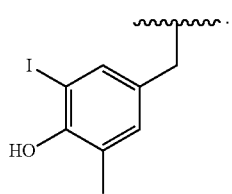 [SMILES: *Cc1cc(C)c(O)c(I)c1]

In some embodiments, $R^{23}$ is

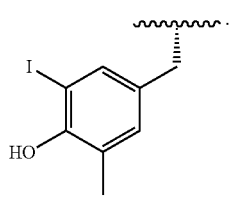

In some embodiments, at least one $R^9$ or $R^5$ is

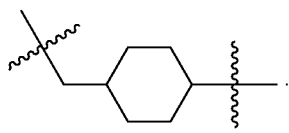 [SMILES: *CC1CCC(*)CC1]

In some embodiments, at least one $R^9$ or $R^5$ is

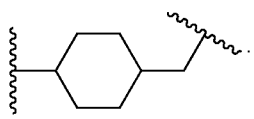 [SMILES: *CC1CCC(*)CC1]

In some embodiments, at least one $R^9$ or $R^5$ is

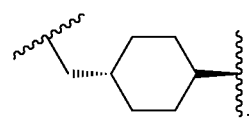

In some embodiments, $R^5$ is

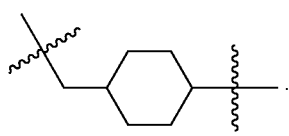

In some embodiments, $R^5$ is

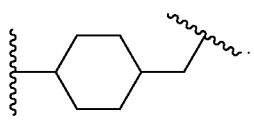 [SMILES: *CC1CCC(*)CC1]

In some embodiments, $R^5$ is

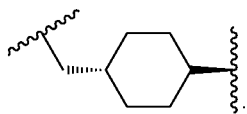

In some embodiments, $R^6$ is hydrogen. In some embodiments, $R^6$ is methyl. In some embodiments, $R^6$ is ethyl.

In some embodiments, $(Xaa^1)_{1-4}$ consists of a single amino acid residue. In some embodiments, $(Xaa^1)_{1-4}$ is a dipeptide, wherein each $Xaa^1$ may be the same or different. In some embodiments, $(Xaa^1)_{1-4}$ is a tripeptide, wherein each $Xaa^1$ may be the same, different or a combination thereof. In some embodiments, $(Xaa^1)_{1-4}$ consists of 4 amino acid residues connected by peptide bonds, wherein each $Xaa^1$ may be the same, different or a combination thereof. In some embodiments, each $Xaa^1$ is independently selected from proteinogenic amino acids and the non-proteinogenic amino acids listed in Table 1, wherein each peptide backbone amino group is optionally methylated.

In some embodiments, at least one $R^9$ is $R^{24}$-$R^{25}$-$R^{26}$, wherein $R^{24}$-$R^{25}$-$R^{26}$ are independently selected from: —$(CH_2)_{0-3}$—; $C_3$-$C_8$ cycloalkylene in which 0-3 carbons are replaced with N, S or O heteroatoms, and optionally substituted with one or more OH, $NH_2$, $NO_2$, halogen, $C_1$-$C_6$ alkyl and/or $C_1$-$C_6$ alkoxyl groups; and $C_4$-$C_{16}$ arylene in which 0-3 carbons are replaced with N, S or O heteroatoms, and optionally substituted with one or more OH, $NH_2$, $NO_2$, halogen, $C_1$-$C_6$ alkyl and/or $C_1$-$C_8$ alkoxyl groups. In some embodiments, $(Xaa^1)_{1-4}$ is $(Xaa^1)_{0-3}NHR^{27}C(O)$, wherein $R^{27}$ is

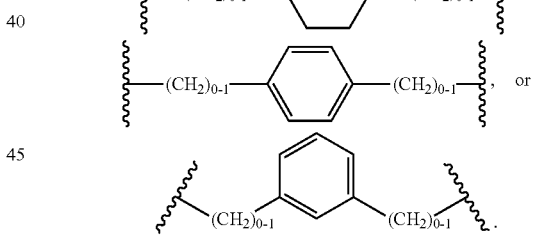

In some embodiments, at least one $R^9$ is

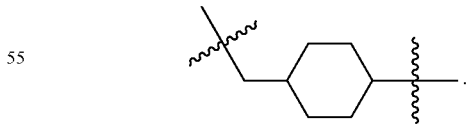

In some embodiments, at least one $R^9$ is

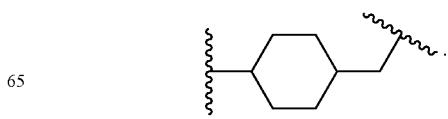

In some embodiments, at least one $R^9$ is

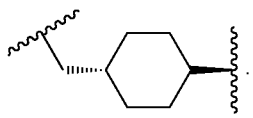

In some embodiments, at least one $R^8$ is hydrogen. In some embodiments, all $R^8$ are hydrogen. In some embodiments, at least one $Xaa^1$ is a tranexamic acid residue. In some embodiments, $(Xaa^1)_{1-4}$ consists of a single tranexamic acid residue.

In some embodiments, $R^3$ is —$(CH_2)_4$— and —$(Xaa^1)_{1-4}N(R^6)R^5R^4$— is

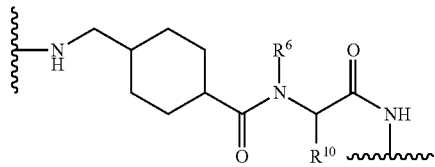

wherein, in alternative embodiments, $R^{10}$ is any $R^{10}$ defined above. In some such embodiments, $R^{10}$ is —$CH^2$—$R^{23}$ and $R^{23}$ is phenyl substituted with 1 or 2 iodo groups and optionally further substituted with 1 oxy group.

In some embodiments, $R^3$ is —$(CH_2)_4$— and —$(Xaa^1)_{1-4}N(R^6)R^5R^4$— is

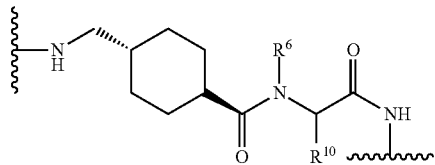

wherein, in alternative embodiments, $R^{10}$ is any $R^{10}$ defined above. In some such embodiments, $R^{10}$ is —$CH^2$—$R^{23}$ and $R^{23}$ is phenyl substituted with 1 or 2 iodo groups and optionally further substituted with 1 oxy group.

Unless otherwise specified, the following definitions apply to any of applicable Formula I/Ia compounds (or salt/solvates thereof), all Formula II/IIa compounds (or salts/solvates thereof) as well as compounds comprising a PSMA-targeting moiety of Formula III/IIIa (or a salts/solvates thereof). The following definitions therefore apply to compounds comprising Formula III/IIIa PSMA-targeting moieties, including but not necessarily limited to when such compounds are Formula II/IIa compounds.

$R^7$ may include a radiolabeling group optionally spaced apart using an amino acid or peptide linker. Accordingly, in some embodiments $R^7$ is $R^X$—$(Xaa^2)_{0-4}$—, wherein $R^X$ bonds to the N-terminus of the N-terminal $Xaa^2$ or an amino acid group of $Xaa^2$ capable of forming an amide bond (e.g. a side chain of an alpha amino acid). An example of a $Xaa^2$ sidechain capable of forming an amide bond with $R^X$ is an amino group. Non-limiting examples of amino acid residues capable of forming an amide with $R^X$ include Lys, Orn, Dab, Dap, Arg, homo-Arg, and the like. In some embodiments, $R^X$ bonds to the N-terminus of the N-terminal $Xaa^2$. In other embodiments, $Xaa^2$ is absent.

In some embodiments, $R^7$ may include two radiolabeling groups in which the amino acid or peptide linker provides two attachment points for the radiolabeling groups. Accordingly, in some embodiments, $R^7$ is

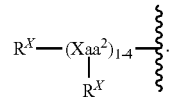

For example, a first $R^X$ may bond to the N-terminus of the N-terminal $Xaa^2$ and a second $R^X$ may bond to a side chain functional group (e.g. an amino group) of a $Xaa^2$. Alternatively, both $R^X$ groups may bond to different $Xaa^2$ side chains or other functional groups.

$R^7$ may include both a radiolabeling group and an albumin-binding group.

Accordingly, in some embodiments with a single $R^X$ group, $R^7$ is

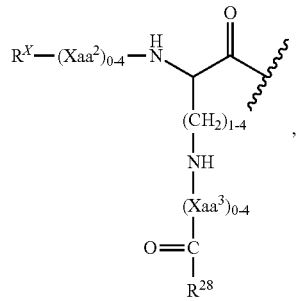

wherein when $(Xaa^2)_{0-4}$ is $(Xaa^2)_{1-4}$ then $R^X$ bonds to the N-terminus of the N-terminal $Xaa^2$ or an amino group of $Xaa^2$ (e.g. a side chain of an alpha amino acid) capable of forming an amide bond, and wherein when $(Xaa^3)_{0-4}$ is $(Xaa^3)_{1-4}$ then $(Xaa^3)_{1-4}$ is oriented to form amide bonds with the adjacent carbonyl and amine groups. In other embodiments with a single $R^X$ group, $R^7$ is

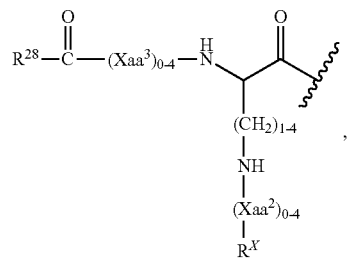

wherein when $(Xaa^2)_{0-4}$ is $(Xaa^2)_{1-4}$ then $R^X$ bonds to the N-terminus of the N-terminal $Xaa^2$ or an amino group of $Xaa^2$ (e.g. a side chain of an alpha amino acid) capable of forming an amide bond, and wherein when $(Xaa^3)_{0-4}$ is $(Xaa^3)_{1-4}$ then $(Xaa^3)_{1-4}$ is oriented to form amide bonds with the adjacent carbonyl and amine groups.

The albumin binding group $R^{28}$ may be any albumin binding group.

In some embodiments, the albumin binding group $R^{28}$ is

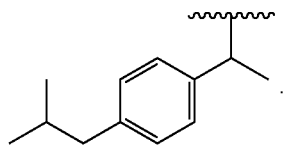 [SMILES: *C(C)c1ccc(CC(C)C)cc1]

In some embodiments, the albumin binding group $R^{28}$ is

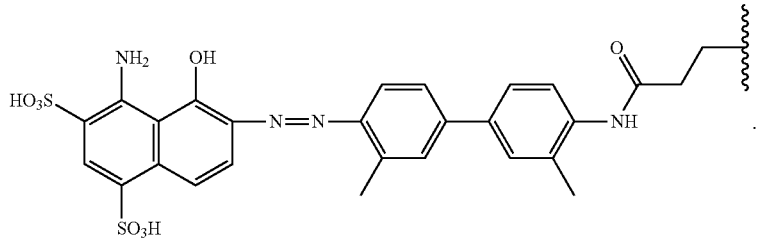 [SMILES: *CCC(=O)Nc1ccc(-c2ccc(N=Nc3ccc4c(S(=O)(=O)O)cc(S(=O)(=O)O)c(N)c4c3O)c(C)c2)cc1C]

In some embodiments, the albumin binding group $R^{28}$ is

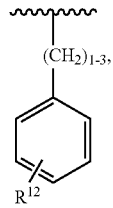

wherein $R^{12}$ is I, Br, F, Cl, H, OH, $OCH_3$, $NH_2$, $NO_2$ or $CH_3$.

In some embodiments, $R^7$ is

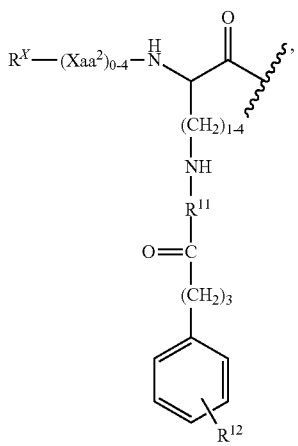

wherein when $(Xaa^2)_{0-4}$ is $(Xaa^2)_{1-4}$ then $R^X$ bonds to the N-terminus of the N-terminal $Xaa^2$ or an amino group of $Xaa^2$ (e.g. a side chain of an alpha amino acid) capable of forming an amide bond.

In other embodiments, $R^7$ is

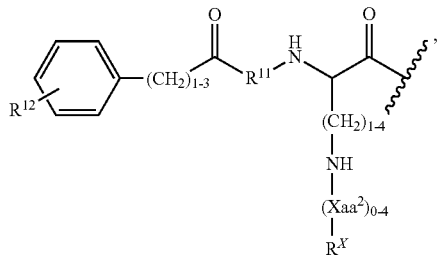

wherein when $(Xaa^2)_{0-4}$ is $(Xaa^2)_{1-4}$ then $R^X$ bonds to the N-terminus of the N-terminal $Xaa^2$ or an amino group of $Xaa^2$ (e.g. a side chain of an alpha amino acid) capable of forming an amide bond.

In other embodiments, $R^7$ is

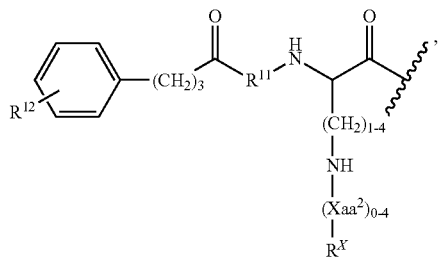

wherein when $(Xaa^2)_{0-4}$ is $(Xaa^2)_{1-4}$ then $R^X$ bonds to the N-terminus of the N-terminal $Xaa^2$ or an amino group of $Xaa^2$ (e.g. a side chain of an alpha amino acid) capable of forming an amide bond.

In some embodiments, $R^{11}$ is absent. In some embodiments, $R^{11}$ is

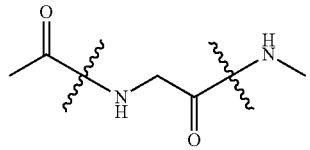

In some embodiments, $R^{11}$ is

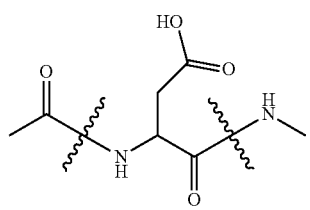

In some embodiments, $R^{11}$ is

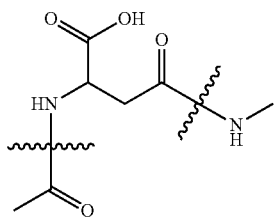

In some embodiments, $R^{11}$ is

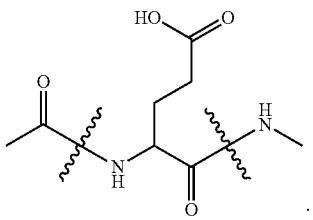

In some embodiments, $R^{11}$ is

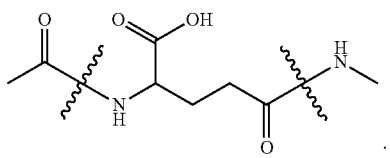

In some embodiments, $R^{11}$ is

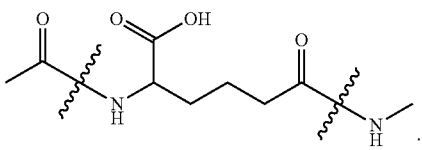

In some embodiments, $R^{11}$ is

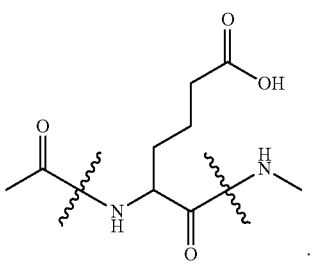

In some embodiments, $R^{11}$ is

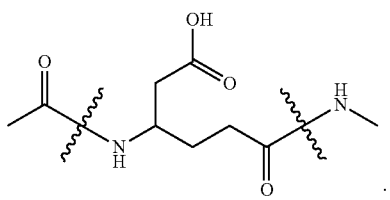

In some embodiments, $R^{11}$ is

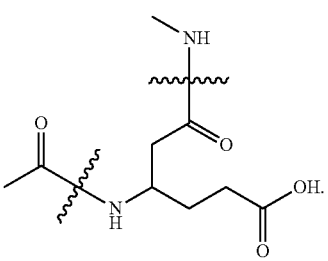

In some embodiments, $R^{12}$ is ortho. In some embodiments, $R^{12}$ is para. In some embodiments, $R^{12}$ is meta. In some embodiments, $R^{12}$ is iodine. In some embodiments, $R^{12}$ is fluorine. In some embodiments, $R^{12}$ is chlorine. In some embodiments, $R^{12}$ is hydrogen. In some embodiments, $R^{12}$ is hydroxide. In some embodiments, $R^{12}$ is $OCH_3$. In some embodiments, $R^{12}$ is $NH_2$. In some embodiments, $R^{12}$ is $NO_2$. In some embodiments, $R^{12}$ is $CH_3$. In some embodiments, $R^{12}$ is $CH_3$ in para position. In some embodiments, $R^{12}$ is iodine in para position. In some embodiments, $R^{12}$ is chlorine in para position. In some embodiments, $R^{12}$ is $OCH_3$ in para position.

In some embodiments, $Xaa^2$ is absent. In some embodiments, $(Xaa^2)_{0-4}$ is a single amino acid residue. In some embodiments, $(Xaa^2)_{0-4}$ is a dipeptide, wherein each $Xaa^2$ may be the same or different. In some embodiments, $(Xaa^2)_{0-4}$ is a tripeptide, wherein each $Xaa^2$ may be the same, different or a combination thereof. In some embodiments, $(Xaa^2)_{0-4}$ consists of 4 amino acid residues connected by peptide bonds, wherein each $Xaa^2$ may be the same, different or a combination thereof. In some embodiments, each $Xaa^2$ is independently selected from proteinogenic amino acids and the non-proteinogenic amino acids listed in Table 1, wherein each peptide backbone amino group is optionally methylated. In some embodiments, each $R^{13}$ in $(Xaa^2)_{1-4}$ is hydrogen. In some embodiments, at least one $R^{13}$ in $(Xaa^2)_{1-4}$ is methyl. In some embodiments, at least one $R^{14}$ in $(Xaa^2)_{1-4}$ is $(CH_2)_2[O(CH_2)_2]_{1-6}$— (e.g. when $Xaa^2$ is a residue of Amino-dPEG™$_4$-acid or Amino-dPEG™$_6$-acid).

In some embodiments, $Xaa^3$ is absent. In some embodiments, $(Xaa^3)_{0-4}$ is a single amino acid residue. In some embodiments, $(Xaa^3)_{0-4}$ is a dipeptide, wherein each $Xaa^3$ may be the same or different. In some embodiments, $(Xaa^3)_{0-4}$ is a tripeptide, wherein each $Xaa^3$ may be the same, different or a combination thereof. In some embodiments, $(Xaa^3)_{0-4}$ consists of 4 amino acid residues connected by peptide bonds, wherein each $Xaa^3$ may be the same, different or a combination thereof. In some embodiments, each $Xaa^3$ is independently selected from proteinogenic amino acids and the non-proteinogenic amino acids listed in Table 1, wherein each peptide backbone amino group is optionally methylated. In some embodiments, each $R^{13}$ in $(Xaa^3)_{1-4}$ is hydrogen. In some embodiments, at least one $R^{13}$ in $(Xaa^3)_{1-4}$ is methyl. In some embodiments, at least one $R^{14}$ in $(Xaa^3)_{1-4}$ is —$(CH_2)_2[O(CH_2)_2]_{1-6}$— (e.g. when $Xaa^3$ is a residue of Amino-dPEG™$_4$-acid or Amino-dPEG™$_6$-acid).

In some embodiments, one or more $R^X$ comprises a radiometal chelator optionally bound by a radiometal. The radiometal chelator may be any radiometal chelator suitable for binding to the radiometal and which is functionalized for attachment to an amino group. Many suitable radiometal chelators are known, e.g. as summarized in Price and Orvig, *Chem. Soc. Rev.*, 2014, 43, 260-290, which is incorporated by reference in its entirety. Non-limiting examples of radioisotope chelators include chelators selected from the group consisting of: DOTA and derivatives; DOTAGA; NOTA; NODAGA; NODASA; CB-DO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; H2-macropa or a derivative thereof; $H_2$dedpa, $H_4$octapa, $H_4$py4pa, $H_4$Pypa, $H_2$azapa, $H_5$decapa, and other picolinic acid derivatives; CP256; PCTA; C-NETA; C-NE3TA; HBED; SHBED; BCPA; CP256; YM103; desferrioxamine (DFO) and DFO derivatives; and $H_6$phospa. Exemplary non-limiting examples of radioisotope chelators and example radioisotopes chelated by these chelators are shown in Table 2. In alternative embodiments, $R^X$ comprises a radioisotope chelator selected from those listed above or in Table 2, or is any other radioisotope chelator. One skilled in the art could replace any of the chelators listed herein with another chelator.

TABLE 2

Exemplary chelators and exemplary isotopes which bind said chelators

| Chelator | Isotopes |
|---|---|
| DOTA, 1,4,7,10-tetraazacyclododecane-1,4,7,10-tetraacetic acid | Cu-64/67<br>Ga-67/68<br>In-111<br>Lu-177<br>Y-86/90<br>Bi-203/212/213<br>Pb-212<br>Ac-225<br>Gd-159<br>Yb-175<br>Ho-166<br>As-211<br>Sc-44/47<br>Pm-149<br>Pr-142<br>Sn-117m<br>Sm-153<br>Tb-149/161<br>Er-165<br>Ra-223/224<br>Th-227 |
| CB-DO2A, 4,10-bis(carboxymethyl)-1,4,7,10-tetraazabicyclo[5.5.2]tetradecane | Cu-64/67 |
| TCMC, 1,4,7,10-tetrakis(carbamoylmethyl)-1,4,7,10-tetraazacyclododecane | Pb-212 |
| 3p-C-DEPA | Bi-212/213 |

TABLE 2-continued

Exemplary chelators and exemplary isotopes which bind said chelators

| Chelator | Isotopes |
|---|---|
| 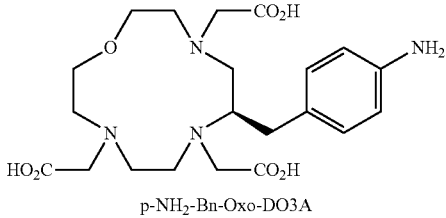 [SMILES: Nc1ccc(C[C@@H]2CN(CC(=O)O)CCOCCN(CC(=O)O)CCN2CC(=O)O)cc1]<br>p-NH$_2$-Bn-Oxo-DO3A | Cu-64/67 |
| 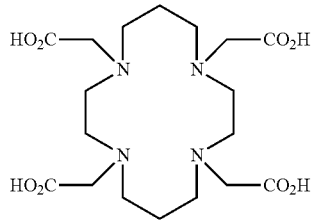<br>TETA, 1,4,8,11-tetraazacyclotetradecane-1,4,8,11-tetraacetic acid | Cu-64/67 |
| 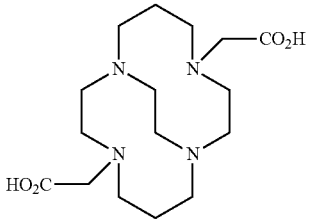<br>CB-TE2A, 4,11-bis-(carboxymethyl)-1,4,8,11-tetraazabicyclo[6.6.2]-hexadecane | Cu-64/67 |
| 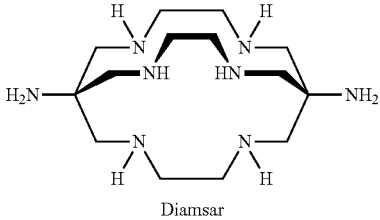<br>Diamsar | Cu-64/67 |
| 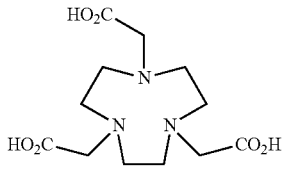<br>NOTA, 1,4,7-triazacyclononane-1,4,7-triacetic acid | Cu-64/67<br>Ga-68<br>In-111<br>Sc-44/47 |
| 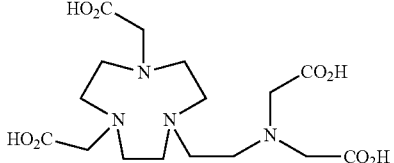<br>NETA, {4-[2-(bis-carboxymethylamino)-ethyl]-7-carboxymethyl-[1,4,7]triazonan-1-yl}-acetic acid | Cu-64/67<br>Ga-68<br>Lu-177<br>Y-86/90<br>Bi-213<br>Pb-212 |

TABLE 2-continued

Exemplary chelators and exemplary isotopes which bind said chelators

| Chelator | Isotopes |
|---|---|
| 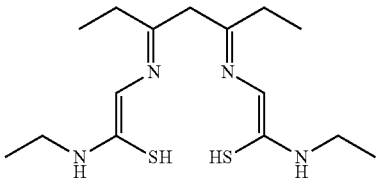<br>HxTSE | Au-198/199 |
| 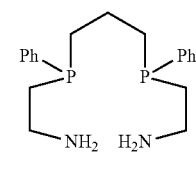<br>P2N2Ph2 | Rh-105 |
| 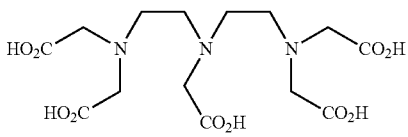<br>DTPA, diethylenetriaminepentaacetic acid | In-111<br>Sc-44/47<br>Lu-177<br>Y-86/90<br>Sn-117m<br>Pd-109 |
| 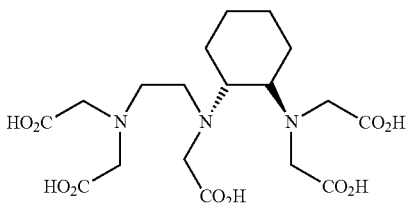<br>CHX-A00-DTPA, 2-(p-isothiocyanatobenzyl)-cyclohexyldiethylenetriaminepentaacetic acid | In-111<br>Lu-177<br>Y-86/90<br>Bi-212/213 |
| 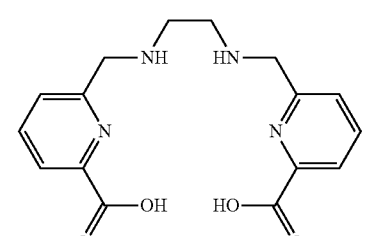<br>H₂dedpa, 1,2-[[6-(carboxy)-pyridin-2-yl]-methylamino]ethane | Cu-64/67 |
| 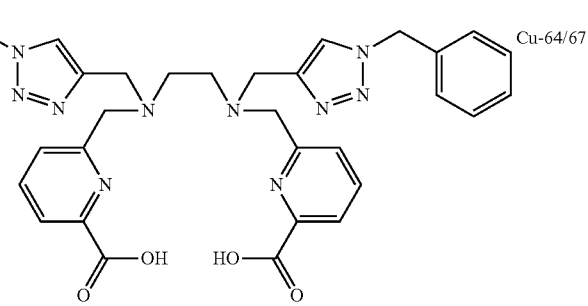<br>H₂azapa, N,N0-[1-benzyl-1,2,3-triazole-4-yl]methyl-N,N0-[6-(carboxy)pyridin-2-yl]-1,2-diaminoethane | Cu-64/67 |

TABLE 2-continued
Exemplary chelators and exemplary isotopes which bind said chelators
| Chelator | Isotopes |
|---|---|
| 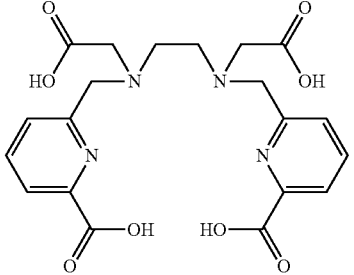<br>H₄octapa | In-111<br>Lu-177<br>Y-86/90<br>Ac-225 |
| 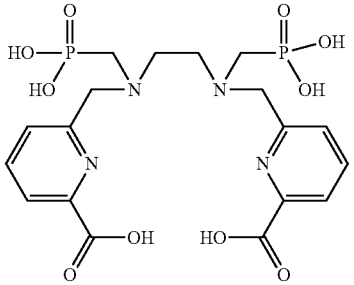<br>H₆phospa | Ac-225 |
| 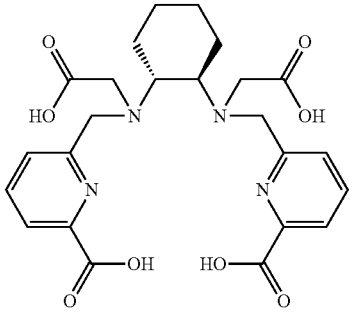<br>H₄CHXoctapa | In-111<br>Ac-225 |
| 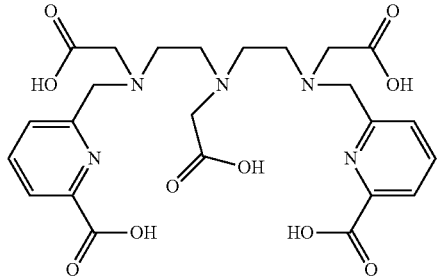<br>H₅decapa | In-111<br>Lu-177<br>Ac-225 |

TABLE 2-continued
Exemplary chelators and exemplary isotopes which bind said chelators
| Chelator | Isotopes |
|---|---|
| 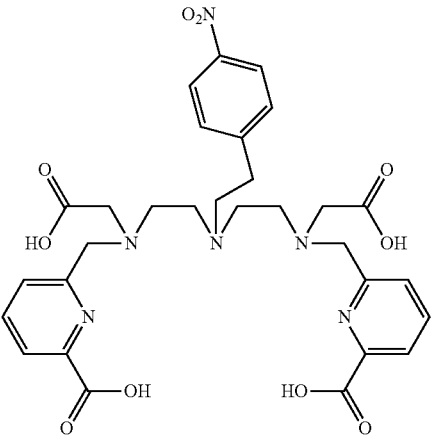<br>H₄neunpa-p-Bn-NO₂ | In-111<br>Lu-177<br>Ac-225 |
| 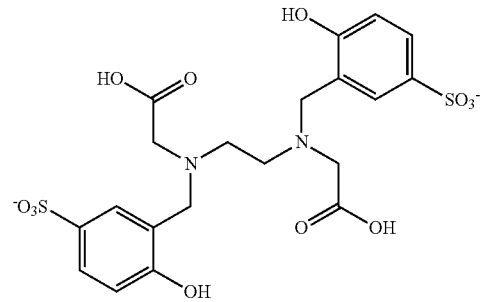<br>SHBED, N,N0-bis(2-hydroxy-5-sulfobenzyl)-ethylenediamine-N,N0-diacetic acid | In-111<br>Ga-68 |
| 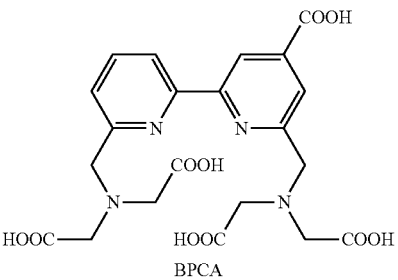 [SMILES: O=C(O)CN(CC(=O)O)Cc1cccc(-c2cc(C(=O)O)cc(CN(CC(=O)O)CC(=O)O)n2)n1]<br>BPCA | In-111 |
| 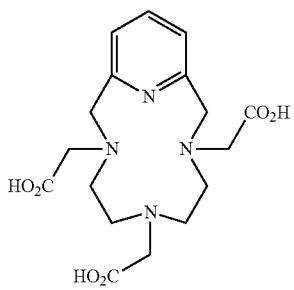<br>PCTA, 3,6,9,15-tetraazabicyclo[9.3.1]-pentadeca-1(15),11,13-triene-3,6,9,-triacetic acid | Cu-64/67 |

TABLE 2-continued

Exemplary chelators and exemplary isotopes which bind said chelators

| Chelator | Isotopes |
|---|---|
| ![H2-MACROPA structure] H2-MACROPA (N,N'-bis[(6-carboxy-2-pyridil)methyl]-4,13-diaza-18-crown-6) | Ac-225 |

In some embodiments, the radioisotope chelator is conjugated with a radioisotope. The conjugated radioisotope may be, without limitation, $^{68}$Ga, $^{61}$Cu, $^{64}$Cu, $^{67}$Ga, $^{99m}$Tc, $^{111}$In, $^{44}$Sc, $^{86}$Y, $^{89}$Zr, $^{90}$Nb, $^{177}$Lu, $^{117m}$Sn, $^{165}$Er, $^{90}$Y, $^{227}$Th, $^{225}$Ac, $^{213}$Bi, $^{212}$Bi, $^{211}$As, $^{203}$Pb, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr, $^{114m}$In, and the like. In some embodiments, the chelator is a chelator from Table 2 and the conjugated radioisotope is a radioisotope indicated in Table 2 as a binder of the chelator.

In some embodiments, the radioisotope chelator is not conjugated to a radioisotope.

In some embodiments, the chelator is: DOTA or a derivative thereof, conjugated with $^{177}$Lu, $^{111}$In, $^{213}$Bi, $^{68}$Ga, $^{203}$Pb, $^{44}$Sc, $^{47}$Sc, $^{90}$Y, $^{86}$Y, $^{225}$Ac, $^{117m}$Sn, $^{153}$Sm, $^{149}$Tb, $^{151}$Tb, $^{165}$Er, $^{213}$Bi, $^{224}$Ra, $^{212}$Bi, $^{227}$Th, $^{223}$Ra, $^{64}$Cu or $^{67}$Cu; H$_2$-MACROPA conjugated with $^{225}$AC; Me-3,2-HOPO conjugated with $^{227}$Th; H$_4$py4pa conjugated with $^{225}$Ac, $^{227}$Th or $^{177}$Lu; H$_4$pypa conjugated with $^{177}$Lu; NODAGA conjugated with $^{68}$Ga; DTPA conjugated with $^{111}$In; or DFO conjugated with $^{89}$Zr.

In some embodiments, the chelator is TETA (1,4,8,11-tetraazacyclotetradecane-1,4,8,11-tetraacetic acid), SarAr (1-N-(4-Aminobenzyl)-3,6,10,13,16,19-hexaazabicyclo[6.6.6]-eicosane-1,8-diamine), NOTA (1,4,7-triazacyclononane-1,4,7-triacetic acid), TRAP (1,4,7-triazacyclononane-1,4,7-tris[methyl(2-carboxyethyl)phosphinic acid), HBED (N,N0-bis(2-hydroxybenzyl)-ethylenediamine-N,N0-diacetic acid), 2,3-HOPO (3-hydroxypyridin-2-one), PCTA (3,6,9,15-tetraazabicyclo[9.3.1]-pentadeca-1(15),11,13-triene-3,6,9,-triacetic acid), DFO (desferrioxamine), DTPA (diethylenetriaminepentaacetic acid), OCTAPA (N,N0-bis(6-carboxy-2-pyridylmethyl)-ethylenediamine-N,N0-diacetic acid) or another picolinic acid derivative.

One or more R$^X$ may comprise a chelator for radiolabeling with $^{99m}$Tc, $^{94m}$Tc, $^{186}$Re, or $^{188}$Re, such as mercaptoacetyl, hydrazinonicotinamide, dimercaptosuccinic acid, 1,2-ethylenediylbis-L-cysteine diethyl ester, methylenediphosphonate, hexamethylpropyleneamineoxime and hexakis (methoxy isobutyl isonitrile, and the like. In some embodiments, one or more R$^X$ comprises a chelator, wherein the chelator is mercaptoacetyl, hydrazinonicotinamide, dimercaptosuccinic acid, 1,2-ethylenediylbis-L-cysteine diethyl ester, methylenediphosphonate, hexamethylpropyleneamineoxime or hexakis(methoxy isobutyl isonitrile). In some of these embodiments, the chelator is bound by a radioisotope. In some such embodiments, the radioisotope is $^{99m}$Tc, $^{94m}$Tc, $^{186}$Re, or $^{188}$Re.

One or more R$^X$ may comprise a chelator that can bind $^{18}$F-aluminum fluoride ([$^{18}$F]AlF), such as 1,4,7-triazacyclononane-1,4-diacetate (NODA) and the like. In some embodiments, the chelator is NODA. In some embodiments, the chelator is bound by [$^{18}$F]AlF.

One or more R$^X$ may comprise a chelator that can bind $^{72}$As or $^{77}$As, such as a trithiol chelate and the like. In some embodiments, the chelator is a trithiol chelate. In some embodiments, the chelator is conjugated to $^{72}$As. In some embodiments, the chelator is conjugated to $^{77}$As.

One or more R$^X$ may comprise an aryl group substituted with a radioisotope. In some embodiments, one or more R$^X$ is

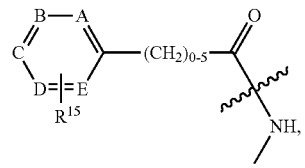

wherein A, B, C, D and E are independently C or N, and R$^{15}$ is a radiohalogen. In some embodiments, one or more R$^X$ is

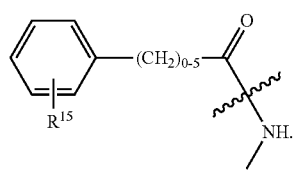

In some embodiments, one or more $R^X$ is

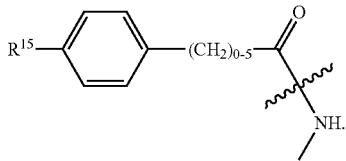

In some embodiments, one or more $R^X$ is

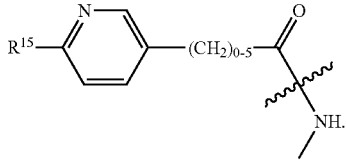

In some embodiments, one or more $R^X$ is

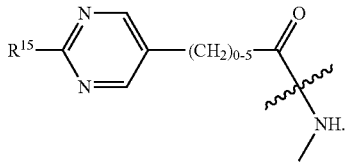

In some embodiments, one or more $R^X$ is

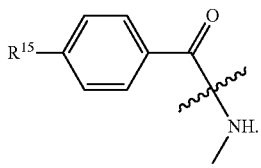

In some embodiments, one or more $R^X$ is

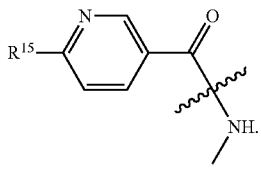

In some embodiments, one or more $R^X$ is

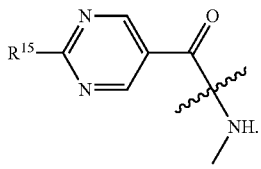

In some embodiments, one or more $R^X$ is

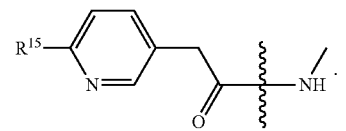

In some of these embodiments, $R^{15}$ is independently $^{211}$At, $^{131}$I, $^{124}$I, $^{123}$I, $^{77}$Br or $^{18}$F. In some of these embodiments, $R^{15}$ is $^{18}$F.

In some embodiments, one or more $R^X$ may comprise a prosthetic group containing a trifluoroborate ($BF_3$), capable of $^{18}$F/$^{19}$F exchange radiolabeling. In such embodiments, one or more $R^X$ may be $R^{16}R^{17}BF_3$, wherein each $R^{16}$ is independently

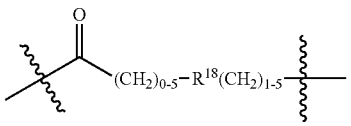

and $R^{18}$ is absent,

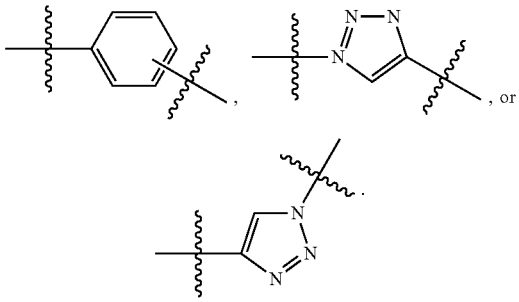

Each —$R^{17}BF_3$ may independently be selected from one or a combination of those listed in Table 3 (below), Table 4 (below), or

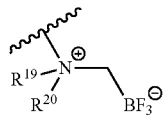

wherein $R^{19}$ and $R^{20}$ are independently $C_1$-$C_5$ linear or branched alkyl groups. For Tables 3 and 4, the R in the pyridine substituted with —OR, —SR, —NR—, —NHR or —NR$_2$ groups is $C_1$-$C_5$ branched or linear alkyl. In some embodiments, one or more —$R^{17}BF_3$ is independently selected from one or a combination of those listed in Table 3. In some embodiments, one or more —$R^{17}BF_3$ is independently selected from one or a combination of those listed in Table 4. In some embodiments, one fluorine is $^{18}$F. In some embodiments, all three fluorines are $^{19}$F.

TABLE 3

Exemplary $R^{17}BF_3$ groups.

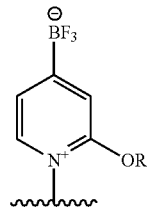

TABLE 3-continued
Exemplary $R^{17}BF_3$ groups.
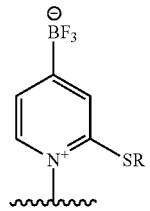
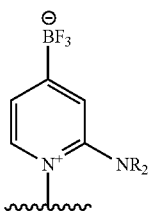
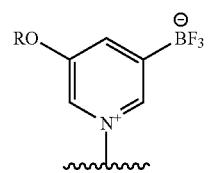
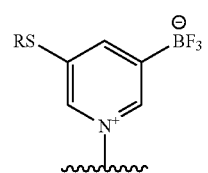
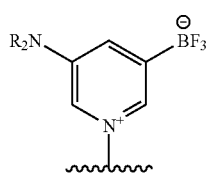
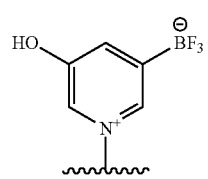
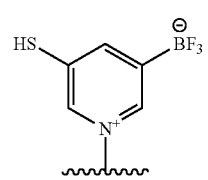
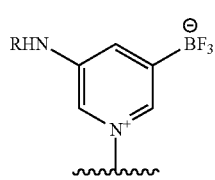
TABLE 3-continued
Exemplary $R^{17}BF_3$ groups.
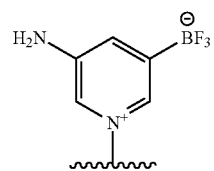
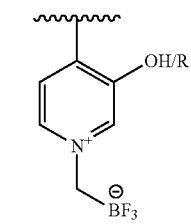
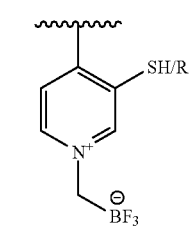
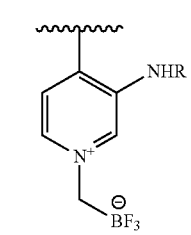
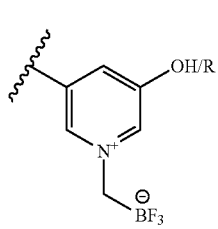
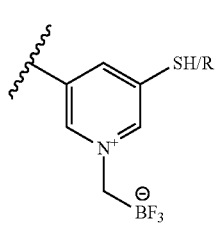
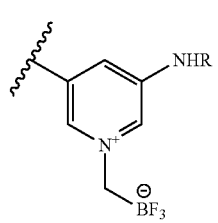

TABLE 3-continued
Exemplary $R^{17}BF_3$ groups.
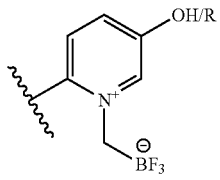
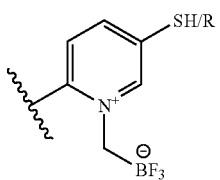
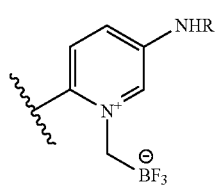
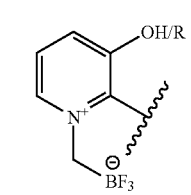
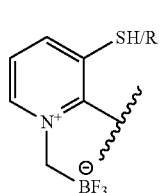
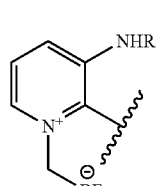
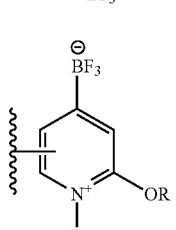
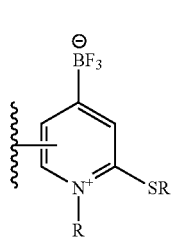
TABLE 3-continued
Exemplary $R^{17}BF_3$ groups.
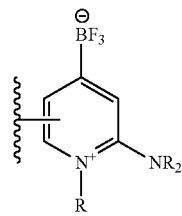
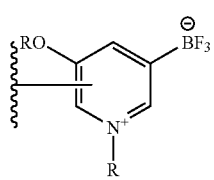
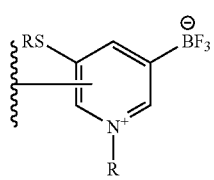
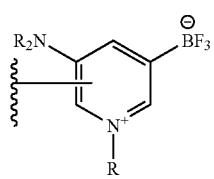
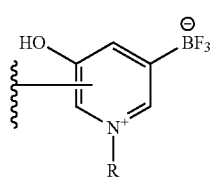
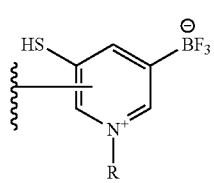
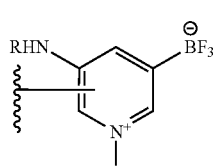
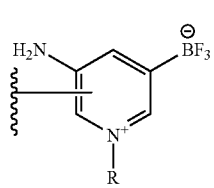

TABLE 3-continued
Exemplary $R^{17}BF_3$ groups.
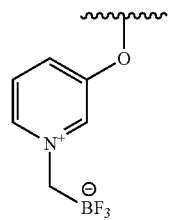
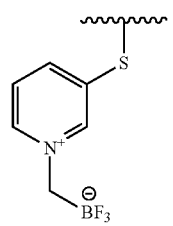
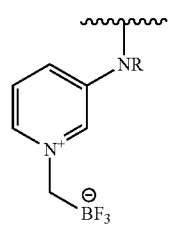
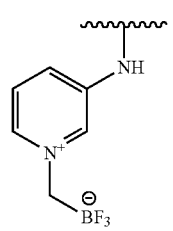
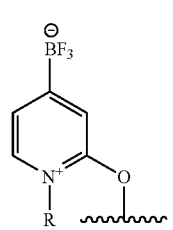
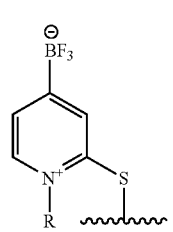
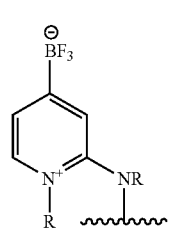
TABLE 3-continued
Exemplary $R^{17}BF_3$ groups.
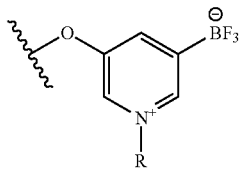
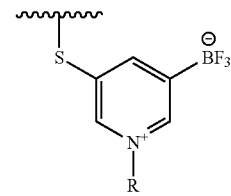
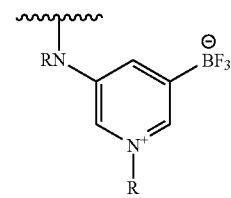
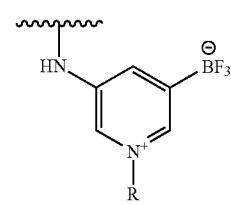
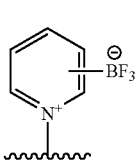
TABLE 4
Exemplary $R^{17}BF_3$ groups.
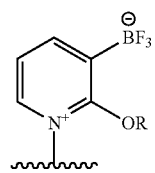
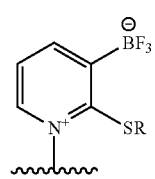
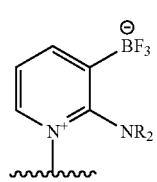

TABLE 4-continued
Exemplary $R^{17}BF_3$ groups.
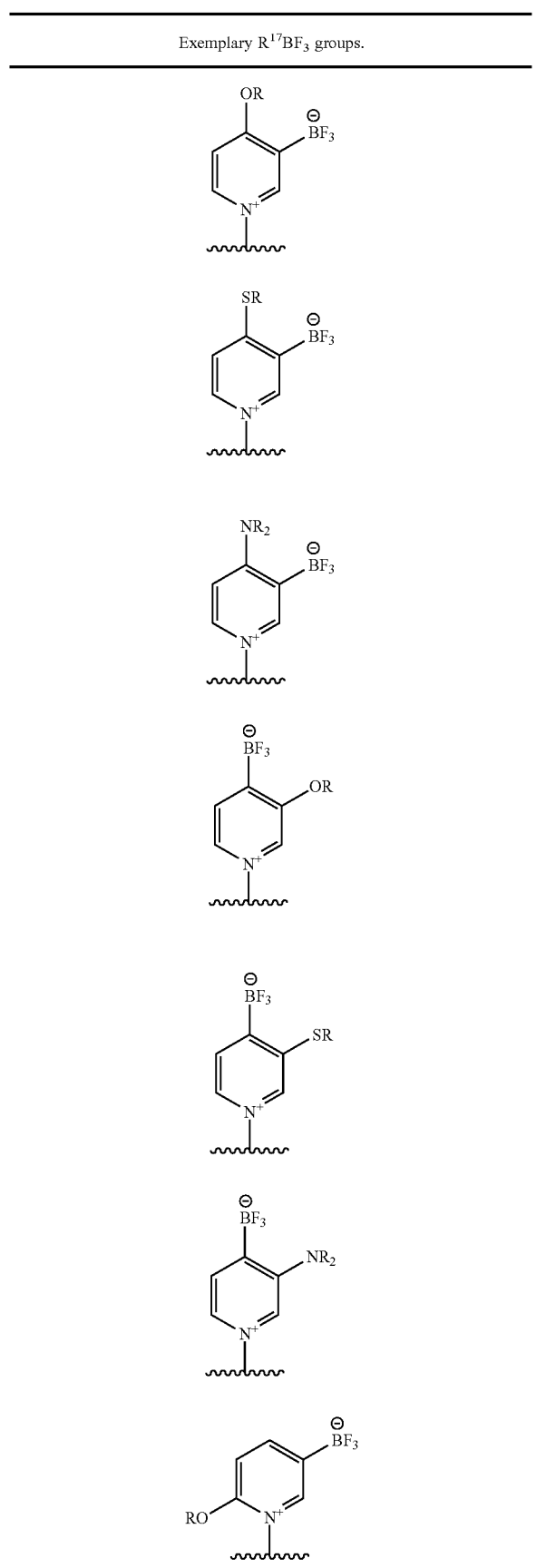
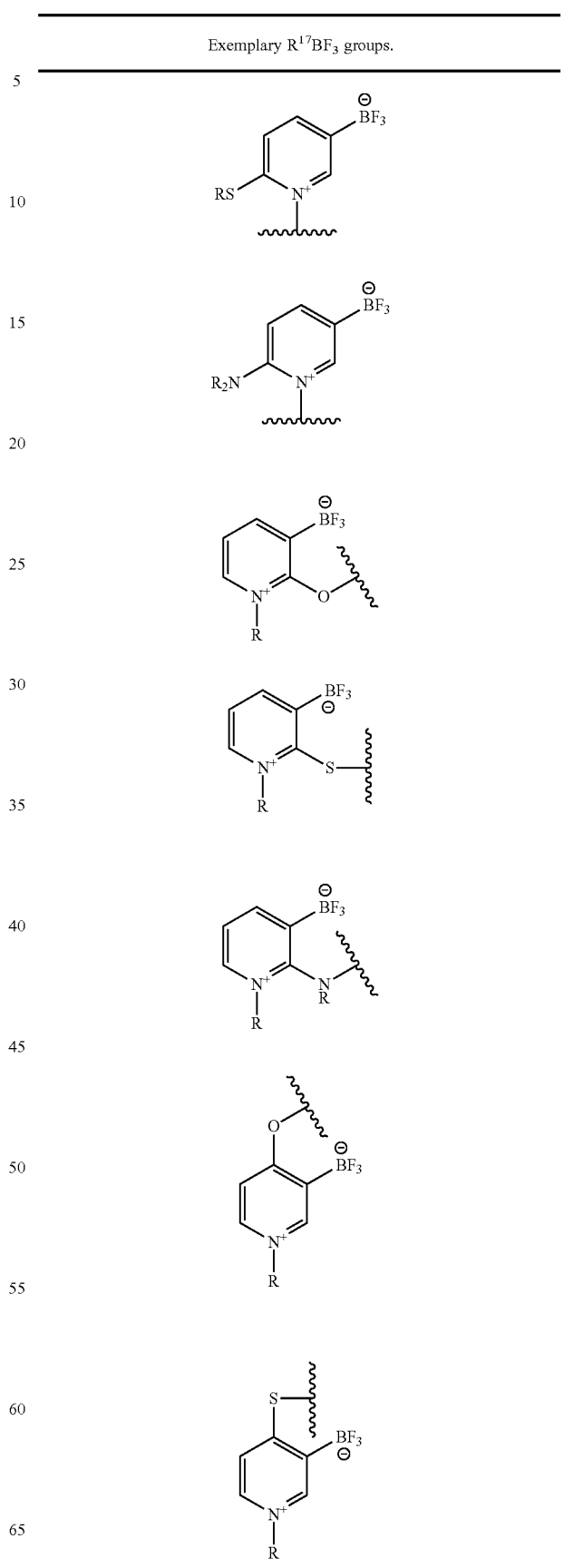

TABLE 4-continued
Exemplary $R^{17}BF_3$ groups.
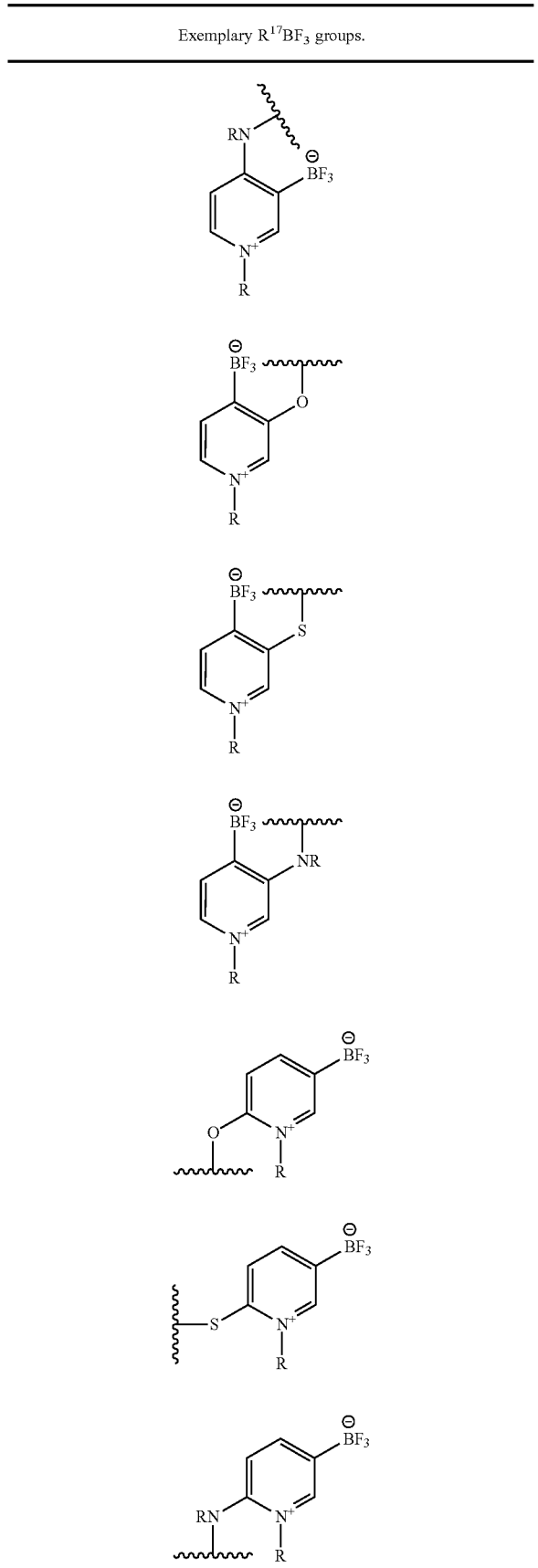
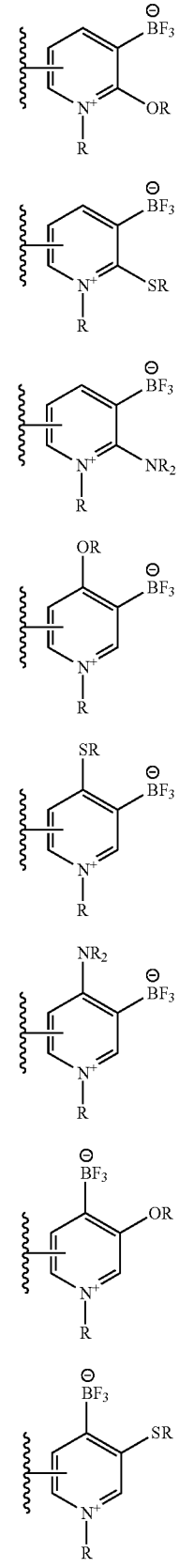

TABLE 4-continued
Exemplary $R^{17}BF_3$ groups.
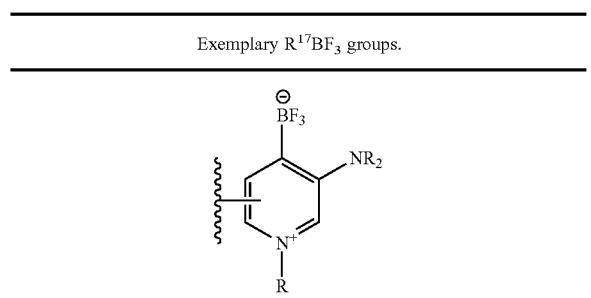
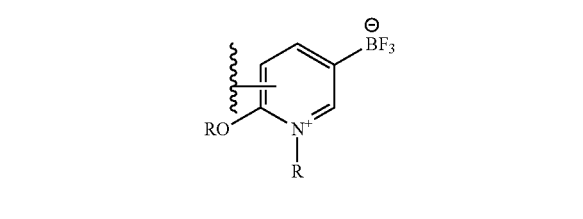
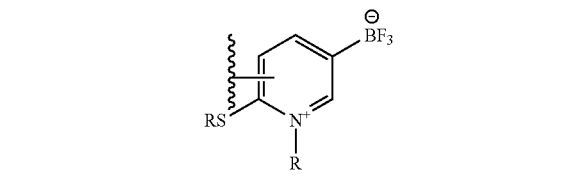
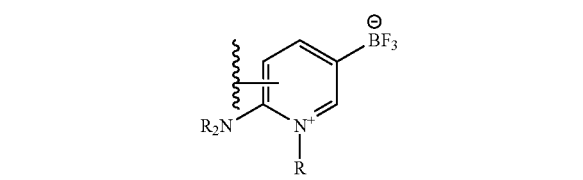
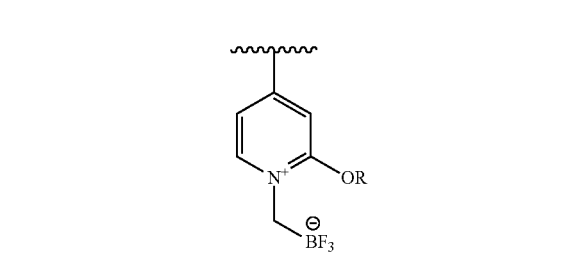
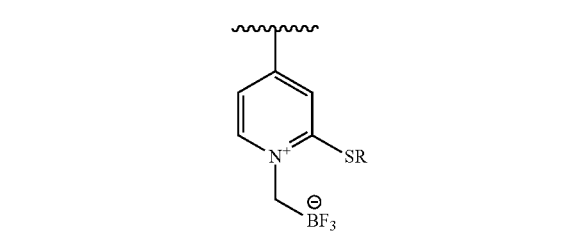
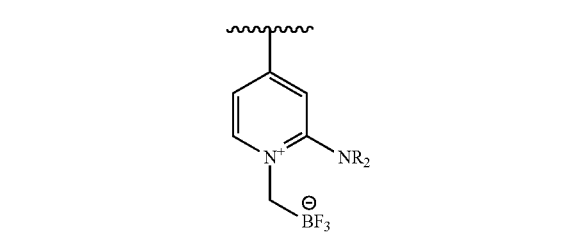
TABLE 4-continued
Exemplary $R^{17}BF_3$ groups.
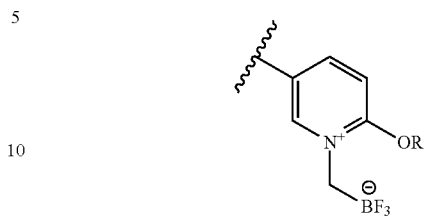
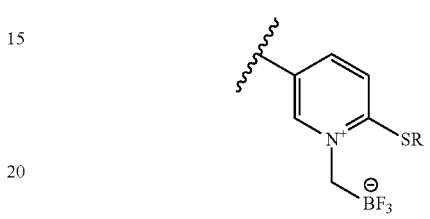
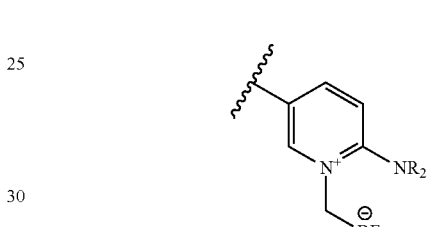
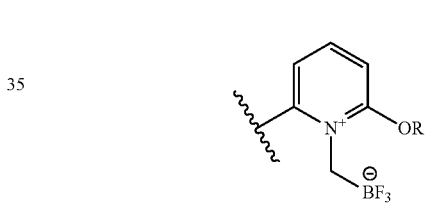
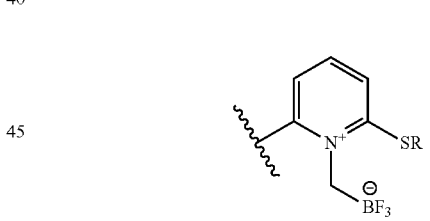
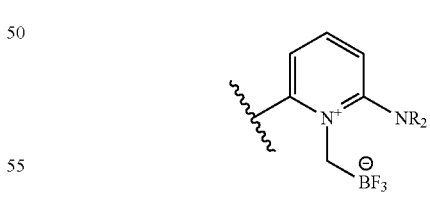
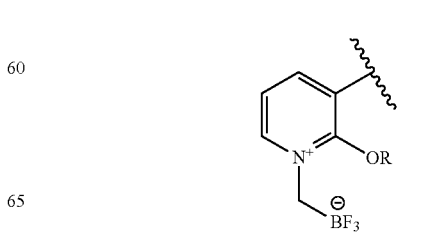

TABLE 4-continued

Exemplary R^17BF_3 groups.

In some embodiments, R^17BF_3 may form

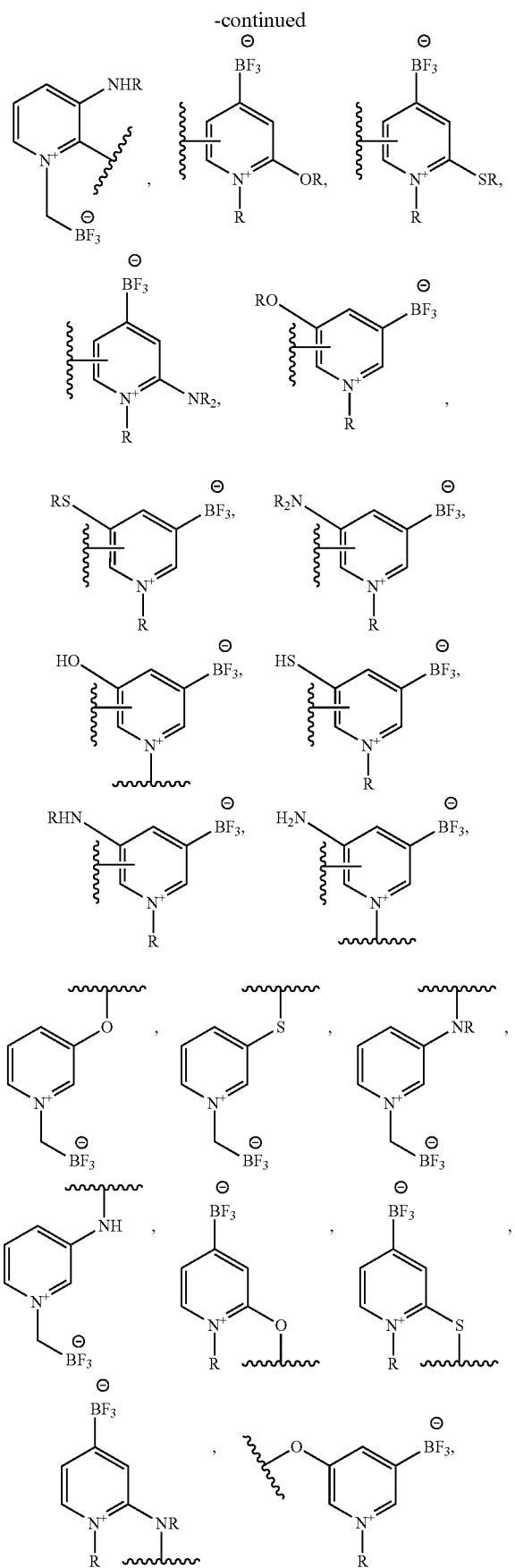
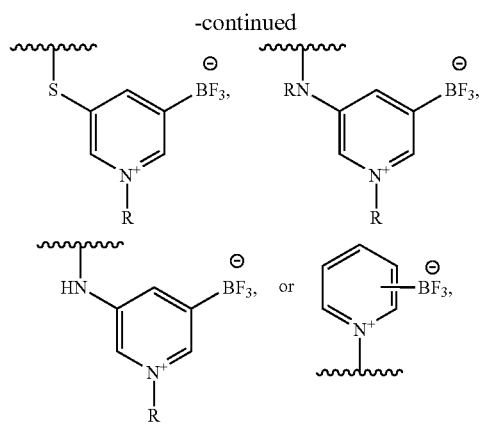

in which the R (when present) in the pyridine substituted —OR, —SR, —NR, —NHR or —NR$_2$ is a branched or linear $C_1$-$C_5$ alkyl. In some embodiments, R is a branched or linear $C_1$-$C_5$ saturated alkyl. In some embodiments, R is methyl. In some embodiments, R is ethyl. In some embodiments, R is propyl. In some embodiments, R is isopropyl. In some embodiments, R is n-butyl. In some embodiments, one fluorine is $^{18}$F. In some embodiments, all three fluorines are $^{19}$F.

In some embodiments, $R^{17}BF_3$ may form

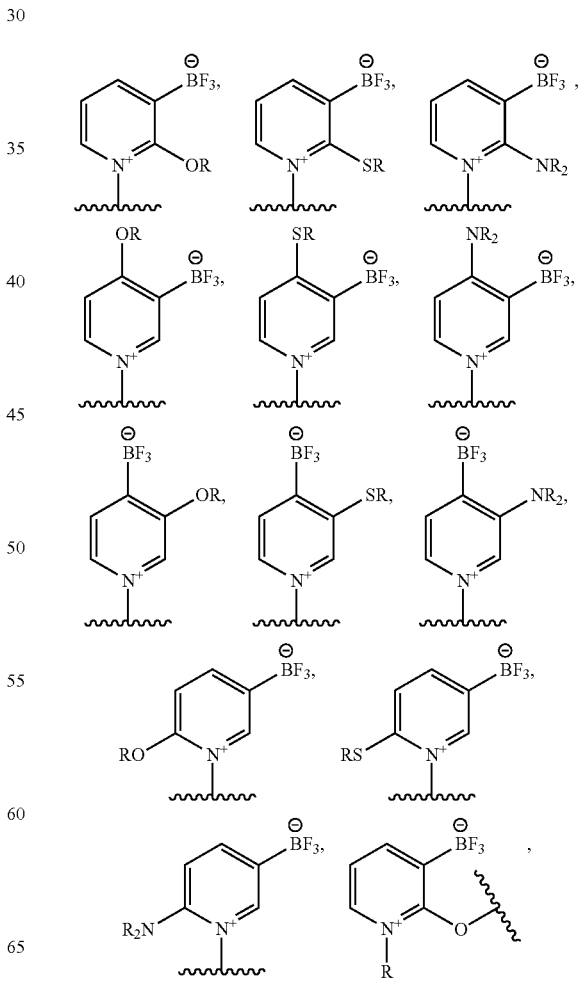

-continued

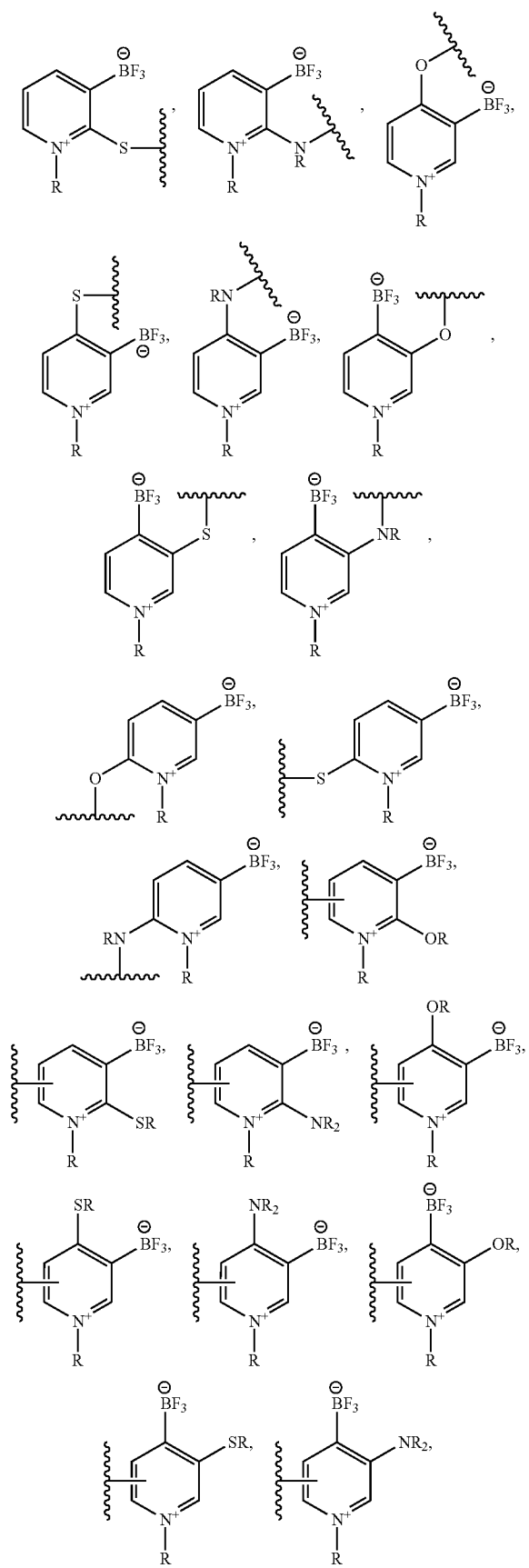

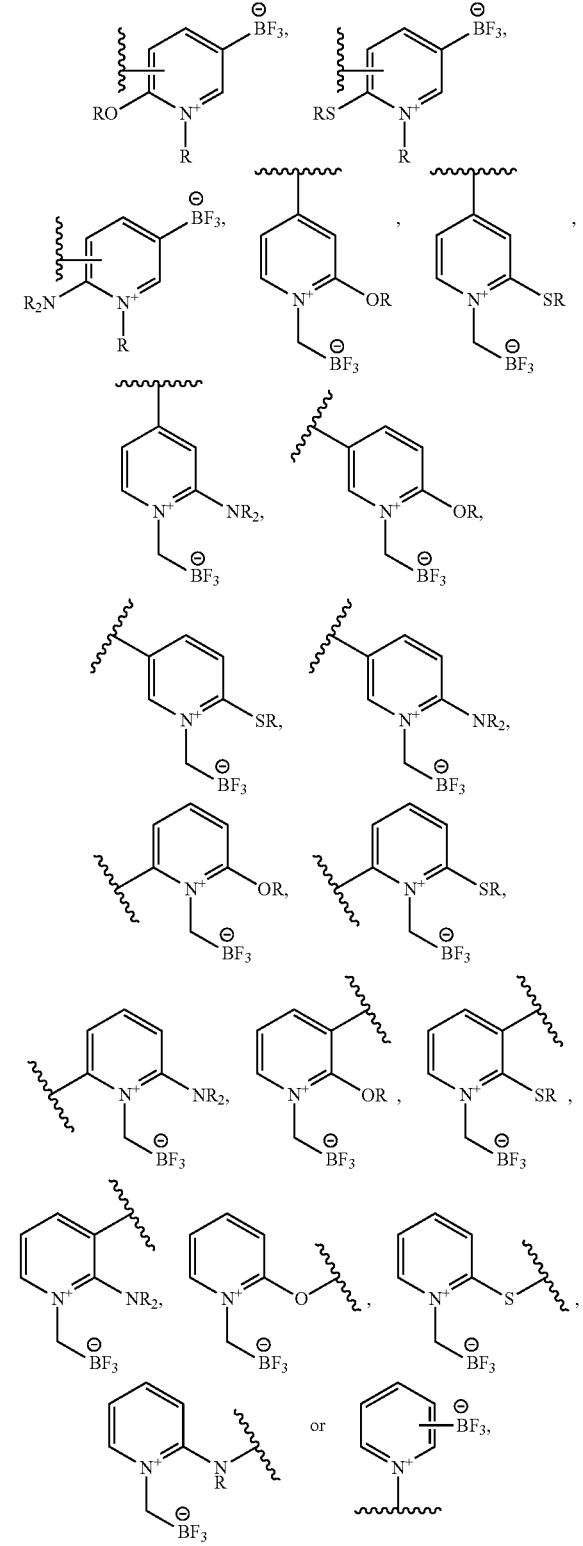

in which the R (when present) in the pyridine substituted —OR, —SR, —NR— or —NR$_2$ is branched or linear C$_1$-C$_5$ alkyl. In some embodiments, R is a branched or linear C$_1$-C$_5$ saturated alkyl. In some embodiments, R is methyl. In some embodiments, R is ethyl. In some embodiments, R is propyl. In some embodiments, R is isopropyl. In some embodiments, R is n-butyl. In some embodiments, one or more —R$^{17}$BF$_3$ is In some embodiments, one or more $-R^{17}BF_3$ is

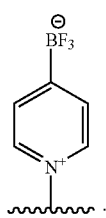

In some embodiments, one fluorine is $^{18}F$. In some embodiments, all three fluorines are $^{19}F$.

In some embodiments, one or more $-R^{17}BF_3$ is

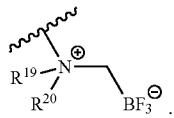

In some embodiments, $R^{19}$ is methyl. In some embodiments, $R^{19}$ is ethyl. In some embodiments, $R^{19}$ is propyl. In some embodiments, $R^{19}$ is isopropyl. In some embodiments, $R^{10}$ is butyl. In some embodiments, $R^{19}$ is n-butyl. In some embodiments, $R^{19}$ is pentyl. In some embodiments, $R^{20}$ is methyl. In some embodiments, $R^{20}$ is ethyl. In some embodiments, $R^{20}$ is propyl. In some embodiments, $R^{20}$ is isopropyl. In some embodiments, $R^{20}$ is butyl. In some embodiments, $R^{20}$ is n-butyl. In some embodiments, $R^{20}$ is pentyl. In some embodiments, $R^{19}$ and $R^{20}$ are both methyl. In some embodiments, one fluorine is $^{18}F$. In some embodiments, all three fluorines are $^{19}F$.

In some embodiments, one or more $R^X$ may comprise a prosthetic group containing a silicon-fluorine-acceptor moiety. In some embodiments, the fluorine of the silicon-fluorine acceptor moiety is $^{18}F$. The prosthetic groups containing a silicon-fluorine-acceptor moiety may be independently selected from one or a combination of the following:

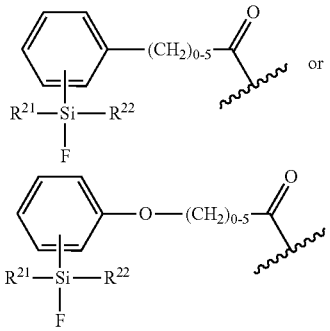

wherein $R^{21}$ and $R^{22}$ are independently a linear or branched, cyclic or acyclic, and/or aromatic or non-aromatic $C_1$-$C_{10}$ alkyl, alkenyl or alkynyl group. In some embodiments, $R^{21}$ and $R^{22}$ are independently selected from the group consisting of phenyl, tert-butyl, sec-propyl or methyl. In some embodiments, the prosthetic group is

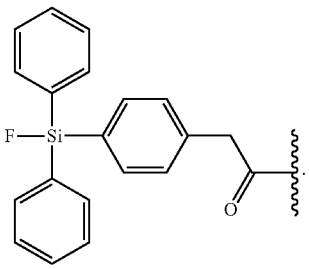 [SMILES: *C(=O)Cc1ccc([Si](F)(c2ccccc2)c2ccccc2)cc1]

In some embodiments, the prosthetic group is

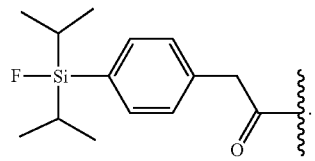 [SMILES: *C(=O)Cc1ccc([Si](F)(C(C)C)C(C)C)cc1]

In some embodiments, the prosthetic group is

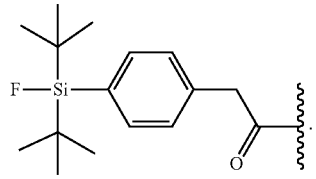

In some embodiments, the prosthetic group is

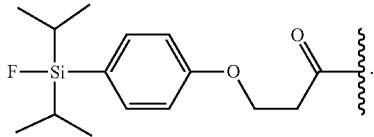 [SMILES: *C(=O)CCOc1ccc([Si](F)(C(C)C)C(C)C)cc1]

In some embodiments, one or more $R^X$ comprise a prosthetic group containing a fluorophosphate. In some embodiments, one or more $R^X$ comprise a prosthetic group containing a fluorosulfate. In some embodiments, one or more $R^X$ comprise a prosthetic group containing a sulfonylfluoride. Such prosthetic groups are well known and are commercially available, and are facile to attach (e.g. via an amide linkage). In some embodiments, the fluorine atom in the fluorophosphate, fluorosulfate or sulfonylfuloride is $^{18}F$. In some embodiments, the fluorine atom in the fluorophosphate, fluorosulfate or sulfonylfuloride is $^{19}F$.

Certain dual labeled compounds (i.e. when $R^7$ comprises two $R^X$ groups), have only a single radioactive atom. For example, but without limitation, one $R^X$ group may be $^{18}F$ labeled and the other $R^X$ group may comprise only $^{19}F$ or the other $R^X$ group may comprise a chelator that is not chelated with a radiometal or is chelated with a metal that is not a radioisotope. In another non-limiting example, one $R^X$ group may comprise an aryl substituted with a radioisotope and the other $R^X$ group may comprise only $^{19}F$ or the other $R^X$ group may comprise a chelator that is not chelated with a radiometal or is chelated with a metal that is not a radioisotope. In yet another non-limiting example, one $R^X$ group may comprise a chelator conjugated with a radioisotope and the other $R^X$ group may comprise only $^{19}F$.

In some embodiments, $R^7$ comprises a first $R^X$ group and a second $R^X$ group, wherein the first $R^X$ group is a radiometal chelator optionally bound by a radiometal and the second $R^X$ group is a prosthetic group containing a trifluoroborate. In some embodiments, $R^7$ comprises a first $R^X$ group and a second $R^X$ group, wherein the first $R^X$ group is a radiometal chelator optionally bound by a radiometal and the second $R^X$ group is a prosthetic group containing a trifluoroborate.

In certain embodiments, the compound is conjugated with a radioisotope for positron emission tomography (PET) or single photon emission computed tomography (SPECT) imaging of PSMA expressing tumors, wherein the compound is conjugated with a radioisotope that is a positron emitter or a gamma emitter. Without limitation, the positron or gamma emitting radioisotope is $^{68}Ga$, $^{67}Ga$, $^{61}Cu$, $^{64}Cu$, $^{99m}Tc$, $^{110m}In$, $^{111}In$, $^{44}Sc$, $^{86}Y$, $^{89}Zr$, $^{90}Nb$, $^{18}F$, $^{131}I$, $^{123}I$, $^{124}I$ and $^{72}As$.

In certain embodiments the compound is conjugated with a radioisotope that is used for therapy of PSMA-expressing tumors. This includes radioisotopes such as $^{165}$Er, $^{212}$Bi, $^{211}$At, $^{166}$Ho, $^{149}$Pm, $^{159}$Gd, $^{105}$Rh, $^{109}$Pd, $^{198}$Au, $^{199}$Au, $^{175}$Yb, $^{142}$Pr, $^{177}$Lu, $^{111}$In, $^{213}$Bi, $^{203}$Pb, $^{212}$Pb, $^{44}$Sc, $^{47}$Sc, $^{90}$Y, $^{225}$Ac, $^{117m}$Sn, $^{153}$Sm, $^{149}$Tb, $^{161}$Tb, $^{224}$Ra, $^{227}$Th, $^{223}$Ra, $^{77}$As, $^{64}$Cu or $^{67}$Cu.

The compound may be HTK03149 or a salt or solvate thereof, optionally conjugated with a radiometal. In some embodiments, the radiometal is $^{177}$Lu, $^{111}$In, $^{213}$Bi, $^{68}$Ga, $^{67}$Ga, $^{203}$Pb, $^{212}$Pb, $^{44}$Sc, $^{47}$Sc, $^{90}$Y, $^{86}$Y, $^{225}$Ac, $^{117m}$Sn, $^{153}$Sm, $^{149}$Tb, $^{161}$Tb, $^{165}$Er, $^{224}$Ra, $^{212}$Bi, $^{227}$Th, $^{223}$Ra, $^{64}$Cu or $^{67}$Cu. In some embodiments, the radiometal is $^{68}$Ga.

The compound may be HTK03169, HTK03161, HTK03177, HTK03187, HTK03153, HTK03170, HTK04053, HTK03189A, HTK03189B, HTK04018, HTK04033, HTK04040, HTK04036, HTK04037, HTK04041, HTK04028, HTK04048, HTK04050, HTK03162, or HTK04055, or a salt or solvate thereof, optionally conjugated with a radiometal. In some embodiments, the radiometal is $^{177}$Lu, $^{111}$In, $^{213}$Bi, $^{68}$Ga, $^{67}$Ga, $^{203}$Pb, $^{212}$Pb, $^{44}$Sc, $^{47}$Sc, $^{90}$Y, $^{86}$Y, $^{225}$Ac, $^{117m}$Sn, $^{153}$Sm, $^{149}$Tb, $^{161}$Tb, $^{165}$Er, $^{224}$Ra, $^{212}$Bi, $^{227}$Th, $^{223}$Ra, $^{64}$Cu or $^{67}$Cu. In some embodiments, the radiometal is $^{68}$Ga. In some embodiments, the radiometal is $^{177}$Lu.

When the radiolabeling group comprises or is conjugated to a diagnostic radioisotope, there is disclosed use of certain embodiments of the compound for preparation of a radiolabeled tracer for imaging PSMA-expressing tissues in a subject. There is also disclosed a method of imaging PSMA-expressing tissues in a subject, in which the method comprises: administering to the subject a composition comprising certain embodiments of the compound and a pharmaceutically acceptable excipient; and imaging tissue of the subject, e.g. using PET or SPECT. When the tissue is a diseased tissue (e.g. a PSMA-expressing cancer), PSMA-targeted treatment may then be selected for treating the subject.

When the radiolabeling group comprises a therapeutic radioisotope, there is disclosed use of certain embodiments of the compound (or a pharmaceutical composition thereof) for the treatment of PSMA-expressing conditions or diseases (e.g. cancer and the like) in a subject. Accordingly, there is provided use of the compound in preparation of a medicament for treating a PSMA-expressing condition or disease in a subject. There is also provided a method of treating PSMA-expressing disease in a subject, in which the method comprises: administering to the subject a composition comprising the compound and a pharmaceutically acceptable excipient. For example, but without limitation, the disease may be a PSMA-expressing cancer.

PSMA expression has been detected in various cancers (e.g. Rowe et al., 2015, *Annals of Nuclear Medicine* 29:877-882; Sathekge et al., 2015, *Eur J Nucl Med Mol Imaging* 42:1482-1483; Verburg et al., 2015, *Eur J Nucl Med Mol Imaging* 42:1622-1623; and Pyka et al., J Nucl Med Nov. 19, 2015 jnumed.115.164442). Accordingly, without limitation, the PSMA-expressing cancer may be prostate cancer, renal cancer, breast cancer, thyroid cancer, gastric cancer, colorectal cancer, bladder cancer, pancreatic cancer, lung cancer, liver cancer, brain tumor, melanoma, neuroendocrine tumor, ovarian cancer or sarcoma. In some embodiments, the cancer is prostate cancer.

Compounds Comprising Retro-Inverso Peptide Linkers

It is well known to those skilled in the art that the concept of retro-inverso peptide design can be applied to further vary the linker constructs defined for the various compounds above. Without prejudice for a given stereoisomer and no necessarily being bound by a given stereoisomer, the use of the retro-inverso approach would require that the preferred stereochemical configuration at certain stereogenic atoms be inverted provided that the polarity of the linking group(s) that bracket the stereogenic atom in question, e.g. N-termini and C-termini have been inverted in the design of a retro-inverso peptide fragment. It is also well known that amide linkages in peptidic linkers can be substituted with alternative linkages and in certain cases extended by an additional group of atoms, e.g. a $CH_2$ or C=O at a given amino acid. As such, it would be obvious to replace any such linker defined above (or elsewhere herein, e.g. in the Examples) with a linker in which the polarity of an amino acid is inverted and/or in which an amide linkage is replaced with an alternative linkage wherein the overall position and 3D conformation of the linker is retained. This principle is demonstrated in the following non-limiting examples of embodiments to illustrate how parts of the molecule that have the same or similar functional groups have been replaced with retro-inverso counterparts, as would be readily appreciated by those skilled in the art of peptide chemistry:

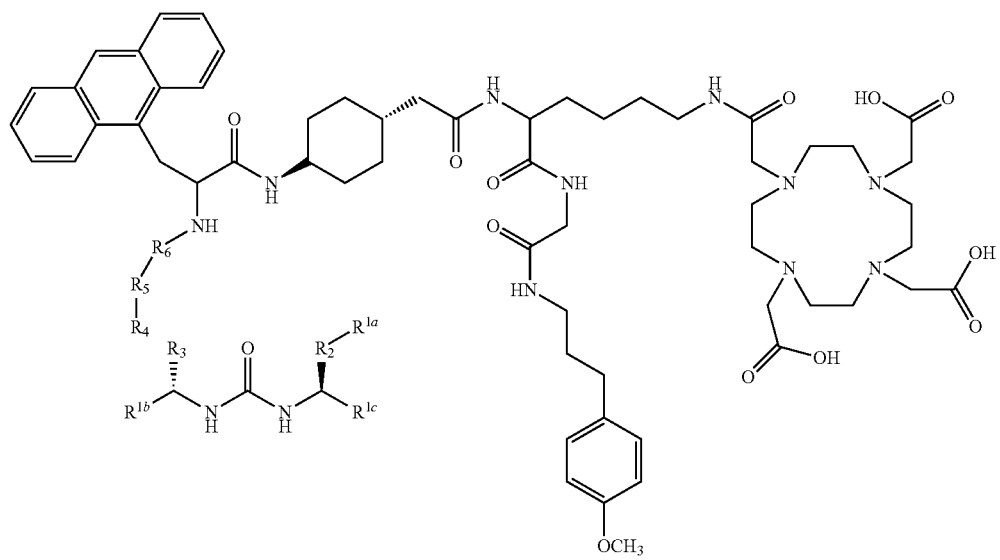

-continued

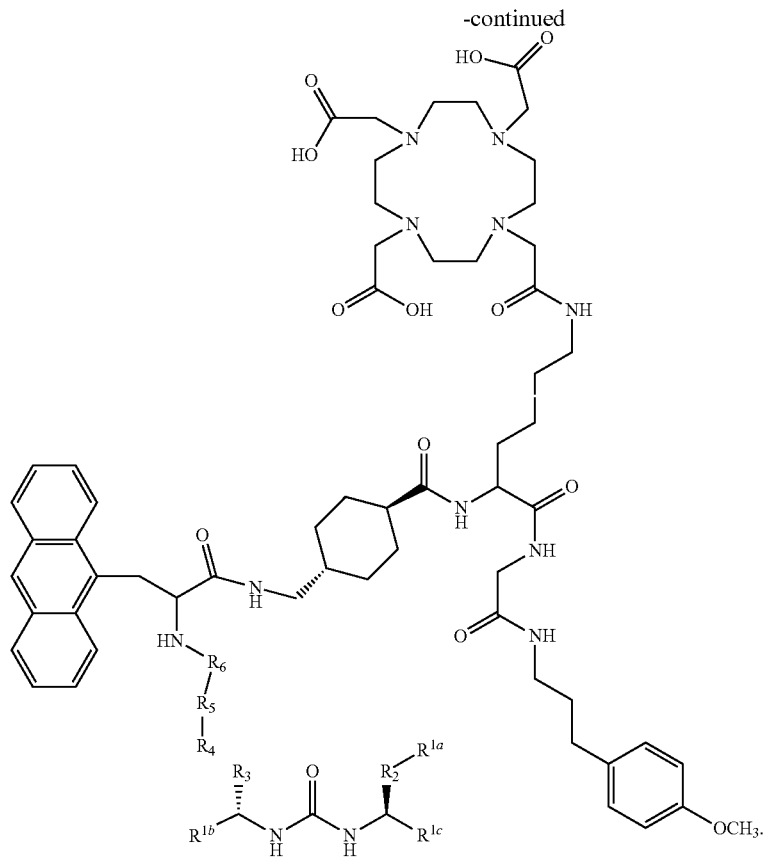

Accordingly, there is also disclosed compounds of Formula IV or Formula V defined below.

There is disclosed a compound, wherein the compound has Formula IV or is a salt or a solvate of Formula IV:

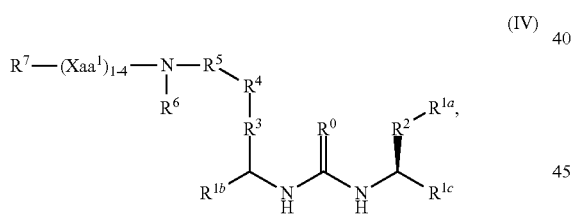
(IV)

wherein:
$R^0$ is S or O;
$R^{1a}$ is —CO$_2$H, —SO$_2$H, —SO$_3$H, —PO$_2$H, —PO$_3$H$_2$, —OPO$_3$H$_2$, —OSO$_3$H, —B(OH)$_2$, or

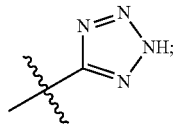 [SMILES: *c1nn[nH]n1]

$R^{1b}$ is —CO$_2$H, —SO$_2$H, —SO$_3$H, —PO$_2$H, —PO$_3$H$_2$, —B(OH)$_2$, or

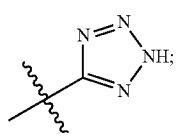 [SMILES: *c1nn[nH]n1]

$R^{1c}$ is —CO$_2$H, —SO$_2$H, —SO$_3$H, —PO$_2$H, —PO$_3$H$_2$, —B(OH)$_2$, or

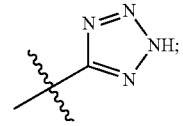 [SMILES: *c1nn[nH]n1]

$R^2$ is —CH$_2$—, —CH(OH)—, —CHF—, —CF$_2$—, —CH(CH$_3$)—, —C(CH$_3$)$_2$—, —CH$_2$CH(OH)—, —CH$_2$CHF—, —CHFCH$_2$—, —CF$_2$CH$_2$—, —CH$_2$CF$_2$—, —CH(OH)CH$_2$—, —CH(CH$_3$)CH$_2$—, —CH$_2$CH(CH$_3$)—, —C(CH$_3$)$_2$CH$_2$—, —CH$_2$C(CH$_3$)$_2$—, —CH$_2$CH(OH)CH$_2$—, —CH$_2$CHFCH$_2$—, —(CH$_2$)$_2$CH(OH)—, —(CH$_2$)$_2$CHF—, —(CH$_2$)$_3$—, —CH$_2$OCH$_2$—, —CH$_2$SCH$_2$—, —CHFCH$_2$CH$_2$—, —CH(OH)CH$_2$CH$_2$—, —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—, —CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —CH$_2$—NH—C(O)—, —C(O)—NH—CH$_2$—,

—C(O)—NH—CH(CH₃)—, —C(O)—NH—C(CH₃)₂—, —CH₂SeCH₂—, —CH(COOH)—, —CH₂CH(COOH)—, —CH₂CH(COOH)CH₂—, —CH₂CH₂CH(COOH)—, —CH=CH—, —CH=CHCH₂—, —C≡CCH₂—, —HC[CH₂]CH—, or —HC[CH₂]CHCH₂—, wherein HC[CH₂]CH represents a cyclopropyl ring;

$R^3$ is a linear or branched, cyclic or acyclic, and/or aromatic or non-aromatic $C_1$-$C_{20}$ alkylenyl or alkenylenyl, or a linear or branched, cyclic or acyclic, and/or aromatic or non-aromatic $X_2$-$X_{20}$ heteroalkylenyl or heteroalkenylenyl;

$R^4$ is —O—, —S—, Se—, S(O)—, —S(O)₂—, —NHC(O)—, —C(O)NH—,

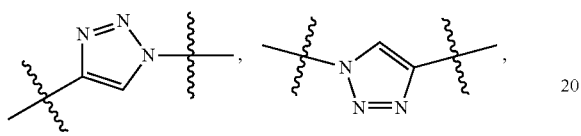

—C(O)—(NH)₂—C(O)—, —OC(O)NH, —NHC(O)O—, —NHC(O)NH—, —OC(S)NH, —NHC(S)O—, —NHC(S)NH—, —NHC(O)C(O)NH—, —S—S—, —S—CH₂—S—, —NH—NH—C(O)—, —C(O)—NH—NH—,

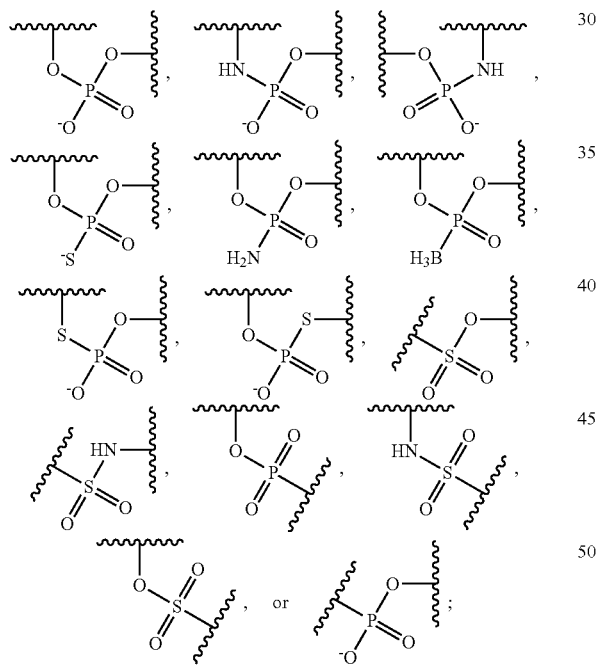

$R^5$ is a linear or branched, cyclic or acyclic, and/or aromatic or non-aromatic $C_1$-$C_{30}$ alkylenyl, alkenylenyl or alkynylenyl, or is a linear or branched, cyclic or acyclic, and/or aromatic or non-aromatic $X_2$-$X_{30}$ heteroalkylenyl, heteroalkenylenyl or heteroalkynylenyl;

$R^6$ is hydrogen or methyl or ethyl;

$Xaa^1$ is an amino acid of formula —N(R⁸)R⁹C(O)—, wherein each $R^8$ is independently hydrogen or methyl, and wherein each $R^9$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl;

at least one $R^9$ or $R^5$ is —(CH₂)₀₋₃CH(R¹⁰)(CH₂)₀₋₃—, wherein $R^{10}$ is:

a linear or branched, cyclic or acyclic, and/or aromatic or non-aromatic $C_2$-$C_{19}$ alkyl, alkenyl or alkynyl; a linear or branched, cyclic or acyclic, and/or aromatic or non-aromatic $X_2$-$X_{19}$ heteroalkyl, heteroalkenyl or heteroalkynyl having only 1-3 heteroatoms;

—CH₂R²³, in which $R^{23}$ is an optionally substituted $C_4$-$C_{16}$ aromatic ring or partially or fully aromatic fused ring system, wherein 0-3 carbons in the aromatic ring or the partially or fully aromatic fused ring system are replaced with N, S and/or O heteroatoms, and wherein the optional substitutions are selected from OH, NH₂, NO₂, halogen, $C_1$-$C_6$ alkyl, and/or $C_1$-$C_6$ alkoxyl groups; or selected from:

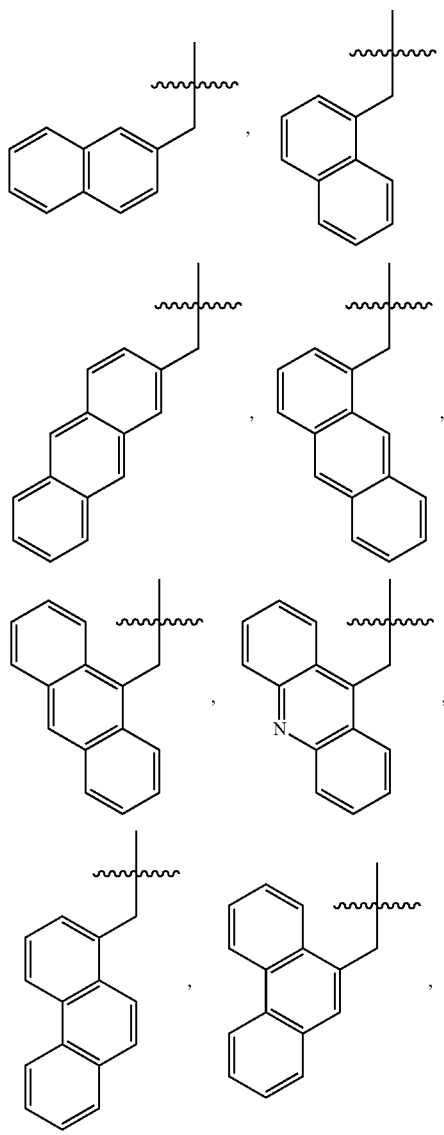

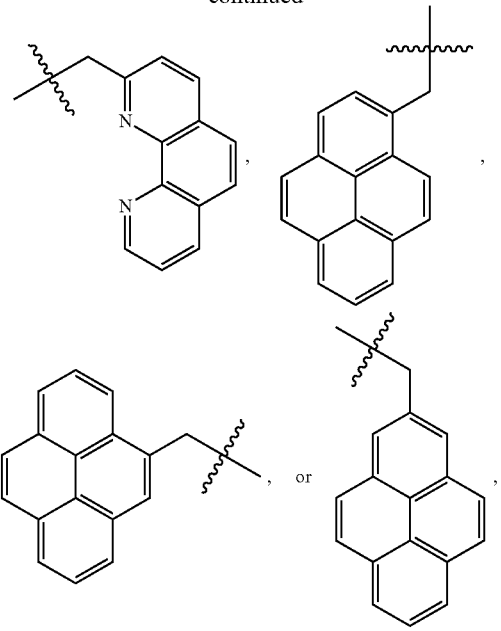

optionally modified with one, more than one, or a combination of: halogen, OMe, SMe, $NH_2$, $NO_2$, CN, OH, or additional endocyclic ring nitrogen atoms;

$R^7$ is $R^X$—$(Xaa^2)_{0-4}$—,

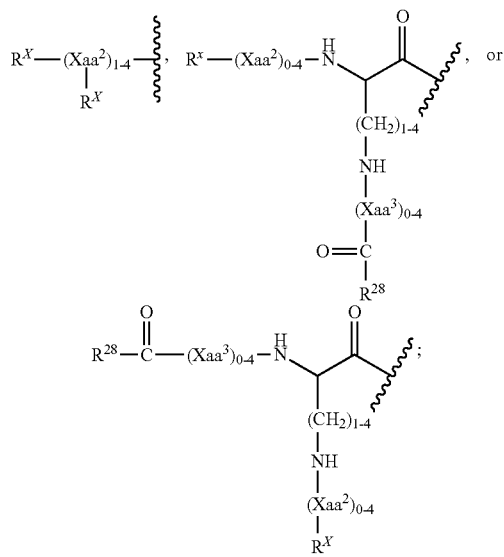

$R^{28}$ is an albumin binder;

$Xaa^2$ and $Xaa^3$, when present, are independently —$N(R^{13})$—$R^{14}C(O)$—, wherein each $R^{13}$ is independently hydrogen or methyl, and wherein each $R^{14}$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl; and each $R^X$ is a radiolabeling group independently selected from: a radiometal chelator optionally bound by a metal;

an aryl or heteroaryl substituted with a radioisotope; a prosthetic group containing a trifluoroborate; or a prosthetic group containing a silicon-fluorine-acceptor moiety, a fluorophosphate, a fluorosulfate, or a sulfonylfluoride;

and wherein any one or any combination of amide linkages within $R^7$—$(Xaa^1)_{1-4}$—$N(R^6)$—$R^5$—$R^4$—$R^3$ is optionally replaced by one or a combination selected from the group consisting of —O—, —S—, —Se—, —S(O)—, —S(O)$_2$—, —NHC(O)—, —C(O)NH—,

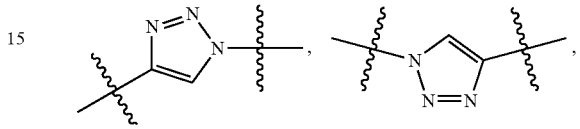

—C(O)—$(NH)_2$—C(O)—, —OC(O)NH, —NHC(O)O—, —NHC(O)NH—, —OC(S)NH, —NHC(S)O—, —NHC(S)NH—, —NHC(O)C(O)NH—, —S—S, —S—$CH_2$—S, —NH—NH—C(O)—, and —C(O)—NH—NH—.

In various embodiments of the compounds of Formula IV, or salts or solvates of Formula IV, the definitions for variables $R^0$, $R^{1a}$, $R^{1b}$, $R^{1c}$, $R^2$, $R^3$, $R^4$, $R^5$, $R^6$, and $R^7$, or any variable defined in the definitions for the foregoing variables, may be any such definition defined for Formula II.

In some embodiments of the compounds of Formula IV, or salts or solvates of Formula IV, —$N(R^6)$—$R^5$—$R^4$— is

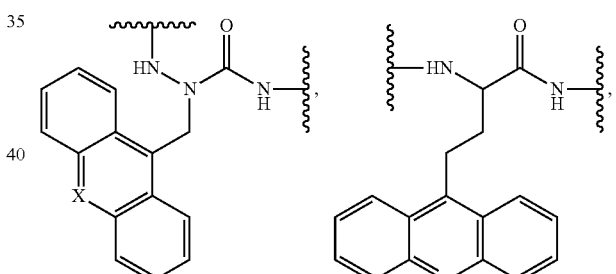

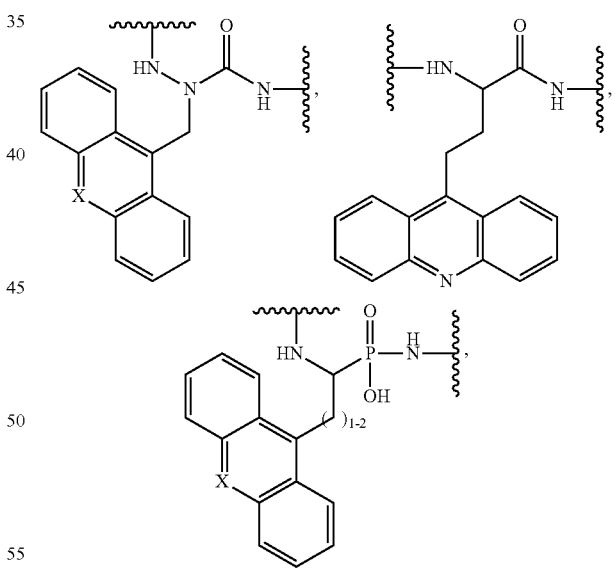

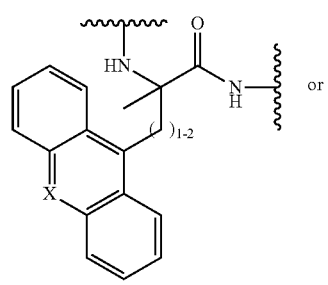

-continued

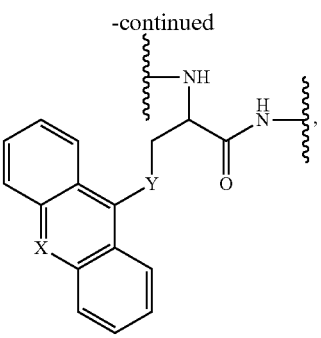

wherein X=CH or N, and Y=NH, S or O, and wherein any of these triaryl/heteroaryl groups is modified optionally with one, more than one, or a combination of halogen, OMe, SMe, NH$_2$, NO$_2$, CN, OH, or one or more additional endocyclic ring nitrogen atoms.

There is also disclosed a compound, wherein the compound has Formula V or is a salt or a solvate of Formula V:

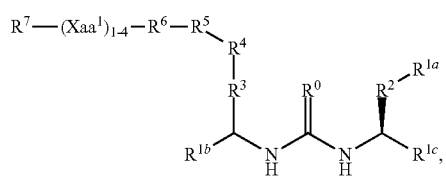

(V)

wherein:
R$^0$ is S or O;
R$^{1a}$ is —CO$_2$H, —SO$_2$H, —SO$_3$H, —PO$_2$H, —PO$_3$H$_2$, —OPO$_3$H$_2$, —OSO$_3$H, —B(OH)$_2$, or

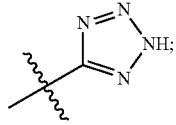 [SMILES: *c1nn[nH]n1]

R$^{1b}$ is —CO$_2$H, —SO$_2$H, —SO$_3$H, —PO$_2$H, PO$_3$H$_2$, —B(OH)$_2$, or

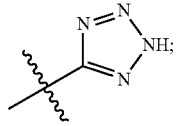 [SMILES: *c1nn[nH]n1]

R$^{1c}$ is —CO$_2$H, —SO$_2$H, —SO$_3$H, —PO$_2$H, —PO$_3$H$_2$, —B(OH)$_2$, or

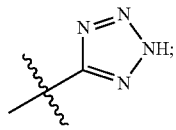

R$^2$ is —CH$_2$—, —CH(OH)—, —CHF—, —CF$_2$—, —CH(CH$_3$)—, —C(CH$_3$)$_2$—, —CH$_2$CH(OH)—, —CH$_2$CHF—, —CHFCH$_2$—, —CF$_2$CH$_2$—, —CH$_2$CF$_2$—, —CH(OH)CH$_2$—, —CH(CH$_3$)CH$_2$—, —CH$_2$CH(CH$_3$)—, —C(CH$_3$)$_2$CH$_2$—, —CH$_2$C(CH$_3$)$_2$—, —CH$_2$CH(OH)CH$_2$—, —CH$_2$CHFCH$_2$—, —(CH$_2$)$_2$CH(OH)—, —(CH$_2$)$_2$CHF—, —(CH$_2$)$_3$—, —CH$_2$OCH$_2$—, —CH$_2$SCH$_2$—, —CHFCH$_2$CH$_2$—, —CH(OH)CH$_2$CH$_2$—, —CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—, —CH(CH$_3$)—O—CH$_2$—, —C(CH$_3$)$_2$—O—CH$_2$—, —CH$_2$—O—CH(CH$_3$)—, —CH$_2$—O—C(CH$_3$)$_2$—, —CH$_2$—S(O)—CH$_2$—, —CH$_2$—S(O)$_2$—CH$_2$—, —CH(CH$_3$)—S—CH$_2$—, —C(CH$_3$)$_2$—S—CH$_2$—, —CH$_2$—S—CH(CH$_3$)—, —CH$_2$—S—C(CH$_3$)$_2$—, —CH(CH$_3$)—S(O)—, CH$_2$—, —C(CH$_3$)$_2$—S(O)—CH$_2$—, —CH$_2$—S(O)—CH(CH$_3$)—, —CH$_2$—S(O)—C(CH$_3$)$_2$—, —CH(CH$_3$)—S(O)$_2$—CH$_2$—, —C(CH$_3$)$_2$—S(O)$_2$—CH$_2$—, —CH$_2$—S(O)$_2$—CH(CH$_3$)—, —CH$_2$—S(O)$_2$—C(CH$_3$)$_2$—, —CH$_2$—NH—C(O)—, —C(O)—NH—CH$_2$—, —C(O)—NH—CH(CH$_3$)—, —C(O)—NH—C(CH$_3$)$_2$—, —CH$_2$SeCH$_2$—, —CH(COOH)—, —CH$_2$CH(COOH)—, —CH$_2$CH(COOH)CH$_2$—, —CH$_2$CH$_2$CH(COOH)—, —CH=CH—, —CH=CHCH$_2$—, —C≡CCH$_2$—, —HC[CH$_2$]CH—, or —HC[CH$_2$]CHCH$_2$—, wherein HC[CH$_2$]CH represents a cyclopropyl ring;

R$^3$ is a linear or branched, cyclic or acyclic, and/or aromatic or non-aromatic C$_1$-C$_{20}$ alkylenyl or alkenylenyl, or a linear or branched, cyclic or acyclic, and/or aromatic or non-aromatic X$_2$-X$_{20}$ heteroalkylenyl or heteroalkenylenyl;

R$^4$ is —O—, —S—, Se—, —S(O)—, —S(O)$_2$—, —NHC(O)—, —C(O)NH—,

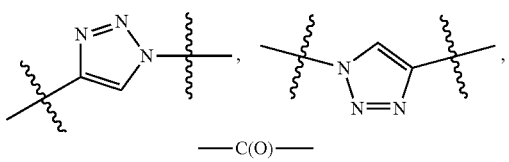

—C(O)—

—C(O)—(NH)$_2$—C(O)—, —OC(O)NH, —NHC(O)O—, —NHC(O)NH—, —OC(S)NH, —NHC(S)O—, —NHC(S)NH—, —NHC(O)C(O)NH—, —S—S—, —S—CH$_2$—S—, —NH—NH—C(O)—, —C(O)—NH—NH—,

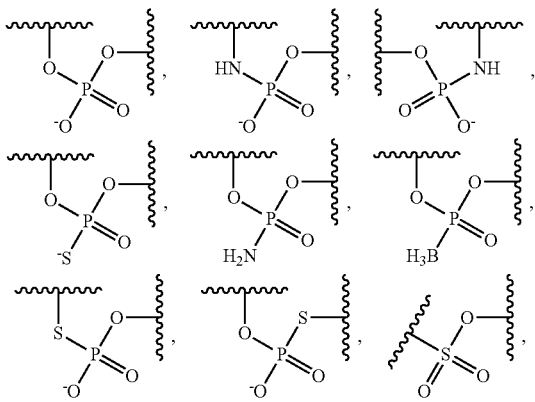

-continued

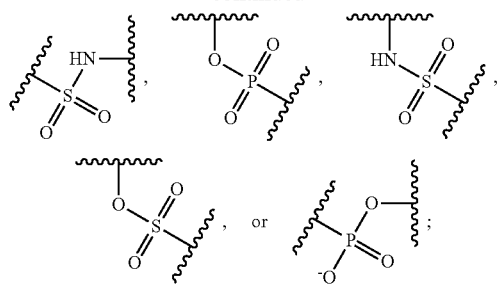

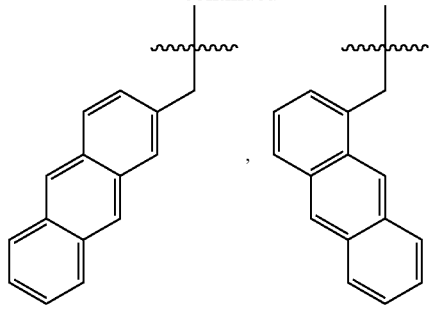

R[5] is a linear or branched, cyclic or acyclic, and/or aromatic or non-aromatic $C_1$-$C_{30}$ alkylenyl, alkenylenyl or alkynylenyl, or is a linear or branched, cyclic or acyclic, and/or aromatic or non-aromatic $X_2$-$X_{30}$ heteroalkylenyl, heteroalkenylenyl or heteroalkynylenyl R[6] is optionally in carbonyl, a phosphoryl or a sulfonyl group that is linked to the alpha-nitrogen in Xaa[1] to respectively give an amide, phosphoramidate/phosphonamidate, or sulfonamide linkage; or alternatively is: —NHC(O)—, —(NH)$_2$—C(O)—, —C(O)—(NH)$_2$—C(O)—, —OC(O)—, —OC(S)—, —NHC(S)—, —NHC(O)C(O)—, —NH—NH—C(O)—, to enjoin the alpha-nitrogen in Xaa[1].

Xaa[1] is an amino acid of formula —N(R[8])R[9]C(O)—, wherein each R[8] is independently hydrogen or methyl, and wherein each R[9] is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl;

at least one R[9] or R[5] is —(CH$_2$)$_{0-3}$CH(R[10])(CH$_2$)$_{0-3}$—, wherein R[10] is:

a linear or branched, cyclic or acyclic, and/or aromatic or non-aromatic $C_2$-$C_{19}$ alkyl, alkenyl or alkynyl; a linear or branched, cyclic or acyclic, and/or aromatic or non-aromatic $X_2$-$X_{19}$ heteroalkyl, heteroalkenyl or heteroalkynyl having only 1-3 heteroatoms;

—CH$_2$R[23], in which R[23] is an optionally substituted $C_4$-$C_{16}$ aromatic ring or partially or fully aromatic fused ring system, wherein 0-3 carbons in the aromatic ring or the partially or fully aromatic fused ring system are replaced with N, S and/or O heteroatoms, and wherein the optional substitutions are selected from OH, NH$_2$, NO$_2$, halogen, $C_1$-$C_6$ alkyl, and/or $C_1$-$C_6$ alkoxyl groups; or selected from:

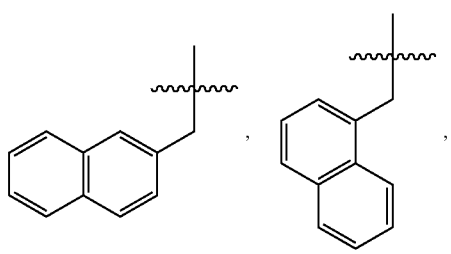

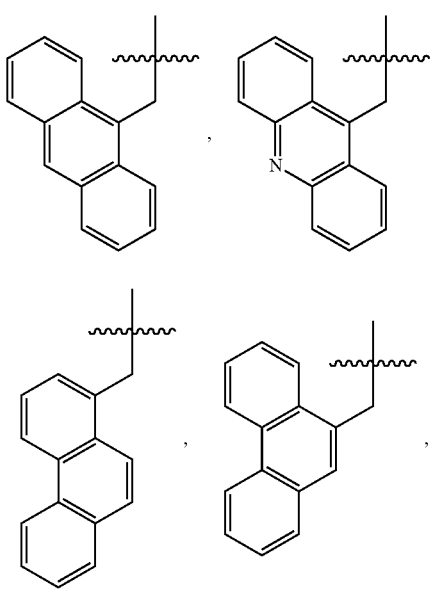

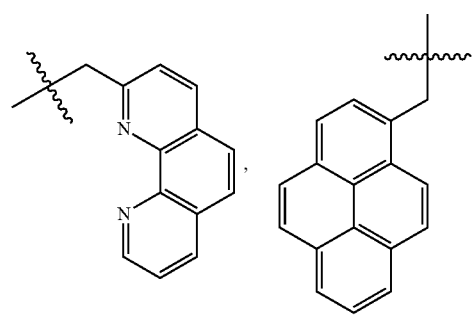

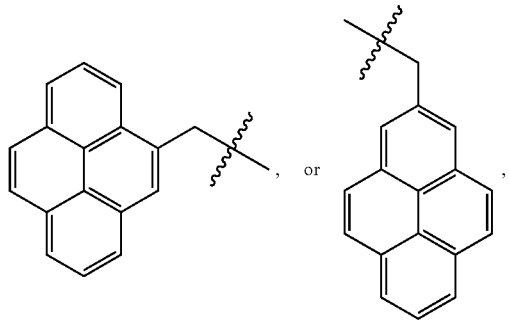

optionally modified with one, more than one, or a combination of: halogen, OMe, SMe, NH$_2$, NO$_2$, CN, OH, or additional endocyclic ring nitrogen atoms;

$R^7$ is $R^X$—$(Xaa^2)_{0-4}$—,

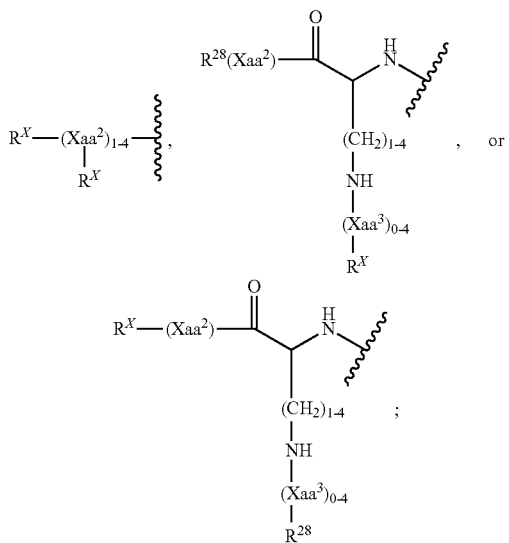

$R^{28}$ is an albumin binder;

Xaa² and Xaa³, when present, are independently —N(R¹³)R¹⁴C(O)—, wherein each $R^{13}$ is independently hydrogen or methyl, and wherein each $R^{14}$ is independently: a linear or branched, cyclic or acyclic, and/or aromatic or non-aromatic $C_1$-$C_{20}$ alkylenyl, alkenylenyl or alkynylenyl; or a linear or branched, cyclic or acyclic, and/or aromatic or non-aromatic $X_2$-$X_{20}$ heteroalkylenyl, heteroalkenylenyl or heteroalkynylenyl; and each $R^X$ is a radiolabeling group independently selected from: a radiometal chelator optionally bound by a metal; an aryl or heteroaryl substituted with a radioisotope; a prosthetic group containing a trifluoroborate; or a prosthetic group containing a silicon-fluorine-acceptor moiety, a fluorophosphate, a fluorosulfate, or a sulfonylfluoride.

In various embodiments of the compounds of Formula V, or salts or solvates of Formula V, the definitions for variables $R^0$, $R^{1a}$, $R^{1b}$, $R^{1c}$, $R^2$, $R^3$, $R^4$, $R^5$, or any variable defined in the definitions for the foregoing variables or for variables $R^6$ or $R^7$, may be any such definition defined for Formula II.

The compounds presented herein incorporate peptides, which may be synthesized by any of a variety of methods established in the art. This includes but is not limited to liquid-phase as well as solid-phase peptide synthesis using methods employing 9-fluorenylmethoxycarbonyl (Fmoc) and/or t-butyloxycarbonyl (Boc) chemistries, and/or other synthetic approaches.

Solid-phase peptide synthesis methods and technology are well-established in the art. For example, peptides may be synthesized by sequential incorporation of the amino acid residues of interest one at a time. In such methods, peptide synthesis is typically initiated by attaching the C-terminal amino acid of the peptide of interest to a suitable resin. Prior to this, reactive side chain and alpha amino groups of the amino acids are protected from reaction by suitable protecting groups, allowing only the alpha carboxyl group to react with a functional group such as an amine group, a hydroxyl group, or an alkyl halide group on the solid support. Following coupling of the C-terminal amino acid to the support, the protecting group on the side chain and/or the alpha amino group of the amino acid is selectively removed, allowing the coupling of the next amino acid of interest. This process is repeated until the desired peptide is fully synthesized, at which point the peptide can be cleaved from the support and purified. A non-limiting example of an instrument for solid-phase peptide synthesis is the Aapptec Endeavor 90 peptide synthesizer.

To allow coupling of additional amino acids, Fmoc protecting groups may be removed from the amino acid on the solid support, e.g. under mild basic conditions, such as piperidine (20-50% v/v) in DMF. The amino acid to be added must also have been activated for coupling (e.g. at the alpha carboxylate). Non-limiting examples of activating reagents include without limitation 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-(7-Aza-1H-benzotriazole-1-yl)-1,1,3,3-tetramethyluronium hexafluorophosphate (HATU), benzotriazole-1-yl-oxy-tris(dimethylamino)phosphoniumhexafluorophosphate (BOP), benzotriazole-1-yl-oxy-tris(pyrrolidino)phosphoniumhexafluorophosphate (PyBOP). Racemization is minimized by using triazoles, such as 1-hydroxy-benzotriazole (HOBt) and 1-hydroxy-7-azabenzotriazole (HOAt). Coupling may be performed in the presence of a suitable base, such as N,N-diisopropylethylamine (DIPEA/DIEA) and the like. For long peptides or if desired, peptide synthesis and ligation may be used.

Apart from forming typical peptide bonds to elongate a peptide, peptides may be elongated in a branched fashion by attaching to side chain functional groups (e.g. carboxylic acid groups or amino groups), either: side chain to side chain; or side chain to backbone amino or carboxylate. Coupling to amino acid side chains may be performed by any known method, and may be performed on-resin or off-resin. Non-limiting examples include: forming an amide between an amino acid side chain containing a carboxyl group (e.g. Asp, D-Asp, Glu, D-Glu, and the like) and an amino acid side chain containing an amino group (e.g. Lys, D-Lys, Orn, D-Orn, Dab, D-Dab, Dap, D-Dap, and the like) or the peptide N-terminus; forming an amide between an amino acid side chain containing an amino group (e.g. Lys, D-Lys, Orn, D-Orn, Dab, D-Dab, Dap, D-Dap, and the like) and either an amino acid side chain containing a carboxyl group (e.g. Asp, D-Asp, Glu, D-Glu, and the like) or the peptide C-terminus; and forming a 1,2,3-triazole via click chemistry between an amino acid side chain containing an azide group (e.g. Lys(N₃), D-Lys(N₃), and the like) and an alkyne group (e.g. Pra, D-Pra, and the like). The protecting groups on the appropriate functional groups must be selectively removed before amide bond formation, whereas the reaction between an alkyne and an azido groups via the click reaction to form an 1,2,3-triazole does not require selective deprotection. Non-limiting examples of selectively removable protecting groups include 2-phenylisopropyl esters (O-2-PhiPr) (e.g. on Asp/Glu) as well as 4-methyltrityl (Mtt), allyloxycarbonyl (alloc), 1-(4,4-dimethyl-2,6-dioxocyclohex-1-ylidene))ethyl (Dde), and 1-(4,4-dimethyl-2,6-dioxocyclohex-1-ylidene)-3-methylbutyl (ivDde) (e.g. on Lys/Orn/Dab/Dap). O-2-PhiPr and Mtt protecting groups can be selectively deprotected under mild acidic conditions, such as 2.5% trifluoroacetic acid (TFA) in DCM. Alloc protecting groups can be selectively deprotected using tetrakis(triphenylphosphine)palladium(0) and phenyl silane in DCM. Dde and ivDde protecting groups can be selectively deprotected using 2-5% of hydrazine in DMF. Deprotected side chains of Asp/Glu (L- or D-forms) and Lys/Orn/Dab/Dap (L- or D-forms) can then be coupled, e.g. by using the coupling reaction conditions described above.

Peptide backbone amides may be N-methylated (i.e. alpha amino methylated). This may be achieved by directly using Fmoc-N-methylated amino acids during peptide synthesis. Alternatively, N-methylation under Mitsunobu conditions may be performed. First, a free primary amine group is protected using a solution of 4-nitrobenzenesulfonyl chloride (Ns—Cl) and 2,4,6-trimethylpyridine (collidine) in NMP. N-methylation may then be achieved in the presence of triphenylphosphine, diisopropyl azodicarboxylate (DIAD) and methanol. Subsequently, N-deprotection may be performed using mercaptoethanol and 1,8-diazabicyclo[5.4.0]undec-7-ene (DBU) in NMP. For coupling protected amino acids to N-methylated alpha amino groups, HATU, HOAt and DIEA may be used.

The PSMA-binding moiety (e.g. Lys-ureido-Aad, and the like) may be constructed on solid phase via the formation of a ureido linkage between the amino groups of two amino acids. This can be done by attaching an Fmoc-protecting amino acid (for example Fmoc-Lys(ivDde)-OH) to Wang resin using standard activation/coupling strategy (for example, Fmoc-protected amino acid (4 eq.), HATU (4 eq.) and N,N-diisopropylethylamine (7 eq.) in N,N-dimethylformamide). The Fmoc-protecting group is then removed by 20% piperidine in N,N-dimethylformamide. To form the ureido linkage, the freed amino group of the solid-phase-attached amino acid is reacted with the $2^{nd}$ amino acid which has its carboxylate group protected with a t-butyl group and its amino group activated and converted to an isocyanate group (—N=C=O). The activation and conversion of an amino group to an isocyanate group can be achieved by reacting the amino group with phosgene or triphosgene. After the formation of the ureido linkage, the side chain functional group of the amino acid (for example ivDde on Lys) can be removed, and then the linker, albumin-binding motif, and/or radiolabeling group (e.g. radiometal chelator and the like) can be subsequently coupled to the PSMA-binding moiety.

The formation of the thioether (—S—) and ether (—O—) linkages (e.g. for $R^4$) can be achieved either on solid phase or in solution phase. For example, the formation of thioether (—S—) linkage can be achieved by coupling between a thiol-containing compound (such as the thiol group on cysteine side chain) and an alkyl halide (such as 3-(Fmoc-amino)propyl bromide and the like) in an appropriate solvent (such as N,N-dimethylformamide and the like) in the presence of base (such as N,N-diisopropylethylamine and the like). The formation of an ether (—O—) linkage can be achieved via the Mitsunobu reaction between an alcohol (such as the hydroxyl group on the side chain of serine or threonine, for example) and a phenol group (such as the side chain of tyrosine, for example) in the presence of triphenylphosphine and diisopropyl azidicarboxylate (DIAD) in an aprotic solvent (such as 1,4-dioxane and the like). If the reactions are carried out in solution phase, the reactants used are preferably in equivalent molar ratio (1 to 1), and the desired products can be purified by flash column chromatography or high performance liquid chromatography (HPLC). If the reactions are carried out on solid phase, meaning one reactant has been attached to a solid phase, then the other reactant is normally used in excess amount (≥3 equivalents of the reactant attached to the solid phase). After the reactions, the excess unreacted reactant and reagents can be removed by sequentially washing the solid phase (resin) using a combination of solvents, such as N,N-dimethylformamide, methanol and dichloromethane, for example.

Non-peptide moieties (e.g. radiolabeling groups, albumin-binding groups and/or linkers) may be coupled to the peptide N-terminus while the peptide is attached to the solid support. This is facile when the non-peptide moiety comprises an activated carboxylate (and protected groups if necessary) so that coupling can be performed on resin. For example, but without limitation, a bifunctional chelator, such as 1,4,7,10-tetraazacyclododecane-1,4,7,10-tetraacetic acid (DOTA) tris(tert-butyl ester) may be activated in the presence of N-hydroxysuccinimide (NHS) and N,N'-dicyclohexylcarbodiimide (DCC) for coupling to a peptide. Alternatively, a non-peptide moiety may be incorporated into the compound via a copper-catalyzed click reaction under either liquid or solid phase conditions. Copper-catalyzed click reactions are well established in the art. For example, 2-azidoacetic acid is first activated by NHS and DCC and coupled to a peptide. Then, an alkyne-containing non-peptide moiety may be clicked to the azide-containing peptide in the presence of $Cu^{2+}$ and sodium ascorbate in water and organic solvent, such as acetonitrile (ACN) and DMF and the like.

The synthesis of radiometal chelators is well-known and many chelators are commercially available (e.g. from Sigma-Aldrich™/Milipore Sigma™ and others). Protocols for conjugation of radiometals to the chelators are also well known (e.g. see Example 1, below). The synthesis of the silicon-fluorine-acceptor moieties can be achieved following previously reported procedures (e.g. Bernard-Gauthier et al. *Biomed Res Int* 2014 2014:454503; Kostikov et al. *Nature Protocols* 2012 7:1956-1963; Kostikov et al. *Bioconjug Chem.* 2012 18:23:106-114; each of which is incorporated by reference in its entirety). The synthesis or acquisition of radioisotope-substituted aryl groups is likewise facile.

The synthesis of the $R^{16}R^{17}BF_3$ component on the PSMA-targeting compounds can be achieved following previously reported procedures (Liu et al. Angew Chem Int Ed 2014 53:11876-11880; Liu et al. J Nucl Med 2015 55:1499-1505; Liu et al. Nat Protoc 2015 10:1423-1432; Kuo et al. J Nucl Med, in press, doi:10.2967/jnumed.118.216598; each of which is incorporated by reference in its entirety). Generally, the $BF_3$-containing motif can be coupled to the linker via click chemistry by forming a 1,2,3-triazole ring between a $BF_3$-containing azido (or alkynyl) group and an alkynyl (or azido) group on the linker, or by forming an amide linkage between a $BF_3$-containing carboxylate and an amino group on the linker. To make the $BF_3$-containing azide, alkyne or carboxylate, a boronic acid ester-containing azide, alkyne or carboxylate is first prepared following by the conversion of the boronic acid ester to $BF_3$ in a mixture of HCl, DMF and $KHF_2$. For alkyl $BF_3$, the boronic acid ester-containing azide, alkyne or carboxylate can be prepared by coupling boronic acid ester-containing alkyl halide (such as iodomethylboronic acid pinacol ester) with an amine-containing azide, alkyne or carboxylate (such as N,N-dimethylpropargylamine). For aryl $BF_3$, the boronic acid ester can be prepared via Suzuki coupling using aryl halide (iodine or bromide) and bis(pinacolato)diboron.

$^{18}F$-Fluorination of the $BF_3$-containing PSMA-targeting compounds via $^{18}F$-$^{19}F$ isotope exchange reaction can be achieved following previously published procedures (Liu et al. *Nat Protoc* 2015 10:1423-1432, incorporated by reference in its entirety). Generally, ~100 nmol of the $BF_3$-containing compound is dissolved in a mixture of 15 µl of pyridazine-HCl buffer (pH=2.0-2.5, 1 M), 15 µl of DMF and 1 µl of a 7.5 mM $KHF_2$ aqueous solution. $^{18}F$-Fluoride solution (in saline, 60 µl) is added to the reaction mixture, and the resulting solution is heated at 80° C. for 20 min. At the end of the reaction, the desired product can be purified by solid phase extraction or by reversed high performance liquid chromatography (HPLC) using a mixture of water and acetonitrile as the mobile phase.

When the peptide has been fully synthesized on the solid support, the desired peptide may be cleaved from the solid support using suitable reagents, such as TFA, tri-isopropylsilane (TIS) and water. Side chain protecting groups, such as Boc, pentamethyldihydrobenzofuran-5-sulfonyl (Pbf), trityl (Trt) and tert-butyl (tBu) are simultaneously removed (i.e. deprotection). The crude peptide may be precipitated and collected from the solution by adding cold ether followed by centrifugation. Purification and characterization of the peptides may be performed by standard separation techniques, such as high performance liquid chromatography (HPLC) based on the size, charge and polarity of the peptides. The identity of the purified peptides may be confirmed by mass spectrometry or other similar approaches.

Figure 2:
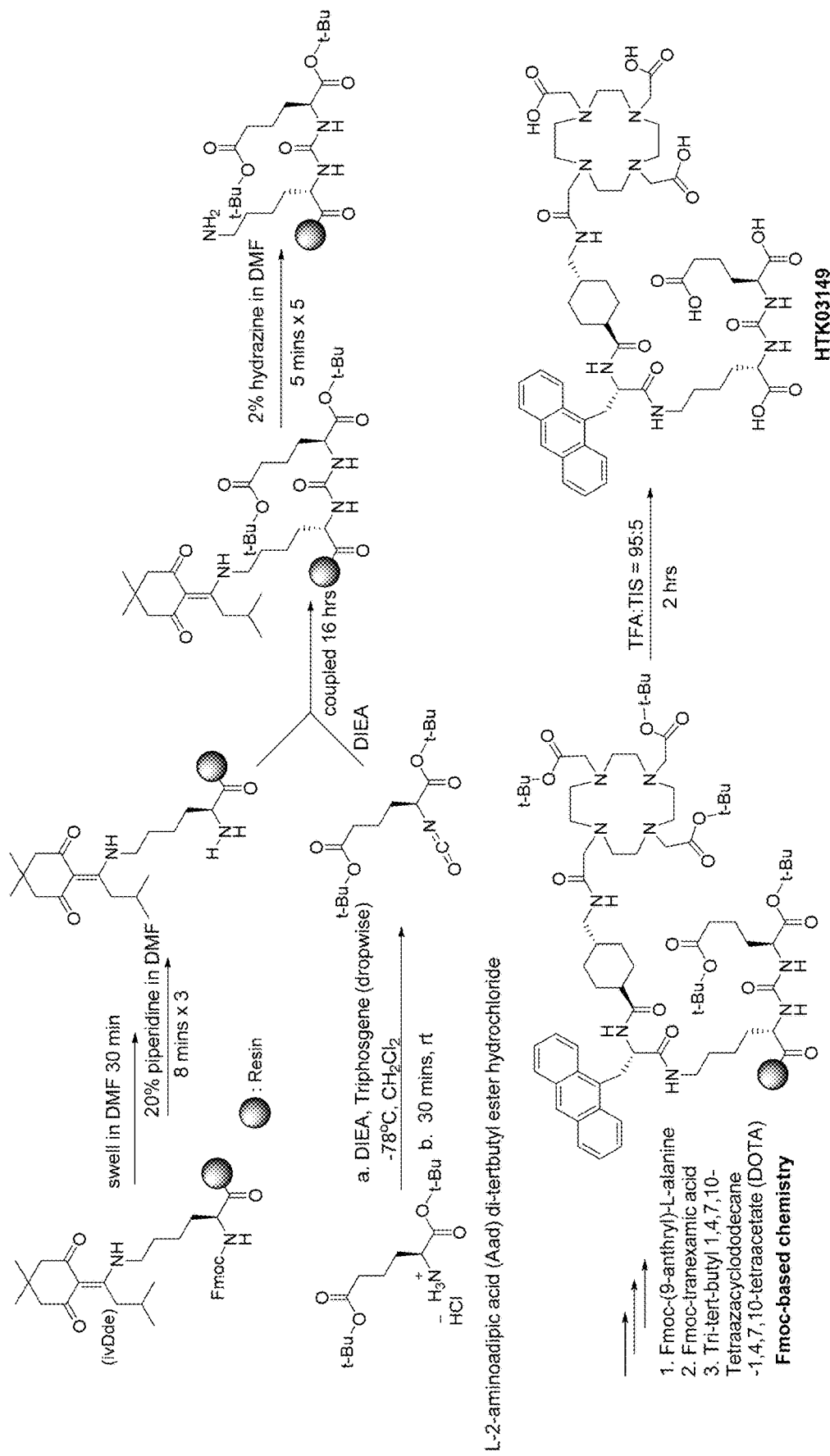
FIG. 2 shows a synthetic scheme for HTK03149 using the solid phase approach.
Figure 3:
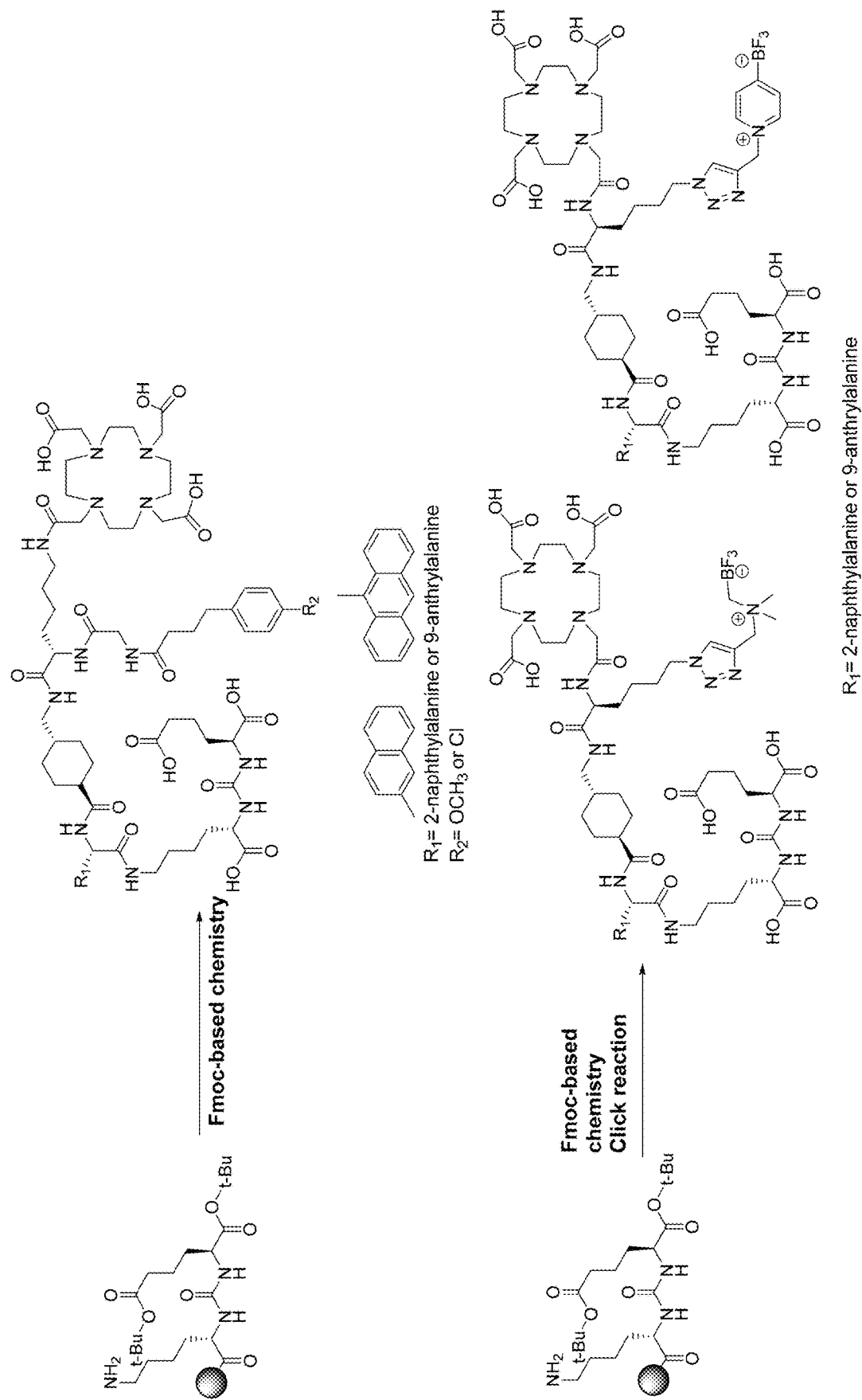
FIG. 3 shows general synthetic schemes for several example compounds incorporating the Lys-ureido-Aad PSMA-binding moiety.
Figure 4:
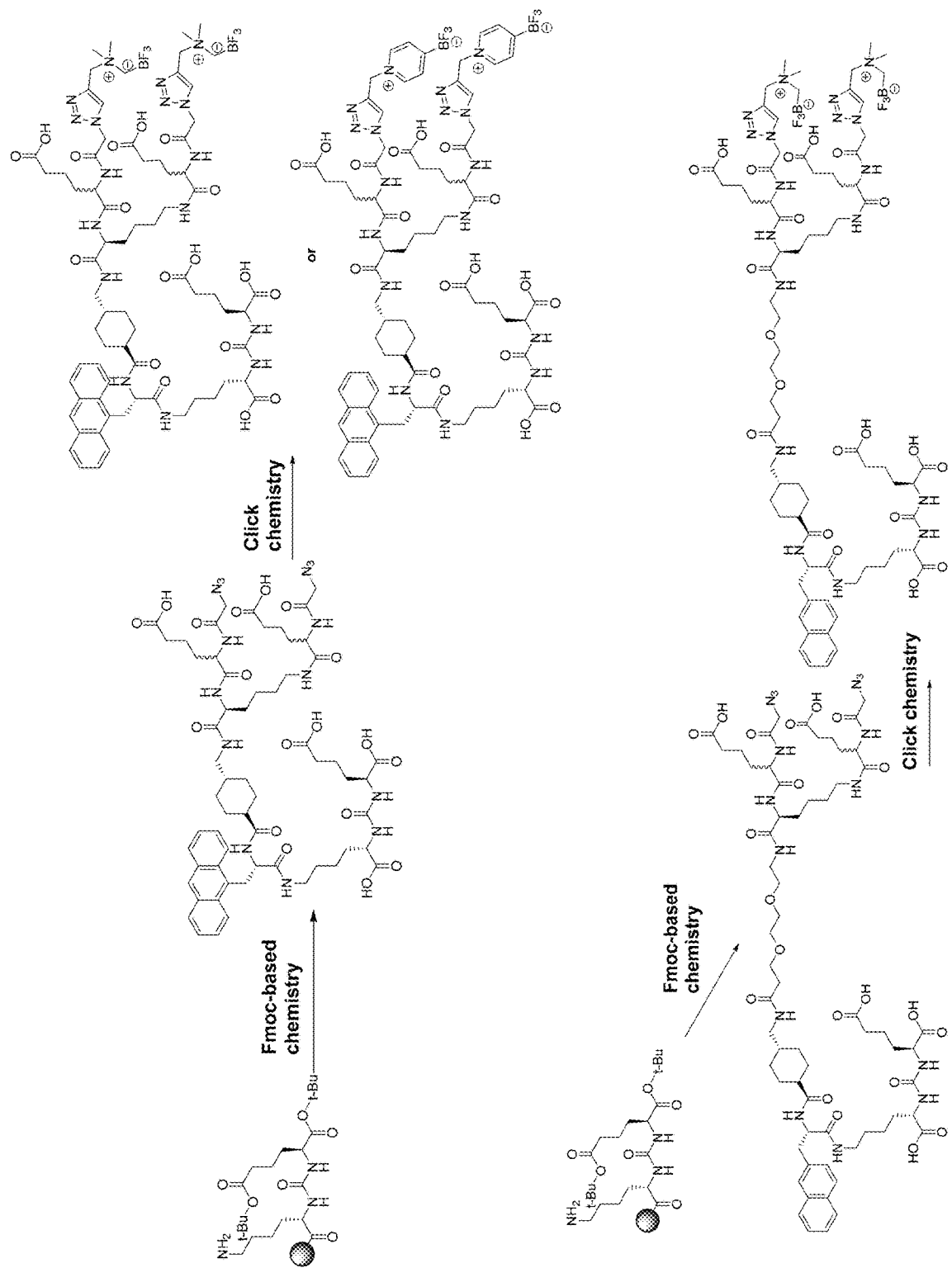
FIG. 4 shows general synthetic schemes for example compounds with two BF₃-labeling groups.

A synthetic scheme for HTK03149 and conjugation with $^{68}$Ga is depicted in FIG. 2 and is explained in further detail in Example 1 below. Examples of general synthetic schemes for additional compounds are shown in FIGS. 3 and 4. Synthesis and testing of exemplary compounds HTK03041, HTK03169, HTK03161, HTK03177, HTK03187, HTK03153, HTK03170, HTK04053, HTK03189 (A and B), HTK04018, HTK04033, HTK04040, HTK04036, HTK04037, HTK04041, HTK04028, HTK04048, HTK04050, HTK03162, and HTK04055 are described in Example 2.

The present invention will be further illustrated in the following examples.

EXAMPLE 1

HTK03149

General Methods

All chemicals and solvents were obtained from commercial sources, and used without further purification. PSMA-targeted peptides were synthesized using a solid phase approach on an AAPPTec (Louisville, Ky.) Endeavor 90 peptide synthesizer. Purification of peptides was performed on an Agilent 1260 Infinity II Preparative System equipped with a model 1260 Infinity II preparative binary pump, a model 1260 Infinity variable wavelength detector (set at 220 nm), and a 1290 Infinity II preparative open-bed fraction collector. The HPLC column used was a preparative column (Gemini, NX-C18, 5μ, 50×30 mm) purchased from Phenomenex. The collected HPLC eluates containing the desired peptide were lyophilized using a Labconco (Kansas City, Mo.) FreeZone 4.5 Plus freeze-drier. Mass analyses were performed using an AB SCIEX (Framingham, Mass.) 4000 QTRAP mass spectrometer system with an ESI ion source. C18 Sep-Pak cartridges (1 cm$^3$, 50 mg) were obtained from Waters (Milford, Mass.). $^{68}$Ga was eluted from an iThemba Labs (Somerset West, South Africa) generator. Radioactivity of $^{68}$Ga-labeled peptides was measured using a Capintec (Ramsey, N.J.) CRC®-25R/W dose calibrator, and the radioactivity of mouse tissues collected from biodistribution studies were counted using a Perkin Elmer (Waltham, Mass.) Wizard2 2480 automatic gamma counter.

Synthesis of HTK03149

The structures of HTK03041 and HTK03149 are shown below, which only differ in that the former has a Glu residue in the PSMA binding moiety (Lys-ureido-Glu) whereas the latter has an Aad in the PSMA binding moiety (Lys-ureido-Aad) and therefore a side chain that is longer by one carbon:

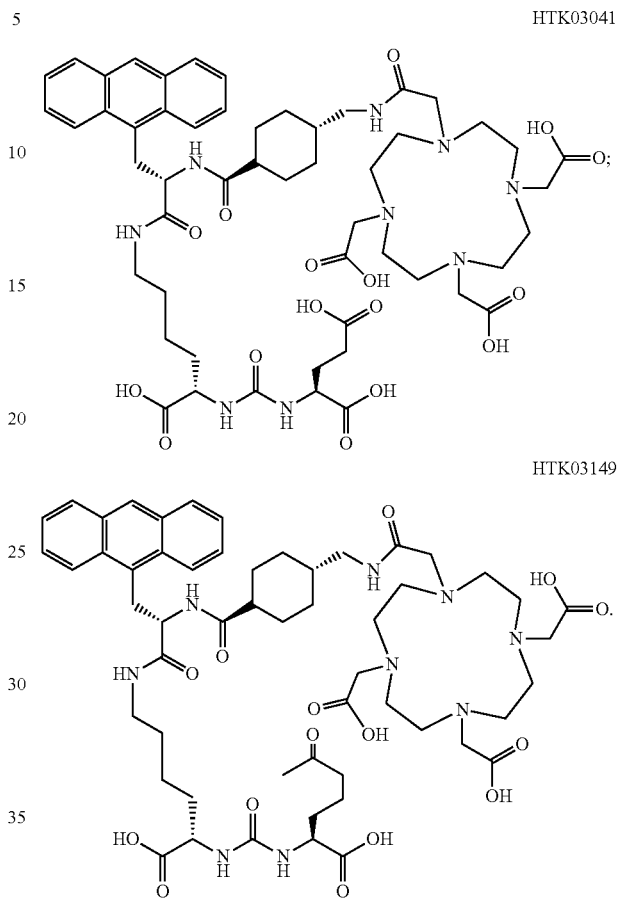

As shown in FIG. 2, the peptidomimetic PSMA-targeting Lys-ureido-Aad moiety was synthesized by solid-phase peptide chemistry. Fmoc-Lys(ivDde)-Wang resin (0.05 mmol, 0.58 mmol/g loading) was suspended in DMF for 30 min. Fmoc was then removed by treating the resin with 20% piperidine in DMF (3×8 min). To generate the isocyanate of the 2-aminoadipyl moiety, a solution of L-2-aminoadipic acid (Aad) di-tertbutyl ester hydrochloride (154.9 mg, 0.5 mmol, 10 eq relative to resin) and diisopropylethylamine (287.4 μL, 1.65 mmol, DIEA) in CH$_2$Cl$_2$ (5 mL) was cooled to −78° C. in a dry ice/acetone bath. Triphosgene (49.0 mg, 0.165 mmol) was dissolved in CH$_2$Cl$_2$ (5 mL), and the resulting solution was added dropwise to the reaction at −78° C. The reaction was then allowed to warm to room temperature and stirred for 30 minutes to give a solution of the isocyanate of the 2-aminoadipyl moiety. After which another 87.1 μL DIEA (0.5 mmole) was added, and then added to the lysine-immobilized resin and reacted for 16 h. After washing the resin with DMF, the ivDde-protecting group was removed with 2% hydrazine in DMF (5×5 min). Fmoc-Ala(9-Anth)-OH was then coupled to the side chain of Lys using Fmoc-protected amino acid (4 eq.), HATU (4 eq.), and N,N-diisopropylethylamine (7 eq.). Afterwards, elongation was continued with the addition of Fmoc-tranexamic acid, and finally DOTA-tris(t-bu)ester (2-(4,7,10-tris(2-(t-butoxy)-2-oxoethyl)-1,4,7,10)-tetraazacyclododecan-1-yl) acetic acid).

The peptide was then deprotected and simultaneously cleaved from the resin by treating with 95/5 trifluoroacetic acid (TFA)/triisopropylsilane (TIS) for 2 h at room temperature. After filtration, the peptide was precipitated by the addition of cold diethyl ether to the TFA solution. The crude peptide was purified by HPLC using the preparative column. The eluates containing the desired peptide were collected, pooled, and lyophilized. The preparative HPLC condition was 24% acetonitrile in water with 0.1% TFA at a flow rate of 30 mL/min. The retention time was 6.9 min. The yield of HTK03149 was 21.4%. ESI-MS: calculated $[M+H]^+$ for HTK03149 $C_{54}H_{75}N_9O_{16}$ 1106.5410; found $[M+H]^+$ 1106.0954.

Synthesis of Ga-HTK03149

To prepare Ga-HTK03149, a solution of HTK03149 was incubated with $GaCl_3$ (5 eq.) in NaOAc buffer (0.1 M, 500 μL, pH 4.2) at 80° C. for 15 min. The reaction mixture was then purified by HPLC using the semi-preparative column, and the HPLC eluates containing the desired peptide were collected, pooled, and lyophilized. The HPLC conditions were 24% acetonitrile in water with 0.1% TFA at a flow rate of 30 mL/min. The retention time was 10.9 min. The yield of Ga-HTK03149 was 90.3%. ESI-MS: calculated $[M+H]^+$ for Ga-HTK03149 $C_{54}H_{74}N_9O_{16}Ga$ 1173.4509; found $[M+H]^+$ 1173.5450.

Cell Culture

LNCaP cell line was obtained from ATCC (LNCaP clone FGC, CRL-1740). It was established from a metastatic site of left supraclavicular lymph node of human prostatic adenocarcinoma. Cells were cultured in PRM I 1640 medium supplemented with 10% FBS, penicillin (100 U/mL) and streptomycin (100 μg/mL) at 37° C. in a humidified incubator containing 5% $CO_2$. Cells grown to 80-90% confluence were then washed with sterile phosphate-buffered saline (1× PBS pH 7.4) and collected by trypsinization. The collected cells concentration was counted with a Hausser Scientific (Horsham, Pa.) Hemacytometer.

PET/CT Imaging and Biodistribution

Imaging and biodistribution experiments were performed using NODSCID 1 L2RγKO male mice. Mice were anesthetized by inhalation with 2% isoflurane in oxygen, and implanted subcutaneously with $1 \times 10^7$ LNCaP cells behind left shoulder. Mice were imaged or used in biodistribution studies when the tumor grew up to reach 5-8 mm in diameter during 5-6 weeks.

Figure 5:
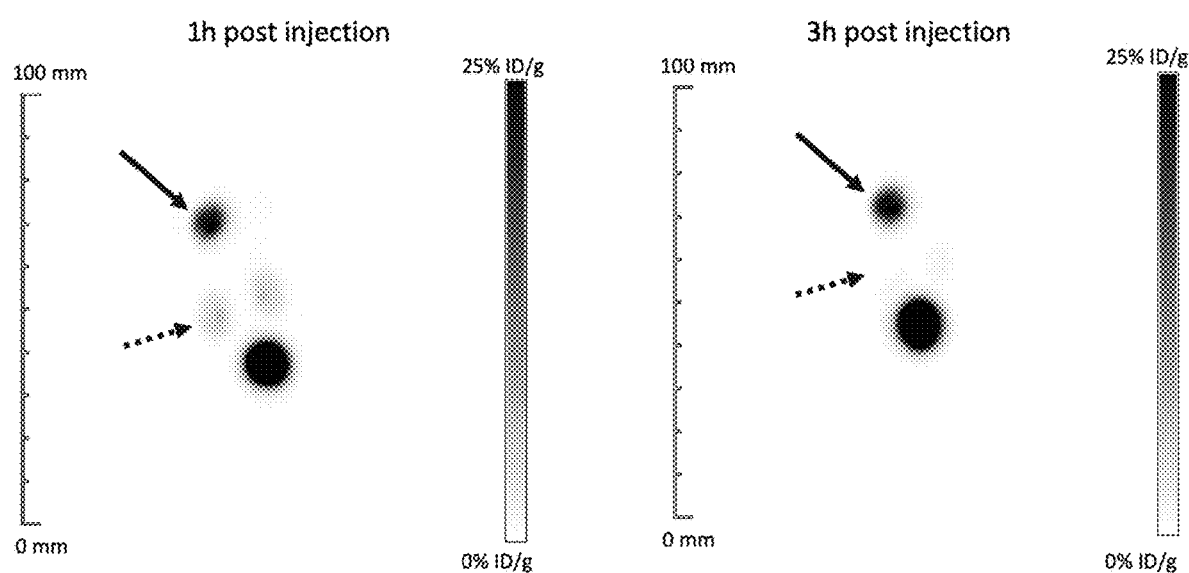
FIG. 5 shows reconstructed ⁶⁸Ga-labeled PET images of a mouse injected with ⁶⁸Ga-HTK03149. Images were obtained at 1 and 3 hours following the intravenous injection of ⁶⁸Ga-HTK03149 in immunodeficient mice bearing LNCaP xenografts. The solid arrow points to very high tumor accumulation. The dotted arrow points to minimal kidney accumulation.
Figure 7:
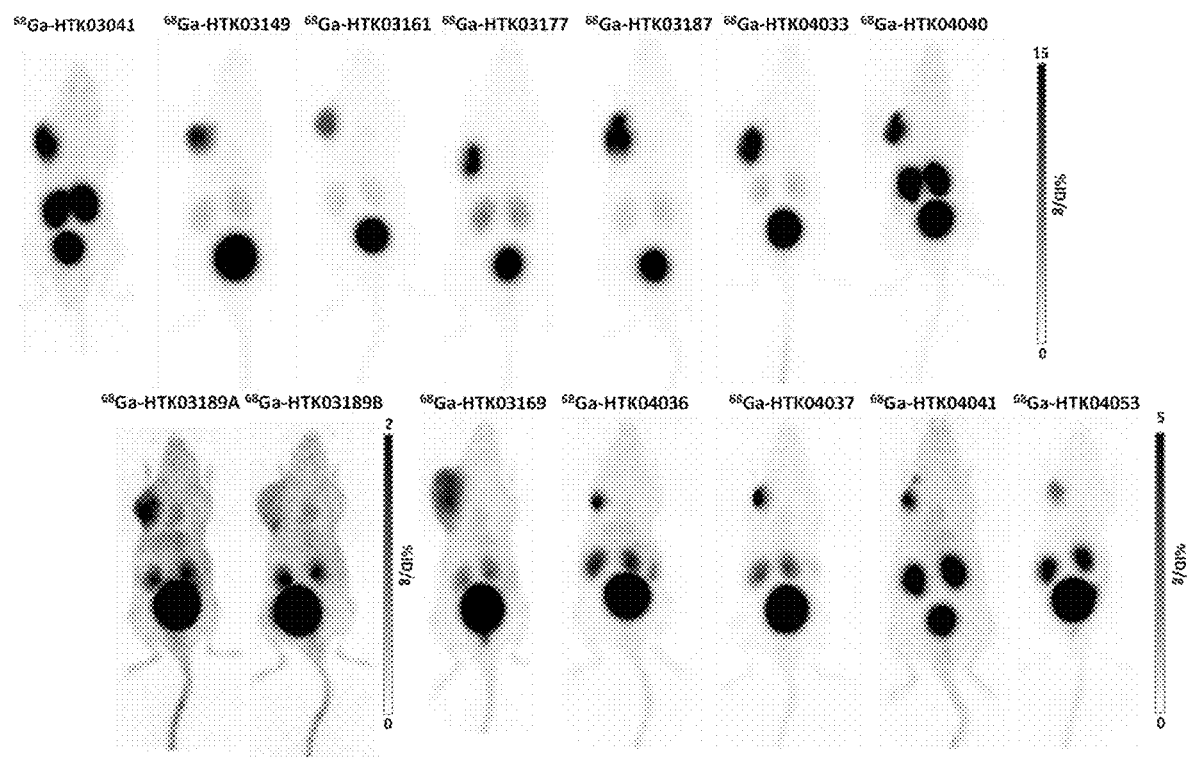
FIG. 7 shows the maximum intensity projection PET/CT images of ⁶⁸Ga-HTK03041, ⁶⁸Ga-HTK03149, ⁶⁸Ga-HTK03161, ⁶⁸Ga-HTK03169, ⁶⁸Ga-HTK03177, ⁶⁸Ga-HTK03187, ⁶⁸Ga-HTK03189A, ⁶⁸Ga-HTK03189B, ⁶⁸Ga-HTK04033, ⁶⁸Ga-HTK04036, ⁶⁸Ga-HTK04037, ⁶⁸Ga-HTK04040, ⁶⁸Ga-HTK04041, and ⁶⁸Ga-HTK04053 acquired at 1 h post-injection.
Figure 8:
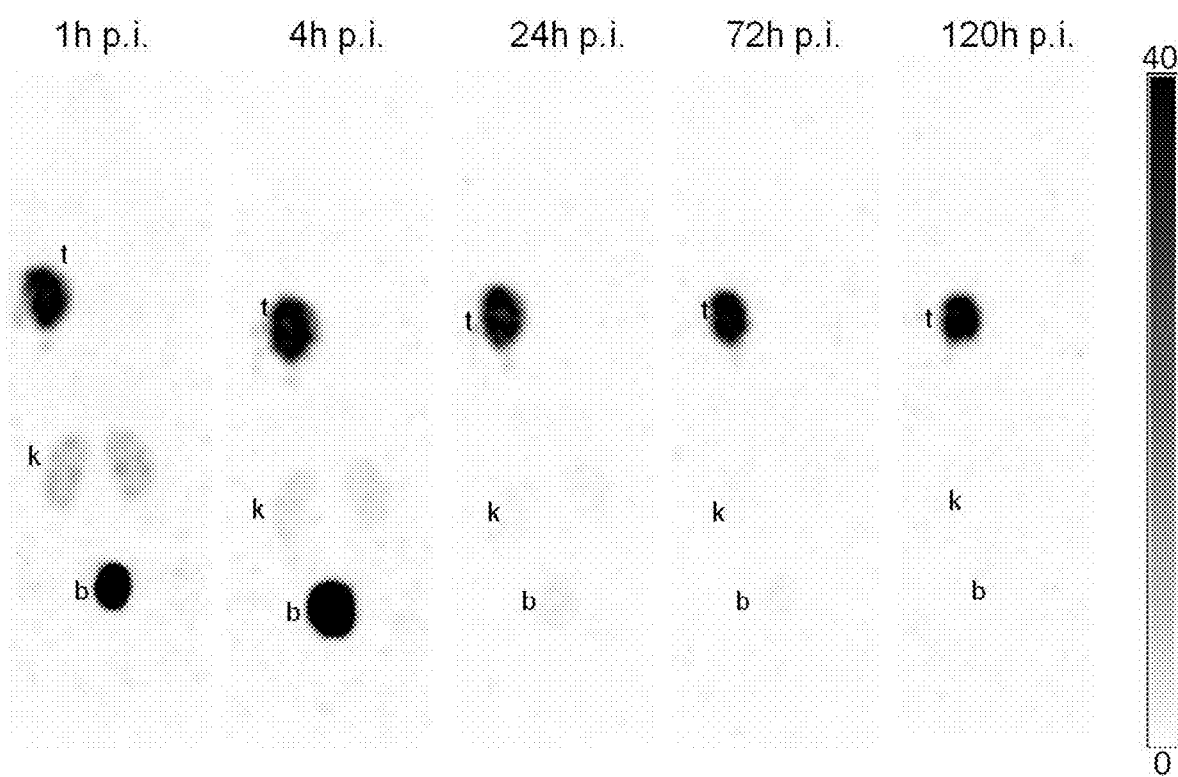
FIG. 8 shows the maximum intensity projection SPECT/CT images of ¹⁷⁷Lu-HTK03149 acquired at 1 h, 4 h, 24 h, 72 h, and 120 h post-injection (t: tumor, k: kidney, b: bladder).
Figure 9:
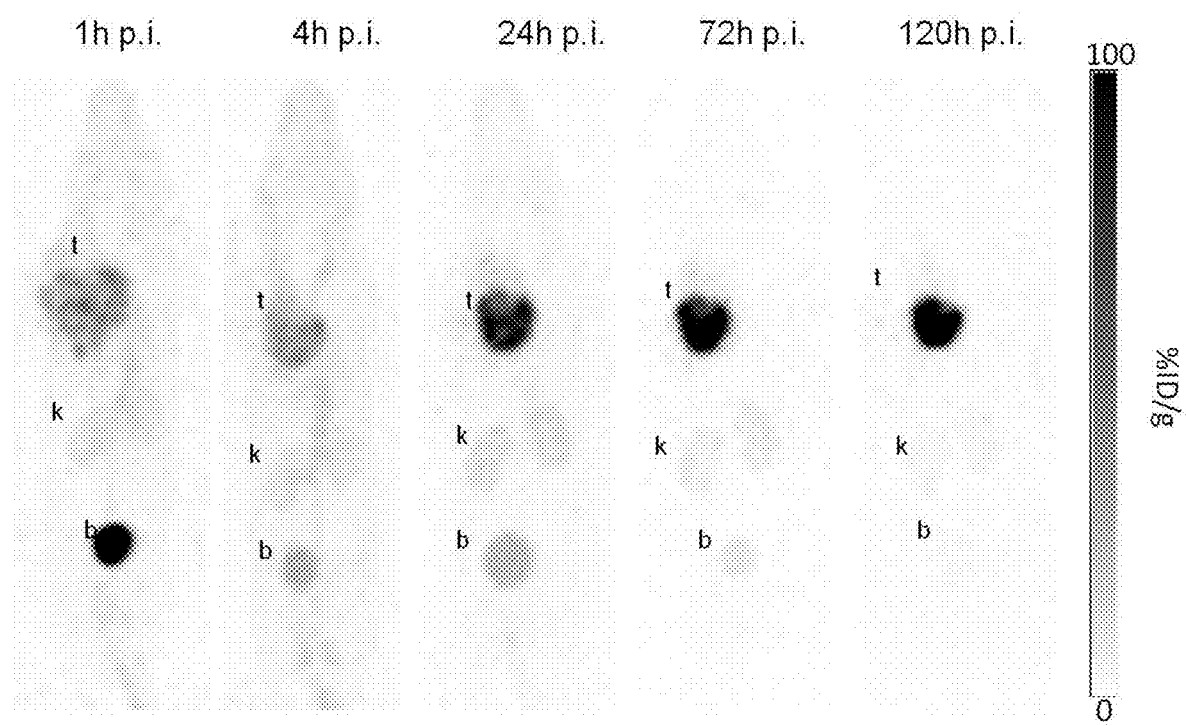
FIG. 9 shows the maximum intensity projection SPECT/CT images of ¹⁷⁷Lu-HTK03153 acquired at 1 h, 4 h, 24 h, 72 h, and 120 h post-injection (t: tumor, k: kidney, b: bladder).
Figure 10:
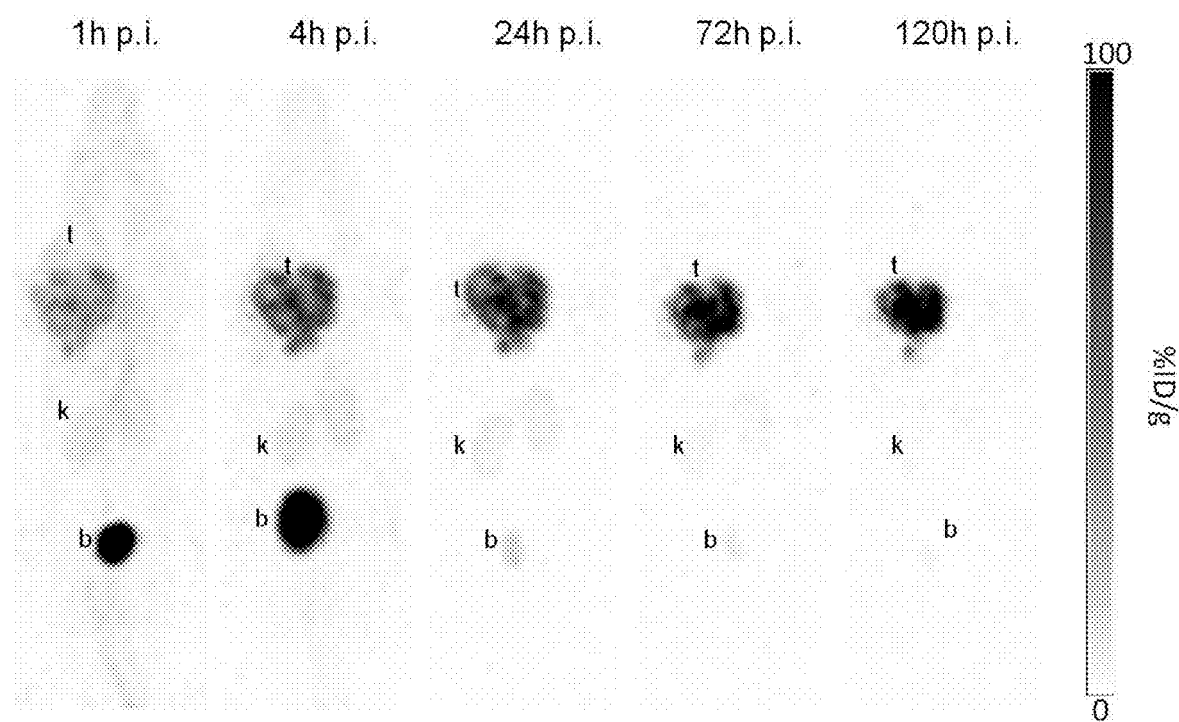
FIG. 10 shows the maximum intensity projection SPECT/CT images of ¹⁷⁷Lu-HTK03170 acquired at 1 h, 4 h, 24 h, 72 h, and 120 h post-injection (t: tumor, k: kidney, b: bladder).
Figure 11:
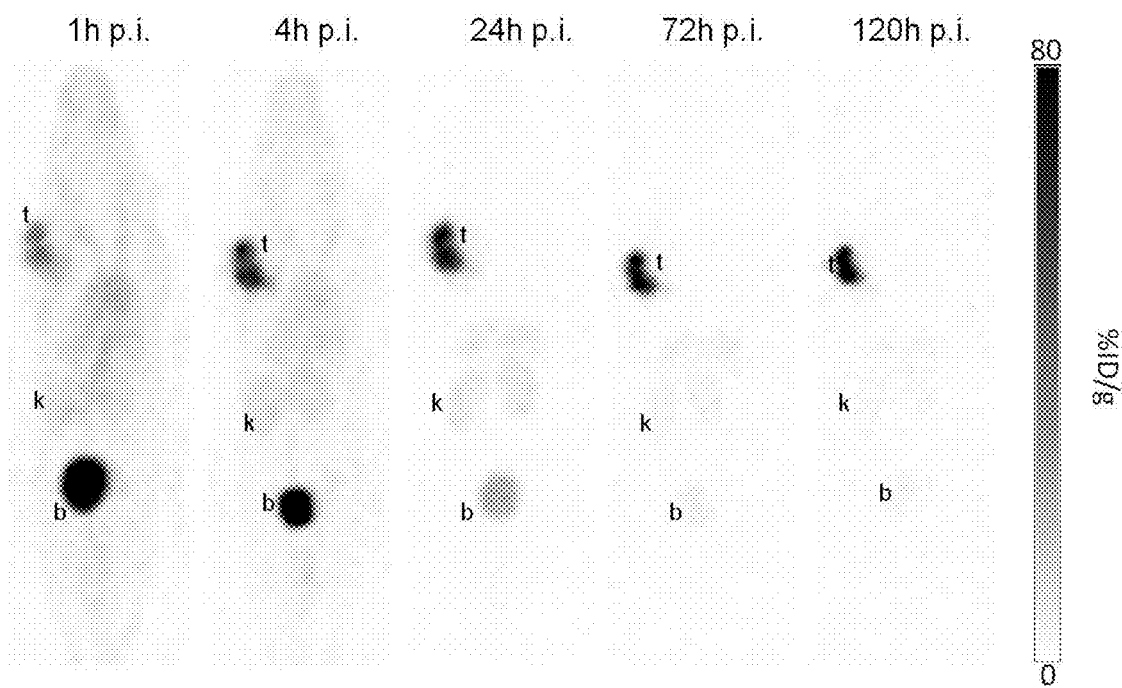
FIG. 11 shows the maximum intensity projection SPECT/CT images of ¹⁷⁷Lu-HTK04028 acquired at 1 h, 4 h, 24 h, 72 h, and 120 h post-injection (t: tumor, k: kidney, b: bladder).
Figure 12:
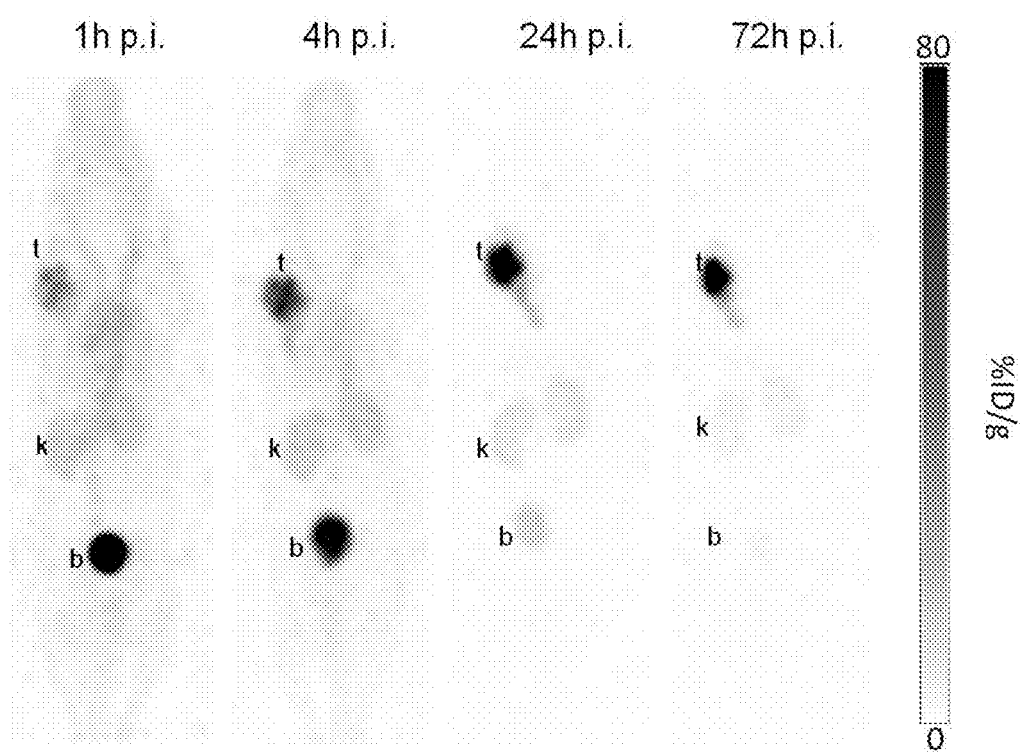
FIG. 12 shows the maximum intensity projection SPECT/CT images of ¹⁷⁷Lu-HTK04048 acquired at 1 h, 4 h, 24 h, 72 h, and 120 h post-injection (t: tumor, k: kidney, b: bladder).
Figure 13:
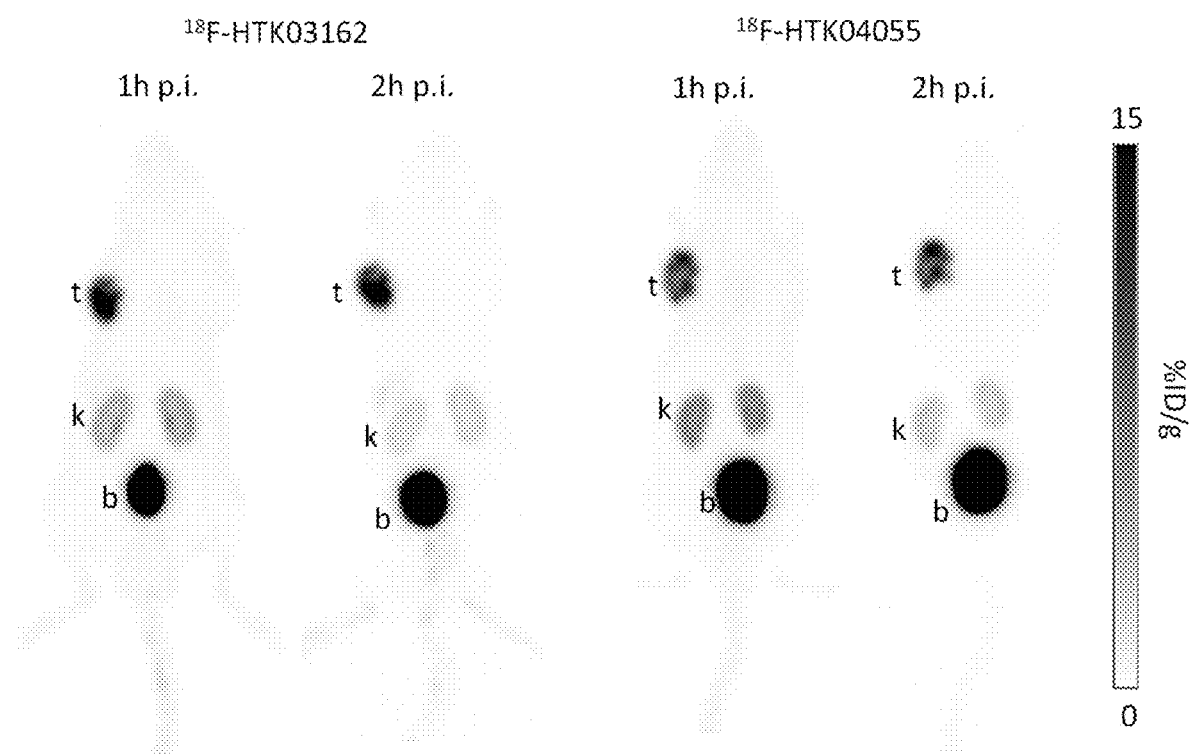
FIG. 13 shows the maximum intensity projection PET/CT images of ¹⁸F-HTK03162 and ¹⁸F-HTK04055 acquired at 1 h and 2 h post-injection (t: tumor, k: kidney, b: bladder).

PET imaging experiments were conducted using Siemens Inveon micro PET/CT scanner. Each tumor bearing mouse was injected 6-8 MBq of Ga-68 labeled tracer through the tail vein under anesthesia (2% isoflurane in oxygen). The mice were allowed to recover and roam freely in their cage. After 50 min, the mice were sedated again with 2% isoflurane in oxygen inhalation and positioned in the scanner. A 10-min CT scan was conducted first for localization and attenuation correction after segmentation for reconstructing the PET images. Then, a 10-min static PET imaging was performed to determined uptake in tumor and other organs. The mice were kept warm by a heating pad during acquisition. For biodistribution studies, the mice were injected with the radiotracer as described above. The mice was anesthetized with 2% isoflurane inhalation, and euthanized by $CO_2$ inhalation. Blood was withdrawn immediately from the heart, and the organs/tissues of interest were collected. The collected organs/tissues were weighed and counted using a Perkin Elmer (Waltham, Mass.) Wizard2 2480 gamma counter. The uptake in each organ/tissue was normalized to the injected dose using a standard curve, and expressed as the percentage of the injected dose per gram of tissue (% ID/g). FIG. 5 shows images obtained at 1 and 3 hours following the intravenous injection of $^{68}$Ga-HTK03149. The images show very high tumour accumulation (solid arrow) with minimal kidney accumulation (dotted arrow) and very low activity in other organs.

Tables 5A and 5B show biodistribution data for HTK03149 at 1 hr and 3 hr post-injection, and Table 6 shows biodistribution data for HTK03041 at 1 hr post-injection.

TABLE 5A

Biodistribution data and tumor-to-background contrast ratios of $^{68}$Ga-labeled HTK03149 in mice bearing PSMA-expressing LNCAP cancer xenografts at 1 h post-injection.

| Tissue (% ID/g) | $^{68}$Ga-HTK03149 (1 hour post injection) | | | | | | | |
|---|---|---|---|---|---|---|---|---|
| | M1 | M2 | M3 | M4 | M5 | M6 | M7 | Average |
| Blood | 0.90 | 0.83 | 0.97 | 1.32 | 0.97 | 0.81 | 0.95 | 0.96 ± 0.17 |
| Urine | 488.21 | 473.17 | 417.73 | 258.22 | 330.48 | 169.39 | 215.32 | 336 ± 127 |
| Fat | 0.09 | 0.06 | 0.16 | | 0.19 | 0.45 | 0.40 | 0.22 ± 0.16 |
| Seminal | 17.94 | 0.68 | 15.91 | 1.91 | 7.13 | 0.49 | 1.14 | 6.46 ± 7.52 |
| Testes | 0.28 | 0.19 | 0.28 | 0.59 | 0.27 | 0.47 | 0.56 | 0.38 ± 0.16 |
| Intestine | 0.35 | 0.22 | 0.41 | 0.26 | 0.26 | 0.34 | 0.26 | 0.30 ± 0.07 |
| Stomach | 0.07 | 0.06 | 0.18 | 0.08 | 0.07 | 0.07 | 0.09 | 0.09 ± 0.04 |
| Spleen | 0.36 | 0.33 | 0.36 | 0.49 | 0.25 | 0.26 | 0.56 | 0.37 ± 0.12 |
| Liver | 0.34 | 0.21 | 0.67 | 0.48 | 0.23 | 0.23 | 0.28 | 0.35 ± 0.17 |
| Pancreas | 0.14 | 0.15 | 0.21 | 0.19 | 0.15 | 0.14 | 0.21 | 0.17 ± 0.03 |
| Adrenal glands | 0.30 | 0.31 | 0.33 | 1.03 | 0.38 | 0.44 | 0.46 | 0.46 ± 0.26 |
| Kidneys | 4.27 | 4.63 | 4.09 | 17.66 | 6.34 | 3.92 | 6.66 | 6.79 ± 4.91 |
| Lungs | 0.67 | 0.63 | 0.73 | 1.63 | 0.68 | 0.54 | 0.87 | 0.82 ± 0.37 |
| Heart | 0.26 | 0.23 | 0.32 | 0.43 | 0.27 | 0.23 | 0.30 | 0.29 ± 0.07 |
| Tumor | 19.95 | 9.52 | 15.18 | 20.15 | 17.76 | 19.78 | 52.40 | 22.1 ± 13.9 |
| Muscle | 0.12 | 0.13 | 0.21 | 0.13 | 0.11 | 0.13 | | 0.14 ± 0.04 |
| Bone | 0.12 | 0.56 | 0.09 | 0.11 | 0.08 | 0.08 | 0.14 | 0.10 ± 0.03 |
| Brain | 0.02 | 0.02 | 0.02 | 0.04 | 0.02 | 0.02 | 0.02 | 0.02 ± 0.01 |
| Tail | 0.68 | 0.45 | 0.69 | 1.45 | 0.71 | 0.45 | 1.59 | 0.86 ± 0.47 |
| Thyroid | 0.23 | 0.23 | 0.27 | 0.44 | 0.27 | 0.24 | 0.35 | 0.29 ± 0.08 |
| Salivary | 0.19 | 0.19 | 0.18 | 0.30 | 0.27 | 0.20 | 0.25 | 0.23 ± 0.05 |
| Lacrimal | 0.11 | 0.15 | 0.05 | 0.13 | 0.10 | 0.08 | 0.10 | 0.10 ± 0.03 |
| Tumor: Muscle | 168.25 | | 119.94 | 95.71 | 139.14 | 176.19 | 410.47 | 185 ± 114 |
| Tumor: Blood | 22.27 | 11.44 | 15.69 | 15.26 | 18.38 | 24.47 | 55.21 | 23.2 ± 14.8 |
| Tumor: Kidney | 4.67 | 2.06 | 3.71 | 1.14 | 2.80 | 5.05 | 7.87 | 3.9 ± 2.2 |
| Tumor: Salivary | 103.76 | 50.85 | 84.60 | 66.28 | 64.67 | 98.55 | 210.42 | 97.0 ± 53.5 |

TABLE 5B

Biodistribution data and tumor-to-background contrast ratios of $^{68}$Ga-labeled HTK03149 in mice bearing PSMA-expressing LNCAP cancer xenografts at 3 h post-injection.

| Tissue | $^{68}$Ga-HTK03149 (3 hours post injection) | | | | | |
|---|---|---|---|---|---|---|
| (% ID/g) | M1 | M2 | M3 | M4 | M5 | Average |
| Blood | 0.21 | 0.22 | 0.38 | 0.40 | 0.54 | 0.35 ± 0.14 |
| Urine | 53.82 | 162.18 | 237.96 | 33.15 | 255.02 | 148 ± 102 |
| Fat | 0.21 | 0.25 | 0.07 | 0.05 | 0.22 | 0.16 ± 0.09 |
| Seminal | 0.08 | 1.97 | 1.78 | 0.05 | 2.09 | 1.19 ± 1.04 |
| Testes | 0.13 | 0.13 | 0.06 | 0.11 | 0.15 | 0.11 ± 0.03 |
| Intestine | 0.17 | 0.13 | 0.17 | 0.24 | 0.21 | 0.18 ± 0.04 |
| Stomach | 0.03 | 0.02 | 0.03 | 0.03 | 0.05 | 0.03 ± 0.01 |
| Spleen | 0.25 | 0.30 | 0.16 | 0.17 | 0.30 | 0.24 ± 0.07 |
| Liver | 0.11 | 0.13 | 0.12 | 0.15 | 0.15 | 0.13 ± 0.02 |
| Pancreas | 0.05 | 0.05 | 0.04 | 0.07 | 0.09 | 0.06 ± 0.02 |
| Adrenal glands | 0.54 | 0.46 | 0.25 | 0.68 | 0.38 | 0.46 ± 0.16 |
| Kidneys | 2.08 | 1.67 | 1.88 | 1.87 | 4.14 | 2.33 ± 1.02 |
| Lungs | 0.20 | 0.20 | 0.17 | 0.27 | 0.27 | 0.22 ± 0.05 |
| Heart | 0.09 | 0.08 | 0.09 | 0.08 | 0.12 | 0.09 ± 0.02 |
| Tumor | 44.05 | 39.21 | 34.49 | 15.81 | 34.21 | 33.55 ± 10.70 |
| Muscle | 0.06 | 0.08 | 0.02 | 0.05 | 0.04 | 0.05 ± 0.02 |
| Bone | 0.10 | 0.14 | 0.06 | 0.04 | 0.09 | 0.08 ± 0.04 |
| Brain | 0.02 | 0.02 | 0.01 | 0.01 | 0.02 | 0.02 ± 0.01 |
| Tail | 0.09 | 0.23 | 0.07 | 0.13 | 0.11 | 0.13 ± 0.06 |
| Thyroid | 0.09 | 0.09 | 0.07 | 0.08 | 0.18 | 0.10 ± 0.04 |
| Salivary | 0.35 | 0.17 | 0.04 | 0.04 | 0.16 | 0.15 ± 0.13 |
| Lacrimal | 0.43 | 0.42 | 0.07 | 0.14 | 0.00 | 0.21 ± 0.20 |
| Tumor: Muscle | 782.04 | 512.04 | 1399.53 | 327.34 | 837.13 | 771 ± 407 |
| Tumor: Blood | 212.16 | 178.07 | 91.50 | 39.81 | 63.38 | 117 ± 75 |
| Tumor: Kidney | 21.21 | 23.42 | 18.37 | 8.47 | 8.27 | 15.95 ± 7.15 |
| Tumor: Salivary | 125.04 | 233.18 | 775.33 | 361.93 | 207.82 | 341 ± 2.57 |

TABLE 6

Biodistribution data and tumor-to-background contrast ratios of $^{68}$Ga-labeled HTK03041 in mice bearing PSMA-expressing LNCAP cancer xenografts at 1 h post-injection.

| Tissue | 68Ga-HTK03041 | | | | | | |
|---|---|---|---|---|---|---|---|
| (% ID/g) | M1 | M2 | M3 | M4 | M5 | M6 | Average |
| Blood | 1.28 | 1.73 | 1.35 | 1.72 | 0.95 | 1.52 | 1.43 ± 0.30 |
| Urine | 108.02 | 143.03 | 360.39 | 142.02 | 136.34 | 146.19 | 172.67 ± 93.01 |
| Fat | 2.31 | 1.91 | 1.63 | 1.58 | 3.14 | 1.82 | 2.06 ± 0.59 |
| Seminal | 1.17 | 0.81 | 1.40 | 1.00 | 1.14 | 0.65 | 1.03 ± 0.27 |
| Testes | 1.14 | 1.41 | 1.36 | 1.57 | 1.53 | 1.03 | 1.34 ± 0.22 |
| Intestine | 1.15 | 1.28 | 1.03 | 1.28 | 1.25 | 0.82 | 1.14 ± 0.18 |
| Stomach | 0.30 | 0.50 | 0.27 | 0.49 | 0.50 | 0.36 | 0.41 ± 0.11 |
| Spleen | 7.04 | 13.14 | 5.11 | 10.87 | 11.23 | 6.31 | 8.95 ± 3.22 |
| Liver | 1.26 | 1.43 | 1.45 | 1.61 | 1.58 | 0.93 | 1.38 ± 0.25 |
| Pancreas | 1.34 | 1.43 | 1.30 | 1.72 | 1.60 | 1.43 | 1.47 ± 0.16 |
| Adrenal glands | 7.48 | 7.13 | 5.34 | 11.16 | 11.24 | 11.02 | 8.90 ± 2.56 |
| Kidneys | 177.26 | 207.66 | 161.12 | 183.52 | 161.36 | 129.20 | 170.02 ± 26.35 |
| Lungs | 3.63 | 4.78 | 4.19 | 5.19 | 4.47 | 3.66 | 4.32 ± 0.62 |
| Heart | 1.66 | 1.96 | 1.72 | 2.06 | 1.97 | 1.54 | 1.82 ± 0.21 |
| Tumor | 33.79 | 24.10 | 19.61 | 16.63 | 25.03 | 19.40 | 23.09 ± 6.11 |
| Muscle | 0.62 | 0.80 | 0.75 | 0.84 | 0.83 | 0.69 | 0.75 ± 0.09 |
| Bone | 0.99 | 1.18 | 0.70 | 1.39 | 1.53 | 1.98 | 1.29 ± 0.45 |
| Brain | 0.07 | 0.07 | 0.06 | 0.11 | 0.12 | 0.18 | 0.10 ± 0.05 |
| Tail | 2.12 | 1.29 | 1.20 | 1.65 | 1.00 | 0.90 | 1.36 ± 0.45 |
| Thyroid | 2.32 | 2.47 | 2.21 | 2.68 | 3.23 | 1.97 | 2.48 ± 0.44 |
| Salivary | 4.15 | 5.60 | 3.83 | 5.47 | 6.10 | 4.82 | 4.99 ± 0.88 |
| Lacrimal | 0.96 | 1.38 | 0.56 | 2.65 | 4.29 | 4.82 | 2.44 ± 1.79 |
| Tumor: Muscle | 54.90 | 30.01 | 26.10 | 19.71 | 30.29 | 28.28 | 31.55 ± 12.08 |
| Tumor: Blood | 26.37 | 13.93 | 14.48 | 9.66 | 26.33 | 12.78 | 17.26 ± 7.24 |
| Tumor: Kidney | 0.19 | 0.12 | 0.12 | 0.09 | 0.16 | 0.15 | 0.14 ± 0.04 |
| Tumor: Salivary | 8.14 | 4.31 | 5.12 | 3.04 | 4.10 | 4.03 | 4.79 ± 1.77 |

Comparing Tables 5A and 5B (HTK03149) to Table 6 (HTK03041), it has therefore been demonstrated that the longer side chain of the Lys-ureido-Aad PSMA-targeting moiety compared to Lys-ureido-Glu significantly decreases the uptake of HTK03149 in kidney and salivary gland compared to HTK03041 without sacrificing the tumour-to-background contrast ratio. Modification of the Glu residue therefore results in an improved imaging and therapeutic agents for PSMA-expressing diseases/conditions.

EXAMPLE 2

HTK03041, HTK03169, HTK03161, HTK03177, HTK03187, HTK03153, HTK03170, HTK04053, HTK03189 (A and B), HTK04018, HTK04033, HTK04040, HTK04036, HTK04037, HTK04041, HTK04028, HTK04048, HTK04050, HTK03162, and HTK04055

General Methods

PSMA-targeted peptides were synthesized using solid phase approach on an AAPPTec (Louisville, Ky.) Endeavor 90 peptide synthesizer. Purification and quality control of cold and radiolabeled peptides were performed on (1) Agilent HPLC systems equipped with a model 1200 quaternary pump, a model 1200 UV absorbance detector (set at 220 nm), and a Bioscan (Washington, D.C.) NaI scintillation detector. The operation of Agilent HPLC systems was controlled using the Agilent ChemStation software. The HPLC columns used were a semi-preparative column (Luna C18, 5μ, 250×10 mm) and an analytical column (Luna C18, 5μ, 250×4.6 mm) purchased from Phenomenex (Torrance, Calif.); or (2) an Agilent 1260 Infinity II Preparative System equipped with a model 1260 Infinity II preparative binary pump, a model 1260 Infinity variable wavelength detector (set at 220 nm), and a 1290 Infinity II preparative open-bed fraction collector. The HPLC column used was a preparative column (Gemini, NX-C18, 5μ, 50×30 mm) purchased from Phenomenex. The collected HPLC eluates containing the desired peptide were lyophilized using a Labconco (Kansas City, Mo.) FreeZone 4.5 Plus freeze-drier. Mass analyses were performed using an AB SCIEX (Framingham, Mass.) 4000 QTRAP mass spectrometer system with an ESI ion source. C18 Sep-Pak cartridges (1 cm$^3$, 50 mg) were obtained from Waters (Milford, Mass.). Radioactivity of $^{68}$Ga-labeled peptides was measured using a Capintec (Ramsey, N.J.) CRC®-25R/W dose calibrator, and the radioactivity of mouse tissues collected from biodistribution studies were counted using a Perkin Elmer (Waltham, Mass.) Wizard2 2480 automatic gamma counter.

The structures of HTK03041, HTK03149, HTK03169, HTK03161, HTK03177, HTK03187, HTK03153, HTK03170, HTK04053, HTK03189A, HTK03189B, HTK04018, HTK04033, HTK04040, HTK04036, HTK04037, HTK04041, HTK04028, HTK04048, HTK04050, HTK03162, and HTK04055 are shown in FIG. 6.

Synthesis of HTK03169 and HTK04053

The peptidomimetic PSMA-targeting Aad-ureido-lysine moiety was synthesized by solid-phase peptide chemistry. Fmoc-Lys(ivDde)-Wang resin (0.10 mmol, 0.58 mmol/g loading) was suspended in DMF for 30 min. Fmoc was then removed by treating the resin with 20% piperidine in DMF (3×8 min). To generate the isocyanate of the 2-aminoadipyl moiety, a solution of L-2-aminoadipic acid (Aad) di-tert-butyl ester hydrochloride (154.9 mg, 0.5 mmol, 5 eq relative to resin) and diisopropylethylamine (287.4 μL, 1.65 mmol, DIEA) in CH$_2$Cl$_2$ (5 mL) was cooled to −78° C. in a dry ice/acetone bath. Triphosgene (49.0 mg, 0.165 mmol) was dissolved in CH$_2$Cl$_2$ (5 mL), and the resulting solution was added dropwise to the reaction at −78° C. The reaction was then allowed to warm to room temperature and stirred for 30 minutes to give a solution of the isocyanate of the 2-aminoadipyl moiety. After which another 87.1 μL DIEA (0.5 mmole) was added, and then added to the lysine-immobilized resin and reacted for 16 h. After washing the resin with DMF, the ivDde-protecting group was removed with 2% hydrazine in DMF (5×5 min). Fmoc-2-naphthylalanine (for HTK03169) or Fmoc-3-iodo-L-phenylalanine (for HTK04053) was then coupled to the side chain of Lys using Fmoc-protected amino acid (4 eq.), HATU (4 eq.), and DIEA (7 eq.). Afterwards, elongation was continued with the addition of Fmoc-tranexamic acid, and finally DOTA-tris(t-bu)ester (2-(4,7,10-tris(2-(t-butoxy)-2-oxoethyl)-1,4,7,10)-tetraazacyclododecan-1-yl)acetic acid).

The peptide was then deprotected and simultaneously cleaved from the resin by treating with 95/5 trifluoroacetic acid (TFA)/triisopropylsilane (TIS) for 2 h at room temperature. After filtration, the peptide was precipitated by the addition of cold diethyl ether to the TFA solution. The crude peptide was purified by HPLC using the preparative or semi-preparative column. The eluates containing the desired peptide were collected and lyophilized. For HTK03169, the preparative HPLC condition was 20% acetonitrile in water with 0.1% TFA at a flow rate of 30 mL/min. The retention time was 9.0 min. The yield was 29.6%. ESI-MS: calculated [M+H]$^+$ for HTK03169 C$_{50}$H$_{73}$N$_9$O$_{16}$ 1056.5254; found [M+H]$^+$ 1056.5647. For HTK04053, the semi-preparative HPLC condition was 24% acetonitrile in water with 0.1% TFA at a flow rate of 4.5 mL/min. The retention time was 11.9 min. The yield was 47.6%. ESI-MS: calculated [M+H]$^+$ for HTK04053 C$_{46}$H$_{70}$N$_9$O$_{16}$I 1132.4063; found [M+H]$^+$ 1132.5523.

Synthesis of HTK03041, HTK03161, HTK03177, HTK03187, HTK03189 (A and B), HTK04018, HTK04033, and HTK04040

The peptidomimetic PSMA-targeting Asp- (for HTK03161), Glu- (for HTK03041), S-carboxymethylcystein- (for HTK03177), and O-carboxymethylserine- (for HTK03187), racemic 2-aminopimelic acid- (for HTK03189A and B), 3-(carboxymethyl)sulfonyl-L-alanine- (for HTK04018), (4R)-4-fluoro-Glu- (for HTK04040) ureido-lysine moieties were synthesized by solid-phase peptide chemistry. Fmoc-Lys(ivDde)-Wang resin (0.1 mmol, 0.58 mmol/g loading) was suspended in DMF for 30 min. Fmoc was then removed by treating the resin with 20% piperidine in DMF (3×8 min). To generate the isocyanate derivative, a solution of L-aspartic acid di-tertbutyl ester hydrochloride (140.9 mg, 0.5 mmol, 5 eq relative to resin), L-glutamic acid di-tertbutyl ester hydrochloride (147.9 mg, 0.5 mmol, 5 eq relative to resin), S-carboxymethylcystein di-tertbutyl ester hydrochloride (163.9 mg, 0.5 mmol, 5 eq relative to resin), O-carboxymethylserine di-tertbutyl ester hydrochloride (155.9 mg, 0.5 mmol, 5 eq relative to resin), 2-aminopimelic acid di-tert-butyl ester hydrochloride (161.9 mg, 0.5 mmol, 5 eq relative to resin), 3-(carboxymethyl)sulfonyl-L-alanine di-tert-butyl ester (179.9 mg, 0.5 mmol, 5 eq relative to resin), (4R)-4-fluoro-L-glutamic acid di-tert-butyl ester hydrochloride (156.6 mg, 0.5 mmol, 5 eq relative to resin), or (4S)-4-fluoro-L-glutamic acid di-tert-butyl ester hydrochloride (156.6 mg, 0.5 mmol, 5 eq relative to resin) and DIEA (287.4 μL, 1.65 mmol, DIEA) in CH$_2$Cl$_2$ (5 mL) was cooled to −78° C. in a dry ice/acetone bath. Triphosgene (49.0 mg, 0.165 mmol) was dissolved in CH$_2$Cl$_2$ (5 mL), and the resulting solution was added dropwise to the reaction at −78° C. The reaction was then allowed to warm to room temperature and stirred for 30 minutes to give a solution of the derivative. After which another 87.1 μL DIEA (0.5 mmole) was added, and then added to the lysine-immobilized resin and reacted for 16 h. After washing the resin with DMF, the ivDde-protecting group was removed with 2% hydrazine in DMF (5×5 min). Fmoc-Ala(9-Anth)-OH was then coupled to the side chain of Lys using Fmoc-protected amino acid (4 eq.), HATU (4 eq.), and DIEA (7 eq.). Afterwards, elongation was continued with the addition of Fmoc-tranexamic acid, and finally DOTA-tris(t-bu)ester.

The peptide was then deprotected and simultaneously cleaved from the resin by treating with 95/5 trifluoroacetic acid (TFA)/triisopropylsilane (TIS) for 2 h at room temperature. After filtration, the peptide was precipitated by the addition of cold diethyl ether to the TFA solution. The crude peptide was purified by HPLC using the preparative or semi-preparative column. The eluates containing the desired peptide were collected and lyophilized. For HTK03161, the preparative HPLC condition was 23% acetonitrile in water with 0.1% TFA at a flow rate of 30 mL/min. The retention time was 7.9 min. The yield was 17.2%. ESI-MS: calculated $[M+H]^+$ for HTK03161 $C_{52}H_{72}N_9O_{16}$ 1078.5097; found $[M+H]^+$ 1078.4720. For HTK03041, the semi-preparative HPLC condition was 31% acetonitrile in water with 0.1% TFA at a flow rate of 4.5 mL/min. The retention time was 7.2 min. The yield was 27%. ESI-MS: calculated $[M+H]^+$ for HTK03161 $C_{53}H_{74}N_9O_{16}$ 1092.5; found $[M+H]^+$ 1092.6. For HTK03177, the preparative HPLC condition was 24% acetonitrile in water with 0.1% TFA at a flow rate of 30 mL/min. The retention time was 8.2 min. The yield was 34.0%. ESI-MS: calculated $[M+H]^+$ for HTK03177 $C_{53}H_{73}N_9O_{16}S$ 1124.4974; found $[M+H]^+$ 1124.4980. For HTK03187, the semi-preparative HPLC condition was 28% acetonitrile in water with 0.1% TFA at a flow rate of 4.5 mL/min. The retention time was 10.4 min. The yield was 30.3%. ESI-MS: calculated $[M+H]^+$ for HTK03187 $C_{53}H_{73}N_9O_{17}$ 1108.5203; found $[M+H]^+$ 1108.5101. For HTK03189, the semi-preparative HPLC condition was 28% acetonitrile in water with 0.1% TFA at a flow rate of 4.5 mL/min. The retention time of HTK03189A was 13.9 min, the yield was 19.7%. The retention time of HTK03189B was 15.5 min, the yield was 15.6%. ESI-MS: calculated $[M+H]^+$ for HTK03189 $C_{55}H_7N_9O_{16}$ 1120.5567; found $[M+H]^+$ 1120.5865 for HTK03189A and 1120.5118 for HTK03189B. For HTK04018, the semi-preparative HPLC condition was 30% acetonitrile in water with 0.1% TFA at a flow rate of 4.5 mL/min. The retention time was 9.2 min. ESI-MS: calculated $[M+H]^+$ for HTK04018 $C_{53}H_{73}N_9O_{18}S$ 1156.4873; found $[M+H]^+$ 1156.3678. For HTK04033, the preparative HPLC condition was 23% acetonitrile in water with 0.1% TFA at a flow rate of 30 mL/min. The retention time was 8.5 min. The yield was 45.7%. ESI-MS: calculated $[M+H]^+$ for HTK04033 $C_{53}H_{72}N_9O_{16}F$ 1110.5159; found $[M+H]^+$ 1110.3887. For HTK04040, the preparative HPLC condition was 23% acetonitrile in water with 0.1% TFA at a flow rate of 30 mL/min. The retention time was 9.4 min. The yield was 33.3%. ESI-MS: calculated $[M+H]^+$ for HTK04040 $C_{53}H_{72}N_9O_{16}F$ 1110.5159; found $[M+H]^+$ 1110.0578.

Synthesis of HTK04036, HTK04037, and HTK04041

The peptidomimetic PSMA-targeting Aad-ureido-lysine moiety was synthesized by solid-phase peptide chemistry. Fmoc-Lys(ivDde)-Wang resin (0.10 mmol, 0.58 mmol/g loading) was suspended in DMF for 30 min. Fmoc was then removed by treating the resin with 20% piperidine in DMF (3×8 min). To generate the isocyanate of the 2-aminoadipyl moiety, a solution of L-2-aminoadipic acid (Aad) di-tert-butyl ester hydrochloride (154.9 mg, 0.5 mmol, 5 eq relative to resin) and DIEA (287.4 μL, 1.65 mmol) in $CH_2Cl_2$ (5 mL) was cooled to −78° C. in a dry ice/acetone bath. Triphosgene (49.0 mg, 0.165 mmol) was dissolved in $CH_2Cl_2$ (5 mL), and the resulting solution was added dropwise to the reaction at −78° C. The reaction was then allowed to warm to room temperature and stirred for 30 minutes to give a solution of the isocyanate of the 2-aminoadipyl moiety. After which another 87.1 μL DIEA (0.5 mmole) was added, and then added to the lysine-immobilized resin and reacted for 16 h. After washing the resin with DMF, the ivDde-protecting group was removed with 2% hydrazine in DMF (5×5 min). Fmoc-Ala(9-Anth)-OH was then coupled to the side chain of Lys using Fmoc-protected amino acid (4 eq.), HATU (4 eq.), and DIEA (7 eq.). Afterwards, elongation was continued with the addition of Fmoc-4-aminomethyl-phenylacetic acid (for HTK04036), Fmoc-3-aminomethyl-phenylacetic acid (for HTK04037), or Fmoc-4-aminobenzoic acid (for HTK04041) and finally DOTA-tris(t-bu)ester.

The peptide was then deprotected and simultaneously cleaved from the resin by treating with 95/5 TFA/TIS for 2 h at room temperature. After filtration, the peptide was precipitated by the addition of cold diethyl ether to the TFA solution. The crude peptide was purified by HPLC using the preparative or semi-preparative column. The eluates containing the desired peptide were collected and lyophilized. For HTK04036, the preparative HPLC condition was 23% acetonitrile in water with 0.1% TFA at a flow rate of 30 mL/min. The retention time was 9.7 min. The yield was 28.2%. ESI-MS: calculated $[M+H]^+$ for HTK04036 $C_{55}H_{71}N_9O_{16}$ 1114.5097; found $[M+H]^+$ 1114.3070. For HTK04037, the preparative HPLC condition was 23% acetonitrile in water with 0.1% TFA at a flow rate of 30 mL/min. The retention time was 11.6 min. The yield was 27.0%. ESI-MS: calculated $[M+H]^+$ for HTK04037 $C_{55}H_{71}N_9O_{16}$ 1114.5097; found $[M+H]^+$ 1114.3629. For HTK04041, the semi-preparative HPLC condition was 23% acetonitrile in water with 0.1% TFA at a flow rate of 4.5 mL/min. The retention time was 10.8 min. The yield was 12.8%. ESI-MS: calculated $[M+H]^+$ for HTK04041 $C_{53}H_{67}N_9O_{16}$ 1086.4784; found $[M+H]^+$ 1086.4066.

Synthesis of HTK03153 and HTK03170

The peptidomimetic PSMA-targeting Aad-ureido-lysine moiety was synthesized by solid-phase peptide chemistry. Fmoc-Lys(ivDde)-Wang resin (0.10 mmol, 0.58 mmol/g loading) was suspended in DMF for 30 min. Fmoc was then removed by treating the resin with 20% piperidine in DMF (3×8 min). To generate the isocyanate of the 2-aminoadipyl moiety, a solution of L-2-aminoadipic acid (Aad) di-tert-butyl ester hydrochloride (154.9 mg, 0.5 mmol, 5 eq relative to resin) and DIEA (287.4 μL, 1.65 mmol) in $CH_2Cl_2$ (5 mL) was cooled to −78° C. in a dry ice/acetone bath. Triphosgene (49.0 mg, 0.165 mmol) was dissolved in $CH_2Cl_2$ (5 mL), and the resulting solution was added dropwise to the reaction at −78° C. The reaction was then allowed to warm to room temperature and stirred for 30 minutes to give a solution of the isocyanate of the 2-aminoadipyl moiety. After which another 87.1 μL DIEA (0.5 mmole) was added, and then added to the lysine-immobilized resin and reacted for 16 h. After washing the resin with DMF, the ivDde-protecting group was removed with 2% hydrazine in DMF (5×5 min). Fmoc-Ala(9-Anth)-OH was then coupled to the side chain of Lys followed by Fmoc-tranexamic acid, Fmoc-Lys(ivDde)-OH, and Fmoc-Gly-OH using Fmoc-based chemistry. All coupling were carried out in DMF using Fmoc-protected amino acid (4 eq.), HATU (4 eq.), and DIEA (7 eq.). Afterwards, elongation was continued with the addition of 4-(p-chlorophenyl)butyric acid (for HTK03153) or 4-(p-methoxyphenyl)butyric acid (for HTK03170) coupled to the same peptide-bound resin using Fmoc-based chemistry. After removal of the ivDde-protecting group with 2% hydrazine in DMF (5×5 min), DOTA-tris(t-bu)ester was then coupled to the side chain of Lys to give the precursors.

The peptide was then deprotected and simultaneously cleaved from the resin by treating with 95/5 TFA/TIS for 2 h at room temperature. After filtration, the peptide was precipitated by the addition of cold diethyl ether to the TFA solution. The crude peptide was purified by HPLC using the preparative or semi-preparative column. The eluates containing the desired peptide were collected and lyophilized. For HTK03153, the preparative HPLC condition was 32% acetonitrile in water with 0.1% TFA at a flow rate of 30 mL/min. The retention time was 7.9 min. ESI-MS: calculated $[M+H]^+$ for HTK03153 $C_{72}H_{99}N_{12}O_{19}Cl$ 1471.6916; found $[M+H]^+$ 1471.1257. For HTK03170, the semi-preparative HPLC condition was 34% acetonitrile in water with 0.1% TFA at a flow rate of 4.5 mL/min. The retention time was 13.1 min. ESI-MS: calculated $[M+2H]^{2+}$ for HTK03170 $C_{73}H_{102}N_{12}O_{20}$ 734.3745; found $[M+2H]^{2+}$ 734.5822

Synthesis of HTK04028, HTK04048 and HTK04050

The synthesis procedures for the construction of the core structures of HTK04028, HTK04048 and HTK04050 were the same as those of HTK03187, HTK03177, and HTK04033, respectively, as described above. After Fmoc-tranexamic acid, elongation was continued with the addition of Fmoc-Lys(ivDde)-OH, Fmoc-Gly-OH, and 4-(p-methoxyphenyl)butyric acid using Fmoc-based chemistry. All coupling were carried out in DMF using Fmoc-protected amino acid (4 eq.), HATU (4 eq.), and DI EA (7 eq.). After removal of the ivDde-protecting group with 2% hydrazine in DMF (5×5 min), DOTA-tris(t-bu)ester was then coupled to the side chain of Lys to give the precursors.

The peptide was then deprotected and simultaneously cleaved from the resin by treating with 95/5 TFA/TIS for 2 h at room temperature. After filtration, the peptide was precipitated by the addition of cold diethyl ether to the TFA solution. The crude peptide was purified by HPLC using the preparative or semi-preparative column. The eluates containing the desired peptide were collected and lyophilized. For HTK04028, the preparative HPLC condition was 28% acetonitrile in water with 0.1% TFA at a flow rate of 30 mL/min. The retention time was 14.8 min. The yield was 21.4%. ESI-MS: calculated $[M+H]^+$ for HTK04028 $C_{72}H_{100}N_{12}O_{21}$ 1469.7204; found $[M+H]^+$ 1469.7000. For HTK04048, the semi-preparative H PLC condition was 35% acetonitrile in water with 0.1% TFA at a flow rate of 4.5 mL/min. The retention time was 11.7 min. The yield was 53.4%. ESI-MS: calculated $[M+H]^+$ for HTK04048 $C_{72}H_{100}N_{12}O_{20}S$ 1485.6976; found $[M+H]^+$ 1485.9910. For HTK04050, the semi-preparative HPLC condition was 35% acetonitrile in water with 0.1% TFA at a flow rate of 4.5 mL/min. The retention time was 11.4 min. The yield was 17.5%. ESI-MS: calculated $[M+H]^+$ for HTK04050 $C_{72}H_{99}N_{12}O_{20}F$ 1471.7161; found $[M+H]^+$ 1471.9511.

Synthesis of Nonradioactive Ga-Complexed Standards

To prepare nonradioactive Ga-complexed standards, a solution of each precursor was incubated with $GaCl_3$ (5 eq.) in NaOAc buffer (0.1 M, 500 µL, pH 4.2) at 80° C. for 15 min. The reaction mixture was then purified by HPLC using the preparative or semi-preparative column, and the HPLC eluates containing the desired peptide were collected, pooled, and lyophilized. For Ga-HTK03041, the semi-preparative HPLC condition was 31% acetonitrile in water with 0.1% TFA at a flow rate of 4.5 mL/min. The retention time was 9.3 min. The yield was 89%. ESI-MS: calculated $[M+H]^+$ for Ga-HTK03041 $C_{53}H_{72}N_9O_{16}Ga$ 1159.4; found $[M+H]^+$ 1159.4. For Ga-HTK03161, the semi-preparative HPLC condition was 29% acetonitrile in water with 0.1% TFA at a flow rate of 4.5 mL/min. The retention time was 11.3 min. The yield was 37.4%. ESI-MS: calculated $[M+H]^+$ for Ga-HTK03161 $C_{52}H_{69}N_9O_{16}Ga$ 1145.4196; found $[M+H]^+$ 1146.1355. For Ga-HTK03169, the semi-preparative HPLC condition was 25% acetonitrile in water with 0.1% TFA at a flow rate of 4.5 mL/min. The retention time was 14.1 min. The yield was 55.0%. ESI-MS: calculated $[M+H]^+$ for Ga-HTK03169 $C_{50}H_{70}N_9O_{16}Ga$ 1122.4275; found $[M+H]^+$ 1122.3041. For Ga-HTK03177, the semi-preparative HPLC condition was 32% acetonitrile in water with 0.1% TFA at a flow rate of 4.5 mL/min. The retention time was 7.8 min. The yield was 55.9%. ESI-MS: calculated $[M+H]^+$ for Ga-HTK03177 $C_{53}H_{70}N_9O_{16}SGa$ 1190.3995; found $[M+H]^+$ 1190.3061. For Ga-HTK03187, the semi-preparative HPLC condition was 29% acetonitrile in water with 0.1% TFA at a flow rate of 4.5 mL/min. The retention time was 13.3 min. The yield was 52.8%. ESI-MS: calculated $[M+H]^+$ for Ga-HTK03187 $C_{53}H_{70}N_9O_{17}Ga$ 1174.4224; found $[M+H]^+$ 1174.3425. For Ga-HTK03189A, the semi-preparative HPLC condition was 30% acetonitrile in water with 0.1% TFA at a flow rate of 4.5 mL/min. The retention time was 13.0 min. The yield was 52.6%. ESI-MS: calculated [M+H]+ for Ga-HTK03189A C55H74N9O16Ga 1186.4588; found [M+H]+ 1186.4164. For Ga-HTK03189B, the semi-preparative HPLC condition was 30% acetonitrile in water with 0.1% TFA at a flow rate of 4.5 mL/min. The retention time was 13.9 min. The yield was 42.1%. ESI-MS: calculated [M+H]+ for Ga-HTK03189B C55H74N9O16Ga 1186.4588; found [M+H]+ 1186.3279. For Ga-HTK04033, the semi-preparative HPLC condition was 29% acetonitrile in water with 0.1% TFA at a flow rate of 4.5 mL/min. The retention time was 13.3 min. The yield was 59.5%. ESI-MS: calculated [M+H]+ for Ga-HTK04033 C53H70N9O16FGa 1177.4259; found [M+H]+ 1178.4800. For Ga-HTK04036, the semi-preparative HPLC condition was 29% acetonitrile in water with 0.1% TFA at a flow rate of 4.5 mL/min. The retention time was 13.1 min. The yield was 61.3%. ESI-MS: calculated [M+H]+ for Ga-HTK04036 C55H69N9O16Ga 1181.4196; found [M+H]+ 1181.4720. For Ga-HTK04037, the semi-preparative HPLC condition was 29% acetonitrile in water with 0.1% TFA at a flow rate of 4.5 mL/min. The retention time was 15.6 min. The yield was 54.2%. ESI-MS: calculated [M+H]+ for Ga-HTK04037 C55H69N9O16Ga 1181.4196; found [M+H]+ 1180.5278. For Ga-HTK04040, the semi-preparative HPLC condition was 30% acetonitrile in water with 0.1% TFA at a flow rate of 4.5 mL/min. The retention time was 10.2 min. The yield was 46.5%. ESI-MS: calculated $[M+H]^+$ for Ga-HTK04040 C53H70N9O16FGa 1177.4259; found [M+H]+ 1176.7043. For Ga-HTK04041, the semi-preparative HPLC condition was 29% acetonitrile in water with 0.1% TFA at a flow rate of 4.5 mL/min. The retention time was 14.4 min. The yield was 55.2%. ESI-MS: calculated [M+H]+ for Ga-HTK04041 C53H65N9O16Ga 1153.3883; found [M+H]+ 1153.5379. For Ga-HTK04053, the semi-preparative HPLC condition was 25% acetonitrile in water with 0.1% TFA at a flow rate of 4.5 mL/min. The retention time was 12.4 min. The yield was 74.7%. ESI-MS: calculated [M+H]+ for Ga-HTK04053 C46H68N9O16Ga 1199.3163; found [M+H]+ 1199.5712.

Synthesis of Ga-68 Labeled Compounds

[$^{68}$Ga]GaCl$_3$ was eluted from an iThemba Labs generator with a total of 4 mL of 0.1 M HCl. The eluted [$^{68}$Ga]GaCl$_3$ solution was added to 2 mL of concentrated HCl. This radioactive mixture was then added to a DGA resin column and washed with 3 mL of 5 M HCl. The column was then dried with air and the [$^{68}$Ga]GaCl$_3$ (0.10-0.50 GBq) was eluted with 0.5 mL of water into a vial containing a solution of the unlabeled precursor (25 µg) in 0.7 mL HEPES buffer (2 M, pH 5.3). The reaction mixture was heated in a microwave oven (Danby; DMW7700WDB) for 1 min at power setting 2. The mixture was purified by the semi-preparative HPLC column and quality control was performed via the analytical HPLC with the co-injection of the unlabeled standard. Radiochemical yields (decay-corrected) were >50% and radiochemical purities were >95%.

Synthesis of Lu-Complexed Standards

To prepare nonradioactive Lu-complexed standards of HTK03149, HTK03153, HTK03170, HTK04028, HTK04048, and HTK04050, a solution of precursor was incubated with LuCl$_3$ (5 eq.) in NaOAc buffer (0.1 M, 500 µL, pH 4.2) at 90° C. for 30 min. The reaction mixture was then purified by HPLC using the semi-preparative column, and the HPLC eluates containing the desired peptide were collected, pooled, and lyophilized. For Lu-HTK03149, the HPLC condition was 29% acetonitrile in water with 0.1% TFA at a flow rate of 4.5 mL/min. The retention time was 8.4 min. The yield of Lu-HTK03149 was 91.3%. ESI-MS: calculated [M+H]$^+$ for Lu-HTK03149 C$_{54}$H$_{74}$N$_9$O$_{16}$Lu 1173.4509; found [M+H]$^+$ 1173.5450. For Lu-HTK03153, the HPLC condition was 39% acetonitrile in water with 0.1% TFA at a flow rate of 4.5 mL/min. The retention time was 8.1 min. The yield of Lu-HTK03153 was 62.5%. ESI-MS: calculated [M+H]$^+$ for Lu-HTK03153 C$_{72}$H$_{96}$N$_{12}$O$_{19}$ClLu 1643.6089; found [M+H]$^+$ 1643.9000. For Lu-HTK03170, the HPLC condition was 34% acetonitrile in water with 0.1% TFA at a flow rate of 4.5 mL/min. The retention time was 15.4 min. The yield of Lu-HTK03170 was 94.7%. ESI-MS: calculated [M+H]$^+$ for Lu-HTK03170 C$_{73}$H$_{99}$N$_{12}$O$_{20}$Lu 1639.6585; found [M+H]$^+$ 1639.6933. For Lu-HTK04028, the HPLC condition was 35% acetonitrile in water with 0.1% TFA at a flow rate of 4.5 mL/min. The retention time was 11.5 min. The yield of Lu-HTK04028 was 29.4%. ESI-MS: calculated [M+H]$^+$ for Lu-HTK04028 C$_{72}$H$_{97}$N$_{12}$O$_{21}$Lu 1641.6377; found [M+H]$^+$ 1641.7775. For Lu-HTK04048, the HPLC condition was 35% acetonitrile in water with 0.1% TFA at a flow rate of 4.5 mL/min. The retention time was 13.9 min. The yield of Lu-HTK04048 was 70.2%. ESI-MS: calculated [M+H]$^+$ for Lu-HTK04048 C$_{72}$H$_{97}$N$_{12}$O$_{20}$SLu 1657.6149; found [M+H]$^+$ 1657.8672. For Lu-HTK04050, the HPLC condition was 35% acetonitrile in water with 0.1% TFA at a flow rate of 4.5 mL/min. The retention time was 13.2 min. The yield of Lu-HTK04050 was 44.9%. ESI-MS: calculated [M+H]$^+$ for Lu-HTK04050 C$_{72}$H$_{96}$N$_{12}$O$_{20}$FLu 1643.6334; found [M+H]$^+$ 1644.7152.

Synthesis of Lu-177 Labeled Compounds

[$^{177}$Lu]LuCl$_3$ was purchased from ITM Isotopen Technologien Munchen AG. [$^{177}$Lu]LuCl$_3$ (100-1000 MBq) in 0.04 M HCl (10-100 µL) was added to a solution of the unlabeled precursor (25 µg) in 0.5 mL of NaOAc buffer (0.1 M, pH 4.5). The reaction mixture was incubated at 100° C. for 15 min. The mixture was purified by the semi-prep HPLC column and the quality control was performed via the analytical HPLC column with the co-injection of the unlabeled standard. Radiochemical yields (decay-corrected) were >50% and radiochemical purities were >95%.

Synthesis of HTK03162 and HTK04055

The di-azide-containing intermediates HTK03156 and HTK04039 for the synthesis of HTK03162 and HTK04055, respectively, were synthesized by solid-phase methods. The synthesis procedures for the preparation of their core structures were the same as the syntheses of HTK03149 (for HTK03156) and HTK03187 (for HTK04039). After coupling Fmoc-tranexamic acid, elongation was continued with the addition of Fmoc-Lys(Fmoc)-OH. The couplings were carried out in DMF using Fmoc-protected amino acid (4 equivalents), HATU (4 equivalents) and DIEA (7 equivalents). After removing the Fmoc-protected group, Fmoc-Aad (OtBu)-OH was then coupled to both side-chain and N-terminus of Lys. The couplings were carried out in DMF using Fmoc-protected amino acid (5 equivalents), HATU (5 equivalents and DI EA (9 equivalents). 2-Azidoacetic acid (5 equivalents) was coupled to the N-terminus with DIEA (5 equivalents) and N-hydroxysuccinimide (6 equivalents) to give the di-azide-containing intermediates. At the end, the peptide was deprotected and simultaneously cleaved from the resin by treating with 95/5 TFA/TIS for 2 h at room temperature. After filtration, the peptide was precipitated by the addition of cold diethyl ether to the TFA solution. The crude peptide was purified by HPLC using the preparative column. The eluates containing the desired peptide were collected, pooled, and lyophilized. For HTK03156, the preparative HPLC condition was 34% acetonitrile in water with 0.1% TFA at a flow rate of 30 mL/min. The retention time was 4.8 min, and the yield of the precursor was 39%. ESI-MS: calculated [M+H]$^+$ C$_{60}$H$_{82}$N$_{15}$O$_{18}$ 1300.5962; found [M+H]$^+$ 1300.6369. For HTK04039, the preparative HPLC condition was 31% acetonitrile in water with 0.1% TFA at a flow rate of 30 mL/min. The retention time was 8.0 min, and the yield of the precursor was 5.8%. ESI-MS: calculated [M+H]$^+$ C$_{59}$H$_{79}$N$_{15}$O$_{19}$ 1302.5755; found [M+H]$^+$ 1302.6022.

To synthesize HTK03162, the di-azide-containing intermediate HTK03156 (7.4 mg, 5.7 µmol), N-propargyl-N,N-dimethylammoniomethyl-trifluoroborate (4.7 mg, 28.5 µmol, 5 eq) were dissolved in 300 µL actonirile, and then adjusting the solution to base condition (pH ~8) by 1M K$_2$CO$_3$. A solution of 1 M CuSO$_4$ (28.5 µL, 5 eq), and 1 M sodium ascorbate (57 µL, 10 eq) was then added, and the reaction mixture was stirred at room temperature for 18 h. The reaction mixture was purified by HPLC using the semi-preparative column eluted with 36% acetonitrile acetonitrile in water with 0.1% TFA at a flow rate of 4.5 mL/min. The retention time was 8.0 min, and the yield of the HTK03162 was 70.7%. ESI-MS: calculated [M+H]$^+$ C$_{72}$H$_{104}$B$_2$F$_6$N$_{17}$O$_{18}$ 1630.7836; found [M+H]$^+$ 1630.8000.

To synthesize HTK04055, the di-azide-containing intermediate HTK04039 (2.0 mg, 1.5 µmol), N-propargyl-N,N-dimethylammoniomethyl-trifluoroborate (1.24 mg, 7.5 µmol, 5 eq) were dissolved in 300 µL actonirile, and then adjusting the solution to base condition (pH ~8) by 1M K$_2$CO$_3$. A solution of 1 M CuSO$_4$ (7.5 µL, 5 eq), and 1 M sodium ascorbate (15 µL, 10 eq) was then added, and the reaction mixture was stirred at room temperature for 18 h. The reaction mixture was purified by HPLC using the semi-preparative column eluted with 33% acetonitrile acetonitrile in water with 0.1% TFA at a flow rate of 4.5 mL/min. The retention time was 11.6 min, and the yield of HTK04055 was 55.9%. ESI-MS: calculated [M+H]$^+$ C$_{71}$H$_{101}$B$_2$F$_6$N$_{17}$O$_{19}$ 1632.7628; found [M+H]$^+$ 1632.6622.

Synthesis of F-18 Labeled Compounds

No-carrier-added [$^{18}$F]fluoride was obtained by bombardment of H$_2$$^{18}$O with 18-MeV protons (Advanced Cyclotron Systems Inc) followed by trapping on an anion exchange resin column (pre-activated with brine and washed with DI water). The [$^{18}$F]fluoride was then eluted from the column using HCl-pyridazine buffer (pH 2.0). Unlabeled trifluoroborate precursor HTK03162 or HTK04055 (100 nmol) was suspended in DMF (15 µL). The eluted [$^{18}$F]fluoride (30-100 GBq) was added into a reaction vessel containing the solution of HTK03162 or HTK04055. The vial was heated at 80° C. for 20 minutes on a heating block and quenched upon the addition of 1 mL of water. The mixture was purified by the semi-preparative HPLC column and the quality control was performed via the analytical HPLC column with the co-injection of the unlabeled standard. Radiochemical yields (decay-corrected) were >10% and radiochemical purities were >95%.

Cell Culture

LNCaP cell line was obtained from ATCC (LNCaP clone FGC, CRL-1740). It was established from a metastatic site of left supraclavicular lymph node of human prostatic adenocarcinoma. Cells were cultured in PRM I 1640 medium supplemented with 10% FBS, penicillin (100 U/mL) and streptomycin (100 µg/mL) at 37° C. in a humidified incubator containing 5% $CO_2$. Cells grown to 80-90% confluence were then washed with sterile phosphate-buffered saline (1× PBS pH 7.4), and collected by trypsinization. The collected cell concentration was counted with a Hausser Scientific (Horsham, Pa.) Hemacytometer.

PET/CT, SPECT/CT Imaging and Biodistribution Studies

Imaging and biodistribution experiments were performed using NODSCID 1L2RγKO male mice. Mice were anesthetized by inhalation with 2% isoflurane in oxygen, and implanted subcutaneously with 1×10$^7$ LNCaP cells behind left shoulder. Mice were imaged or used in biodistribution studies when the tumor grew up to reach 5-8 mm in diameter during 5-6 weeks.

PET imaging experiments were conducted using Siemens Inveon micro PET/CT scanner. Each tumor bearing mouse was injected 6-8 MBq of Ga-68 or F-18 labeled tracer through the tail vein under anesthesia (2% isoflurane in oxygen). The mice were allowed to recover and roam freely in their cage. After 50 min, the mice were sedated again with 2% isoflurane in oxygen inhalation and positioned in the scanner. A 10-min CT scan was conducted first for localization and attenuation correction after segmentation for reconstructing the PET images. Then, a 10-min static PET imaging was performed to determined uptake in tumor and other organs.

SPECT/CT imaging experiments were conducted using the MILabs (Utrecht, the Netherlands) U-SPECT-I I/CT scanner. Each tumor bearing mouse was injected with ~37 MBq of $^{177}$Lu-labeled tracer through the tail vein under anesthesia (2% isoflurane in oxygen). The mice were allowed to recover and roam freely in their cage and imaged at 1, 4, 24, 72 and 120 hours after injection. At each time point, the mice were sedated again and positioned in the scanner. A 5-min CT scan was conducted first for anatomical reference with a voltage setting at 60 kV and current at 615 µA followed by a 60-min static emission scan acquired in list mode using an ultra-high resolution multi-pinhole rat-mouse (1 mm pinhole size) collimator. Data were reconstructed using the U-SPECT II software with a 20% window width on three energy windows. The photopeak window was centered at 208 keV, with lower scatter and upper scatter windows centered at 170 and 255 keV, respectively. Reconstruction parameters used maximum-likelihood expectation maximization (3 iterations), pixel-based ordered subset expectation maximization (16 subsets), and a post-processing filter (Gaussian blurring) of 0.5 mm. Images were decay corrected to injection time in PMOD (PMOD Technologies, Switzerland) then converted to DICOM for qualitative visualization in Inveon Research Workplace (Siemens Medical Solutions USA, Inc.).

For biodistribution studies, the mice were injected with the radiotracer as described above. At predetermined time points (1 h for $^{68}$Ga studies; 1, 4, 24, 72, or 120 h for $^{177}$Lu studies), the mice was anesthetized with 2% isoflurane inhalation, and euthanized by $CO_2$ inhalation. Blood was withdrawn immediately from the heart, and the organs/tissues of interest were collected. The collected organs/tissues were weighed and counted using a Perkin Elmer (Waltham, Mass.) Wizard2 2480 gamma counter. The uptake in each organ/tissue was normalized to the injected dose using a standard curve, and expressed as the percentage of the injected dose per gram of tissue (% ID/g).

The results for Example 2 are shown in Tables 7A, 7B, and 8-13 below and FIGS. 7-13.

TABLE 7A

Biodistribution data and tumor-to-background contrast ratios of $^{68}$Ga-labeled HTK03149, HTK03161, HTK03169, HTK3177, HTK03187, HTK03189A, and HTK03189B in mice bearing PSMA-expressing LNCaP cancer xenografts.

| Tissue (% ID/g) | $^{68}$Ga-HTK03149 1 h (n = 6) | $^{68}$Ga-HTK03161 1 h (n = 4) | $^{68}$Ga-HTK03169 1 h (n = 5) | $^{68}$Ga-HTK03177 1 h (n = 5) | $^{68}$Ga-HTK03187 1 h (n = 5) | $^{68}$Ga-HTK03189A 1 h (n =5) | $^{68}$Ga-HTK03189B 1 h (n =5) |
|---|---|---|---|---|---|---|---|
| Blood | 0.70 ± 0.17 | 1.13 ± 0.19 | 0.63 ± 0.36 | 0.70 ± 0.06 | 0.67 ± 0.10 | 0.89 ± 0.22 | 1.06 ± 0.25 |
| Urine | 319 ± 183 | 363 ± 155 | 421 ± 187 | 400 ± 262 | 444 ± 192 | 343 ± 54.4 | 441 ± 138 |
| Fat | 0.17 ± 0.15 | 0.15 ± 0.04 | 0.09 ± 0.04 | 0.09 ± 0.04 | 0.07 ± 0.02 | 0.18 ± 0.11 | 0.17 ± 0.10 |
| Seminal | 3.66 ± 5.36 | 6.22 ± 12.2 | 3.83 ± 2.93 | 0.28 ± 0.38 | 0.65 ± 0.80 | 3.61 ± 4.59 | 2.62 ± 4.74 |
| Testes | 0.23 ± 0.13 | 0.54 ± 0.51 | 0.13 ± 0.07 | 0.25 ± 0.07 | 0.15 ± 0.03 | 0.23 ± 0.11 | 0.26 ± 0.05 |
| Intestine | 0.24 ± 0.05 | 0.31 ± 0.09 | 0.23 ± 0.16 | 0.21 ± 0.02 | 0.23 ± 0.05 | 0.31 ± 0.18 | 0.28 ± 0.07 |
| Stomach | 0.07 ± 0.01 | 0.10 ± 0.04 | 0.09 ± 0.11 | 0.15 ± 0.09 | 0.08 ± 0.05 | 0.11 ± 0.06 | 0.11 ± 0.03 |
| Spleen | 0.27 ± 0.05 | 0.27 ± 0.06 | 0.13 ± 0.06 | 0.42 ± 0.15 | 0.17 ± 0.02 | 0.21 ± 0.10 | 0.20 ± 0.05 |
| Liver | 0.25 ± 0.06 | 0.28 ± 0.05 | 0.21 ± 0.16 | 0.33 ± 0.20 | 0.21 ± 0.05 | 0.34 ± 0.15 | 0.39 ± 0.08 |
| Pancreas | 0.13 ± 0.02 | 0.18 ± 0.03 | 0.11 ± 0.05 | 0.14 ± 0.01 | 0.12 ± 0.02 | 0.15 ± 0.04 | 0.18 ± 0.05 |
| Adrenal glands | 0.33 ± 0.11 | 0.41 ± 0.07 | 0.24 ± 0.08 | 0.46 ± 0.17 | 0.26 ± 0.06 | 0.35 ± 0.06 | 0.37 ± 0.15 |
| Kidneys | 4.15 ± 1.46 | 4.41 ± 1.26 | 2.18 ± 0.48 | 7.76 ± 1.00 | 2.83 ± 0.45 | 2.65 ± 0.69 | 2.13 ± 0.45 |
| Lungs | 0.53 ± 0.09 | 0.75 ± 0.13 | 0.38 ± 0.17 | 0.61 ± 0.08 | 0.52 ± 0.09 | 0.68 ± 0.12 | 0.82 ± 0.22 |
| Heart | 0.21 ± 0.03 | 0.32 ± 0.05 | 0.14 ± 0.07 | 0.21 ± 0.01 | 0.19 ± 0.04 | 0.24 ± 0.06 | 0.30 ± 0.06 |
| Tumor | 19.1 ± 6.37 | 12.7 ± 1.91 | 3.19 ± 0.70 | 24.7 ± 6.85 | 21.1 ± 3.62 | 2.10 ± 0.28 | 0.67 ± 0.15 |
| Muscle | 0.11 ± 0.04 | 0.15 ± 0.04 | 0.08 ± 0.05 | 0.18 ± 0.18 | 0.09 ± 0.01 | 0.14 ± 0.04 | 0.12 ± 0.03 |
| Bone | 0.11 ± 0.04 | 0.11 ± 0.02 | 0.08 ± 0.03 | 0.10 ± 0.03 | 0.13 ± 0.03 | 0.12 ± 0.03 | 0.10 ± 0.02 |

TABLE 7A-continued

Biodistribution data and tumor-to-background contrast ratios of $^{68}$Ga-labeled HTK03149, HTK03161, HTK03169, HTK3177, HTK03187, HTK03189A, and HTK03189B in mice bearing PSMA-expressing LNCaP cancer xenografts.

| Tissue (% ID/g) | $^{68}$Ga-HTK03149 1 h (n = 6) | $^{68}$Ga-HTK03161 1 h (n = 4) | $^{68}$Ga-HTK03169 1 h (n = 5) | $^{68}$Ga-HTK03177 1 h (n = 5) | $^{68}$Ga-HTK03187 1 h (n = 5) | $^{68}$Ga-HTK03189A 1 h (n =5) | $^{68}$Ga-HTK03189B 1 h (n =5) |
|---|---|---|---|---|---|---|---|
| Brain | 0.02 ± 0.00 | 0.02 ± 0.00 | 0.02 ± 0.01 | 0.02 ± 0.00 | 0.02 ± 0.00 | 0.02 ± 0.00 | 0.03 ± 0.00 |
| Tail | 0.58 ± 0.14 | 0.55 ± 0.10 | 0.48 ± 0.20 | 0.74 ± 0.12 | 0.46 ± 0.10 | 0.77 ± 0.30 | 0.90 ± 0.29 |
| Thyroid | 0.20 ± 0.05 | 0.29 ± 0.05 | 0.16 ± 0.07 | 0.23 ± 0.01 | 0.18 ± 0.02 | 0.25 ± 0.05 | 0.29 ± 0.08 |
| Salivary | 0.22 ± 0.06 | 0.23 ± 0.05 | 0.14 ± 0.03 | 0.22 ± 0.02 | 0.16 ± 0.02 | 0.20 ± 0.04 | 0.22 ± 0.04 |
| Lacrimal | 0.15 ± 0.09 | 0.12 ± 0.06 | 0.13 ± 0.06 | 0.12 ± 0.06 | 0.09 ± 0.03 | 0.18 ± 0.18 | 0.13 ± 0.04 |
| Tumor: Blood | 29.5 ± 15.8 | 11.4 ± 1.73 | 6.09 ± 2.24 | 36.1 ± 12.5 | 32.2 ± 8.53 | 2.41 ± 0.29 | 0.65 ± 0.15 |
| Tumor: Muscle | 185 ± 79.6 | 89.4 ± 36.1 | 47.1 ± 12.3 | 220 ± 135 | 249 ± 61.2 | 16.5 ± 4.08 | 5.68 ± 1.12 |
| Tumor: Kidney | 5.44 ± 3.88 | 3.03 ± 0.84 | 1.47 ± 0.16 | 3.25 ± 1.16 | 7.67 ± 2.10 | 0.83 ± 0.21 | 0.32 ± 0.05 |
| Tumor: Salivary | 97.3 ± 59.2 | 57.2 ± 7.11 | 23.2 ± 1.91 | 112 ± 33.1 | 133 ± 14.0 | 10.5 ± 1.07 | 3.08 ± 0.53 |
| Blood: Salivary | 3.21 ± 0.64 | 5.08 ± 0.62 | 4.39 ± 2.06 | 3.14 ± 0.19 | 4.27 ± 0.74 | 4.39 ± 0.44 | 4.86 ± 1.16 |

TABLE 7B

Biodistribution data and tumor-to-background contrast ratios of $^{68}$Ga-labeled HTK04033, HTK04040, HTK04036, HTK04037, HTK04041 and HTK04053 in mice bearing PSMA-expressing LNCaP cancer xenografts.

| Tissue (% ID/g) | $^{68}$Ga-HTK04033 1 h (n = 4) | $^{68}$Ga-HTK04040 1 h (n = 4) | $^{68}$Ga-HTK04036 1 h (n = 4) | $^{68}$Ga-HTK04037 1 h (n = 5) | $^{68}$Ga-HTK04041 1 h (n = 5) | $^{68}$Ga-HTK04053 1 h (n = 5) |
|---|---|---|---|---|---|---|
| Blood | 0.59 ± 0.12 | 0.94 ± 0.12 | 0.69 ± 0.35 | 0.51 ± 0.12 | 1.00 ± 0.09 | 0.29 ± 0.05 |
| Urine | 440 ± 211 | 325 ± 66.8 | 422 ± 163 | 396 ± 114 | 396 ± 92.3 | 523 ± 330 |
| Fat | 0.10 ± 0.03 | 0.60 ± 0.30 | 0.09 ± 0.05 | 0.06 ± 0.01 | 0.11 ± 0.03 | 0.04 ± 0.01 |
| Seminal | 0.10 ± 0.04 | 0.51 ± 0.12 | 2.08 ± 3.09 | 8.45 ± 10.0 | 1.68 ± 3.44 | 7.61 ± 12.5 |
| Testes | 0.17 ± 0.05 | 0.74 ± 0.04 | 0.25 ± 0.14 | 0.18 ± 0.04 | 0.31 ± 0.05 | 0.11 ± 0.02 |
| Intestine | 0.20 ± 0.04 | 0.53 ± 0.04 | 0.41 ± 0.23 | 0.28 ± 0.03 | 0.19 ± 0.04 | 0.15 ± 0.03 |
| Stomach | 0.07 ± 0.03 | 0.23 ± 0.08 | 0.12 ± 0.11 | 0.12 ± 0.05 | 0.07 ± 0.03 | 0.06 ± 0.04 |
| Spleen | 0.19 ± 0.03 | 2.58 ± 0.80 | 0.27 ± 0.13 | 0.24 ± 0.05 | 0.40 ± 0.11 | 0.12 ± 0.03 |
| Liver | 0.29 ± 0.09 | 0.94 ± 0.11 | 0.48 ± 0.67 | 0.20 ± 0.03 | 0.37 ± 0.08 | 0.13 ± 0.07 |
| Pancreas | 0.15 ± 0.08 | 0.61 ± 0.08 | 0.13 ± 0.07 | 0.11 ± 0.01 | 0.15 ± 0.02 | 0.06 ± 0.02 |
| Adrenal glands | 0.16 ± 0.03 | 2.68 ± 0.70 | 0.30 ± 0.16 | 0.19 ± 0.03 | 0.31 ± 0.05 | 0.12 ± 0.03 |
| Kidneys | 3.31 ± 0.34 | 76.0 ± 22.6 | 5.82 ± 5.00 | 4.47 ± 0.90 | 6.82 ± 2.93 | 3.48 ± 2.39 |
| Lungs | 0.50 ± 0.05 | 2.01 ± 0.21 | 0.55 ± 0.26 | 0.46 ± 0.09 | 0.82 ± 0.08 | 0.28 ± 0.04 |
| Heart | 0.18 ± 0.06 | 0.88 ± 0.08 | 0.22 ± 0.12 | 0.15 ± 0.03 | 0.30 ± 0.03 | 0.09 ± 0.02 |
| Tumor | 18.5 ± 4.05 | 18.8 ± 5.06 | 12.1 ± 2.15 | 13.1 ± 4.69 | 12.2 ± 3.15 | 4.96 ± 2.75 |
| Muscle | 0.09 ± 0.04 | 0.64 ± 0.50 | 0.11 ± 0.06 | 0.08 ± 0.03 | 0.13 ± 0.03 | 0.05 ± 0.01 |
| Bone | 0.08 ± 0.01 | 0.18 ± 0.03 | 0.10 ± 0.03 | 0.07 ± 0.01 | 0.13 ± 0.02 | 0.04 ± 0.01 |
| Brain | 0.02 ± 0.00 | 0.25 ± 0.43 | 0.02 ± 0.01 | 0.02 ± 0.00 | 0.02 ± 0.00 | 0.01 ± 0.00 |
| Tail | 0.66 ± 0.50 | 0.85 ± 0.54 | 0.42 ± 0.18 | 0.41 ± 0.16 | 0.57 ± 0.05 | 0.20 ± 0.07 |
| Thyroid | 0.18 ± 0.03 | 1.14 ± 0.14 | 0.22 ± 0.12 | 0.16 ± 0.03 | 0.29 ± 0.04 | 0.09 ± 0.01 |
| Salivary | 0.13 ± 0.02 | 1.29 ± 0.24 | 0.18 ± 0.08 | 0.14 ± 0.03 | 0.26 ± 0.04 | 0.06 ± 0.02 |
| Lacrimal | 0.04 ± 0.03 | 0.06 ± 0.02 | 0.06 ± 0.03 | 0.07 ± 0.04 | 0.11 ± 0.05 | 0.05 ± 0.01 |
| Tumor: Blood | 31.7 ± 5.00 | 20.4 ± 6.02 | 21.0 ± 8.58 | 26.3 ± 10.5 | 12.4 ± 3.62 | 16.8 ± 7.00 |
| Tumor: Muscle | 221 ± 53.4 | 43.2 ± 24.9 | 139 ± 62.4 | 165 ± 52.9 | 95.1 ± 33.7 | 93.7 ± 27.0 |
| Tumor: kidney | 5.64 ± 1.37 | 0.26 ± 0.08 | 3.02 ± 1.44 | 3.02 ± 1.22 | 2.06 ± 0.89 | 1.84 ± 1.26 |
| Tumor: Salivary | 138 ± 21.1 | 14.9 ± 4.40 | 75.1 ± 28.2 | 92.2 ± 34.5 | 48.2 ± 12.2 | 84.3 ± 32.1 |
| Blood: Salivary | 4.38 ± 0.57 | 0.73 ± 0.06 | 3.68 ± 0.41 | 3.55 ± 0.46 | 3.96 ± 0.51 | 5.19 ± 1.73 |

TABLE 8

Biodistribution data and tumor-to-background contrast ratios of $^{177}$Lu-labeled HTK03149 in mice bearing PSMA-expressing LNCaP cancer xenografts.

| Tissue (% ID/g) | $^{177}$Lu-HTK03149 | | | | |
|---|---|---|---|---|---|
| | 1 h (n = 4) | 4 h (n = 4) | 24 h (n = 4) | 72 h (n = 4) | 120 h (n = 4) |
| Blood | 0.88 ± 0.07 | 0.17 ± 0.03 | 0.12 ± 0.01 | 0.07 ± 0.02 | 0.02 ± 0.01 |
| Urine | 460 ± 199 | 60.6 ± 30.4 | 1.29 ± 0.98 | 0.47 ± 0.44 | 0.33 ± 0.23 |
| Fat | 0.14 ± 0.05 | 0.02 ± 0.00 | 0.02 ± 0.00 | 0.04 ± 0.04 | 0.01 ± 0.01 |
| Seminal | 0.38 ± 0.47 | 0.04 ± 0.03 | 0.02 ± 0.00 | 0.03 ± 0.01 | 0.01 ± 0.00 |
| Testes | 0.26 ± 0.02 | 0.06 ± 0.00 | 0.05 ± 0.00 | 0.05 ± 0.01 | 0.03 ± 0.01 |
| Intestine | 0.27 ± 0.06 | 0.19 ± 0.07 | 0.09 ± 0.05 | 0.09 ± 0.03 | 0.31 ± 0.48 |
| Stomach | 0.10 ± 0.02 | 0.05 ± 0.02 | 0.13 ± 0.11 | 0.14 ± 0.10 | 0.24 ± 0.31 |
| Spleen | 0.26 ± 0.05 | 0.09 ± 0.02 | 0.09 ± 0.01 | 0.14 ± 0.06 | 0.13 ± 0.08 |

TABLE 8-continued

Biodistribution data and tumor-to-background contrast ratios of $^{177}$Lu-labeled HTK03149 in mice bearing PSMA-expressing LNCaP cancer xenografts.

| | $^{177}$Lu-HTK03149 | | | | |
|---|---|---|---|---|---|
| Tissue (% ID/g) | 1 h (n = 4) | 4 h (n = 4) | 24 h (n = 4) | 72 h (n = 4) | 120 h (n = 4) |
| Liver | 0.26 ± 0.03 | 0.11 ± 0.01 | 0.10 ± 0.01 | 0.13 ± 0.03 | 0.08 ± 0.04 |
| Pancreas | 0.17 ± 0.03 | 0.03 ± 0.00 | 0.03 ± 0.00 | 0.03 ± 0.00 | 0.02 ± 0.01 |
| Adrenal glands | 0.35 ± 0.07 | 0.08 ± 0.01 | 0.07 ± 0.02 | 0.12 ± 0.05 | 0.02 ± 0.03 |
| Kidneys | 7.67 ± 1.35 | 1.67 ± 0.38 | 0.60 ± 0.11 | 0.68 ± 0.39 | 0.28 ± 0.06 |
| Lungs | 0.72 ± 0.06 | 0.17 ± 0.01 | 0.12 ± 0.01 | 0.11 ± 0.02 | 0.09 ± 0.08 |
| Heart | 0.28 ± 0.04 | 0.07 ± 0.01 | 0.06 ± 0.00 | 0.06 ± 0.01 | 0.03 ± 0.01 |
| Tumor | 14.0 ± 2.16 | 20.9 ± 2.99 | 13.8 ± 2.88 | 17.1 ± 4.70 | 16.4 ± 11.0 |
| Muscle | 0.18 ± 0.14 | 0.02 ± 0.01 | 0.02 ± 0.00 | 0.02 ± 0.00 | 0.01 ± 0.00 |
| Bone | 0.07 ± 0.02 | 0.02 ± 0.01 | 0.03 ± 0.00 | 0.03 ± 0.01 | 0.01 ± 0.01 |
| Brain | 0.02 ± 0.00 | 0.01 ± 0.00 | 0.01 ± 0.00 | 0.00 ± 0.00 | 0.00 ± 0.00 |
| Tail | 0.52 ± 0.13 | 0.20 ± 0.14 | 0.14 ± 0.14 | 0.08 ± 0.02 | 0.04 ± 0.01 |
| Thyroid | 0.27 ± 0.02 | 0.07 ± 0.01 | 0.06 ± 0.00 | 0.08 ± 0.01 | 0.04 ± 0.01 |
| Salivary | 0.23 ± 0.06 | 0.05 ± 0.01 | 0.05 ± 0.01 | 0.05 ± 0.02 | 0.03 ± 0.01 |
| Lacrimal | 0.02 ± 0.01 | 0.03 ± 0.01 | 0.00 ± 0.00 | 0.01 ± 0.01 | 0.00 ± 0.00 |
| Tumor: Blood | 16.0 ± 2.44 | 12.6 ± 1.11 | 120 ± 31.1 | 258 ± 74.7 | 780 ± 451 |
| Tumor: Muscle | 101 ± 48.3 | 1028 ± 227 | 842 ± 216 | 985 ± 342 | 1336 ± 566 |
| Tumor: Kidney | 1.83 ± 0.21 | 12.9 ± 2.72 | 24.0 ± 7.26 | 28.1 ± 6.86 | 56.8 ± 26.2 |
| Tumor: Salivary | 63.4 ± 13.6 | 415 ± 60.5 | 286 ± 88.4 | 349 ± 109 | 533 ± 218 |
| Blood: Salivary | 3.98 ± 0.65 | 3.32 ± 0.59 | 2.37 ± 0.24 | 1.45 ± 0.69 | 0.75 ± 0.19 |

TABLE 9

Biodistribution data and tumor-to-background contrast ratios of $^{177}$Lu-labeled HTK03153 in mice bearing PSMA-expressing LNCaP cancer xenografts.

| | $^{177}$Lu-HTK03153 | | | | |
|---|---|---|---|---|---|
| Tissue (% ID/g) | 1 h (n = 7) | 4 h (n = 7) | 24 h (n = 7) | 72 h (n = 7) | 120 h (n = 6) |
| Blood | 24.7 ± 2.11 | 18.8 ± 1.16 | 7.44 ± 1.12 | 1.46 ± 0.58 | 0.37 ± 0.13 |
| Urine | 36.9 ± 21.8 | 35.6 ± 11.1 | 22.3 ± 7.35 | 4.92 ± 3.36 | 2.65 ± 1.27 |
| Fat | 1.61 ± 0.36 | 1.46 ± 0.36 | 0.66 ± 0.16 | 0.30 ± 0.13 | 0.19 ± 0.09 |
| Seminal | 1.30 ± 0.32 | 1.20 ± 0.32 | 0.70 ± 0.50 | 0.23 ± 0.11 | 0.15 ± 0.05 |
| Testes | 3.24 ± 0.40 | 3.45 ± 0.40 | 2.15 ± 0.33 | 1.38 ± 0.48 | 0.98 ± 0.22 |
| Intestine | 1.56 ± 0.16 | 1.22 ± 0.16 | 0.78 ± 0.10 | 0.30 ± 0.10 | 0.18 ± 0.08 |
| Stomach | 0.89 ± 0.15 | 0.71 ± 0.15 | 0.68 ± 0.15 | 0.31 ± 0.17 | 0.15 ± 0.10 |
| Spleen | 2.54 ± 0.27 | 1.54 ± 0.27 | 1.21 ± 0.24 | 1.03 ± 0.46 | 1.53 ± 0.71 |
| Liver | 3.61 ± 0.65 | 3.19 ± 0.65 | 1.52 ± 0.25 | 0.73 ± 0.21 | 0.40 ± 0.03 |
| Pancreas | 2.17 ± 0.21 | 1.60 ± 0.21 | 0.77 ± 0.09 | 0.29 ± 0.13 | 0.15 ± 0.04 |
| Adrenal glands | 4.52 ± 0.46 | 3.50 ± 0.46 | 2.35 ± 0.47 | 1.20 ± 0.26 | 0.82 ± 0.19 |
| Kidneys | 10.0 ± 1.09 | 9.10 ± 1.09 | 8.81 ± 1.06 | 4.95 ± 2.39 | 2.81 ± 0.35 |
| Lungs | 10.8 ± 1.38 | 9.40 ± 1.38 | 3.93 ± 0.41 | 1.87 ± 1.31 | 0.56 ± 0.12 |
| Heart | 5.95 ± 0.44 | 4.26 ± 0.44 | 1.90 ± 0.25 | 0.68 ± 0.25 | 0.32 ± 0.07 |
| Tumor | 14.2 ± 7.67 | 27.9 ± 7.67 | 57.2 ± 10.1 | 69.1 ± 13.4 | 86.4 ± 8.05 |
| Muscle | 1.54 ± 0.16 | 1.19 ± 0.16 | 0.56 ± 0.10 | 0.18 ± 0.07 | 0.07 ± 0.01 |
| Bone | 1.26 ± 0.15 | 0.83 ± 0.15 | 0.40 ± 0.08 | 0.16 ± 0.06 | 0.06 ± 0.04 |
| Brain | 0.35 ± 0.03 | 0.27 ± 0.03 | 0.13 ± 0.02 | 0.05 ± 0.02 | 0.03 ± 0.00 |
| Tail | 5.38 ± 5.96 | 6.89 ± 5.96 | 1.55 ± 0.34 | 0.44 ± 0.15 | 0.24 ± 0.04 |
| Thyroid | 4.80 ± 0.32 | 3.57 ± 0.32 | 1.95 ± 0.32 | 0.85 ± 0.28 | 0.52 ± 0.12 |
| Salivary | 3.56 ± 0.39 | 2.86 ± 0.39 | 1.25 ± 0.14 | 0.68 ± 0.22 | 0.37 ± 0.04 |
| Lacrimal | 0.35 ± 0.07 | 0.35 ± 0.14 | 0.18 ± 0.06 | 0.05 ± 0.05 | 0.02 ± 0.02 |
| Tumor: Blood | 0.58 ± 0.17 | 1.48 ± 0.34 | 7.80 ± 1.51 | 49.4 ± 8.48 | 217 ± 40.7 |
| Tumor: Muscle | 9.24 ± 2.53 | 23.5 ± 5.88 | 106 ± 25.1 | 406 ± 76.4 | 1073 ± 218 |
| Tumor: Kidney | 1.44 ± 0.50 | 3.06 ± 0.76 | 6.49 ± 0.85 | 18.1 ± 14.4 | 27.9 ± 7.77 |
| Tumor: Salivary | 3.96 ± 1.02 | 10.0 ± 3.38 | 45.6 ± 6.71 | 105 ± 17.1 | 237 ± 33.3 |
| Blood: Salivary | 6.95 ± 0.67 | 6.67 ± 0.91 | 5.99 ± 1.07 | 2.10 ± 0.21 | 0.99 ± 0.30 |

TABLE 10

Biodistribution data and tumor-to-background contrast ratios of $^{177}$Lu-labeled HTK03170 in mice bearing PSMA-expressing LNCaP cancer xenografts.

| Tissue (% ID/g) | $^{177}$Lu-HTK03170 | | | | |
|---|---|---|---|---|---|
| | 1 h (n = 6) | 4 h (n = 6) | 24 h (n = 6) | 72 h (n = 6) | 120 h (n = 6) |
| Blood | 16.9 ± 1.97 | 8.34 ± 1.67 | 0.59 ± 0.13 | 0.06 ± 0.02 | 0.02 ± 0.01 |
| Urine | 201 ± 45.6 | 117 ± 17.7 | 11.1 ± 4.32 | 3.55 ± 2.05 | 2.36 ± 1.36 |
| Fat | 1.38 ± 0.45 | 0.60 ± 0.13 | 0.12 ± 0.04 | 0.04 ± 0.02 | 0.03 ± 0.03 |
| Seminal | 1.22 ± 0.40 | 0.49 ± 0.10 | 0.08 ± 0.02 | 0.04 ± 0.01 | 0.02 ± 0.01 |
| Testes | 2.17 ± 0.32 | 1.83 ± 0.58 | 0.64 ± 0.53 | 0.24 ± 0.04 | 0.14 ± 0.06 |
| Intestine | 1.19 ± 0.25 | 0.61 ± 0.17 | 0.18 ± 0.07 | 0.14 ± 0.11 | 0.04 ± 0.03 |
| Stomach | 0.59 ± 0.12 | 0.42 ± 0.15 | 0.25 ± 0.13 | 0.28 ± 0.33 | 0.05 ± 0.08 |
| Spleen | 1.64 ± 0.83 | 0.96 ± 0.29 | 0.45 ± 0.10 | 0.38 ± 0.15 | 0.49 ± 0.38 |
| Liver | 2.67 ± 0.37 | 1.89 ± 0.69 | 0.69 ± 0.27 | 0.36 ± 0.13 | 0.23 ± 0.13 |
| Pancreas | 1.41 ± 0.31 | 0.74 ± 0.18 | 0.12 ± 0.03 | 0.04 ± 0.01 | 0.02 ± 0.02 |
| Adrenal glands | 3.34 ± 0.45 | 1.78 ± 0.45 | 0.50 ± 0.16 | 0.27 ± 0.11 | 0.22 ± 0.18 |
| Kidneys | 13.2 ± 1.87 | 9.23 ± 2.18 | 5.80 ± 1.24 | 2.56 ± 0.62 | 1.30 ± 0.55 |
| Lungs | 8.06 ± 1.48 | 4.35 ± 0.82 | 0.72 ± 0.19 | 0.18 ± 0.04 | 0.06 ± 0.03 |
| Heart | 3.60 ± 0.52 | 1.91 ± 0.40 | 0.26 ± 0.04 | 0.09 ± 0.03 | 0.04 ± 0.02 |
| Tumor | 27.2 ± 7.55 | 47.6 ± 13.5 | 57.2 ± 15.3 | 59.3 ± 16.0 | 61.9 ± 22.3 |
| Muscle | 1.15 ± 0.19 | 0.58 ± 0.13 | 0.08 ± 0.02 | 0.02 ± 0.01 | 0.01 ± 0.01 |
| Bone | 0.89 ± 0.27 | 0.45 ± 0.13 | 0.06 ± 0.04 | 0.03 ± 0.02 | 0.02 ± 0.01 |
| Brain | 0.23 ± 0.04 | 0.13 ± 0.03 | 0.02 ± 0.01 | 0.01 ± 0.00 | 0.00 ± 0.00 |
| Tail | 6.11 ± 3.05 | 2.66 ± 0.90 | 0.31 ± 0.06 | 0.19 ± 0.12 | 0.08 ± 0.06 |
| Thyroid | 2.90 ± 0.41 | 1.62 ± 0.42 | 0.37 ± 0.06 | 0.15 ± 0.01 | 0.08 ± 0.05 |
| Salivary | 2.43 ± 0.33 | 1.31 ± 0.30 | 0.28 ± 0.04 | 0.11 ± 0.03 | 0.05 ± 0.04 |
| Lacrimal | 0.27 ± 0.08 | 0.15 ± 0.07 | 0.04 ± 0.03 | 0.01 ± 0.01 | 0.00 ± 0.00 |
| Tumor: Blood | 1.58 ± 0.26 | 5.81 ± 1.58 | 105 ± 57.4 | 1029 ± 459 | 3996 ± 2182 |
| Tumor: Muscle | 23.5 ± 4.66 | 83.1 ± 17.0 | 736 ± 333 | 3374 ± 1417 | 12777 ± 19955 |
| Tumor: Kidney | 2.07 ± 0.55 | 5.38 ± 1.91 | 10.5 ± 4.77 | 24.0 ± 6.93 | 46.4 ± 21.3 |
| Tumor: Salivary | 11.3 ± 2.76 | 36.4 ± 5.35 | 202 ± 49.3 | 566 ± 236 | 1167 ± 533 |
| Blood: Salivary | 7.04 ± 0.86 | 6.48 ± 1.02 | 2.11 ± 0.47 | 0.57 ± 0.17 | 0.31 ± 0.06 |

TABLE 11

Biodistribution data and tumor-to-background contrast ratios of $^{177}$Lu-labeled HTK04028 in mice bearing PSMA-expressing LNCaP cancer xenografts.

| Tissue (% ID/g) | $^{177}$Lu-HTK04028 | | | | |
|---|---|---|---|---|---|
| | 1 h (n = 5) | 4 h (n = 5) | 24 h (n = 5) | 72 h (n = 5) | 120 h (n = 6) |
| Blood | 17.7 ± 2.10 | 12.2 ± 1.66 | 0.82 ± 0.11 | 0.05 ± 0.01 | 0.02 ± 0.00 |
| Urine | 95.3 ± 21.1 | 101 ± 40.6 | 16.2 ± 4.19 | 1.73 ± 0.89 | 1.59 ± 0.44 |
| Fat | 1.26 ± 0.21 | 0.89 ± 0.24 | 0.14 ± 0.02 | 0.06 ± 0.02 | 0.03 ± 0.01 |
| Seminal | 1.53 ± 0.97 | 0.90 ± 0.20 | 0.12 ± 0.02 | 0.05 ± 0.01 | 0.05 ± 0.03 |
| Testes | 2.26 ± 0.46 | 2.66 ± 0.41 | 0.55 ± 0.05 | 0.31 ± 0.05 | 0.22 ± 0.01 |
| Intestine | 1.23 ± 0.24 | 1.04 ± 0.12 | 0.23 ± 0.05 | 0.07 ± 0.03 | 0.08 ± 0.05 |
| Stomach | 0.51 ± 0.18 | 0.45 ± 0.06 | 0.31 ± 0.10 | 0.07 ± 0.07 | 0.10 ± 0.10 |
| Spleen | 1.53 ± 0.23 | 1.44 ± 0.31 | 0.48 ± 0.14 | 0.49 ± 0.16 | 0.69 ± 0.36 |
| Liver | 2.93 ± 0.51 | 2.29 ± 0.55 | 0.54 ± 0.09 | 0.22 ± 0.02 | 0.31 ± 0.30 |
| Pancreas | 1.53 ± 0.22 | 1.24 ± 0.04 | 0.15 ± 0.02 | 0.05 ± 0.01 | 0.03 ± 0.00 |
| Adrenal glands | 3.25 ± 0.34 | 2.18 ± 0.33 | 0.73 ± 0.13 | 0.48 ± 0.17 | 0.33 ± 0.05 |
| Kidneys | 8.30 ± 1.58 | 9.21 ± 2.76 | 4.32 ± 0.58 | 1.77 ± 0.25 | 1.16 ± 0.13 |
| Lungs | 7.88 ± 1.77 | 5.79 ± 0.44 | 1.08 ± 0.72 | 0.18 ± 0.02 | 0.09 ± 0.01 |
| Heart | 4.15 ± 0.31 | 2.67 ± 0.31 | 0.36 ± 0.03 | 0.12 ± 0.03 | 0.07 ± 0.01 |
| Tumor | 19.0 ± 5.86 | 42.6 ± 11.6 | 30.2 ± 2.74 | 26.1 ± 7.29 | 28.4 ± 5.11 |
| Muscle | 1.32 ± 0.19 | 0.83 ± 0.09 | 0.11 ± 0.02 | 0.03 ± 0.01 | 0.02 ± 0.00 |
| Bone | 0.99 ± 0.21 | 0.63 ± 0.10 | 0.11 ± 0.02 | 0.05 ± 0.02 | 0.04 ± 0.02 |
| Brain | 0.26 ± 0.03 | 0.19 ± 0.02 | 0.02 ± 0.00 | 0.01 ± 0.00 | 0.00 ± 0.00 |
| Tail | 4.85 ± 1.59 | 2.21 ± 0.18 | 0.31 ± 0.10 | 0.15 ± 0.04 | 0.10 ± 0.03 |
| Thyroid | 3.30 ± 0.42 | 2.30 ± 0.30 | 0.52 ± 0.08 | 0.24 ± 0.04 | 0.13 ± 0.02 |
| Salivary | 2.55 ± 0.21 | 1.75 ± 0.25 | 0.45 ± 0.10 | 0.19 ± 0.05 | 0.11 ± 0.03 |
| Lacrimal | 0.51 ± 0.23 | 0.39 ± 0.19 | 0.05 ± 0.04 | 0.01 ± 0.01 | 0.00 ± 0.00 |
| Tumor: Blood | 1.11 ± 0.45 | 3.60 ± 1.24 | 37.2 ± 4.22 | 550 ± 108 | 1714 ± 320 |
| Tumor: Muscle | 14.5 ± 4.46 | 52.2 ± 17.4 | 275 ± 35.3 | 886 ± 181 | 1825 ± 415 |
| Tumor: Kidney | 2.39 ± 0.99 | 4.89 ± 1.58 | 7.06 ± 0.86 | 14.6 ± 2.72 | 24.9 ± 5.16 |
| Tumor: Salivary | 7.60 ± 2.89 | 24.5 ± 5.95 | 69.3 ± 15.8 | 144 ± 35.6 | 284 ± 87.9 |
| Blood: Salivary | 6.93 ± 0.33 | 7.09 ± 1.45 | 1.88 ± 0.42 | 0.26 ± 0.06 | 0.17 ± 0.04 |

TABLE 12

Biodistribution data and tumor-to-background contrast ratios of $^{177}$Lu-labeled HTK04048 in mice bearing PSMA-expressing LNCaP cancer xenografts.

| | $^{177}$Lu-HTK04048 | | | | |
|---|---|---|---|---|---|
| Tissue (% ID/g) | 1 h (n = 4) | 4 h (n = 4) | 24 h (n = 4) | 72 h (n = 4) | 120 h (n = 5) |
| Blood | 17.7 ± 2.05 | 12.3 ± 1.56 | 0.68 ± 0.11 | 0.12 ± 0.01 | 0.05 ± 0.02 |
| Urine | 232 ± 4.59 | 102 ± 27.2 | 11.5 ± 2.99 | 2.00 ± 0.58 | 1.34 ± 0.72 |
| Fat | 1.32 ± 0.17 | 1.00 ± 0.13 | 0.15 ± 0.06 | 0.08 ± 0.03 | 0.06 ± 0.03 |
| Seminal | 1.14 ± 0.17 | 0.92 ± 0.20 | 0.11 ± 0.03 | 0.06 ± 0.01 | 0.04 ± 0.01 |
| Testes | 2.25 ± 0.30 | 2.68 ± 0.16 | 0.73 ± 0.32 | 0.34 ± 0.03 | 0.26 ± 0.04 |
| Intestine | 1.26 ± 0.20 | 1.03 ± 0.10 | 0.49 ± 0.41 | 0.15 ± 0.09 | 0.05 ± 0.02 |
| Stomach | 0.74 ± 0.14 | 0.81 ± 0.04 | 0.89 ± 0.84 | 0.23 ± 0.16 | 0.03 ± 0.01 |
| Spleen | 2.54 ± 0.60 | 2.10 ± 0.39 | 0.60 ± 0.05 | 0.62 ± 0.14 | 0.92 ± 0.30 |
| Liver | 3.95 ± 0.83 | 2.16 ± 0.17 | 0.45 ± 0.04 | 0.26 ± 0.01 | 0.22 ± 0.08 |
| Pancreas | 1.70 ± 0.17 | 1.21 ± 0.14 | 0.17 ± 0.03 | 0.07 ± 0.01 | 0.04 ± 0.01 |
| Adrenal glands | 3.95 ± 0.34 | 2.10 ± 0.22 | 0.49 ± 0.04 | 0.34 ± 0.03 | 0.37 ± 0.09 |
| Kidneys | 14.5 ± 3.33 | 12.4 ± 1.36 | 5.06 ± 0.91 | 2.28 ± 0.24 | 1.69 ± 0.58 |
| Lungs | 9.01 ± 0.91 | 6.35 ± 0.78 | 1.09 ± 0.33 | 0.29 ± 0.05 | 0.15 ± 0.05 |
| Heart | 4.41 ± 0.22 | 2.99 ± 0.36 | 0.36 ± 0.04 | 0.16 ± 0.01 | 0.10 ± 0.02 |
| Tumor | 15.6 ± 2.98 | 46.5 ± 28.4 | 54.3 ± 10.6 | 66.3 ± 18.7 | 74.0 ± 35.5 |
| Muscle | 1.42 ± 0.11 | 1.00 ± 0.10 | 0.11 ± 0.01 | 0.04 ± 0.01 | 0.05 ± 0.05 |
| Bone | 1.04 ± 0.20 | 0.74 ± 0.09 | 0.11 ± 0.02 | 0.07 ± 0.01 | 0.07 ± 0.01 |
| Brain | 0.31 ± 0.02 | 0.18 ± 0.02 | 0.03 ± 0.00 | 0.01 ± 0.00 | 0.01 ± 0.00 |
| Tail | 3.57 ± 0.35 | 2.72 ± 0.61 | 0.40 ± 0.17 | 0.15 ± 0.03 | 0.19 ± 0.13 |
| Thyroid | 3.79 ± 0.23 | 2.69 ± 0.26 | 0.55 ± 0.07 | 0.31 ± 0.04 | 0.19 ± 0.01 |
| Salivary | 2.70 ± 0.29 | 2.01 ± 0.17 | 0.42 ± 0.07 | 0.20 ± 0.03 | 0.14 ± 0.02 |
| Lacrimal | 0.50 ± 0.05 | 0.32 ± 0.13 | 0.05 ± 0.01 | 0.01 ± 0.01 | 0.01 ± 0.01 |
| Tumor:Blood | 0.89 ± 0.20 | 4.01 ± 3.07 | 82.9 ± 26.3 | 533 ± 154 | 1338 ± 455 |
| Tumor:Muscle | 11.1 ± 2.19 | 48.9 ± 36.0 | 476 ± 80.2 | 1625 ± 244 | 1860 ± 673 |
| Tumor:Kidney | 1.12 ± 0.34 | 3.88 ± 2.77 | 11.0 ± 2.91 | 28.9 ± 7.09 | 44.0 ± 16.4 |
| Tumor:Salivary | 5.75 ± 0.54 | 23.6 ± 15.5 | 133 ± 31.7 | 351 ± 138 | 537 ± 257 |
| Blood:Salivary | 6.60 ± 0.83 | 6.14 ± 0.72 | 1.67 ± 0.42 | 0.65 ± 0.10 | 0.40 ± 0.16 |

TABLE 13

Biodistribution data and tumor-to-background contrast ratios of $^{18}$F-labeled HTK03162 and HTK04055 in mice bearing PSMA-expressing LNCaP cancer xenografts.

| | $^{18}$F-HTK03162 | | $^{18}$F-HTK04055 | |
|---|---|---|---|---|
| Tissue (% ID/g) | 1 h (n = 5) | 2 h (n = 5) | 1 h (n = 4) | 2 h (n = 4) |
| Blood | 0.47 ± 0.10 | 0.07 ± 0.01 | 0.36 ± 0.08 | 0.16 ± 0.03 |
| Urine | 363 ± 115 | 143 ± 46.6 | 329 ± 118 | 149 ± 34.2 |
| Fat | 0.15 ± 0.02 | 0.03 ± 0.01 | 0.11 ± 0.04 | 0.03 ± 0.01 |
| Seminal | 3.82 ± 4.70 | 0.44 ± 0.71 | 0.60 ± 1.05 | 2.79 ± 5.49 |
| Testes | 0.23 ± 0.04 | 0.05 ± 0.01 | 0.17 ± 0.04 | 0.08 ± 0.01 |
| Intestine | 0.26 ± 0.08 | 0.25 ± 0.28 | 0.16 ± 0.03 | 0.19 ± 0.03 |
| Stomach | 0.07 ± 0.01 | 1.03 ± 2.09 | 0.07 ± 0.04 | 0.03 ± 0.01 |
| Spleen | 0.27 ± 0.14 | 0.06 ± 0.02 | 0.23 ± 0.04 | 0.11 ± 0.02 |
| Liver | 0.17 ± 0.07 | 0.05 ± 0.01 | 0.13 ± 0.02 | 0.10 ± 0.01 |
| Pancreas | 0.15 ± 0.05 | 0.02 ± 0.01 | 0.09 ± 0.02 | 0.07 ± 0.05 |
| Adrenal glands | 0.44 ± 0.10 | 0.08 ± 0.01 | 0.17 ± 0.06 | 0.10 ± 0.02 |
| Kidneys | 14.2 ± 6.55 | 2.50 ± 0.45 | 4.10 ± 1.05 | 2.98 ± 0.45 |
| Lungs | 0.52 ± 0.10 | 0.14 ± 0.03 | 0.36 ± 0.06 | 0.19 ± 0.04 |
| Heart | 0.17 ± 0.04 | 0.03 ± 0.01 | 0.13 ± 0.03 | 0.06 ± 0.01 |
| Tumor | 14.1 ± 3.71 | 13.9 ± 2.93 | 8.48 ± 2.31 | 10.2 ± 2.44 |
| Muscle | 0.12 ± 0.06 | 0.10 ± 0.11 | 0.09 ± 0.04 | 0.04 ± 0.02 |
| Bone | 0.15 ± 0.06 | 0.10 ± 0.03 | 0.10 ± 0.04 | 0.08 ± 0.02 |
| Brain | 0.01 ± 0.00 | 0.01 ± 0.00 | 0.02 ± 0.01 | 0.01 ± 0.00 |
| Tail | 0.46 ± 0.07 | 0.43 ± 0.63 | 0.49 ± 0.28 | 0.14 ± 0.03 |
| Thyroid | 0.20 ± 0.04 | 0.04 ± 0.01 | 0.16 ± 0.04 | 0.06 ± 0.01 |
| Salivary | 0.18 ± 0.03 | 0.05 ± 0.01 | 0.15 ± 0.06 | 0.05 ± 0.01 |
| Lacrimal | 0.06 ± 0.03 | 0.03 ± 0.02 | 0.03 ± 0.01 | 0.03 ± 0.01 |
| Tumor: Blood | 30.1 ± 6.62 | 200 ± 37.8 | 23.2 ± 2.96 | 67.5 ± 25.1 |
| Tumor: Muscle | 143 ± 73.8 | 423 ± 452 | 105 ± 46.5 | 277 ± 107 |
| Tumor: Kidney | 1.11 ± 0.39 | 5.57 ± 0.43 | 2.06 ± 0.06 | 3.53 ± 1.33 |

Example 1 shows that modifying the Glu sidechain in the Lys-ureido-Glu PSMA-targeting moiety in Formula I, II and III compounds (e.g. by lengthening the Glu sidechain) can significantly decrease the uptake of the tracer in kidney and salivary gland without sacrificing the tumour-to-background contrast ratio in a radiolabeled tracer (compare HTK03041 to HTK03149). The results in Example 2 further confirm that modification of the Glu sidechain provides improved imaging and therapeutic agents for PSMA-expressing diseases/conditions. In particular, it is noted that reduced kidney and salivary gland uptake is demonstrated for Formula I, II or III compounds in which $R^2$ is methylene (—CH$_2$—) or propylene (—CH$_2$—CH$_2$—CH$_2$—), or their closely related derivatives (e.g. —CH$_2$—O—CH$_2$—, —CH$_2$—S—CH$_2$—, or —CH2-CHF—), while retaining binding of PSMA-expressing tumors. In contrast, the results in Example 2 further demonstrate that substituting $R^2$ with butylene (—CH$_2$—CH$_2$—CH$_2$—CH$_2$—), or a derivative thereof, results in poor uptake in PSMA-expressing tumors (see compounds HTK03189A and HTK03189B), indicating that binding to PSMA is severely weakened.

It is further shown in Example 2 that Formula I, II and III compounds in which $R^2$ is a derivative of ethylene (—CH$_2$—CH$_2$—) can result in reduced kidney and salivary gland uptake while retaining binding of PSMA-expressing tumors, such as when $R^2$ is substituted ethylene or other ethylene derivative. For example, when $R^2$ is —CH$_2$—CHF— (HTK04033 and HTK04040), the present results show that compounds of the invention can still bind well to PSMA and have much less kidney and salivary gland uptake. Notably, although HTK04040 (the S-isomer) has a relatively higher kidney uptake (76% ID/g), this is still much less than that of HTK03041 (170% ID/g), which lacks the fluoro substituent. These results therefore show that small substituents (e.g. F, CH$_3$, OH) do not abrogate PSMA-binding.

The results further show that the conjugation of an albumin binder further enhances tumor uptake, resulting in improved tumor-to-kidney and tumor-to-salivary gland uptake ratios, especially at later time points.

The present invention has been described with regard to one or more embodiments. However, it will be apparent to persons skilled in the art that a number of variations and modifications can be made without departing from the scope of the invention as defined in the following claims. The scope of the invention should therefore not be limited by the preferred embodiments set forth in the above Examples, but should be given the broadest interpretation consistent with the description as a whole.

The contents of U.S. provisional application No. 63/006,643, filed Apr. 7, 2020, and U.S. provisional application No. 62/865,088, filed Jun. 21, 2019, are herein incorporated by reference in their entirety. To the extent that there may be any inconsistency between the definitions therein, the definitions herein in the above paragraphs shall prevail.

The invention claimed is:

1. A compound of Formula II:

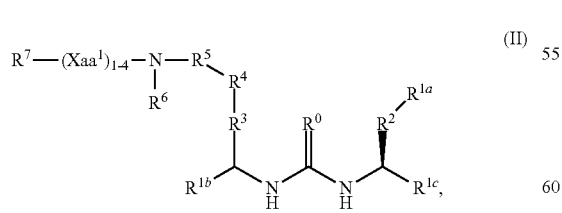

wherein:
$R^0$ is O;
$R^{1a}$, $R^{1b}$, and $R^{1c}$ are each —CO$_2$H;
$R^2$ is —CH$_2$— or —(CH$_2$)$_3$—;
$R^3$ is a linear C$_4$ alkylenyl;

—(Xaa$^1$)$_{1-4}$N(R$^6$)R$^5$R$^4$— is:

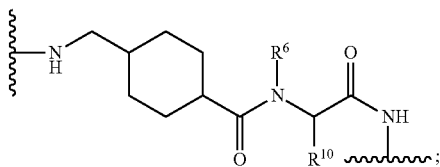

$R^6$ is H, methyl or ethyl;
$R^7$ is:

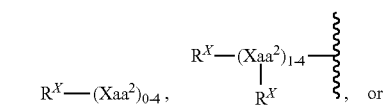

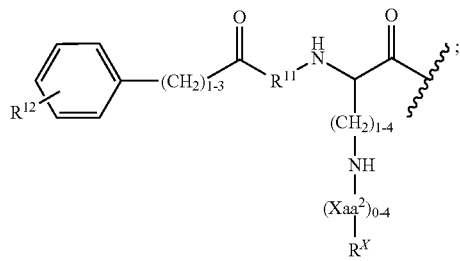

(Xaa$^2$)$_{0-4}$ is absent;
(Xaa$^2$)$_{1-4}$ is a tripeptide;
$R^{10}$ is:

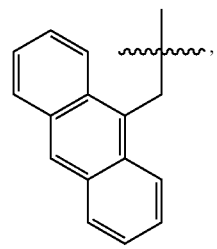

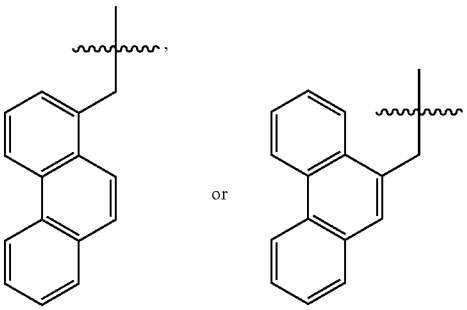

optionally modified with one or more of halogen, —OCH$_3$, —NH$_2$, —NO$_2$, —CN, —OH, or additional endocyclic ring nitrogen atoms, or combinations thereof;

$R^{11}$ is absent,

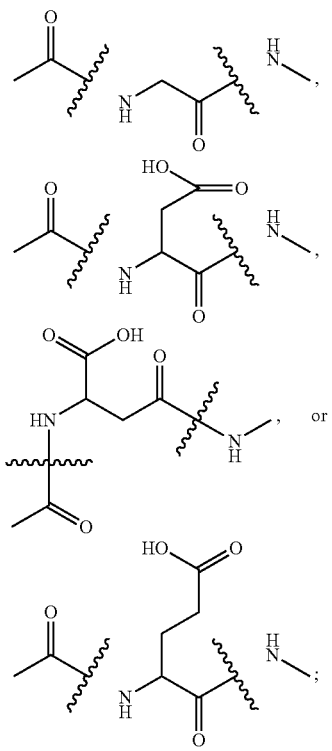

$R^{12}$ is I, Br, F, Cl, H, —OH, —OCH$_3$, —NH$_2$, —NO$_2$, or —CH$_3$; and $R^X$ is a radiometal chelator optionally bound to a radiometal, or a prosthetic group containing a trifluoroborate.

2. The compound of claim 1, wherein $R^6$ is H.

3. The compound of claim 1, wherein $R^7$ is:

$R^X$—(Xaa$^2$)$_{0-4}$ or

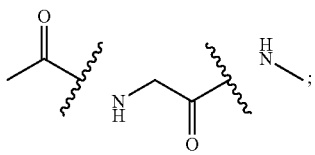

4. The compound of claim 1, wherein $R^{10}$ is

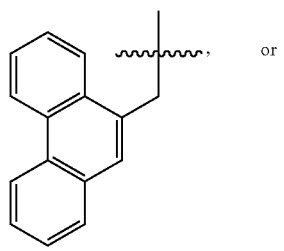

or

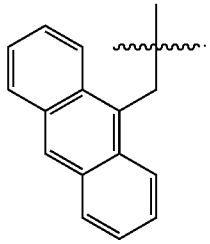

5. The compound of claim 1, wherein:

$R^{11}$ is

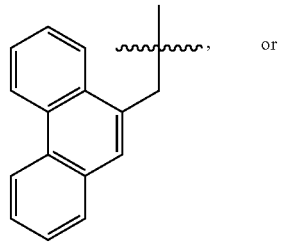

and $R^{12}$ is —OCH$_3$ or Cl.

6. The compound of claim 1, wherein $R^X$ is DOTA, H$_2$macropa, H$_4$py4pa, or H$_4$Pypa, each of which is optionally bound to a radiometal.

7. The compound of claim 3, wherein $R^{10}$ is

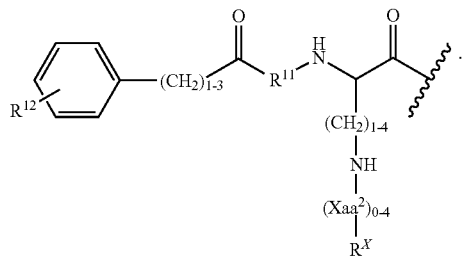

or

8. The compound of claim 3, wherein:

$R^{11}$ is

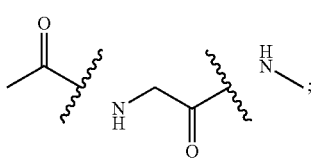

and $R^{12}$ is —OCH$_3$ or Cl.

9. The compound of claim 7, wherein:
R$^{11}$ is

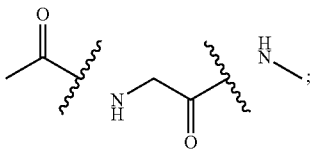

and
R$^{12}$ is —OCH$_3$ or Cl.

10. The compound of claim 1 which is

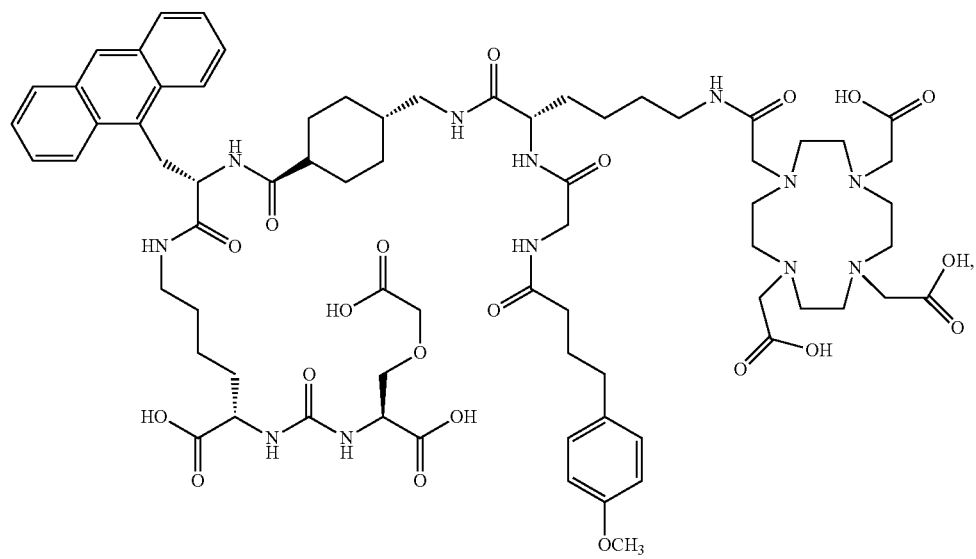

and the compound is optionally bound to a radiometal.

11. The compound of claim 1, wherein the radiometal is selected from the group consisting of $^{177}$Lu, $^{111}$In, $^{213}$Bi, $^{68}$Ga, $^{67}$Ga, $^{203}$Pb, $^{212}$Pb, $^{44}$Sc, $^{47}$Sc, $^{90}$Y, $^{86}$Y, $^{225}$Ac, $^{117m}$Sn, $^{153}$Sm, $^{149}$Tb, $^{161}$Tb, $^{165}$Er, $^{212}$Bi, $^{227}$Th, $^{64}$Cu and $^{67}$Cu.

12. The compound of claim 10, wherein the radiometal is selected from the group consisting of $^{177}$Lu and $^{225}$Ac.

13. The compound of claim 1, wherein R$^7$ is R$^X$—(Xaa$^2$)$_{0-4}$— and R$^X$ is DOTA, optionally chelated with $^{68}$Ga, $^{177}$Lu, or $^{225}$Ac.

14. The compound of claim 1, wherein R$^7$ is

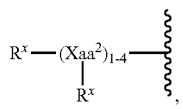

(Xaa$^2$)$_{1-4}$ is a tripeptide, and each R$^X$ is independently —C(O)—(CH$_2$)$_{0-5}$ R$^{18}$—(CH$_2$)$_{1-5}$R$^{17}$B$^{18}$F$_3$, wherein R$^{18}$ is

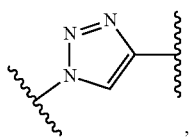 [SMILES: *c1cn(*)nn1]

and R$^{17}$B$^{18}$F$_3$ is

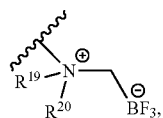

and R$^{19}$ and R$^{20}$ are independently C$_1$—c$_5$ linear or branched alkyl groups.

15. A method of treating a PSMA-expressing condition or disease, comprising administering to a patient in need thereof a therapeutically effective amount of a compound of claim 1.

16. A method of treating a PSMA-expressing condition or disease, comprising administering to a patient in need thereof a therapeutically effective amount of a compound of claim 10.

17. The method of claim 15, wherein the PSMA-expressing condition or disease is a cancer selected from the group consisting of prostate cancer, renal cancer, breast cancer, thyroid cancer, gastric cancer, colorectal cancer, bladder cancer, pancreatic cancer, lung cancer, liver cancer, brain tumor, melanoma, neuroendocrine tumor, ovarian cancer, and sarcoma.

18. The method of claim 17, wherein the PSMA-expressing condition or disease is prostate cancer.

19. A method of imaging PSMA-expressing tissues, comprising administering to a patient in need of such imaging an effective amount of a compound of claim 1; and imaging the tissues of the patient.

20. The method of claim 19, wherein said imaging is performing PET or SPECT imaging.

* * * * *

UNITED STATES PATENT AND TRADEMARK OFFICE
CERTIFICATE OF CORRECTION

PATENT NO. : 11,504,441 B2  
APPLICATION NO. : 17/371587  
DATED : November 22, 2022  
INVENTOR(S) : Lin et al.

Page 1 of 3

It is certified that error appears in the above-identified patent and that said Letters Patent is hereby corrected as shown below:

In the Claims

At Claim 1, Column 137, Lines 2-8, please replace " 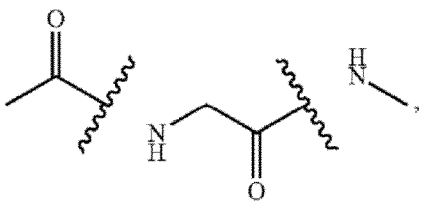 " with

" 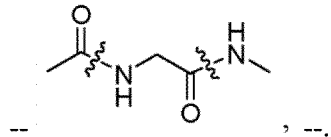 , --.

At Claim 1, Column 137, Lines 8-15, please replace " 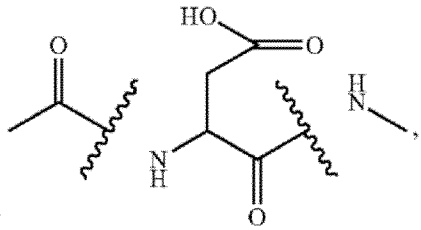 " with

" 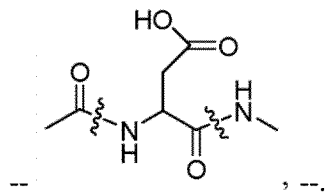 , --.

Signed and Sealed this  
Sixteenth Day of May, 2023

*Katherine Kelly Vidal*

Katherine Kelly Vidal  
*Director of the United States Patent and Trademark Office*

CERTIFICATE OF CORRECTION (continued)
U.S. Pat. No. 11,504,441 B2

At Claim 1, Column 137, Lines 23-32, please replace " 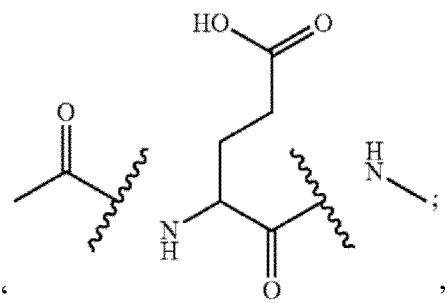 " with 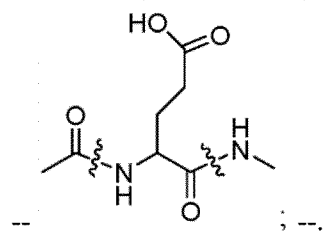 ; --.

At Claim 5, Column 138, Lines 17-22, please replace " 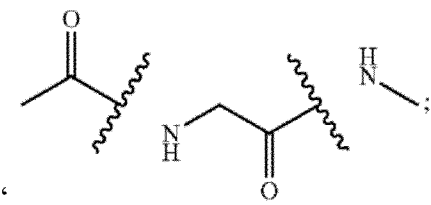 " with 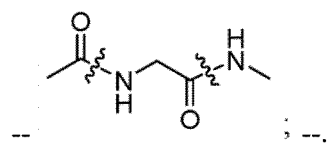 ; --.

At Claim 8, Column 138, Lines 58-63, please replace " 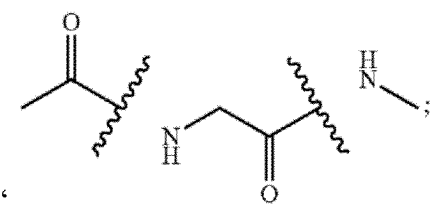 " with 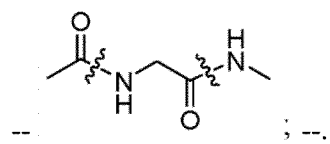 ; --.

At Claim 9, Column 139, Lines 5-10, please replace " 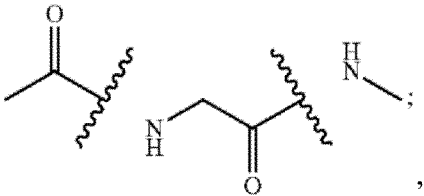 " with

CERTIFICATE OF CORRECTION (continued)
U.S. Pat. No. 11,504,441 B2

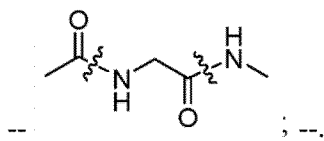

-- ; --.

At Claim 10, Column 139, Lines 15-38, please replace

" 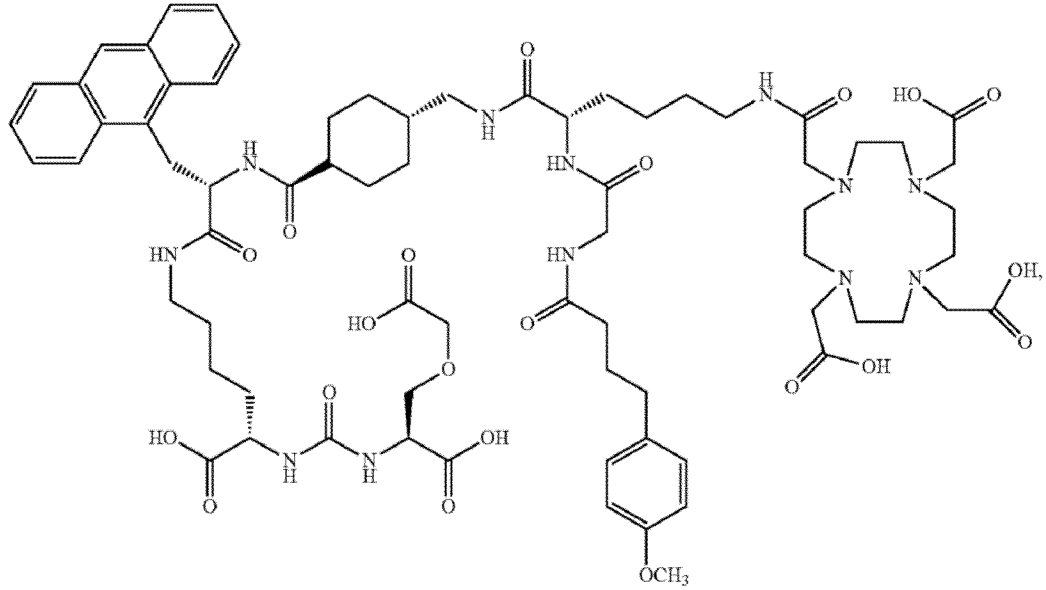 " with

" 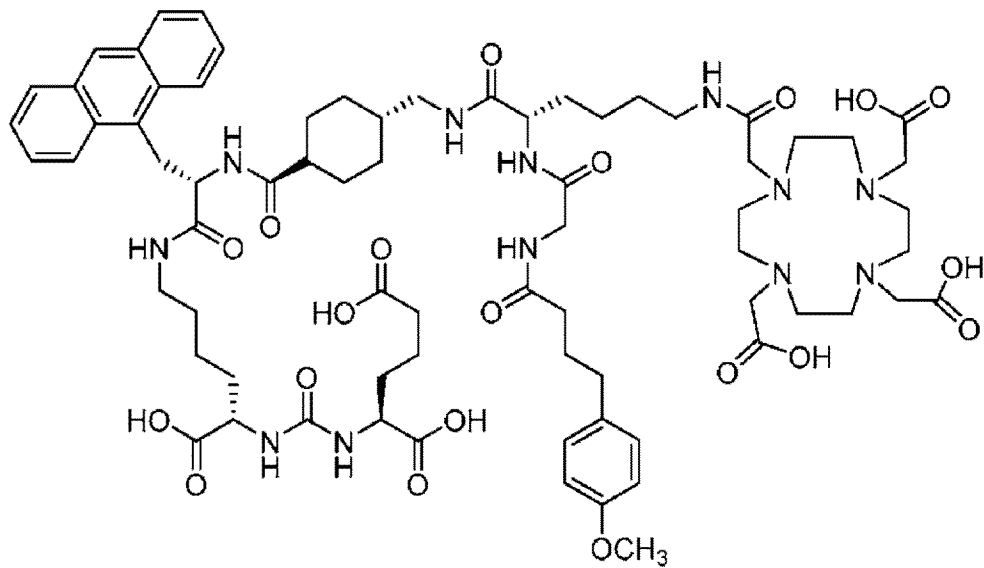 ' --.

At Claim 12, Column 139, Line 46, please replace "$^{225}$AC." with -- $^{225}$Ac. --.

At Claim 14, Column 139, Line 59, please replace
"-C(O)-(CH$_2$)$_{0-5}$ R$^{18}$-(CH$_2$)$_{1-5}$R$^{17}$B$^{18}$F$_3$," with -- -C(O)-(CH$_2$)$_{0-5}$R$^{18}$-(CH$_2$)$_{1-5}$R$^{17}$B$^{18}$F$_3$, --.

At Claim 14, Column 140, Line 13, please replace "C$_1$-c$_5$" with -- C$_1$-C$_5$ --.